(12) United States Patent
Nikolovska-Coleska et al.

(10) Patent No.: US 9,486,422 B2
(45) Date of Patent: Nov. 8, 2016

(54) SMALL MOLECULE INHIBITORS OF MCL-1 AND THE USES OF THEREOF

(71) Applicants: THE REGENTS OF THE UNIVERSITY OF MICHIGAN, Ann Arbor, MI (US); WAYNE STATE UNIVERSITY, Detroit, MI (US)

(72) Inventors: Zaneta Nikolovska-Coleska, Ann Arbor, MI (US); Hollis D. Showalter, Ann Arbor, MI (US); Chenzhong Liao, Anhui (CN); Ramzi Mohammad, Troy, MI (US); Fardokht Abulwerdi, Ann Arbor, MI (US)

(73) Assignees: THE REGENTS OF THE UNIVERSITY OF MICHIGAN, Ann Arbor, MI (US); WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 14/346,584

(22) PCT Filed: Oct. 8, 2012

(86) PCT No.: PCT/US2012/059216
§ 371 (c)(1),
(2) Date: Mar. 21, 2014

(87) PCT Pub. No.: WO2013/052943
PCT Pub. Date: Apr. 11, 2013

(65) Prior Publication Data
US 2014/0235702 A1    Aug. 21, 2014

Related U.S. Application Data

(60) Provisional application No. 61/544,133, filed on Oct. 6, 2011.

(51) Int. Cl.
| | | |
|---|---|---|
| C07C 321/18 | (2006.01) |
| A61K 31/165 | (2006.01) |
| A61K 31/381 | (2006.01) |
| C07D 333/34 | (2006.01) |
| C07C 311/21 | (2006.01) |
| C07D 403/12 | (2006.01) |
| C07D 215/38 | (2006.01) |
| C07D 215/40 | (2006.01) |
| C07D 333/62 | (2006.01) |
| C07C 311/20 | (2006.01) |
| C07D 409/12 | (2006.01) |
| C07C 323/49 | (2006.01) |
| C07C 323/52 | (2006.01) |
| C07C 323/60 | (2006.01) |
| C07D 257/04 | (2006.01) |
| C07D 295/096 | (2006.01) |
| C07D 295/26 | (2006.01) |
| A61K 31/196 | (2006.01) |
| A61K 45/06 | (2006.01) |

C07C 321/28    (2006.01)
A61K 31/18     (2006.01)
(Continued)

(52) U.S. Cl.
CPC ............ A61K 31/165 (2013.01); A61K 31/18 (2013.01); A61K 31/196 (2013.01); A61K 31/216 (2013.01); A61K 31/381 (2013.01); A61K 31/402 (2013.01); A61K 31/41 (2013.01); A61K 31/4453 (2013.01); A61K 31/47 (2013.01); A61K 31/4709 (2013.01); A61K 31/495 (2013.01); A61K 31/551 (2013.01); A61K 31/664 (2013.01); A61K 45/06 (2013.01); C07C 311/20 (2013.01); C07C 311/21 (2013.01); C07C 321/28 (2013.01); C07C 323/49 (2013.01); C07C 323/52 (2013.01); C07C 323/60 (2013.01); C07D 215/38 (2013.01); C07D 215/40 (2013.01); C07D 257/04 (2013.01); C07D 295/096 (2013.01); C07D 295/26 (2013.01); C07D 333/34 (2013.01); C07D 333/62 (2013.01); C07D 403/12 (2013.01); C07D 409/12 (2013.01); *C07C 2101/02* (2013.01); *C07C 2101/08* (2013.01); *C07C 2101/14* (2013.01); *C07C 2101/18* (2013.01)

(58) Field of Classification Search
CPC .................................................. C07C 321/18
See application file for complete search history.

(56) References Cited

U.S. PATENT DOCUMENTS 4,108,663 A * 8/1978 Okazaki et al. .............. 430/505
4,492,749 A   1/1985 Scheler
(Continued)

FOREIGN PATENT DOCUMENTS

WO   WO 2009149192 A1 * 12/2009
WO       2010/005534       1/2010
(Continued)

OTHER PUBLICATIONS

Han, H.K. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
(Continued)

*Primary Examiner* — Noble Jarrell
*Assistant Examiner* — John S Kenyon
(74) *Attorney, Agent, or Firm* — Casimir Jones, SC

(57) ABSTRACT

This invention is in the field of medicinal chemistry. In particular, the invention relates to a new class of small-molecules having sulfonamido-1-hydroxynaphthalene structure which function as inhibitors of Mcl-1 protein, and their use as therapeutics for the treatment of cancer and other diseases.

3 Claims, 33 Drawing Sheets

(51) Int. Cl.

| | |
|---|---|
| A61K 31/216 | (2006.01) |
| A61K 31/402 | (2006.01) |
| A61K 31/41 | (2006.01) |
| A61K 31/4453 | (2006.01) |
| A61K 31/47 | (2006.01) |
| A61K 31/4709 | (2006.01) |
| A61K 31/495 | (2006.01) |
| A61K 31/551 | (2006.01) |
| A61K 31/664 | (2006.01) |

(56) References Cited

U.S. PATENT DOCUMENTS

2005/0282818 A1 12/2005 Ramesh
2007/0203236 A1 8/2007 Smith

FOREIGN PATENT DOCUMENTS

| | | | |
|---|---|---|---|
| WO | WO2010005534 A2 * | 1/2010 | |
| WO | WO 2010005534 A2 * | 1/2010 | |
| WO | WO 2010102286 A2 * | 9/2010 | |
| WO | WO 2010151799 A2 * | 12/2010 | ............ A61K 31/70 |
| WO | WO 2012178036 A2 * | 12/2012 | |

OTHER PUBLICATIONS

Xu, X., et al. "Chemical Probes that Competitively and Selectively Inhibit Stat3 Activation." PLoS ONE. (2009), vol. 4(3), pp. 1-12.*
Soares, K.M., et al. "Profiling the NIH Small Molecule Repository for Compounds That Generate H2O2 by Redox Cycling in Reducing Environments." ASSAY and Drug Development Technologies. (Apr. 2010), pp. 152-174.*
Bodner Research Web. "The Chemistry of the Halogens." (c) Apr. 2009. Available from: < http://web.archive.org/web/20090414155348/http://chemed.chem.purdue.edu/genchem/topicreview/bp/ch10/group7.php >.*
Hanahan, D., et al., Cell, 2000, 100: 57-70.
Griffiths, GJ, et al., J Cell Biol. 1999, 144:903-14.
Day, CL, et al., J. Biol. Chem., 2005; 280:4738-44.
Day, CL, et al., J. Mol. Biol. 2008;280:958-71.
Zhou, P., et al., Blood, 1997; 89:630-43.
Miyamoto, Y., et al., Oncology, 1999;56-73-82.
Schniewind, B., et al., Int. J. Cancer, 2004;109:182-8.
Ren, LN, et al., Biochem. Biophys Res. Commun. 2009;386-35-9.
Wei, SH, et al., Cancer Chemother Pharmacol. 2008;62:1055-64.
Guoan, X., et al., Surgery, 2010; 147-553-61.
Huang, S., et al., Cancer Res. 2008;68-2944-51.
Oltersdorf, T., et al., Nature, 2005;435:677-81.
Tse, C., et al., Cancer Res. 2008;68-3421-8.
Chen, S., et al., Cancer Res. 2007;67:782-91.
International Search Report, International Patent Application No. PCT/US2012/059216, mailed Mar. 25, 2013.
Park et al. "Characterization of molecular recognition of STAT3 SH2 domain inhibitors through molecular simulation." J. Mol. Recognit. 2011, vol. 24, pp. 254-265.

* cited by examiner

A

SMALL MOLECULE INHIBITORS OF MCL-1 AND THE USES OF THEREOF

CROSS-REFERENCE TO RELATED APPLICATIONS

The present application is a 371 U.S. National Phase Entry of pending International Patent Application No. PCT/US2012/059216, international filing date Oct. 8, 2012, which claims priority to U.S. Provisional Patent Application No. 61/544,133, filed Oct. 6, 2011, the contents of which are incorporated by reference in its entirety.

STATEMENT REGARDING FEDERALLY SPONSORED RESEARCH OR DEVELOPMENT

This invention was made with government support under CA149442 and CA158976 awarded by the National Institutes of Health. The government has certain rights in the invention.

FIELD OF THE INVENTION

This invention is in the field of medicinal chemistry. In particular, the invention relates to a new class of small-molecules having sulfonamido-1-hydroxynaphthalene structure which function as inhibitors of Mcl-1 protein, and their use as therapeutics for the treatment of cancer and other diseases.

INTRODUCTION

Pancreatic cancer is the fourth most common cause of cancer death across the globe (see, e.g., Hariharan, D., et al., HPB 10 (1): 58-62; herein incorporated by reference in its entirety). Pancreatic cancer often has a poor prognosis: for all stages combined, the 1- and 5-year relative survival rates are 25% and 6%, respectively (see, e.g., American Cancer Society: Cancer Facts & Figures 2010; herein incorporated by reference in its entirety); for local disease the 5-year survival is approximately 20% (see, e.g., American Cancer Society: Cancer Facts & Figures 2010; National Cancer Institute. General Information About Pancreatic Cancer; each herein incorporated by reference in its entirety) while the median survival for locally advanced and for metastatic disease, which collectively represent over 80% of individuals (see, e.g., National Cancer Institute. General Information About Pancreatic Cancer; herein incorporated by reference in its entirety), is about 10 and 6 months respectively (see, e.g., Benson A B, Myerson R J, and Sasson A R. Pancreatic, Neuroendocrine G I, and Adrenal Cancers. Cancer Management 13th edition; herein incorporated by reference in its entirety).

Improved methods for treating this disease are needed.

SUMMARY OF THE INVENTION

A hallmark of cancer cells is defects in the apoptotic cell death program (see, e.g., Hanahan D, et al., Cell. 2000; 100:57-70; herein incorporated by reference in its entirety). The broad resistance of pancreatic cancer (PC) to existing chemotherapeutic agents and radiation therapy is due, in large part, to defects in apoptotic signaling pathways. Mcl-1 is a potent anti-apoptotic protein and an important survival factor for many cancers, including PC. Its overexpression has been associated with tumor initiation, progression and resistance to current anticancer therapies. Recent independent studies using a genetic approach to down-regulation of Mcl-1 provided a significant proof-of-concept that selective, small-molecule Mcl-1 inhibitors may have potential as a new treatment for PC by overcoming the apoptosis resistance of cancer cells to current therapeutic agents. Mcl-1 is a homologous protein related to other anti-apoptotic proteins such as Bcl-2 and Bcl-x$_L$, but it has a distinctly different structure and exhibits selective binding to the pro-apoptotic BH3-only proteins. This suggests that specific targeting of the Mcl-1 protein is possible and that drugs specific to Mcl-1 can be developed.

Using high throughput screening, experiments conducted during the course of developing embodiments for the present invention identified a new class of small-molecules having sulfonamido-1-hydroxynaphthalen structure which function as inhibitors of Mcl-1 protein.

Accordingly, the present invention contemplates that exposure of animals (e.g., humans) suffering from cancer (e.g., and/or cancer related disorders) to therapeutically effective amounts of drug(s) (e.g., small molecules) that inhibit the activity of Mcl-1 will inhibit the growth of cancer cells or supporting cells outright and/or render such cells as a population more susceptible to the cell death-inducing activity of cancer therapeutic drugs or radiation therapies. In some embodiments, the inhibition of Mcl-1 activity occurs through, for example, inhibiting the interaction between Mcl-1 and Bak and/or Bax. In some embodiments, the inhibition of Mcl-1 activity occurs through, for example, binding the BH3 binding groove of Mcl-1. The present invention contemplates that inhibitors of Mcl-1 activity satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain sulfonamido-1-hydroxynaphthalene compounds function as inhibitors of Mcl-1 protein, and serve as therapeutics for the treatment of cancer and other diseases. Thus, the present invention relates to sulfonamido-1-hydroxynaphthalene compounds useful for inhibiting Mcl-1 activity (e.g., thereby facilitating cell apoptosis), and increasing the sensitivity of cells to inducers of apoptosis and/or cell cycle arrest. Certain sulfonamido-1-hydroxynaphthalene compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, sulfonamido-1-hydroxynaphthalene compounds have Formula I:

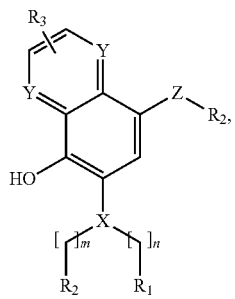

Formula II:

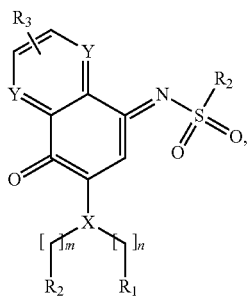

or Formula III:

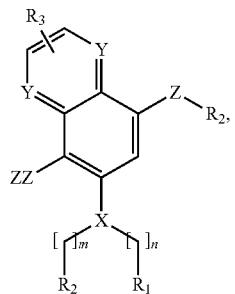

including pharmaceutically acceptable salts, solvates, and/or prodrugs thereof.

Formulas I, II and/or III are not limited to a particular chemical moiety for R1, R2, R3, m, n, X, Y, Z and ZZ. In some embodiments, R1, R2, R3, m, n, X, Y, Z and ZZ is independently include any chemical moiety that permits the resulting compound to bind with an Mcl-1 protein.

In some embodiments, X is selected from O, S, N or C.

In some embodiments, Y is selected from C or N.

In some embodiments, Z is selected from

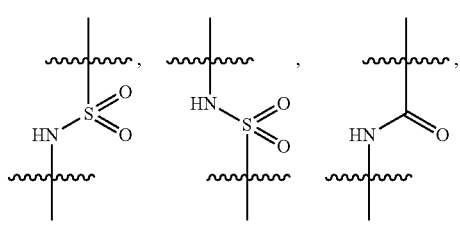

-continued

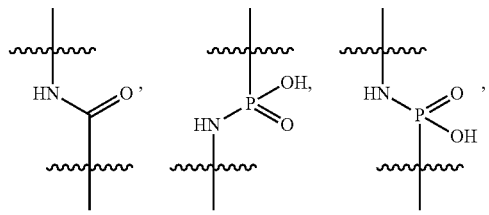

etc.

In some embodiments, ZZ is selected from the group consisting of OH, OCH$_3$, =O, and

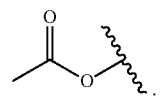

In some embodiments, m is between 0 and 6.

In some embodiments, n is between 0 and 4.

In some embodiments, R1 is selected from H, —COOH,

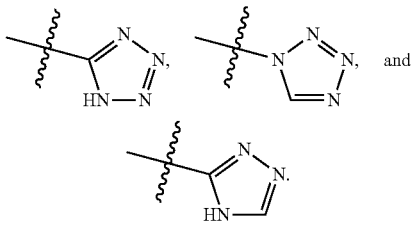

In some embodiments, R1 is any chemical moiety having hydrogen bond acceptors. In some embodiments, R1 is any negatively charged chemical moiety having hydrogen bond acceptors.

In some embodiments, R1 is absent.

In some embodiments, R2 is independently selected from —H,

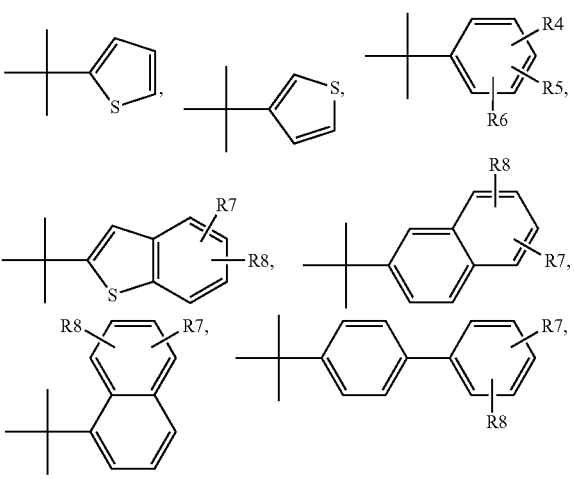

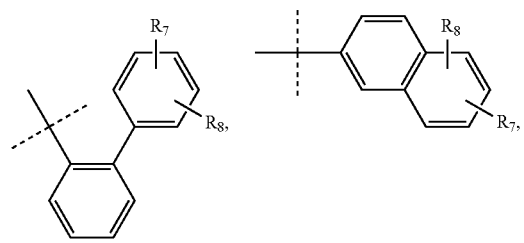
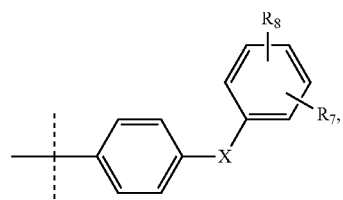
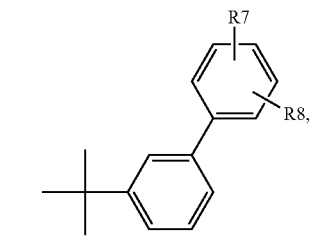
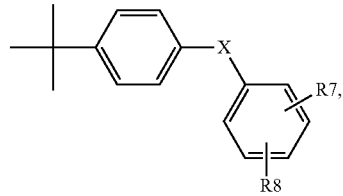
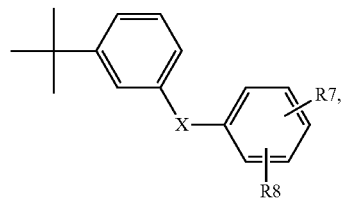
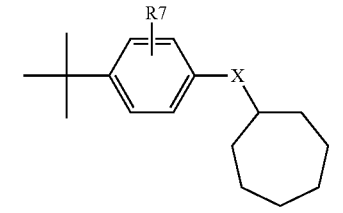
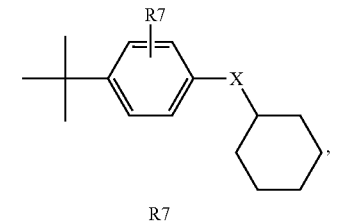
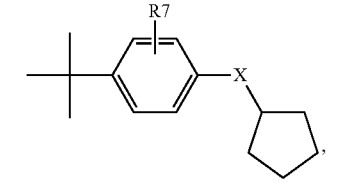
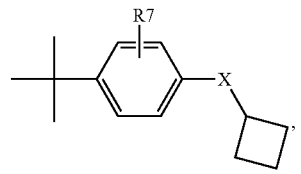
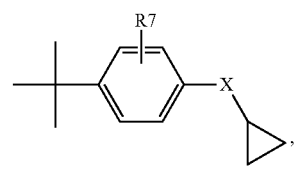
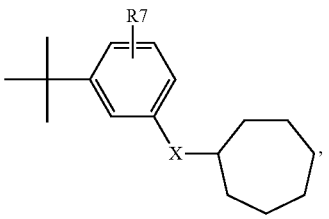
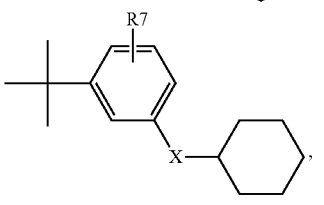
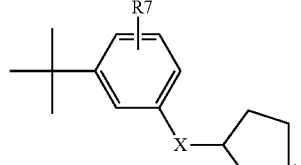
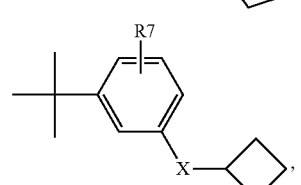
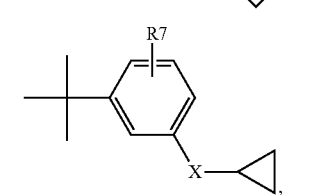
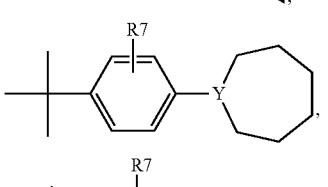
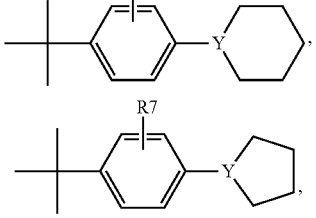

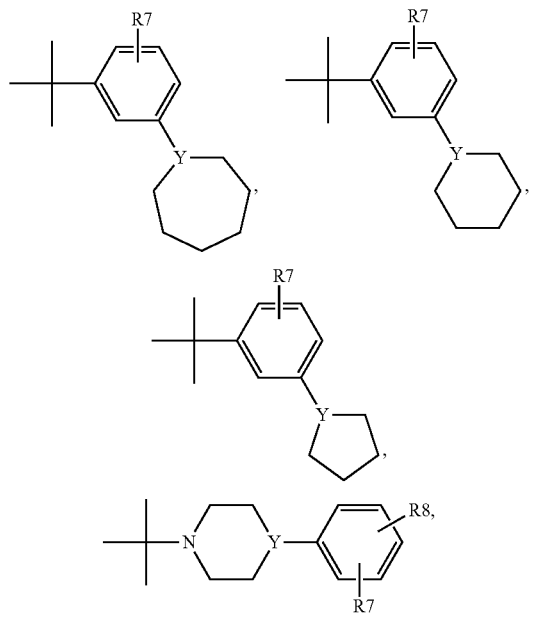
etc.
In some embodiments, R2 is independently selected from the group consisting of H,
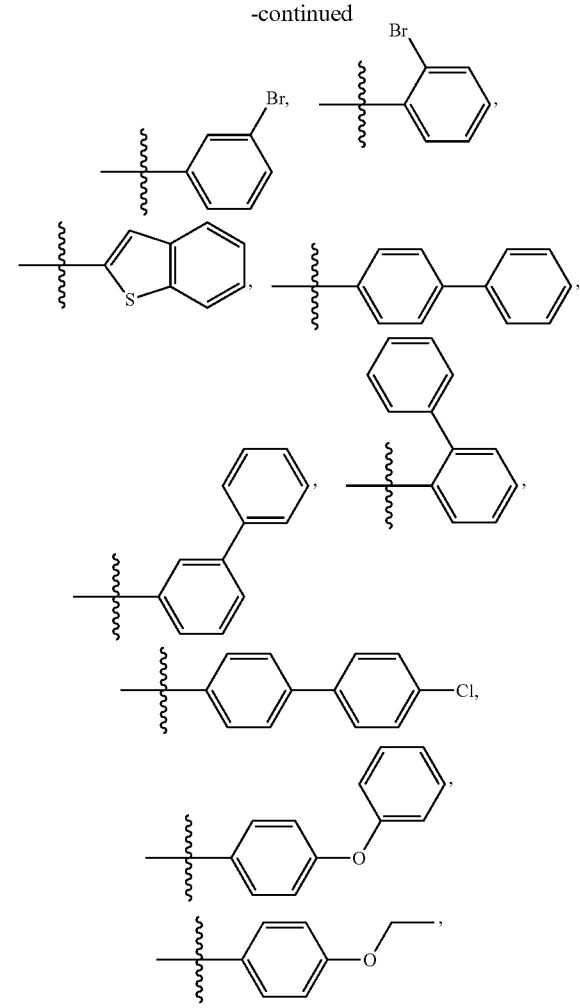
In some embodiments, R2 is absent.
In some embodiments, R3 is selected from —H, —F, —Cl, —Br, —CH$_3$, —CF$_3$, —OCH$_3$, etc.
In some embodiments, R3 is absent.
In some embodiments,
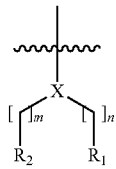
is selected from the group consisting of Cl, H,
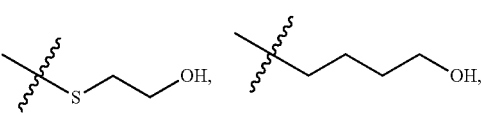

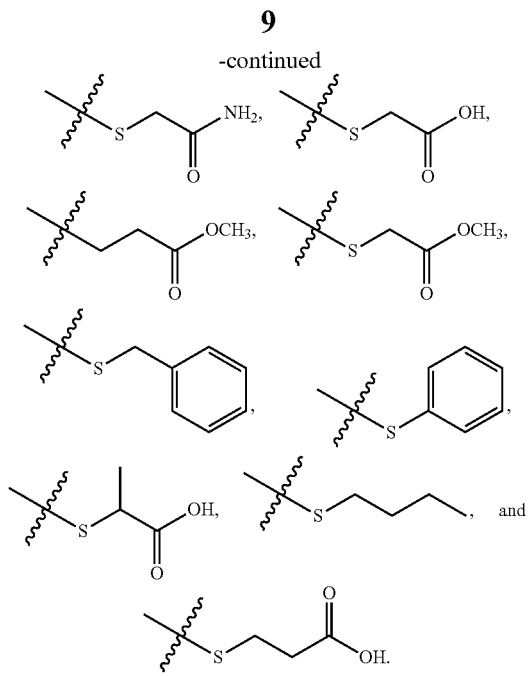
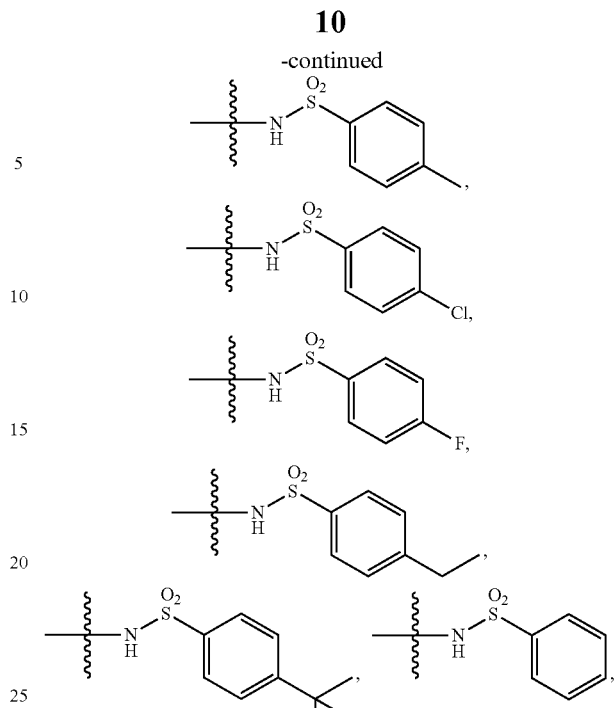
In some embodiments,
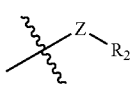
is selected from the group consisting of
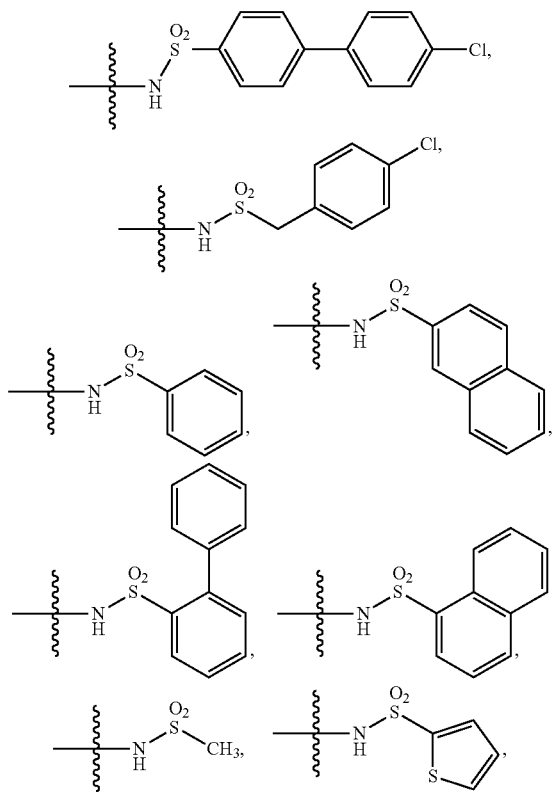
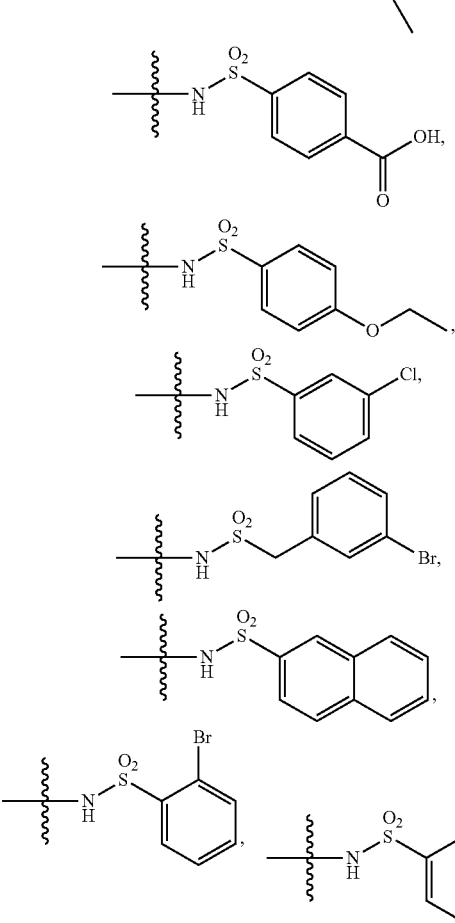

-continued

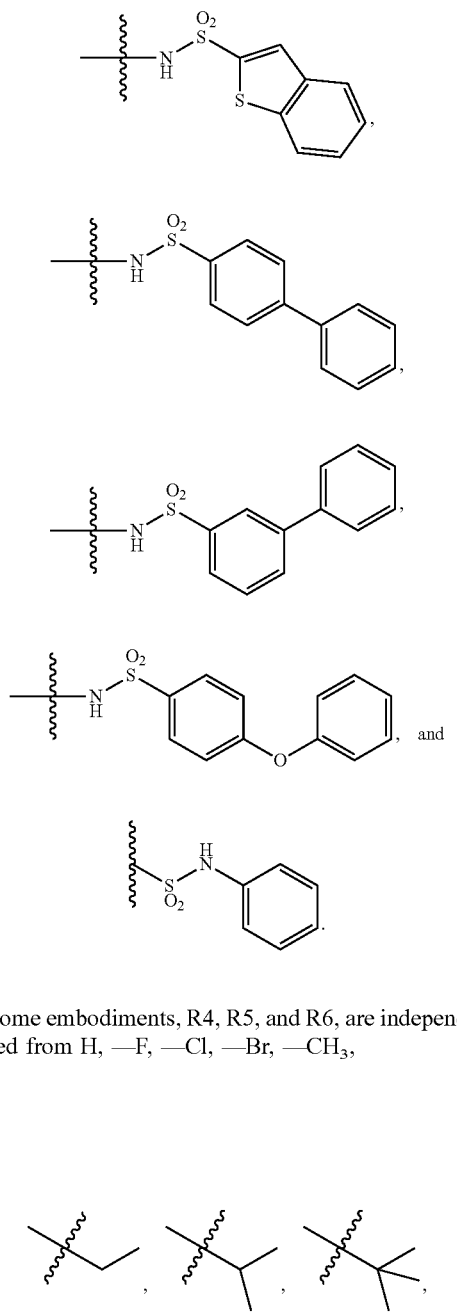

In some embodiments, R4, R5, and R6, are independently selected from H, —F, —Cl, —Br, —CH₃,

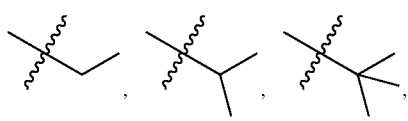

or any other alkyl groups (substituted or unsubstituted), —CF₃, —OH, —OCH₃, —OC₂H₅, —OCF₃, —NO₂, —COOH, etc.

In some embodiments, R7 and R8 are independently selected from —H, —F, —Cl, —Br, —CH₃, or any other alkyl groups (substituted or unsubstituted), —CF₃, —OH, —OCH₃, —OC₂H₅, etc.

Tables 2, 3, 4 and 5 shows binding affinities (IC$_{50}$ values were determined with fluorescence polarizing binding assay) for various compounds encompassed and inhibition against Mcl-1 within Formulas I, II and/or III.

In some embodiments, the following compounds are contemplated for Formula I, Formula II, and Formula III:

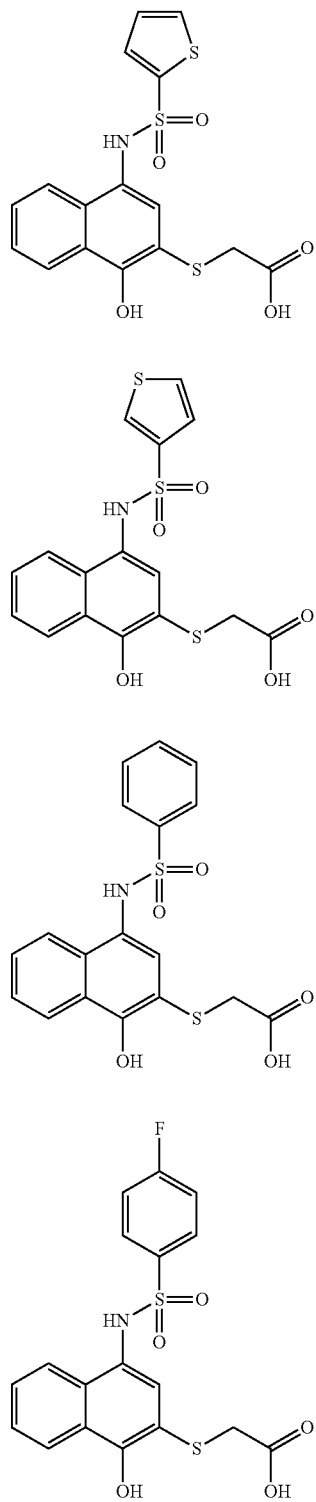

-continued
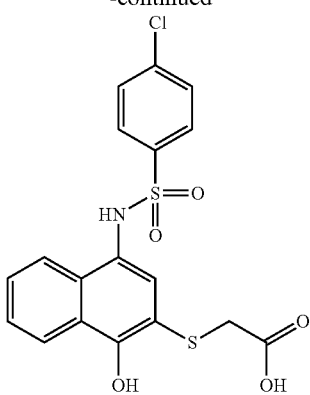
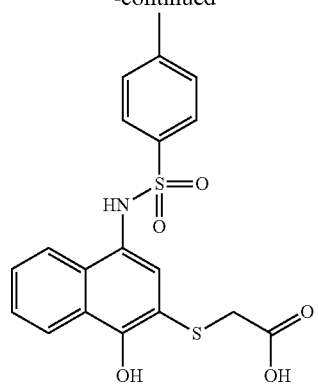
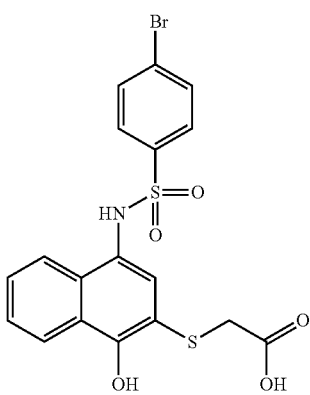
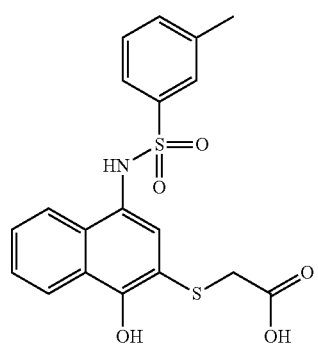
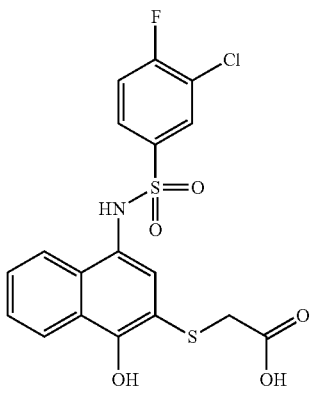
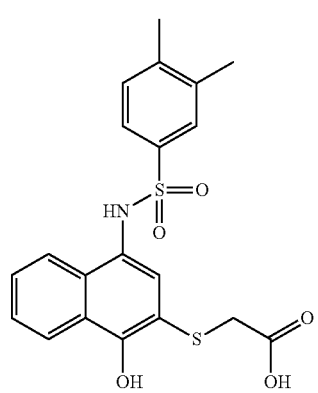
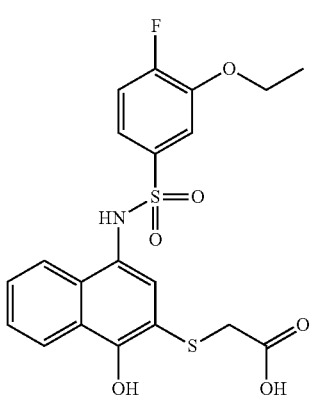
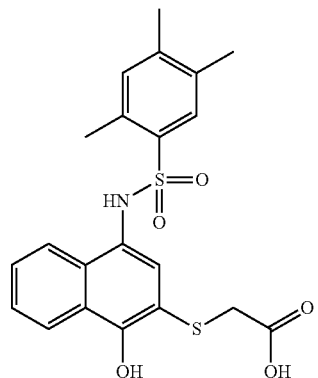

-continued
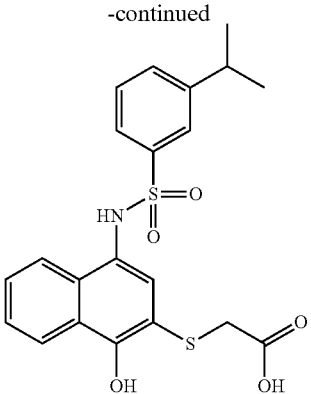
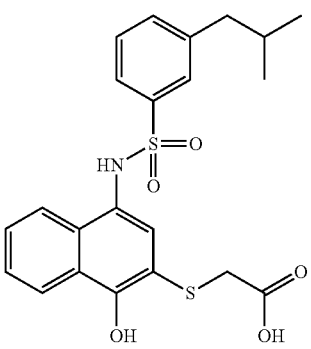
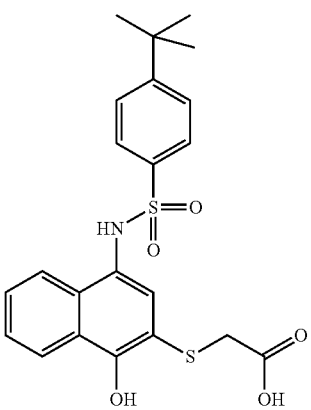
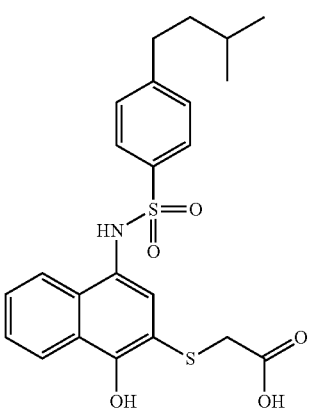
-continued
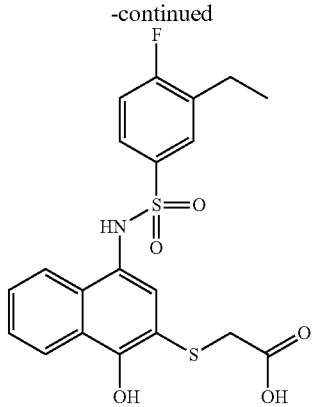
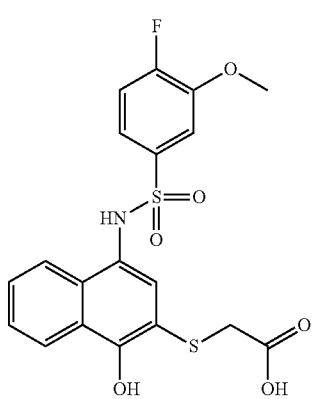
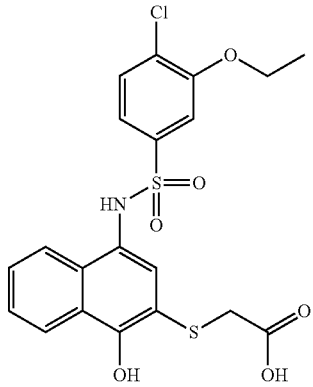
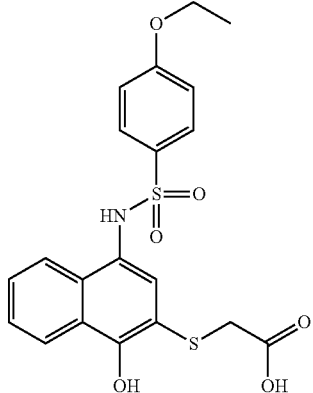

-continued
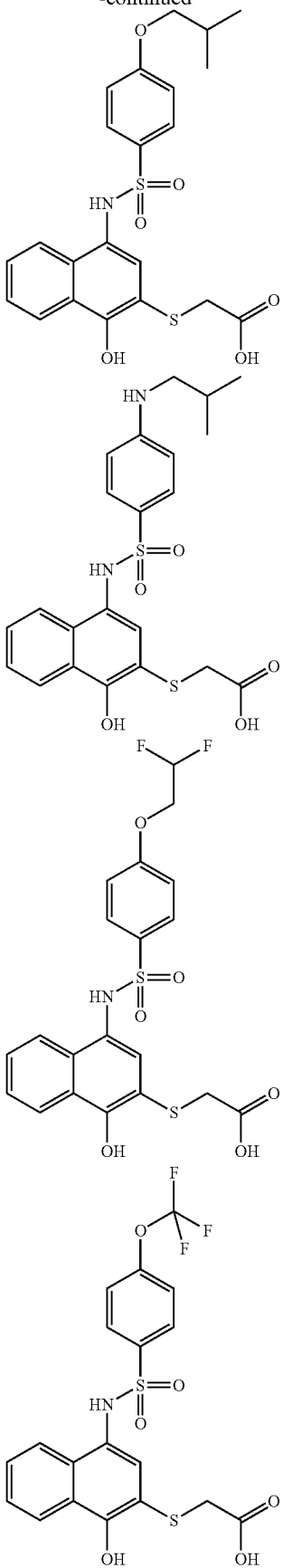
-continued
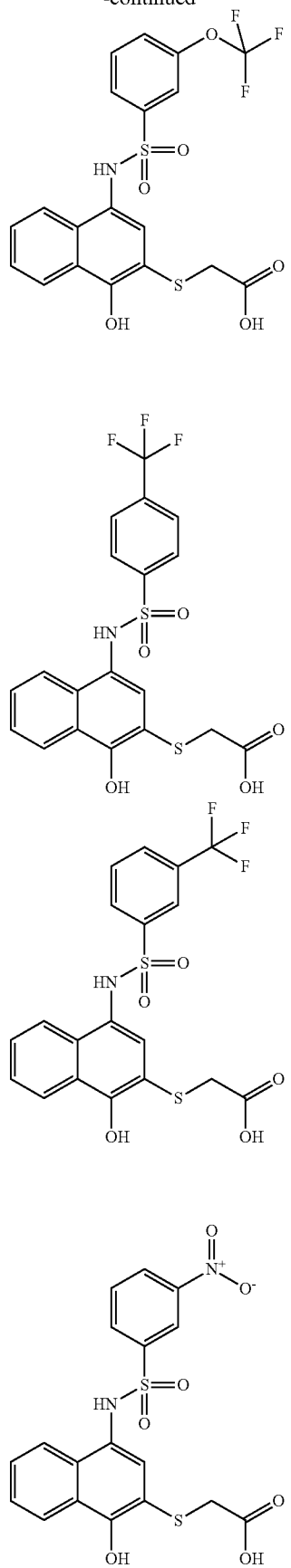

-continued
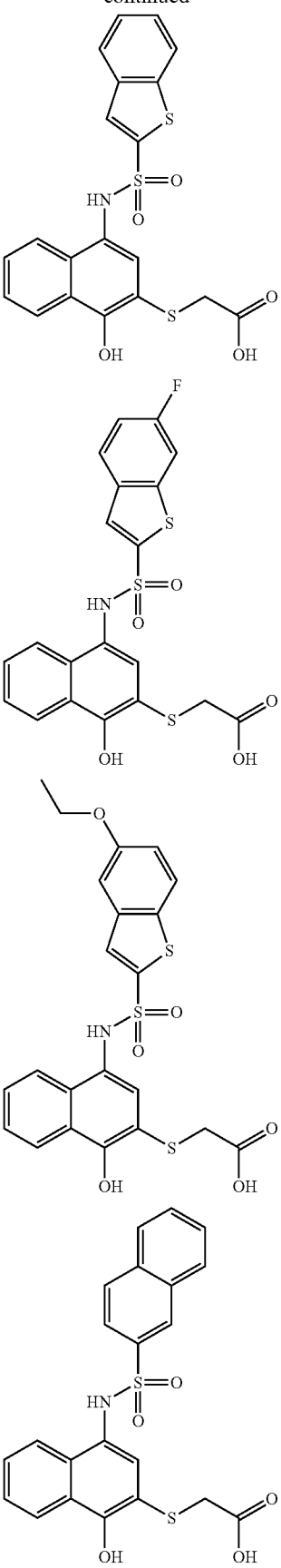
-continued
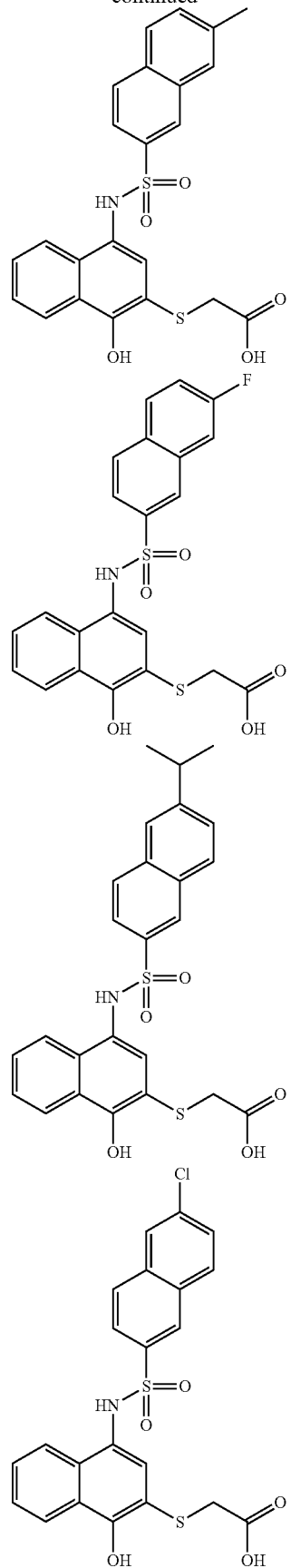

21
-continued
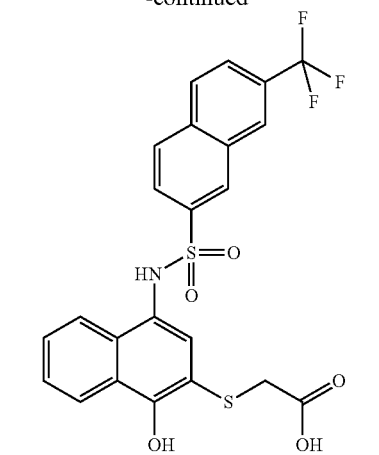
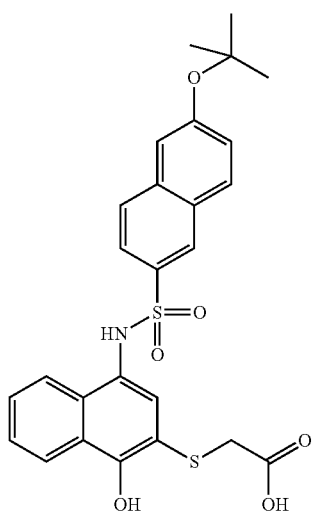
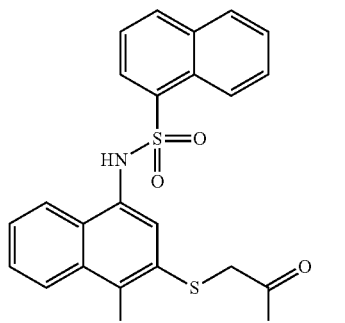
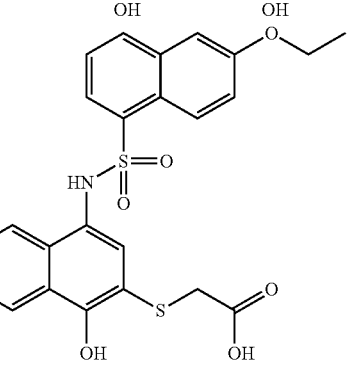
22
-continued
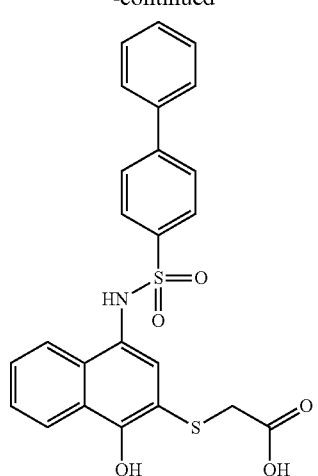
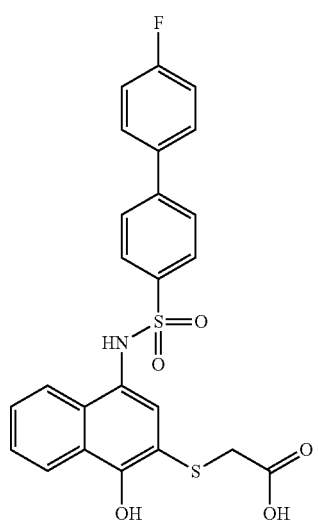
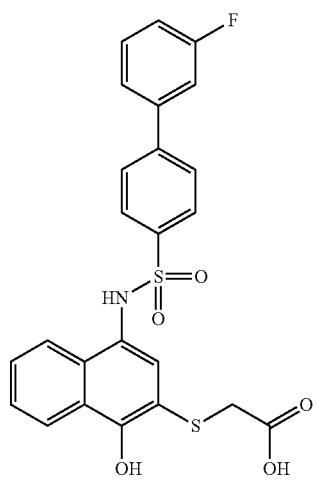

-continued
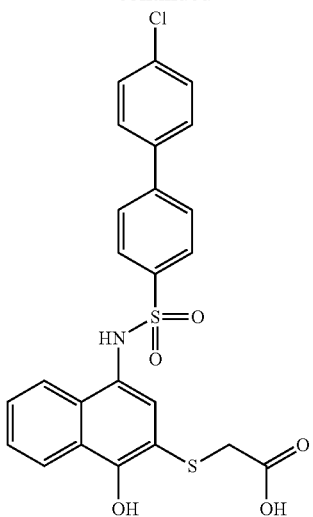
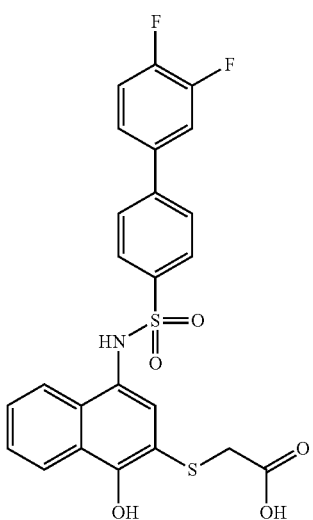
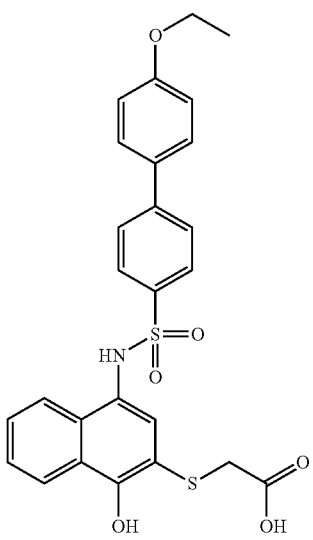
-continued
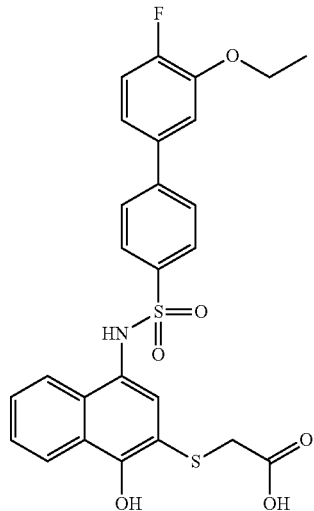
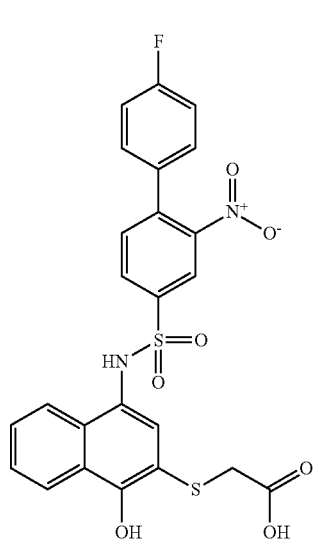
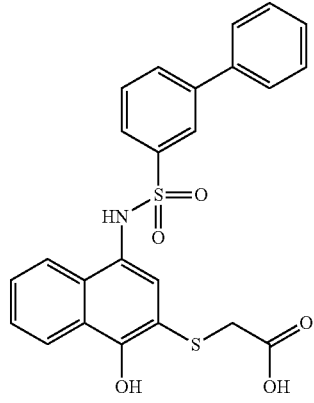

25
-continued
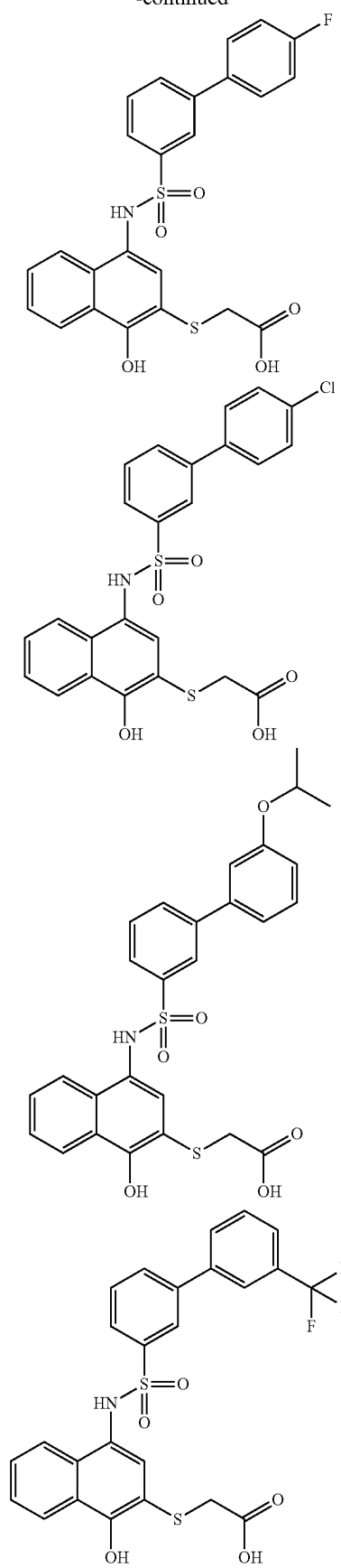
26
-continued
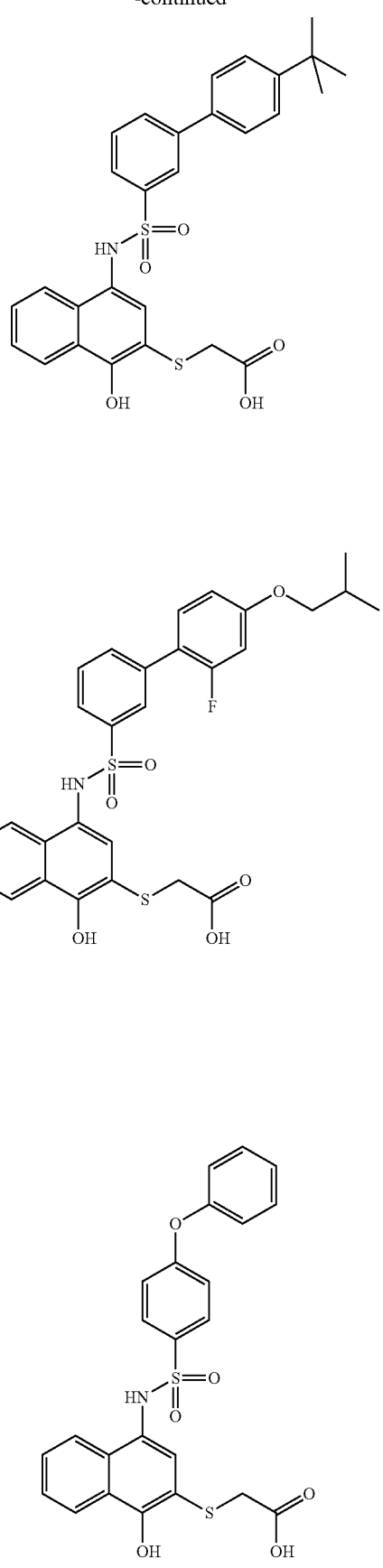

27
-continued
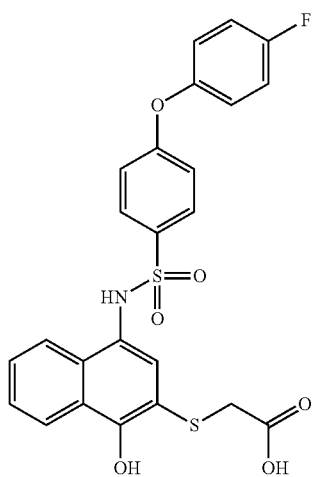
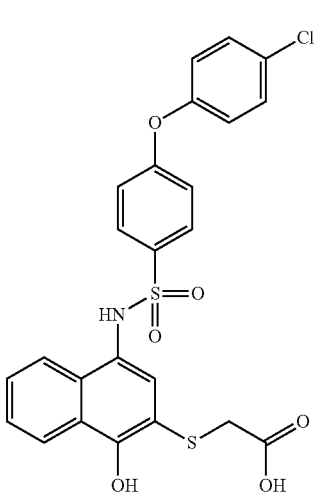
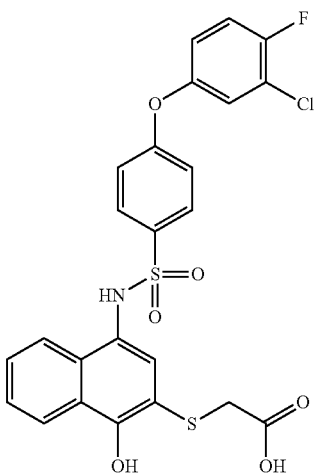
28
-continued
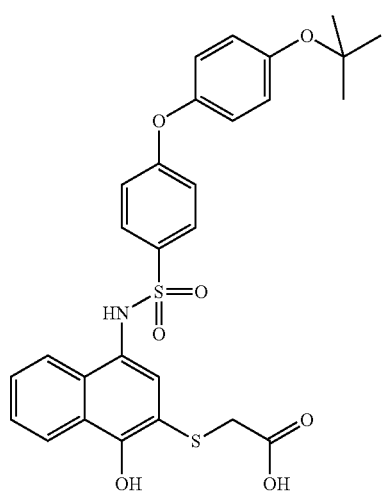
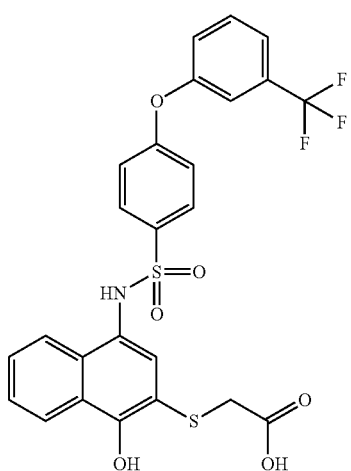
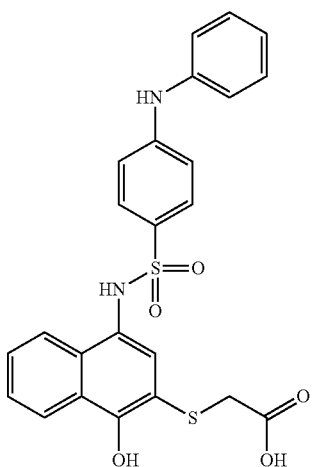

29
-continued
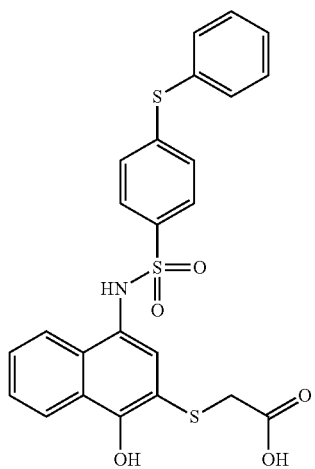
30
-continued
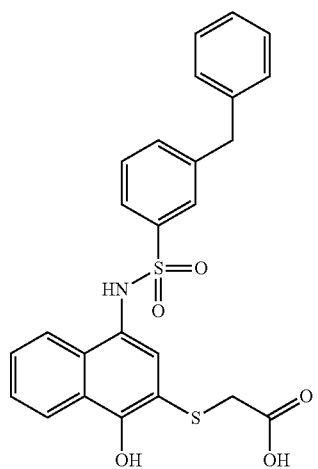
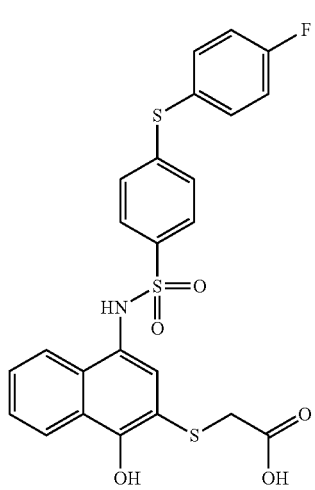
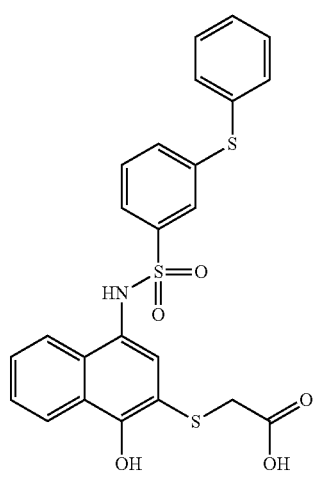
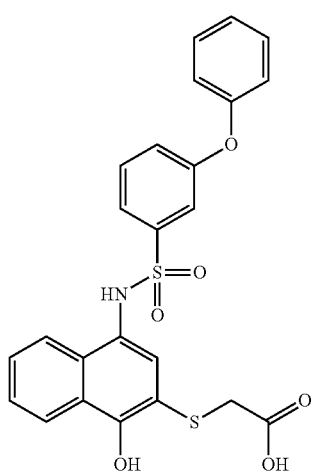
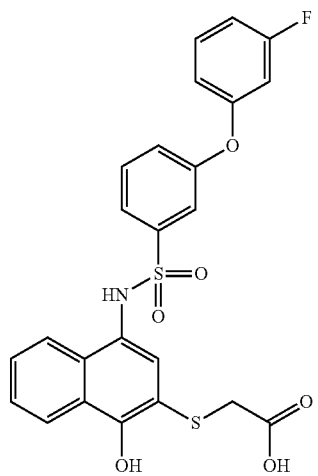

31
-continued
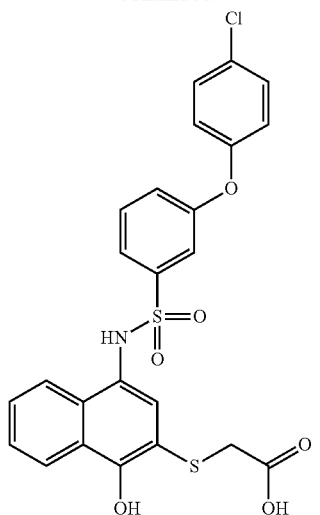
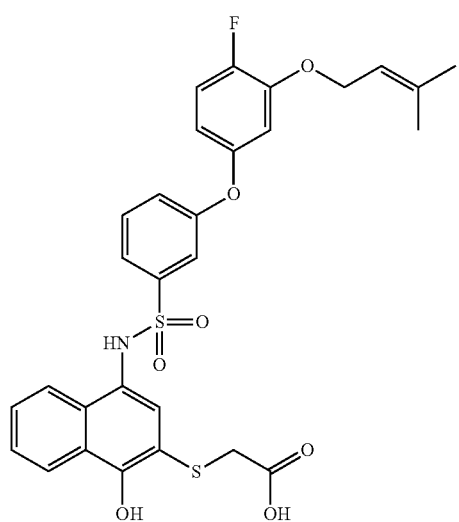
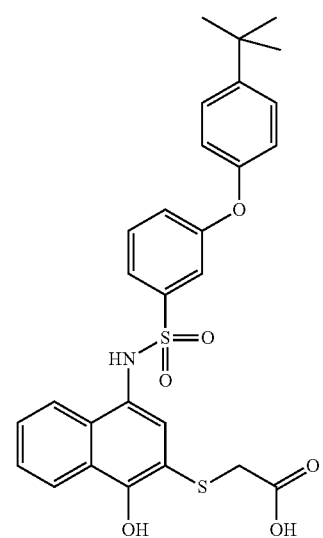
32
-continued
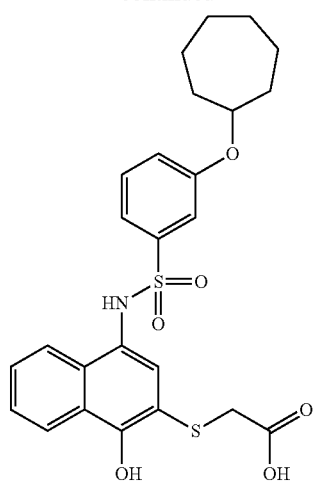
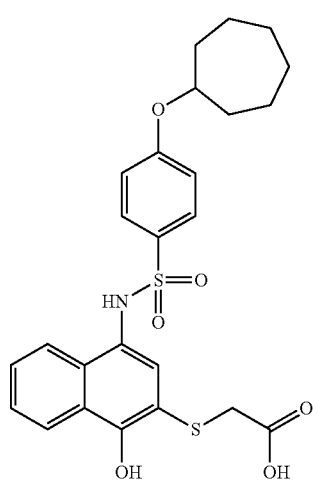
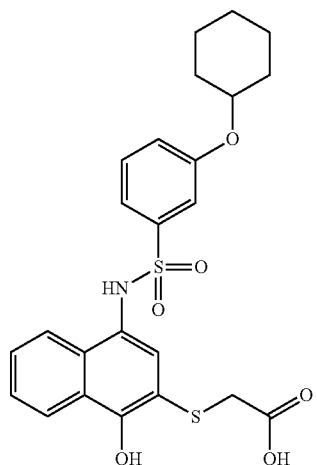

33
-continued
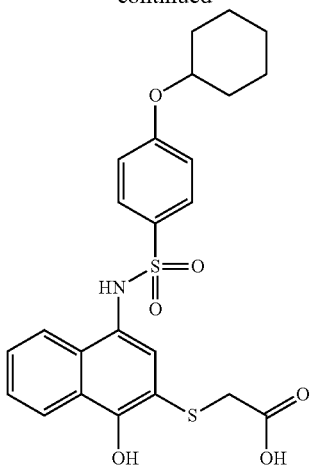
34
-continued
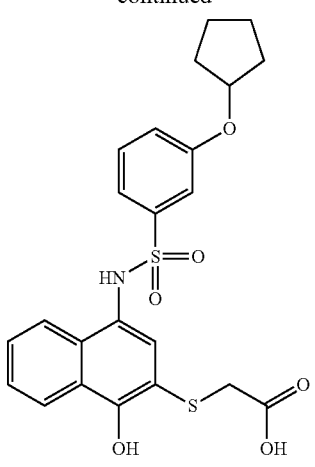
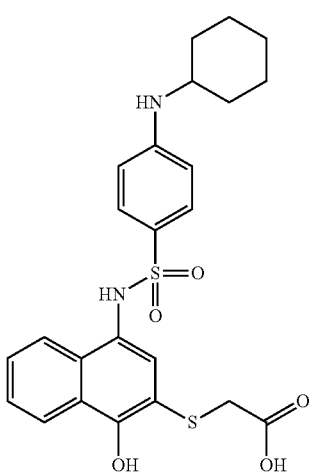
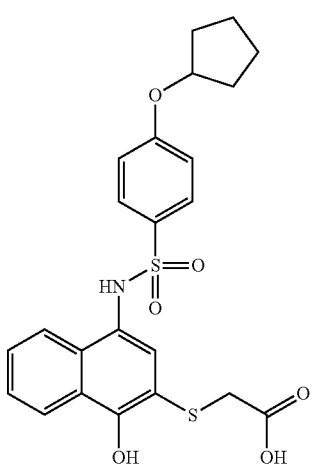
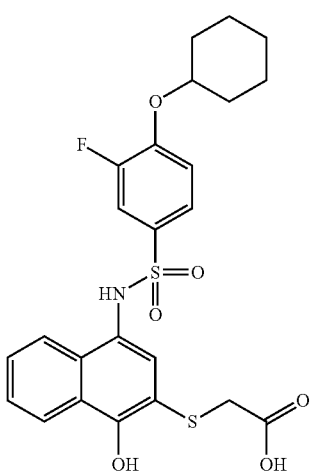
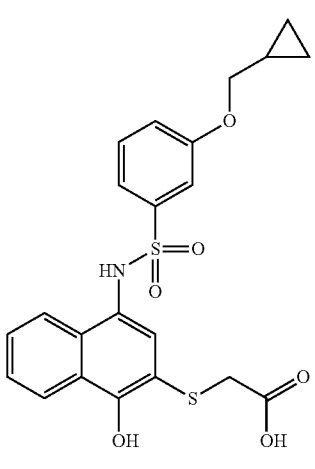

35
-continued
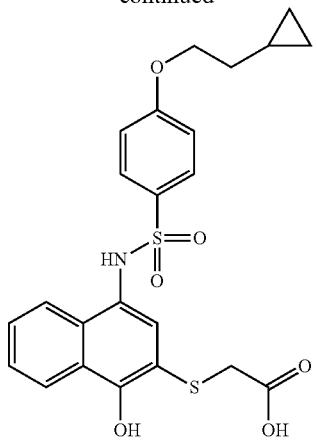
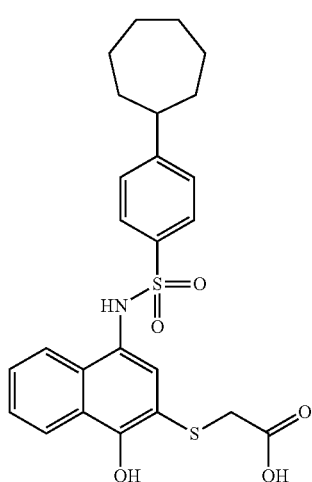
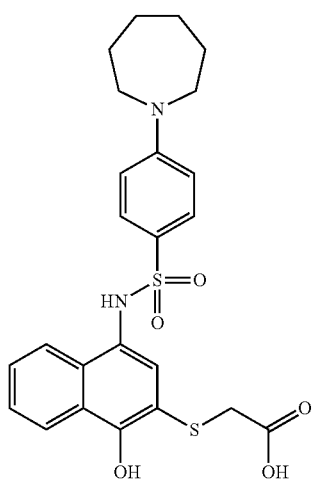
36
-continued
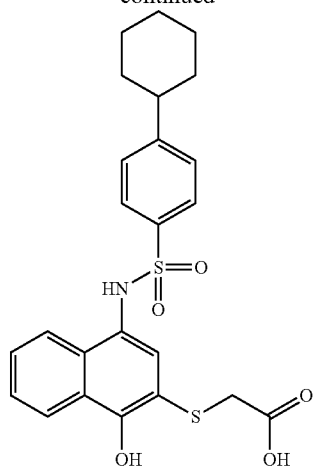
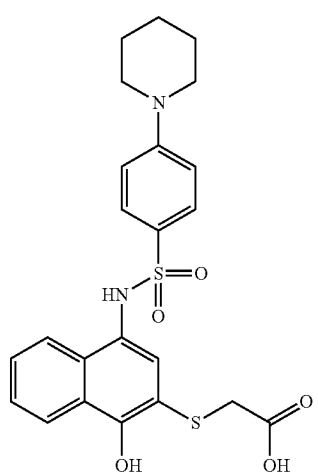
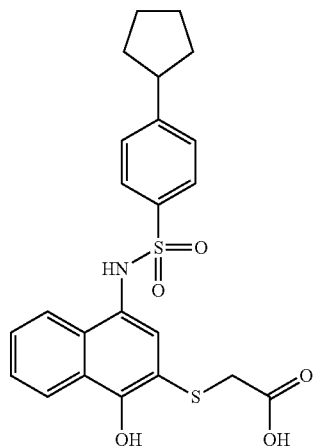

37
-continued
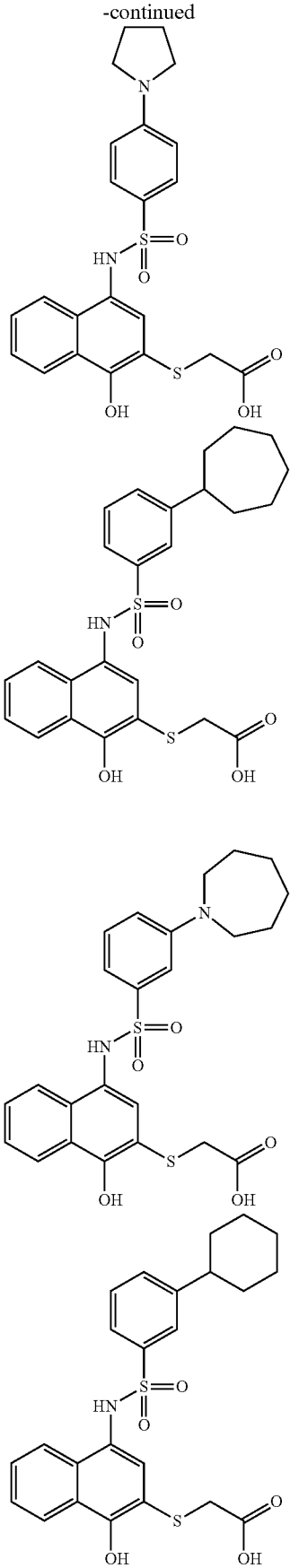
38
-continued
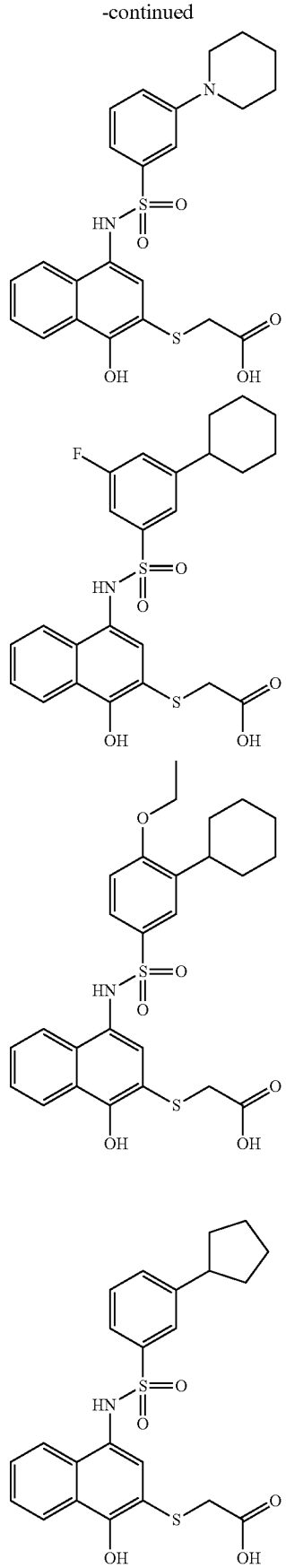

39
-continued
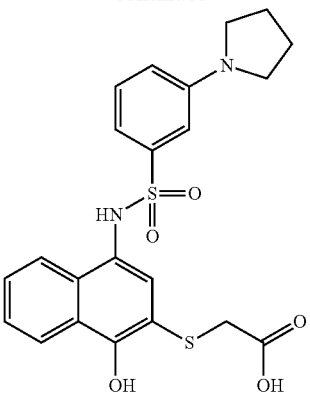
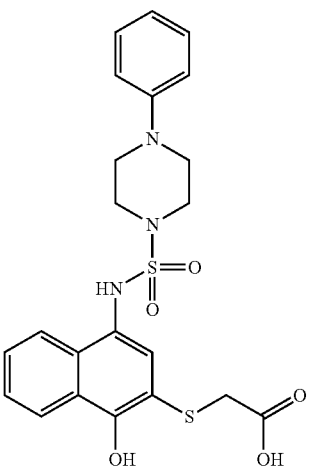
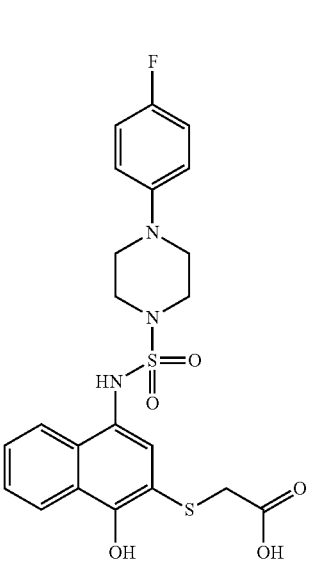
40
-continued
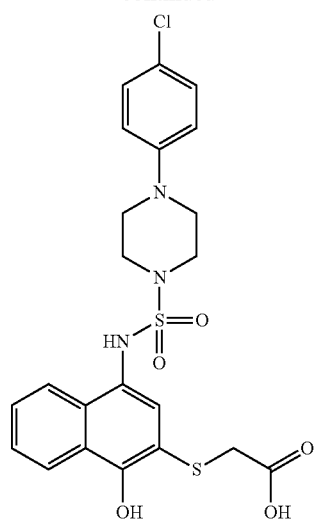
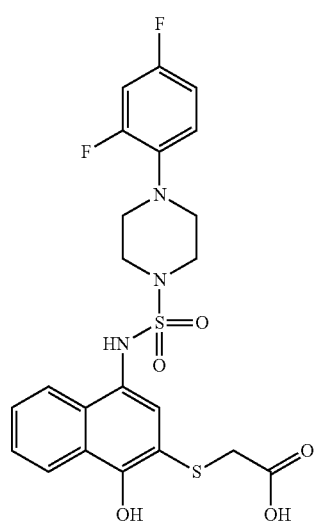
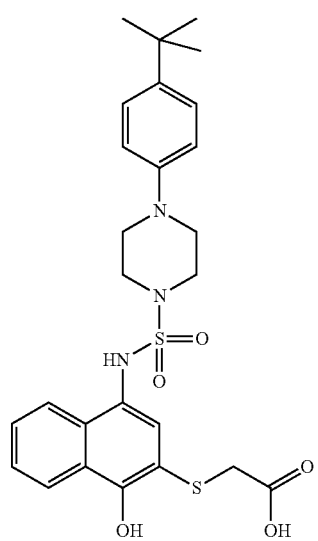

-continued
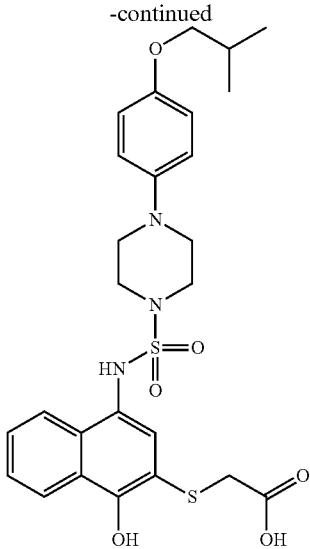
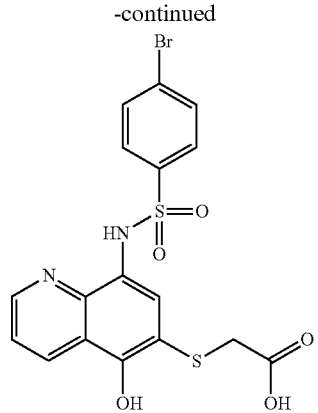
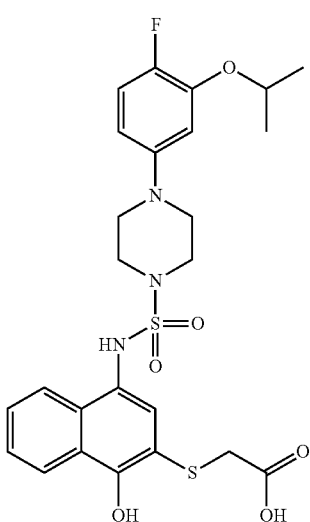
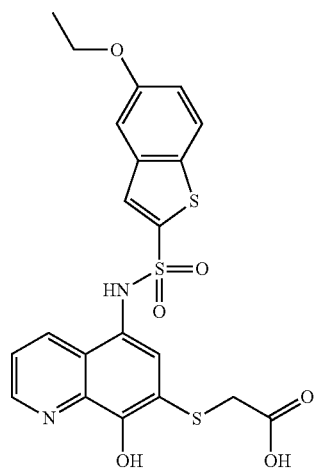
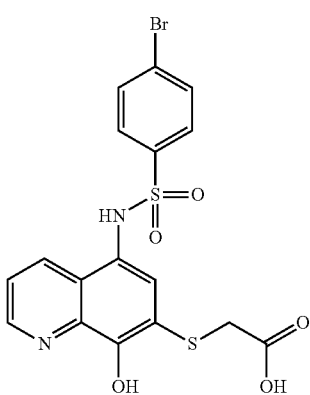
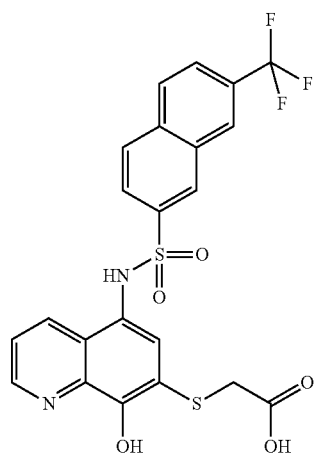

43
-continued
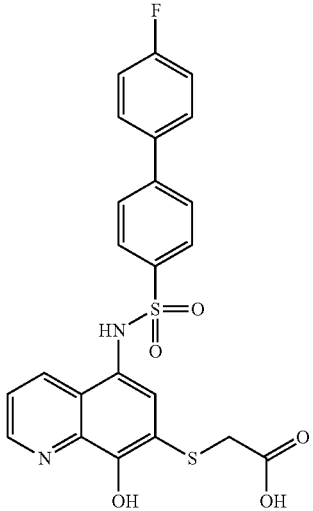
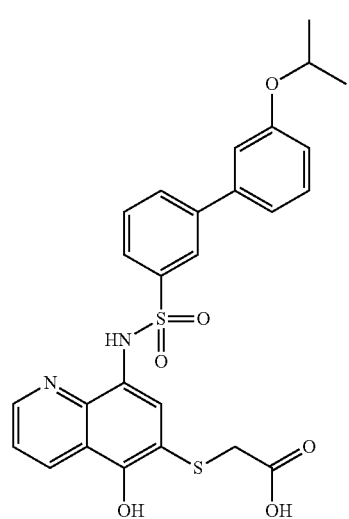
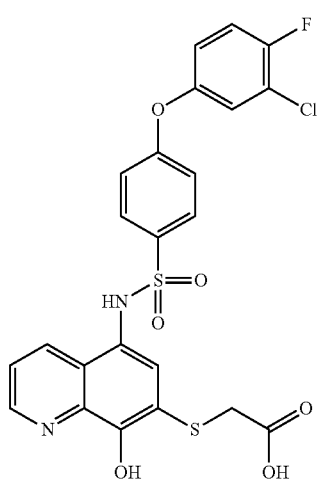
44
-continued
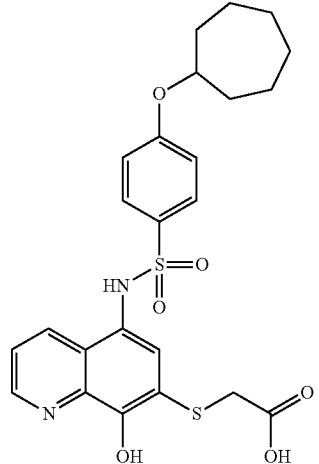
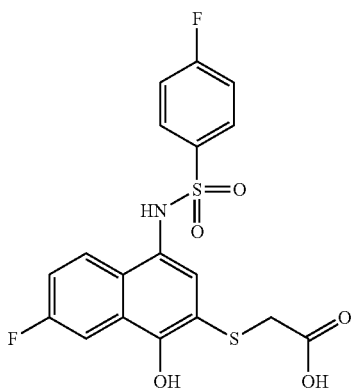
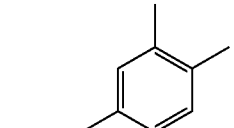
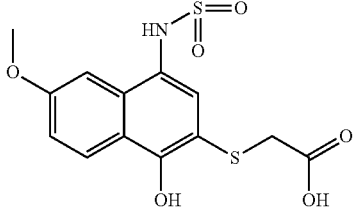
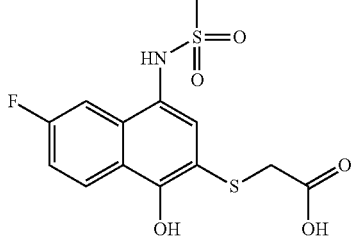

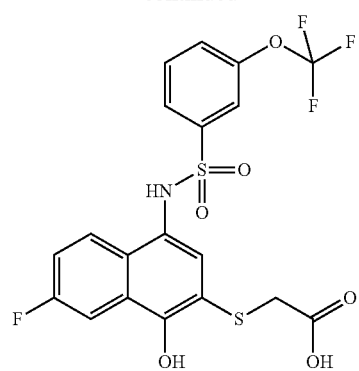
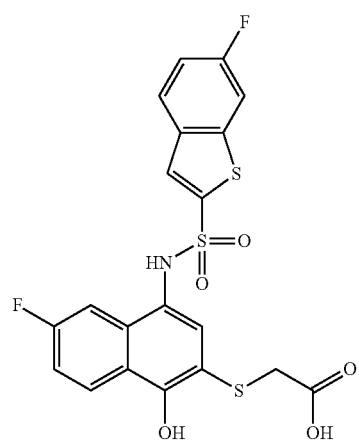
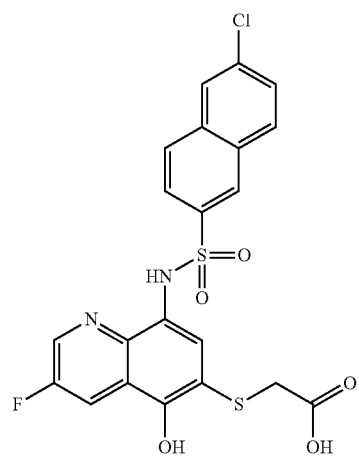
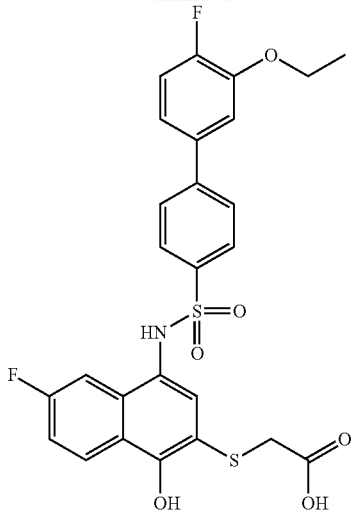
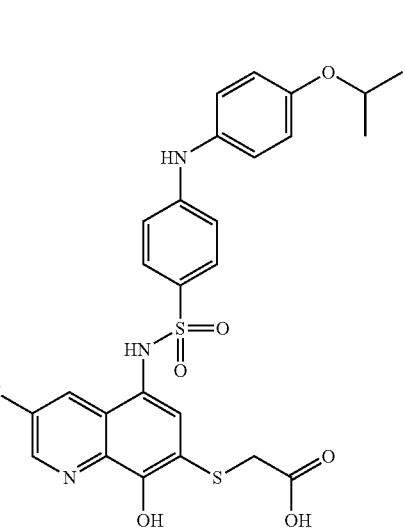
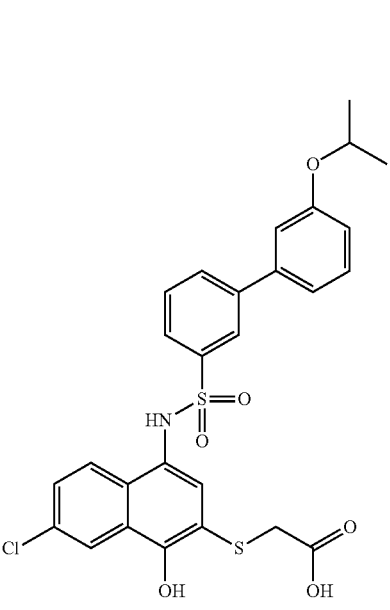

-continued
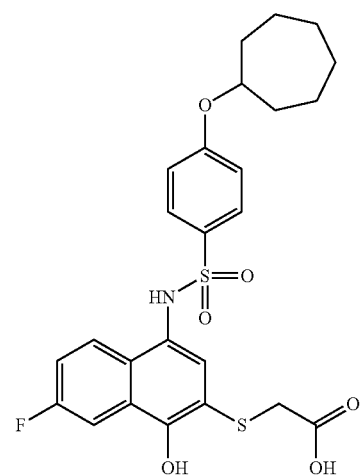
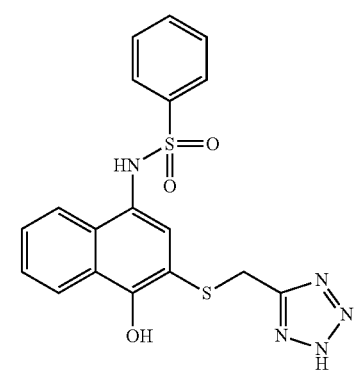
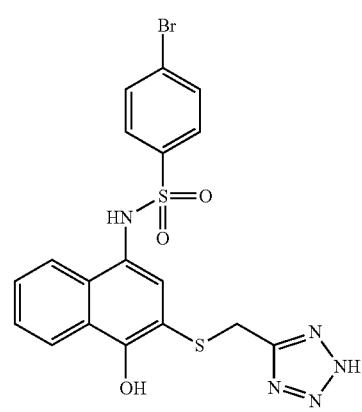
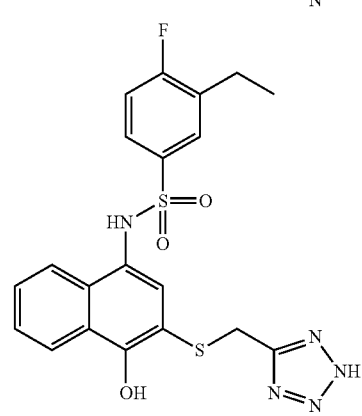
-continued
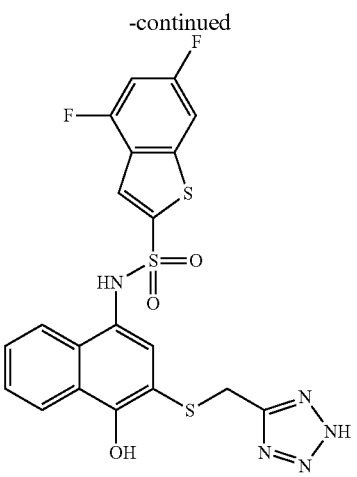
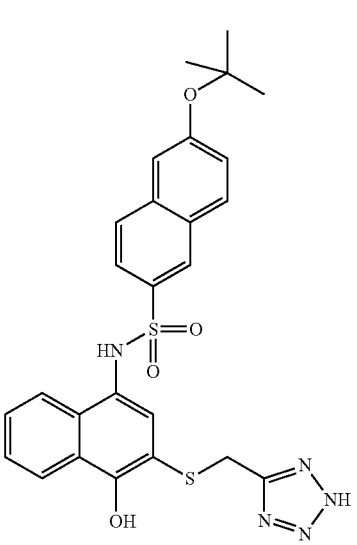
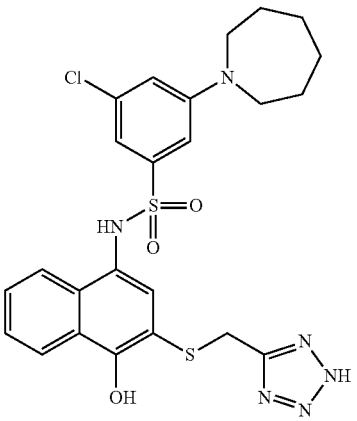

US 9,486,422 B2
49
-continued
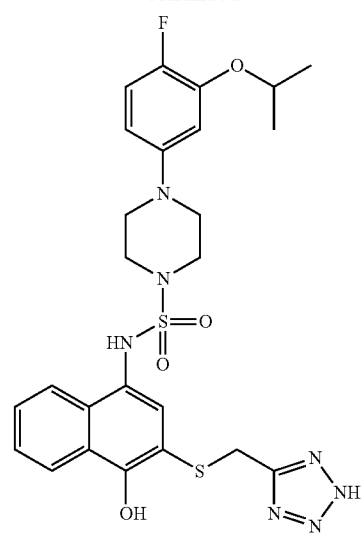
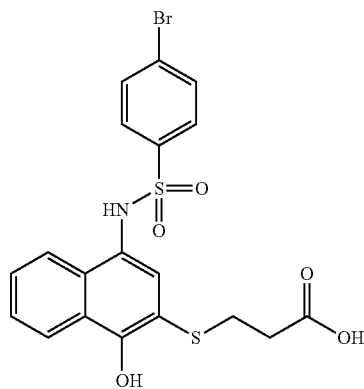
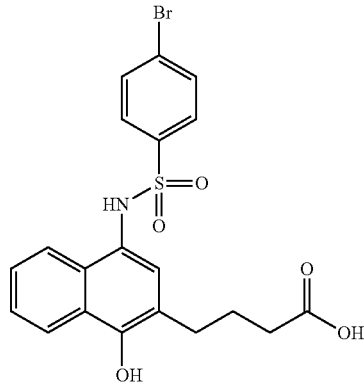
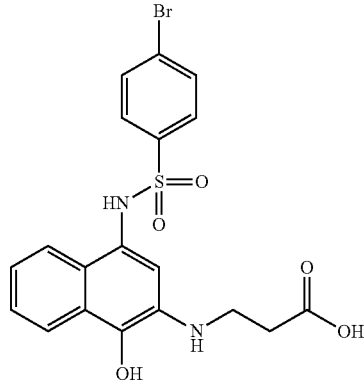
50
-continued
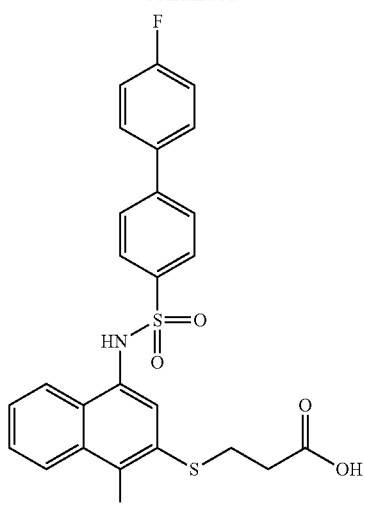
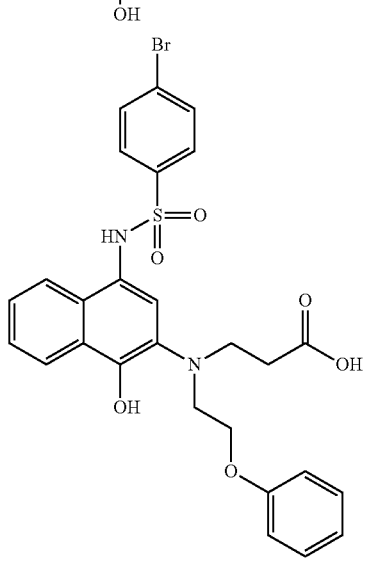
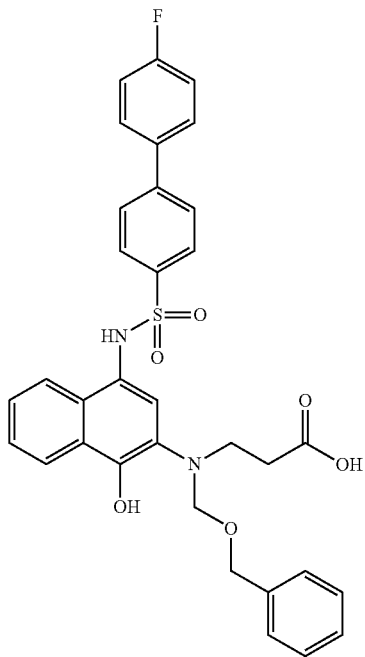

51
-continued
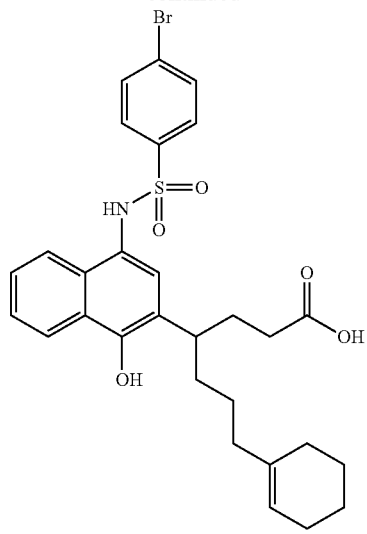
52
-continued
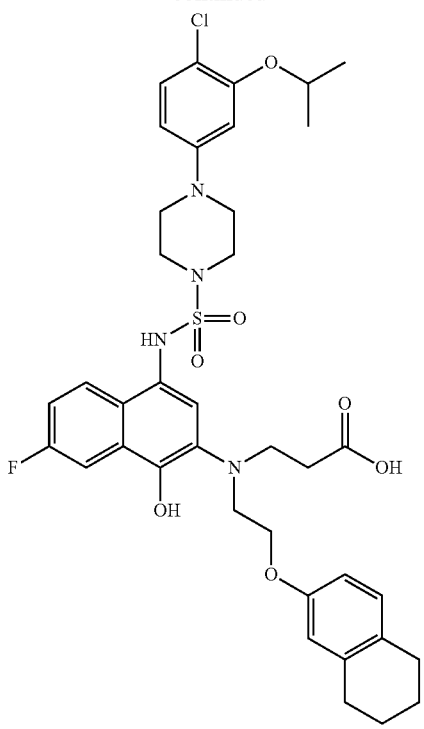
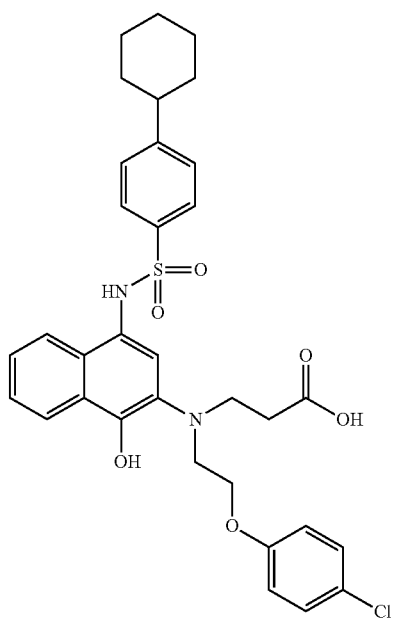
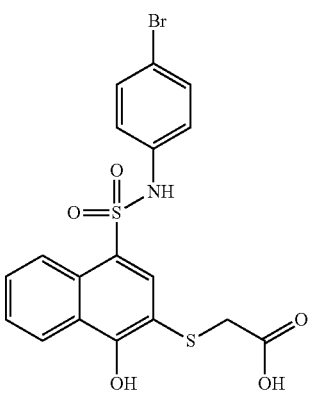
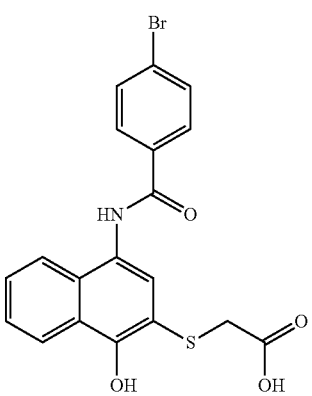

53
-continued
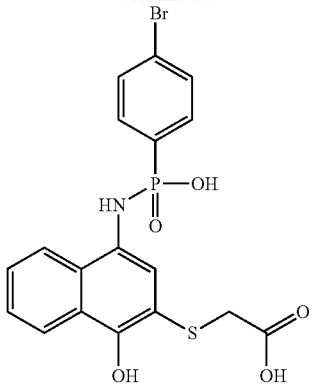
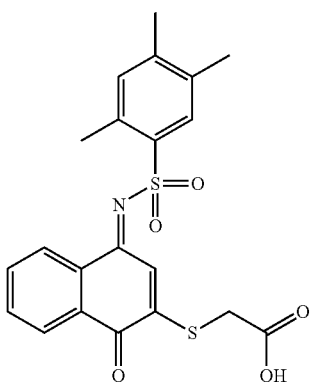
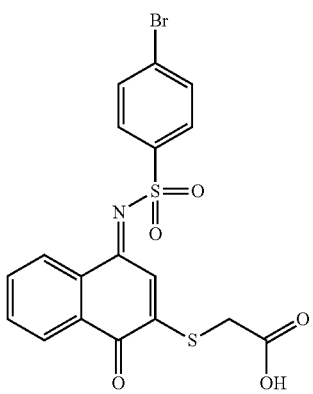
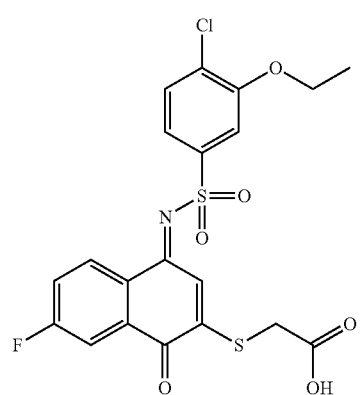
54
-continued
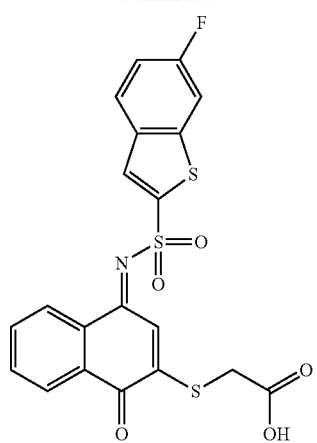
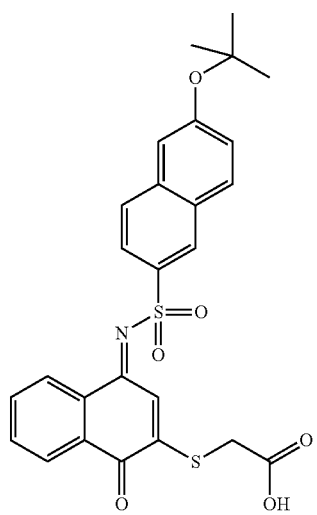
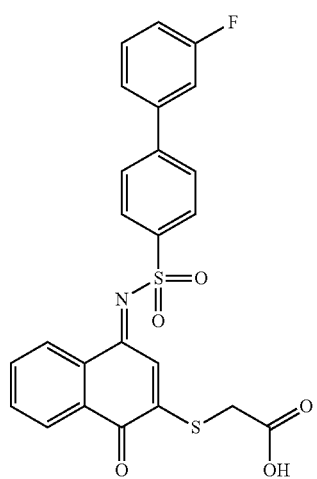

55
-continued
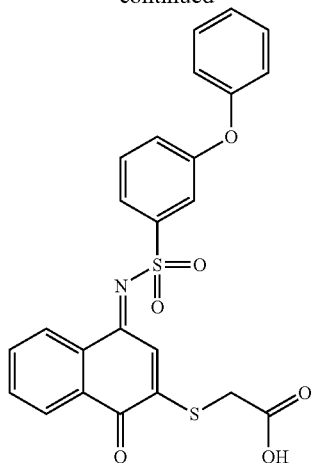
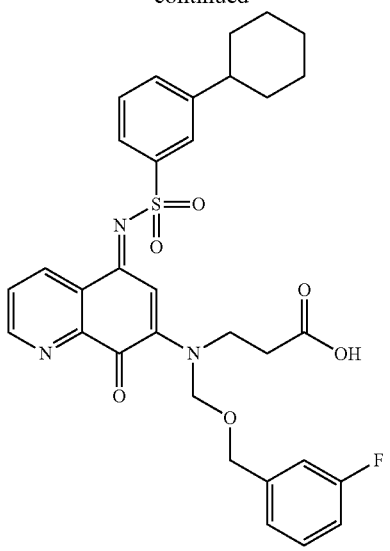
56
-continued
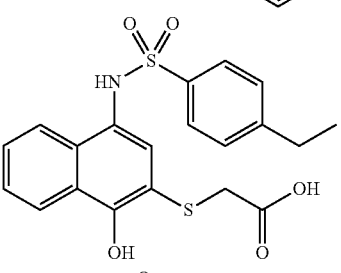
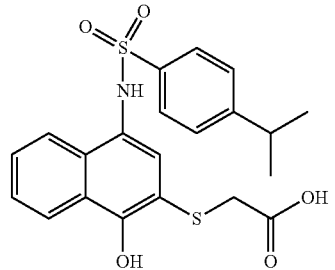
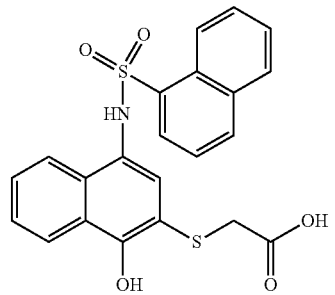
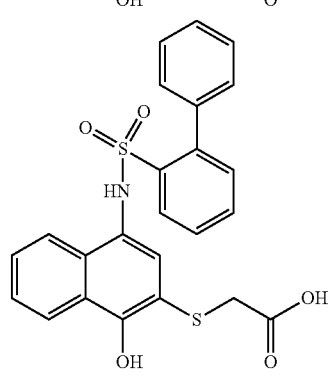

57
-continued
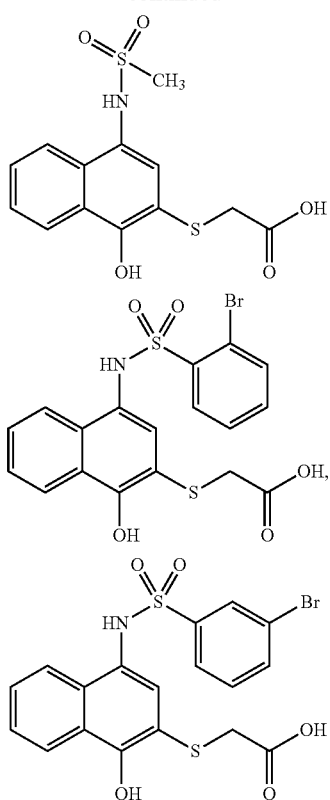
58
-continued
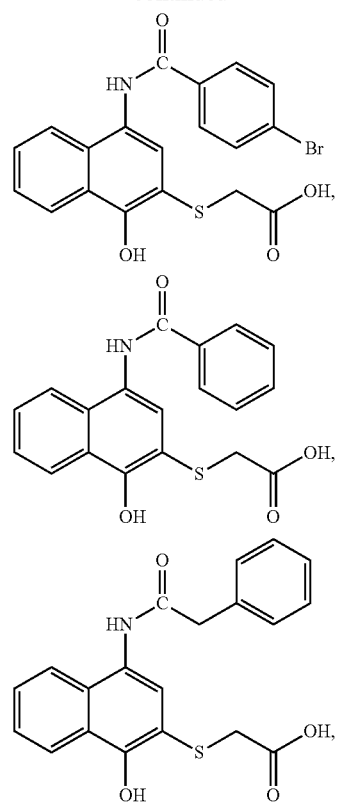
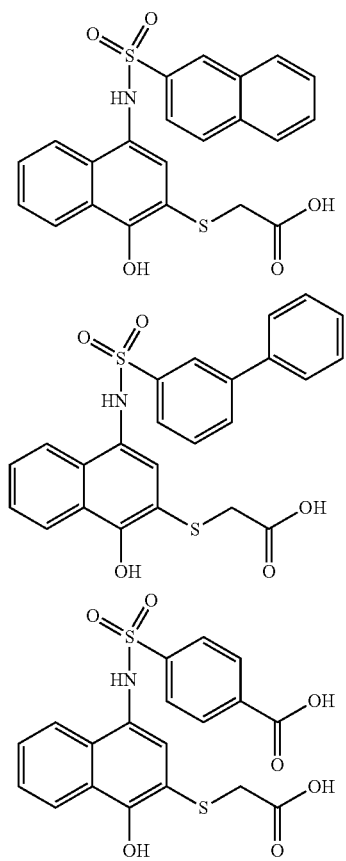

59
-continued
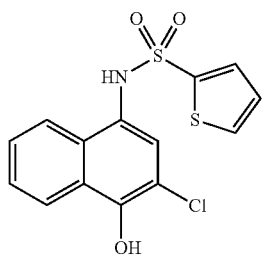
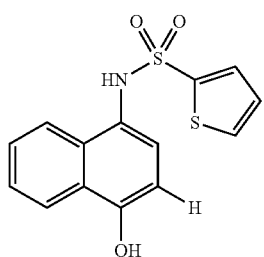
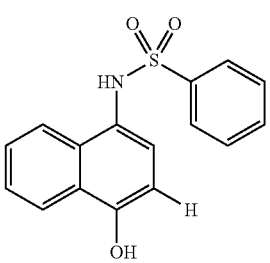
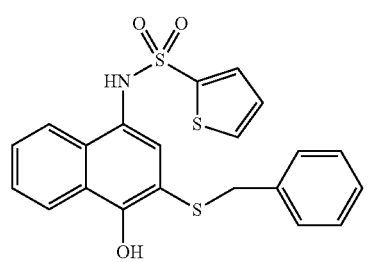
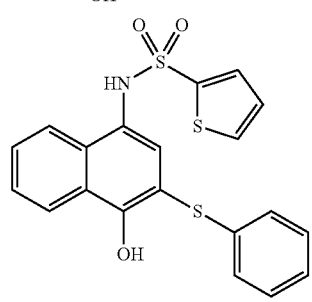
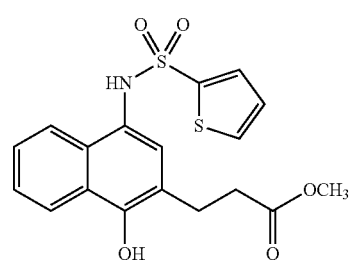
60
-continued
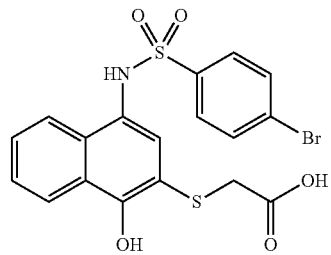
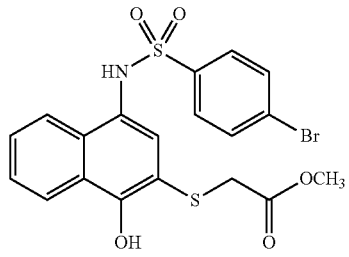
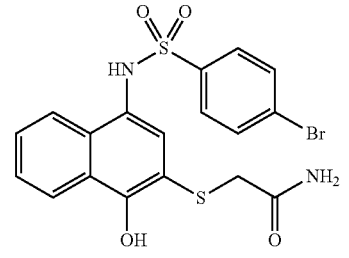
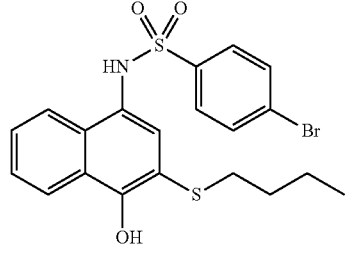
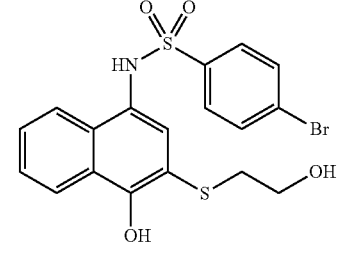
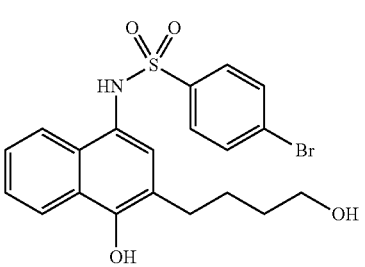

-continued
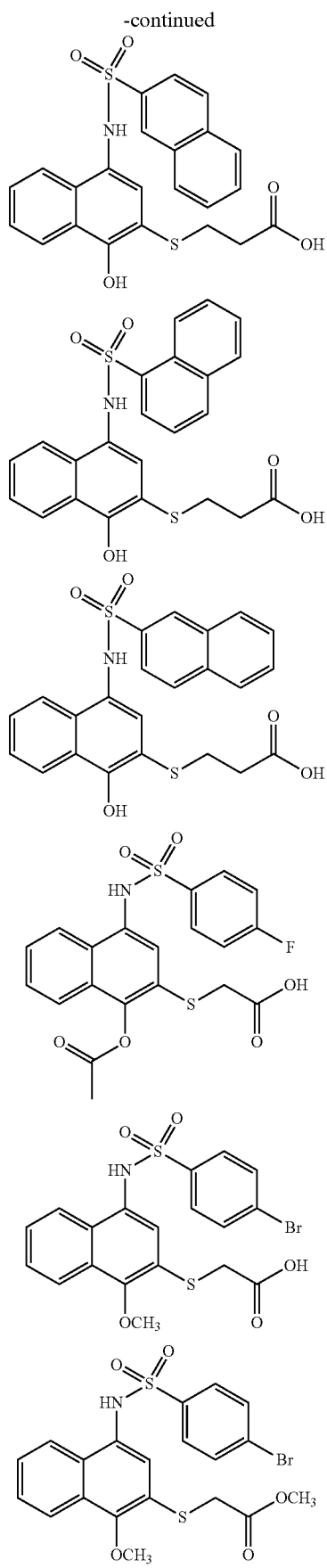
-continued
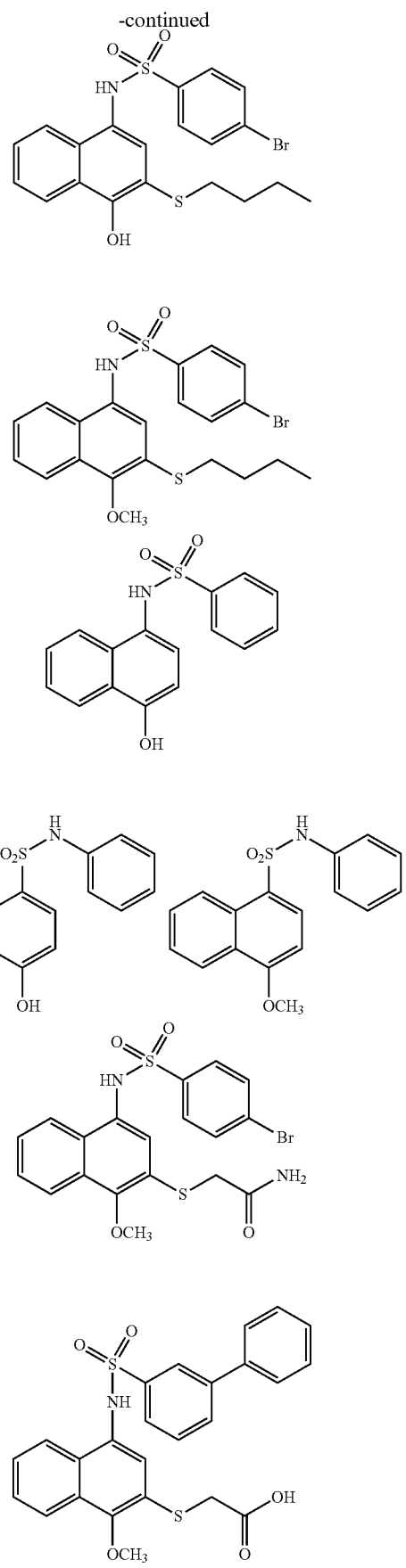

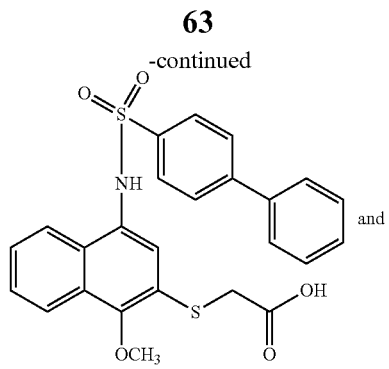

and

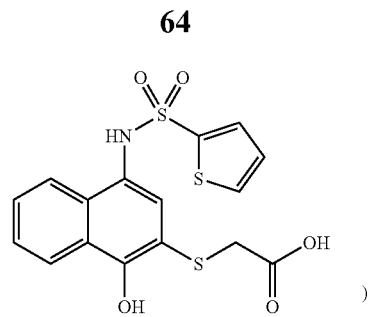

as a selective Mcl-1 inhibitor. Further chemical modifications identified a more potent Mcl-1 small-molecule inhibitor, UMI-77

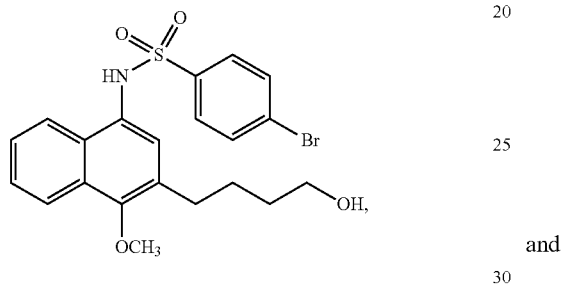

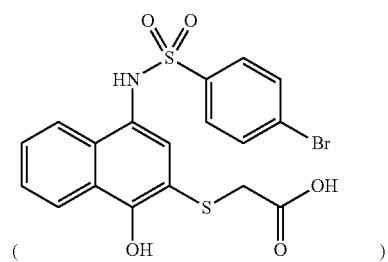

and or a pharmaceutically acceptable salt, solvate, or prodrug thereof.

The invention also provides the use of compounds to induce cell cycle arrest and/or apoptosis in cells containing functional Mcl-1 proteins. The invention also relates to the use of compounds for sensitizing cells to additional agent(s), such as inducers of apoptosis and/or cell cycle arrest, and chemoprotection of normal cells through the induction of cell cycle arrest prior to treatment with chemotherapeutic agents.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In certain embodiments, the cancer is multiple myeloma. In other embodiments, the compounds can be used to treat hyperproliferative diseases characterized by expression of functional Mcl-1 and/or Mcl-1 related proteins.

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents.

Experiments conducted during the course of developing embodiments for the present invention further identified UMI-59

(compound 17), which were shown to selectively bind Mcl-1 protein. UMI-77 was further shown to have in vitro and in vivo anticancer effects against PC. Indeed, in vitro FP and SPR based binding studies showed that UMI-77 selectively binds to Mcl-1 with $K_i$ of 490 nM, with significantly lower binding affinities to Bcl-2 and Bcl-$x_L$.

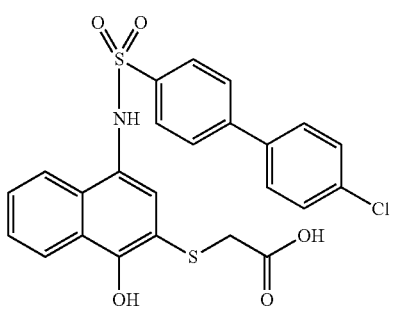 [SMILES: O=C(O)CSc1cc(NS(=O)(=O)c2ccc(-c3ccc(Cl)cc3)cc2)c2ccccc2c1O]

(compound 17) showed an $IC_{50}$ of 0.68±0.14 µM and a $K_i$ of 0.17±0.04 µM against Mcl-1 and selectively inhibited Mcl-1 over other anti-apoptotic Bcl-2 family proteins.

Docking and NMR binding studies provided conclusive evidence that UMI-77 binds to the BH3-binding groove of Mcl-1 protein. The predicted computational model supported by the HSQC NMR experiments showed that the interaction between UMI-77 and Mcl-1 is mediated by highly conserved BH3 elements forming the hydrophobic pockets two, h2, (Leu 267, Val 253, Phe 270 and Met 231) and three, h3, (His 224, Phe 228, Met 231 and Val 220) and hydrogen bonding network including the conserved hydrogen bond interaction with Arg 263.

From a functional standpoint, UMI-77 was shown to effectively target native Mcl-1, and induce apoptosis in a time-dependent and dose-dependent manner and apoptosis induction occurred at a low micro molar doses that reflected the affinity of this compound to Mcl-1 as well as its potency in inhibition of the PC cell growth. Mechanistically, apoptosis induction by UMI-77 was preceded by release of cytochrome c, disrupting the Mcl-1/Bak and Mcl-1/Bax and liberation of Bak and Bax, which were previously reported to promote apoptosis (see, e.g., Griffiths G J, et al., J. Cell Biol. 1999; 144:903-14; herein incorporated by reference in its entirety). Furthermore, in the absence of Bak/Bax, apoptosis induced by UMI-77 was abolished indicating that this compound functions as BH3 mimetic and exhibits specific and mechanism-based cell growth inhibition. Using siRNA interference approach, knocking down the Mcl-1 expression significantly decreased induction of apoptosis and protected PC cells from killing induced by UMI-77, demonstrating that Mcl-1 is a major mediator of cell sensitivity to this compound and the effect is Mcl-1 dependent. UMI-77 demonstrated robust anti-tumor efficacy in a resistant PC xenograft model with no toxicity to the surrounding tissue and minimal discomfort to the host. Molecular analysis of remnant tumor tissue showed increase level of pro-apoptotic proteins Bax and Bak consistent with co-immunoprecipitation results that UMI-77 can inhibit the endogenous protein-protein interactions of Bax and Bak with Mcl-1 and release them. Furthermore, significant decrease in anti-apoptotic protein survivin which potently inhibits apoptosis through antagonizing caspases activity was detected in the remnant tumor tissue. In situ apoptosis detection assays confirmed that UMI-77 induced clear apoptosis in the tumor tissue, but not in the control treated tumors. Moreover, as described in Example 9, bone marrow derived cells from patients having multiple myeloma showed loss in viability post Mcl-1 (e.g., UMI-77) treatment.

Accordingly, the present invention further provides methods for treating cancer through administration of therapeutic amounts of UMI-77 and/or UMI-59 to a subject suffering from cancer. The methods are not limited to a particular type of cancer. In some embodiments, the cancer is any cancer having Mcl-1 protein activity. In some embodiments, administration of UMI-77 and/or UMI-59 results in inhibition of Mcl-1 protein activity. In some embodiments, the administered UMI-77 and/or UMI-59 binds Mcl-1 protein within its BH3 groove. In some embodiments, the administered UMI-77 and/or UMI-59 inhibits cell growth and increases cellular apoptosis for cells having Mcl-1 activity. In some embodiments, the UMI-77 and/or UMI-59 are co-administered with one or more anticancer agents.

Moreover, the present invention provides methods for inhibiting Mcl-1 protein activity in cells through exposing such cells to one or more of the sulfonamido-1-hydroxynaphthalene compounds of the present invention. In some embodiments, the sulfonamido-1-hydroxynaphthalene compound is UMI-77. In some embodiments, the sulfonamido-1-hydroxynaphthalene compound is UMI-59. In some embodiments, the sulfonamido-1-hydroxynaphthalene compounds bind Mcl-1 protein thereby inhibiting the Mcl-1 protein activity. In some embodiments, the sulfonamido-1-hydroxynaphthalene compounds bind the BH3 groove within the Mcl-1 protein.

F) Induction of apoptosis in WT and Bax/Bak-deficient (DKO) MEFs cells after 24 h treatment with 10 µM of UMI-77. G) UMI-77 induces Bax activation in Panc-1 cells Immunocytochemistry analysis demonstrated the increased number of positive cells stained with anti-Bax(6A7) antibody, which specifically detect the active form of Bax, 24 h after UMI-77 treatment in Panc-1 cells. Conversely, DMSO control did not induce the active form of Bax (greyish-green: anti-Bax(6A7) antibody, greyish-blue: DAPI). Scale bar, 100 µm.

Figure 7:
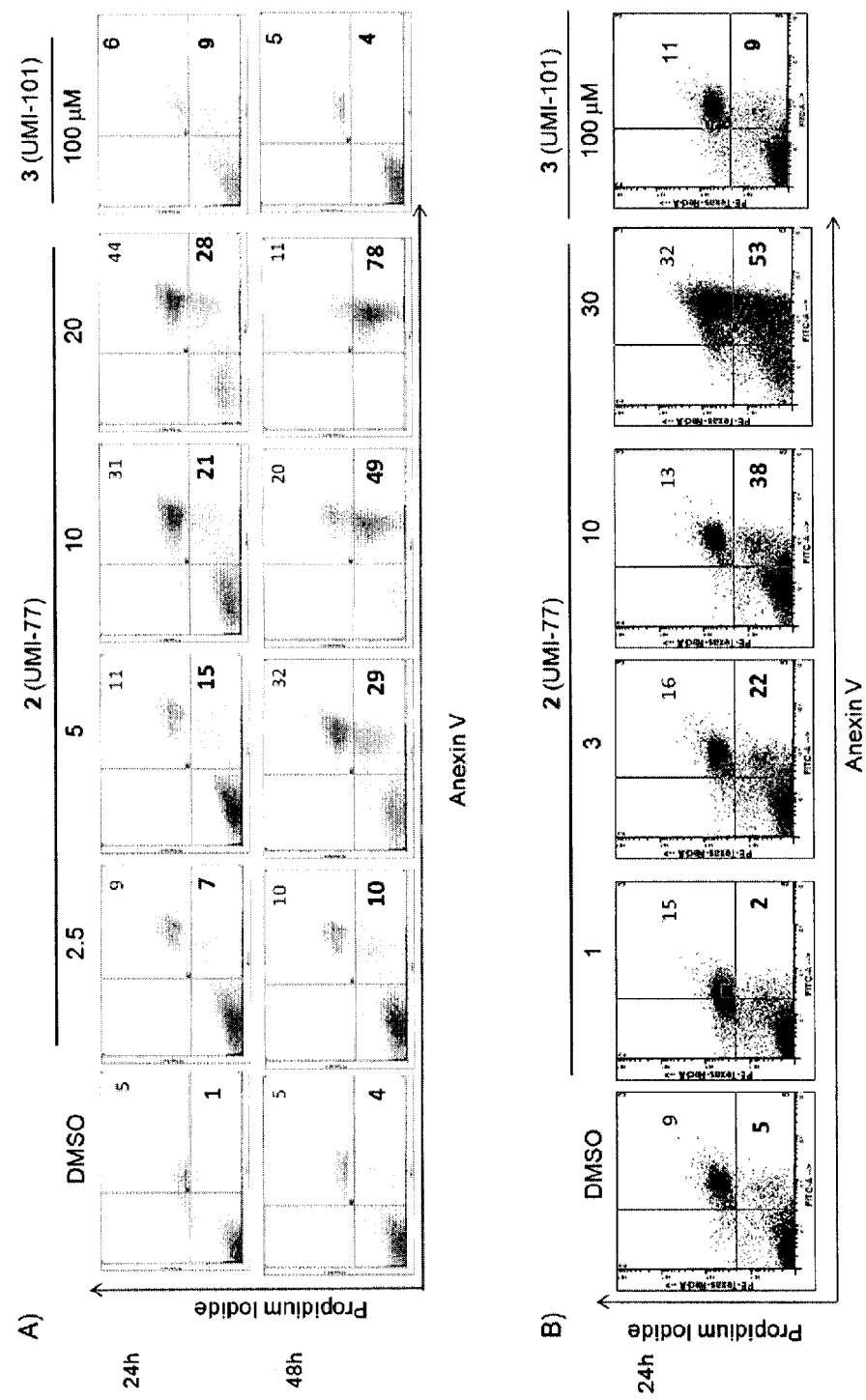

FIG. 7 shows time and dose dependent apoptosis induction in (A) Panc-1 and (B) BxPC-3 cells.

Figure 8:
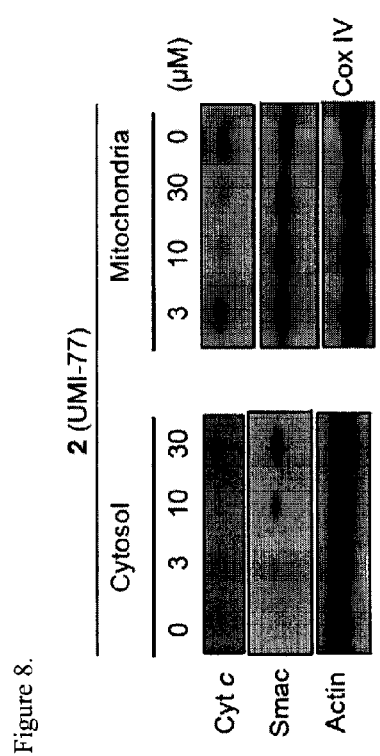

FIG. 8 shows release of cytochrome c and Smac from mitochondria in BxPC-3 cells after 24 h treatment with UMI-77.

Figure 9:
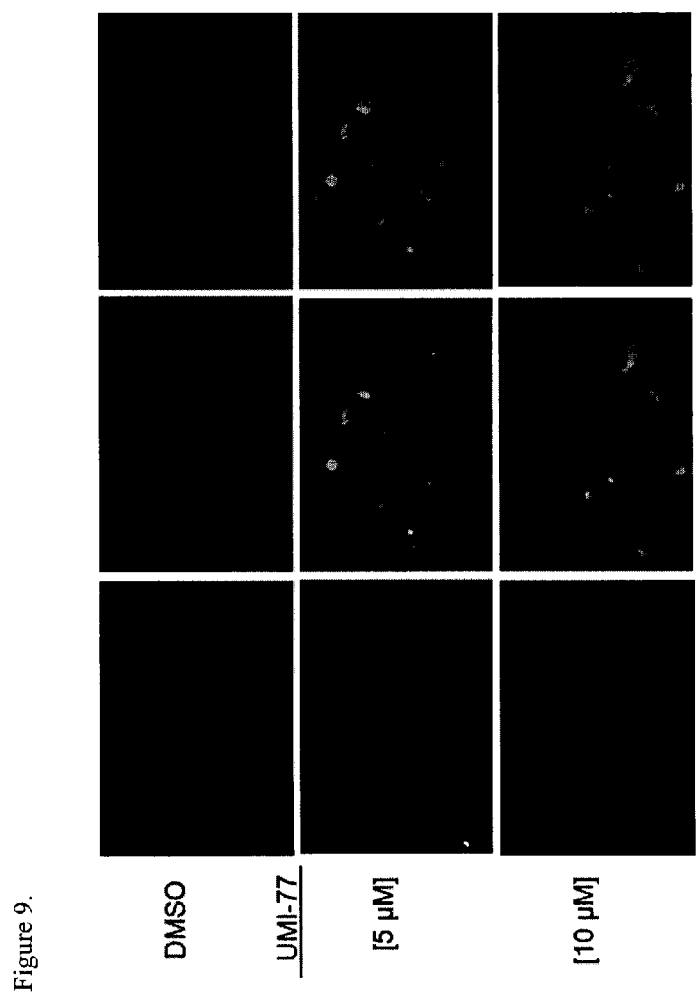

FIG. 9 shows UMI-77 induces Bax activation in BxPC-3 cells Immunocytochemistry analysis demonstrated the increased number of positive cells stained with anti-Bax (6A7) antibody, which specifically detect the active form of Bax, 24 h after UMI-77 treatment in BxPC-3 cells. Conversely, DMSO control did not induce the active form of Bax (greyish-green: anti-Bax(6A7) antibody, greyish-blue: DAPI). Scale bar, 100 µm.

Figure 10:
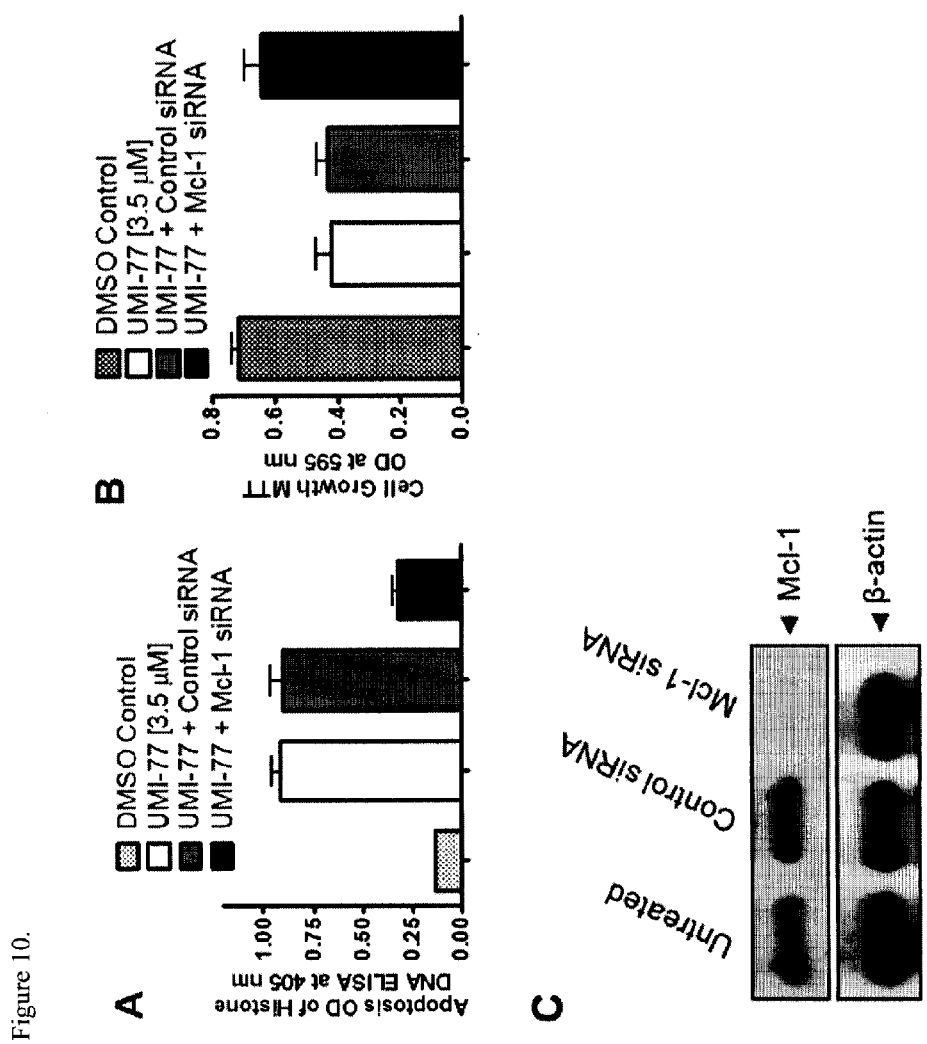

FIG. 10 shows down-regulation of Mcl-1 by siRNA in BxPC-3 cells blocks growth inhibition and apoptosis induced by UMI-77. A) Induction of apoptosis by UMI-77 is abolished in the presence of Mcl-1 siRNA. BxPC-3 cells were treated with respective siRNA's as described in Materials and Methods section. After the siRNA treatment, cells were incubated with UMI-77 for 72 hrs. Apoptosis was detected using Histone/DNA ELISA assay. B) Cell growth inhibition by UMI-77 is decreased in the presence of Mcl-1 siRNA. Cell growth was detected with MTT assay. C) Western blot of untreated; control siRNA and Mcl-1 siRNA treated cells showing down regulation of Mcl-1.

Figure 11:
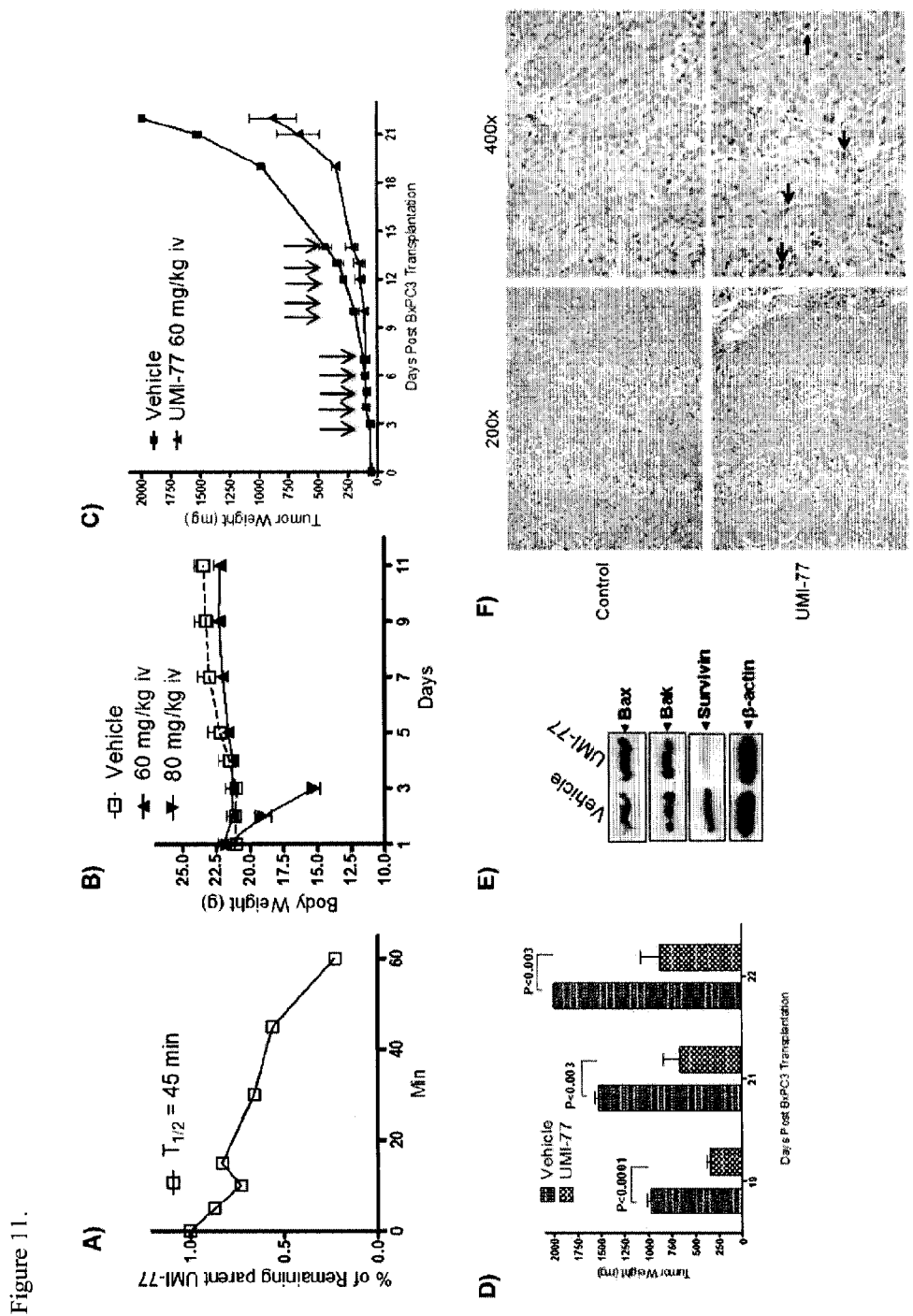

FIG. 11 shows in vivo characterization of UMI-77. A) Determination of the microsome stability of UMI-77 (expressed as $T_{1/2}$). B) Evaluation of the effect of UMI-77 on weight loss of SCID mice. UMI-77 was administrated two cycles i.v. for 5 days per week in two tested concentrations 60 and 80 mg/kg. C) In vivo efficacy of UMI-77 in BxPC-3 xenograft animal model. BxPC-3 xenografts were inoculated subcutaneously in SCID mice. Once transplanted, fragments developed into palpable tumors, about 60 mg, groups of 4 animals with bi-lateral tumors were removed randomly and assigned to two treatment groups. Mice were administered UMI-77 i.v 60 mg/kg for 5 consecutive days a week for two weeks. [■] vehicle treated group and [▲] UMI-77 treated groups. D) UMI-77 treated groups showed significant reduction of the tumor growth when compared to treatments with vehicle on day 19 (p<0.0001), 20 (p<0.003) and 21 (p<0.003). E) Western blots analysis for different pro-apoptotic and survival markers on lysates isolated from tumours harvested from mice of different treatment groups showing enhancement of pro-apoptotic Bax and Bak and down-regulation of survivin compared with control. F) Immunohistochemical staining of BxPC-3 tumor xenografts using Apoptag Kit. No positively-staining nuclei are present in the control samples. Several positively-staining cells (open arrows) are present, as is apoptotic debris (closed arrows) in presented field (400× original magnification).

Figure 12:
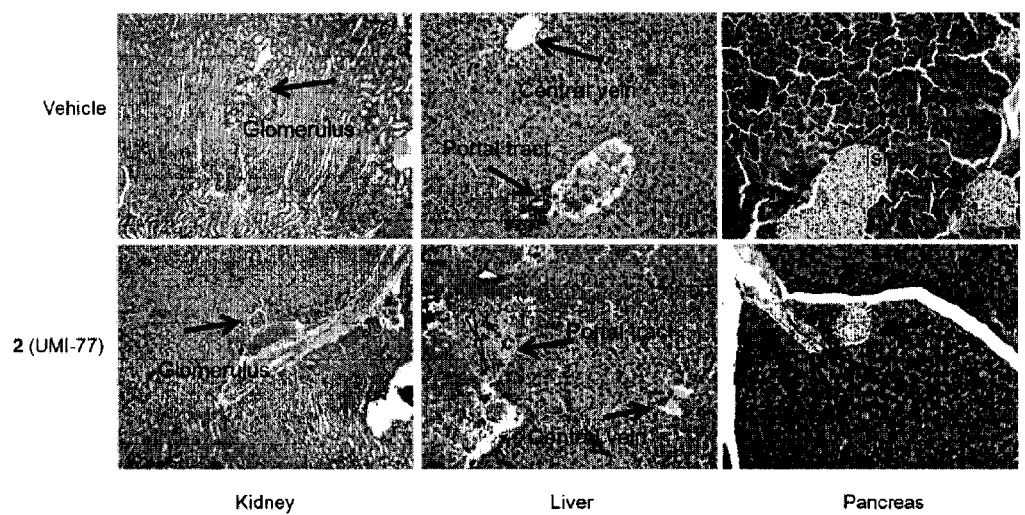

FIG. 12 shows H&E analyses of normal mouse tissues after treatment with UMI-77.

Figure 13:
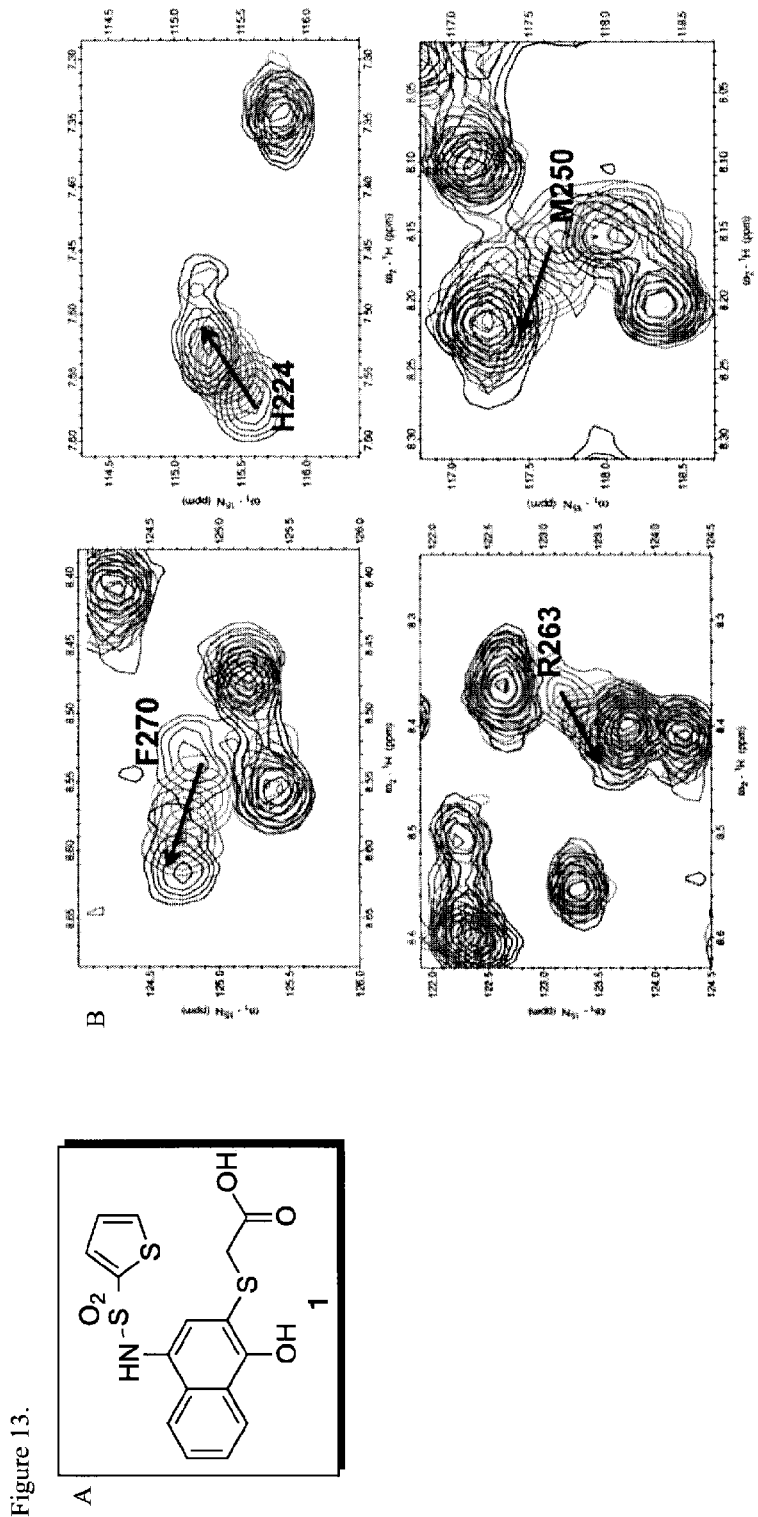
Figure 13:
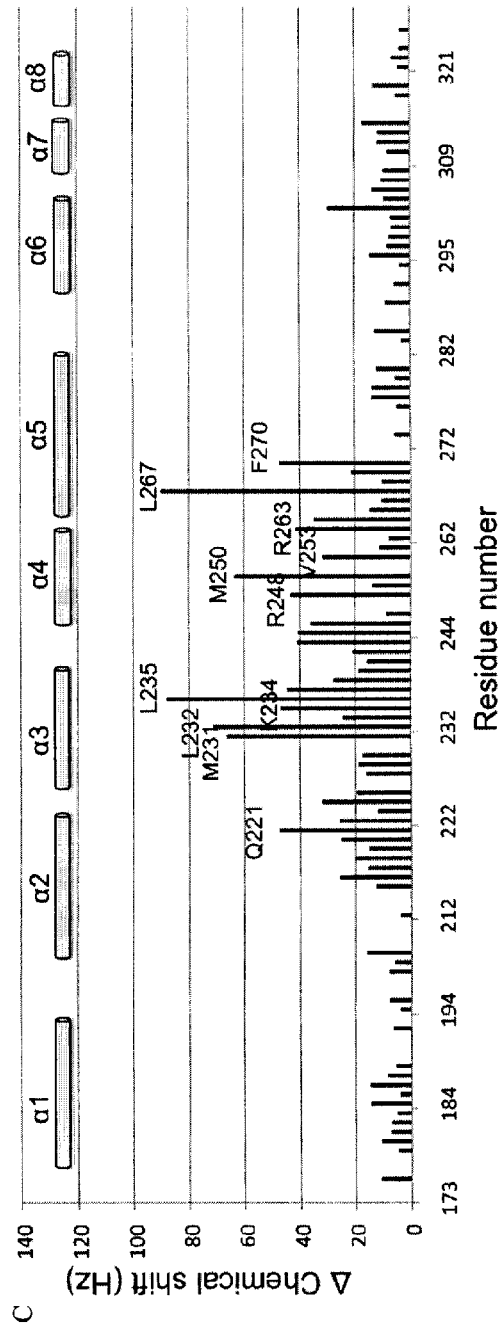
Figure 13:

FIG. 13. (A) The structure of the HTS lead 1 (UMI-59). (B) Slices of overlaid $^{15}$N—$^1$H HSQC spectra of Mcl-1 (greyish-red), and in presence of 1 (Mcl-1:1 ratio of 1 to 2) (black), (Mcl-1:1 ratio of 1 to 1) (greyish-purple), (Mcl-1:1 ratio of 1 to 0.5) (greyish-green). The arrows show the direction of chemical shift changes upon binding of 1. (C) Plot of chemical shift changes calculated as $((\Delta^1 H\ Hz)^2+(\Delta^{15}N\ Hz)^2)^{0.5}$ of Mcl-1 amide upon addition of 1 (Mcl-1:1 ratio of 1 to 2) as a function of Mcl-1 residue numbers. (D) The putative binding mode of 1 to Mcl-1 (2NLA). The surface of Mcl-1 protein is colored according to the chemical shift intensity. Significant shift (>60 Hz) is represented with greyish-red, moderate shift (>20 Hz and <60 Hz) represented with greyish-pink.

Figure 14:
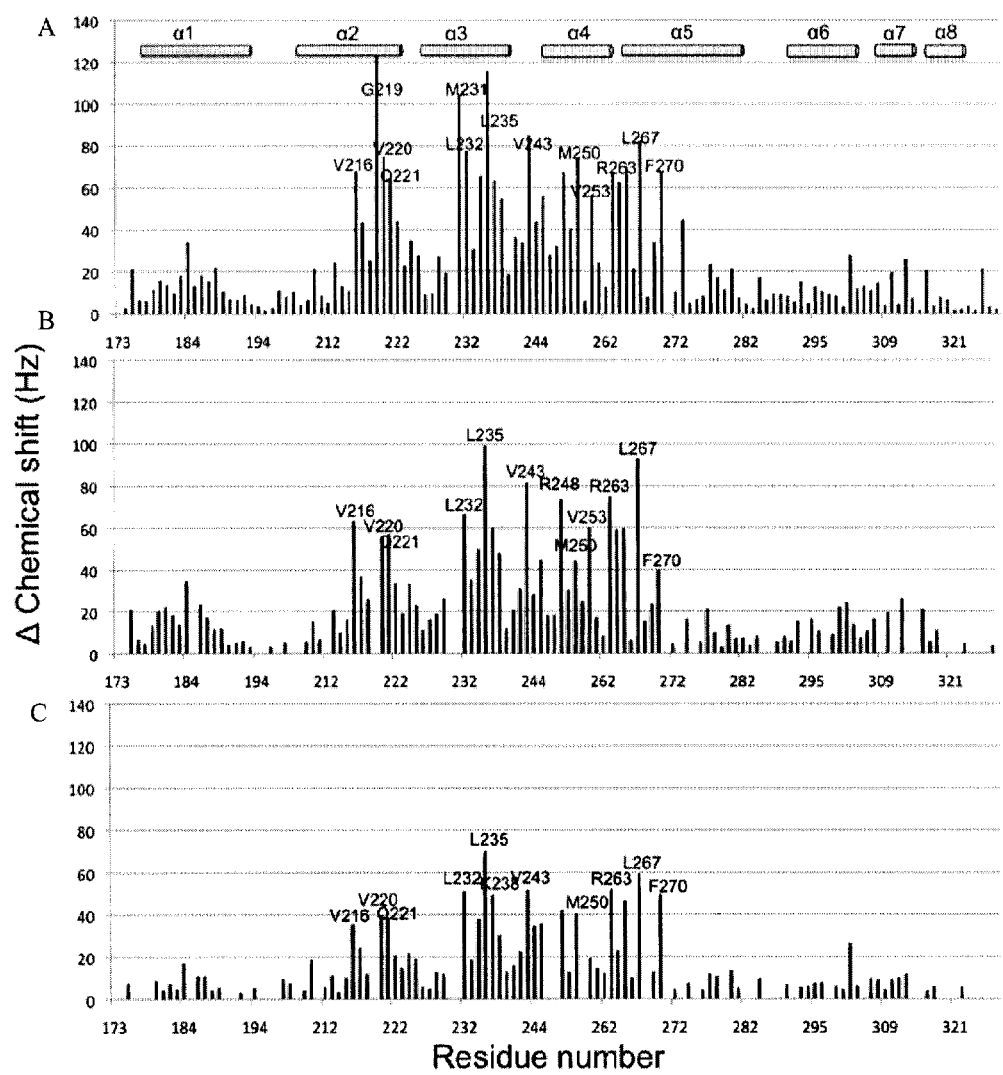
Figure 14:
Figure 14:
Figure 14:
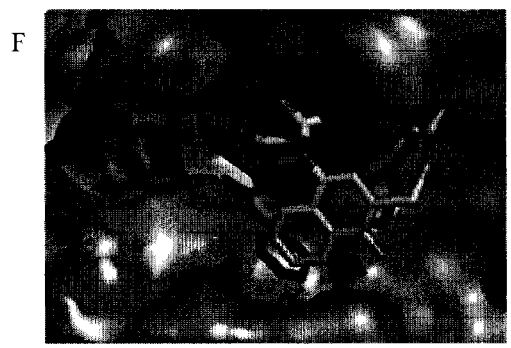

FIG. 14 shows plots of chemical shift changes calculated as $((\Delta^1 H\ Hz)^2+(\Delta^{15}N\ Hz)^2)^{0.5}$ of Mcl-1 amide upon addition of (A) 9 (Mcl-1:9 ratio of 1 to 2) (B) 10 (Mcl-1:10 ratio of 1 to 2) (C) 11 (Mcl-1:11 ratio of 1 to 2) as a function of Mcl-1 residue numbers. The putative binding modes of (D) 9, (E) 10, (F) 11 to Mcl-1. The surface of Mcl-1 protein is colored according to the chemical shift intensity. Significant shift (>60 Hz) is represented with greyish-red, moderate shift (>20 Hz and <60 Hz) represented with greyish-pink.

Figure 15:
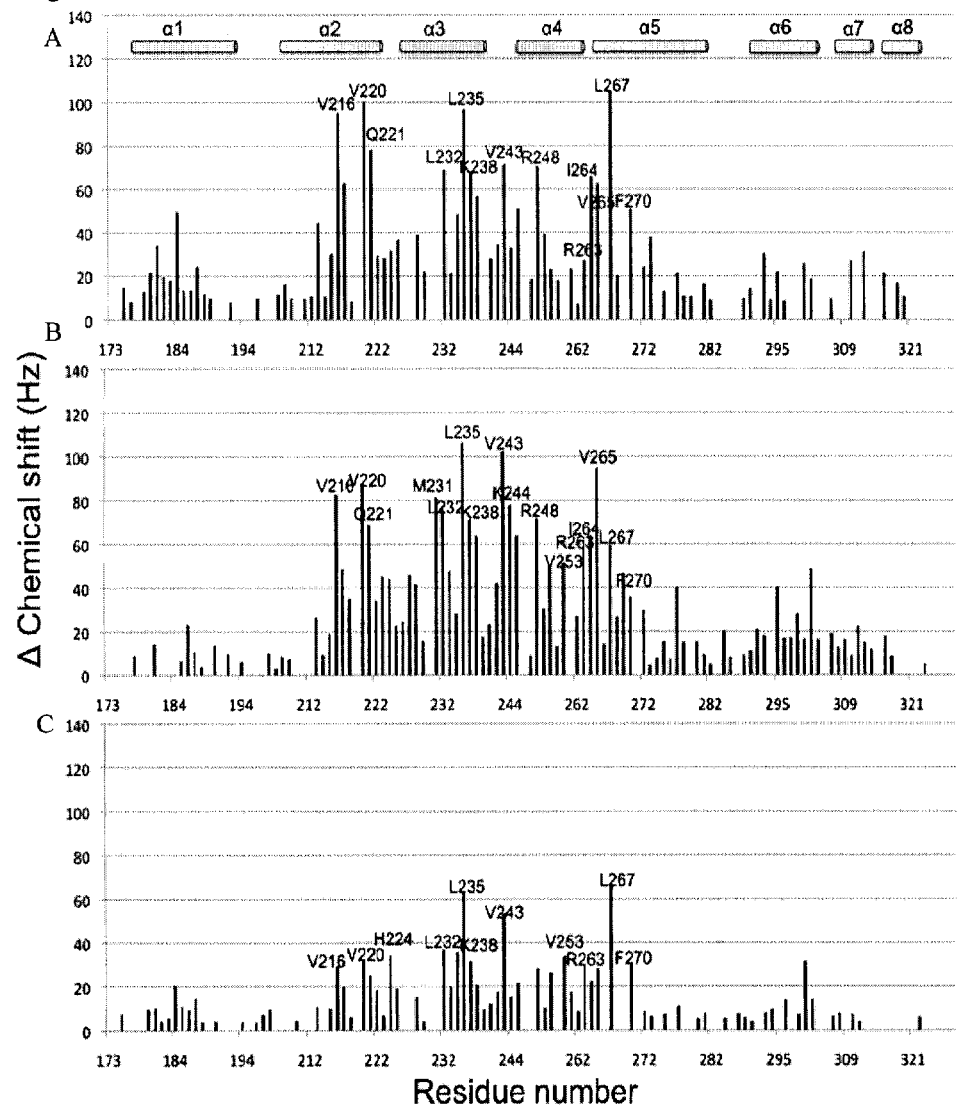
Figure 15:
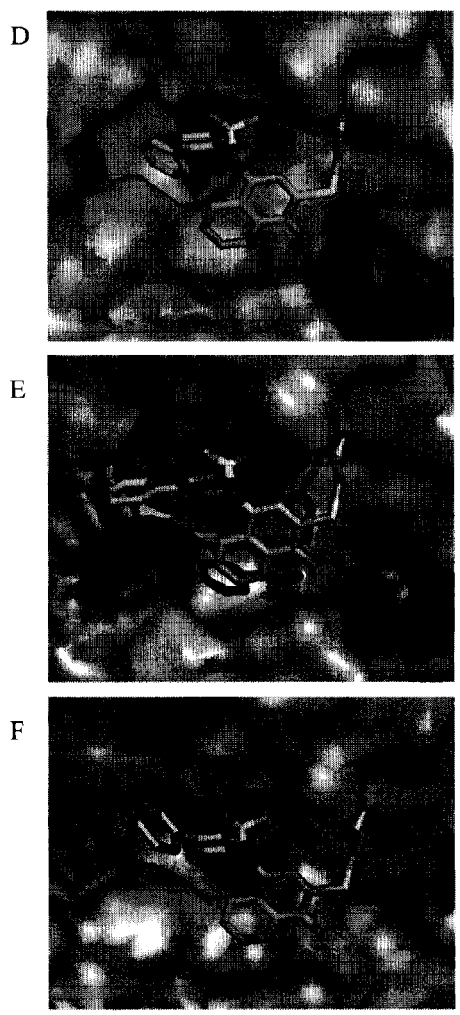

FIG. 15 shows plots of chemical shift changes calculated as $((\Delta^1 H\ Hz)^2+(\Delta^{15}N\ Hz)^2)^{0.5}$ of Mcl-1 amide upon addition of (A) 14 (Mcl-1:14 ratio of 1 to 2) (B) 15 (Mcl-1:15 ratio of 1 to 2) (C) 16 (Mcl-1:16 ratio of 1 to 2) as a function of Mcl-1 residue numbers. The putative binding modes of (D) 14, (E) 15, (F) 16 to Mcl-1. The surface of Mcl-1 protein is colored according to the chemical shift intensity. Significant shift (>60 Hz) is represented with greyish-red, moderate shift (>20 Hz and <60 Hz) represented with greyish-pink.

Figure 16:
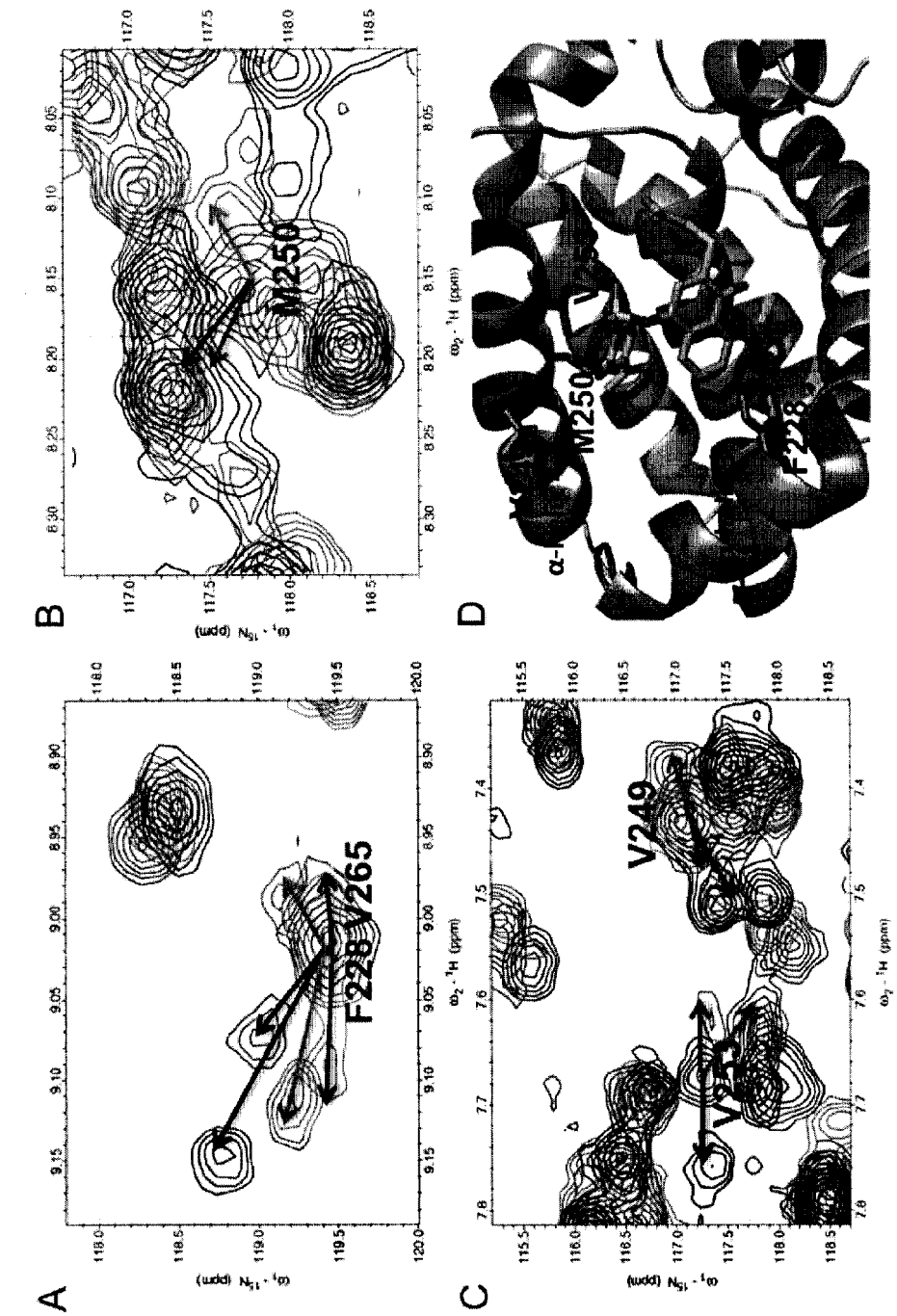

FIG. 16 shows slices of overlaid $^{15}$N—$^1$H HSQC spectra of Mcl-1 (red), and in presence of 14 (Mcl-1:14 ratio of 1 to 2) (greyish-purple), 15 (Mcl-1:15 ratio of 1 to 2) (black), 16 (Mcl-1:16 ratio of 1 to 2) (greyish-green) for (A) Phe 228 (B) Met 250 (C) Val 249 and Val 253. The arrows show the direction of chemical shift changes upon binding of compounds. (D) The putative binding mode of 14 to Mcl-1 highlighting in greyish-purple Val 249, Met 250, and Val 253 located on the helix 4 and Phe 228 located on the helix 3 of Mcl-1.

Figure 17:
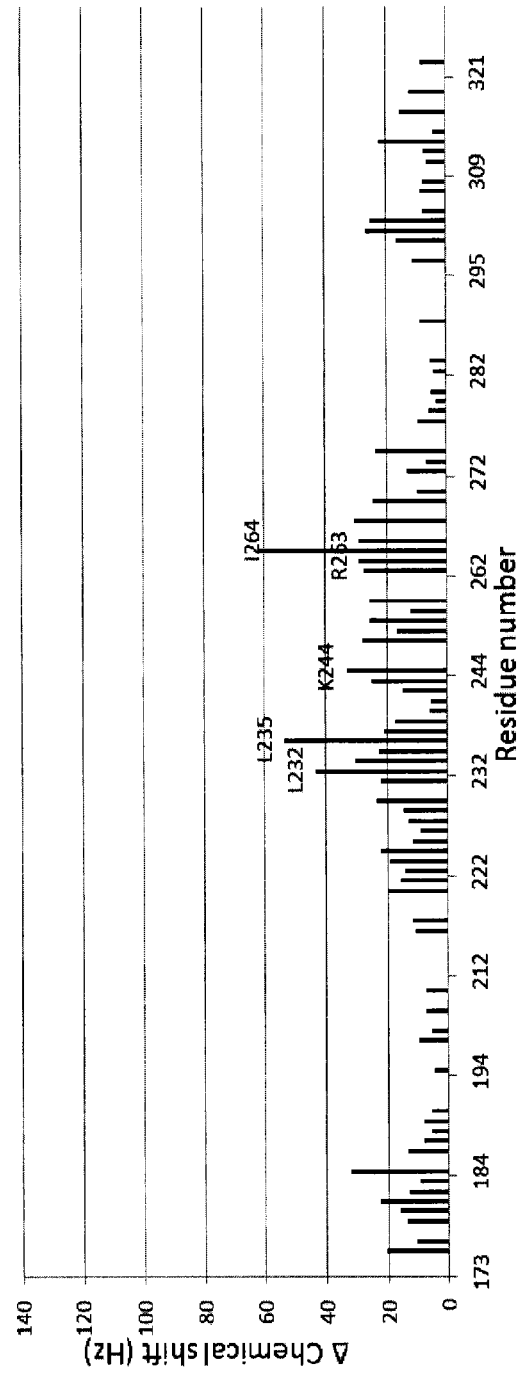

FIG. 17 shows plot of chemical shift changes calculated as $((\Delta^1 H\ Hz)^2+(\Delta^{15}N\ Hz)^2)^{0.5}$ of Mcl-1 amide upon addition of 23 (Mcl-1:23 ratio of 1 to 2).

Figure 18:
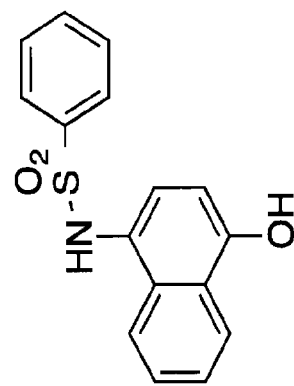
Figure 18:
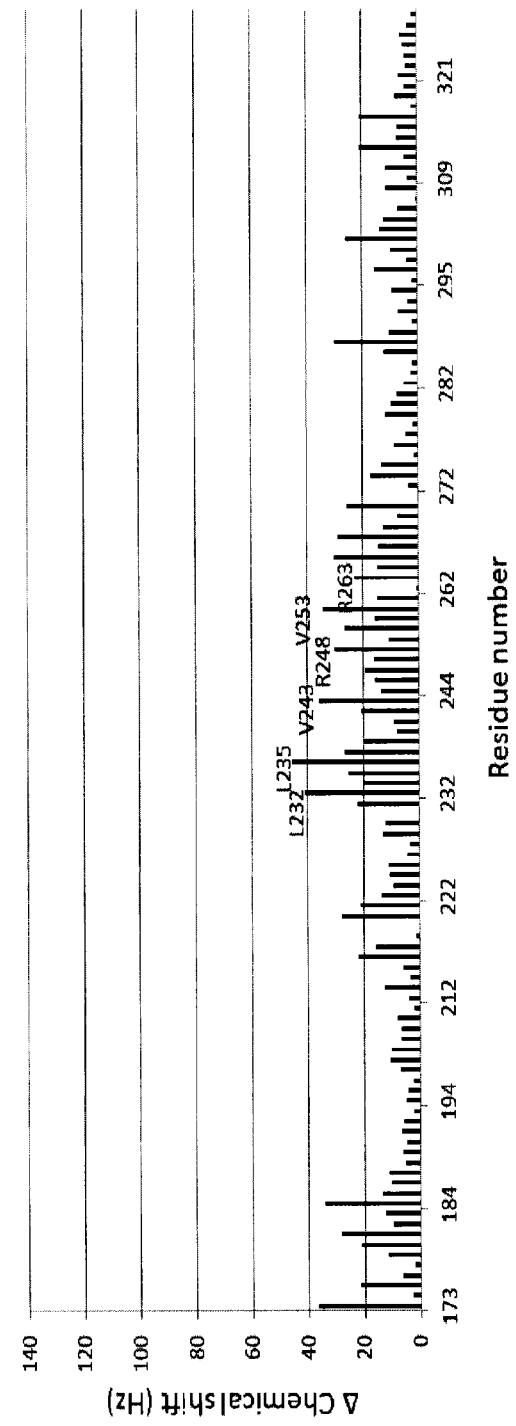

FIG. 18 shows plot of chemical shift changes calculated as $((\Delta^1 H\ Hz)^2+(\Delta^{15}N\ Hz)^2)^{0.5}$ of Mcl-1 amide upon addition of 27 (Mcl-1:27 ratio of 1 to 2).

Figure 19:
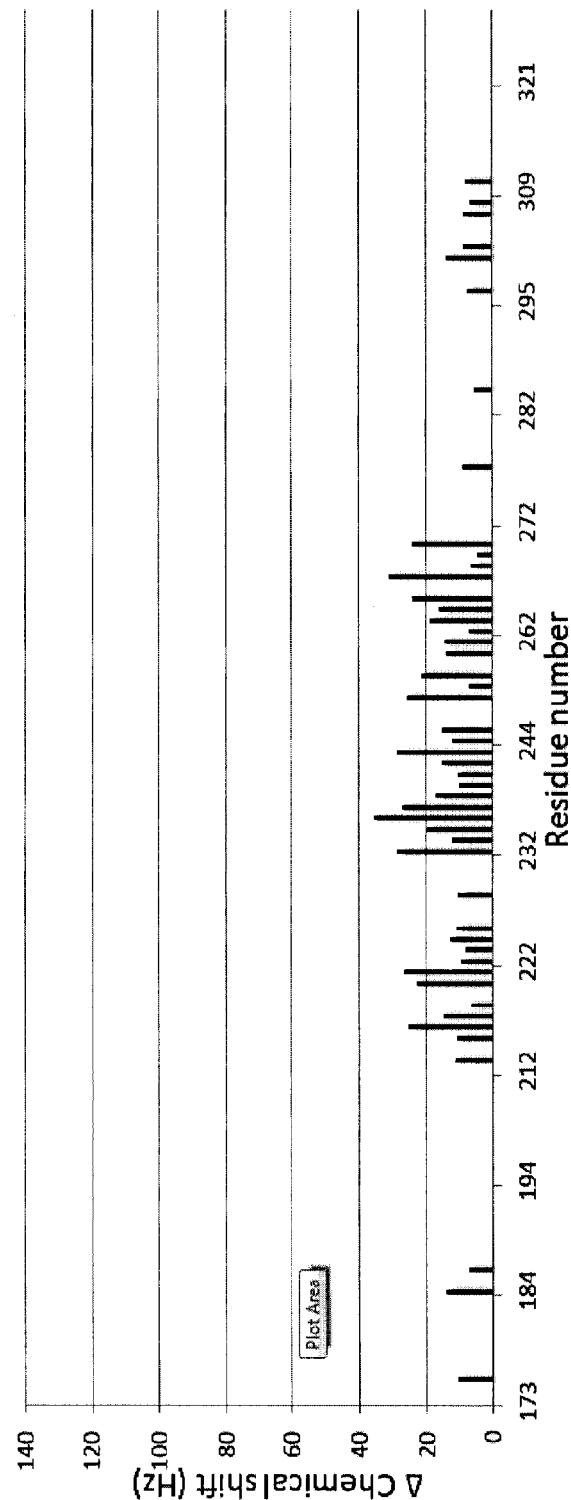

FIG. 19 shows plot of chemical shift changes calculated as $((\Delta^1 H\ Hz)^2+(\Delta^{15}N\ Hz)^2)^{0.5}$ of Mcl-1 amide upon addition of 29 (Mcl-1:29 ratio of 1 to 2).

Figure 20:
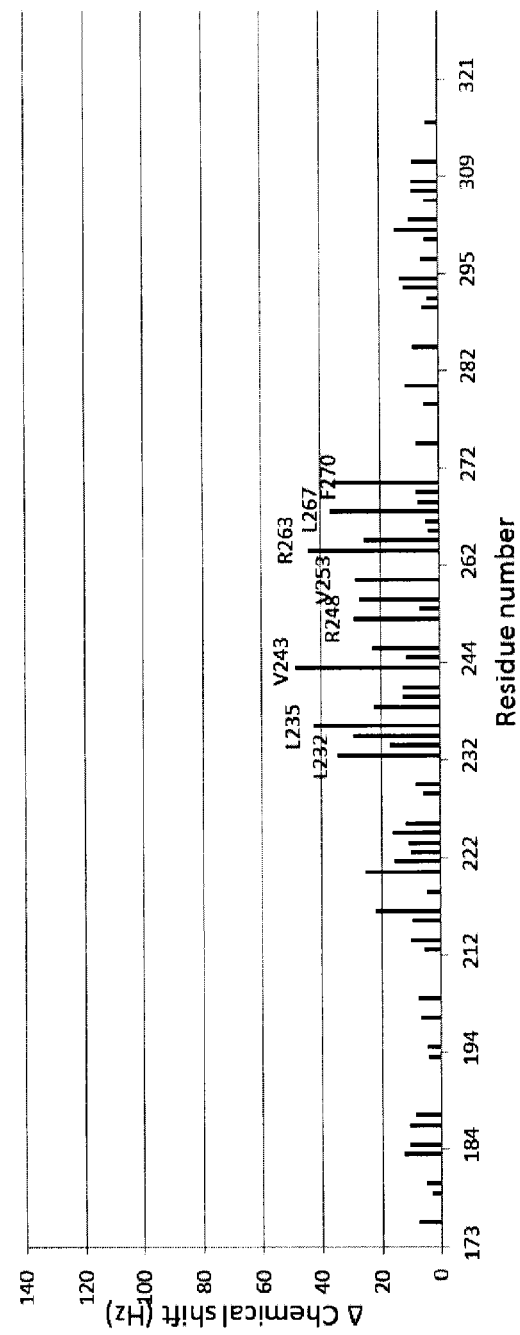
Figure 20:
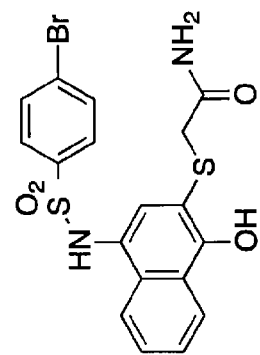

FIG. 20 shows plot of chemical shift changes calculated as $((\Delta^1 H\ Hz)^2+(\Delta^{15}N\ Hz)^2)^{0.5}$ of Mcl-1 amide upon addition of 33 (Mcl-1:33 ratio of 1 to 2).

Figure 21:
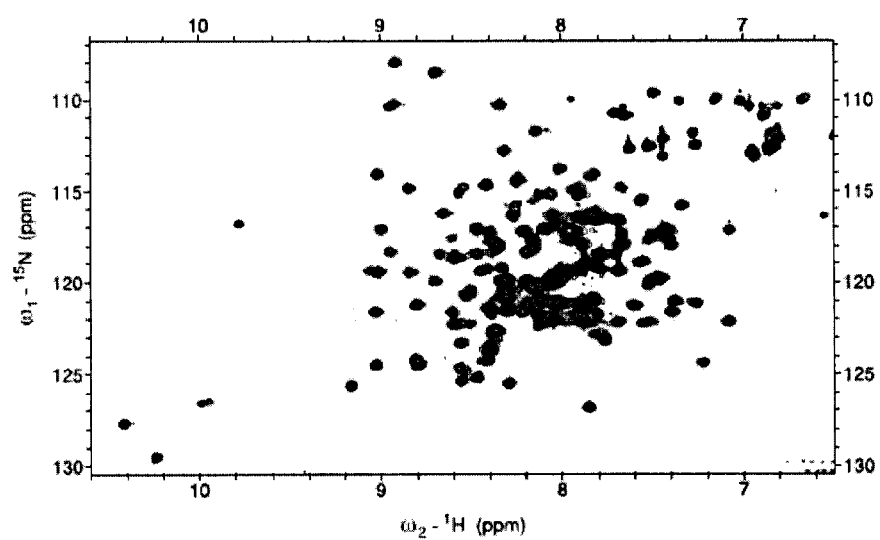

FIG. 21 shows overlaid $^{15}$N,$^1$H—HSQC NMR spectra of Mcl-1 (greyish-red) and in presence of 40d (Mcl-1:40d ratio of 1 to 2) (greyish-blue).

Figure 22:
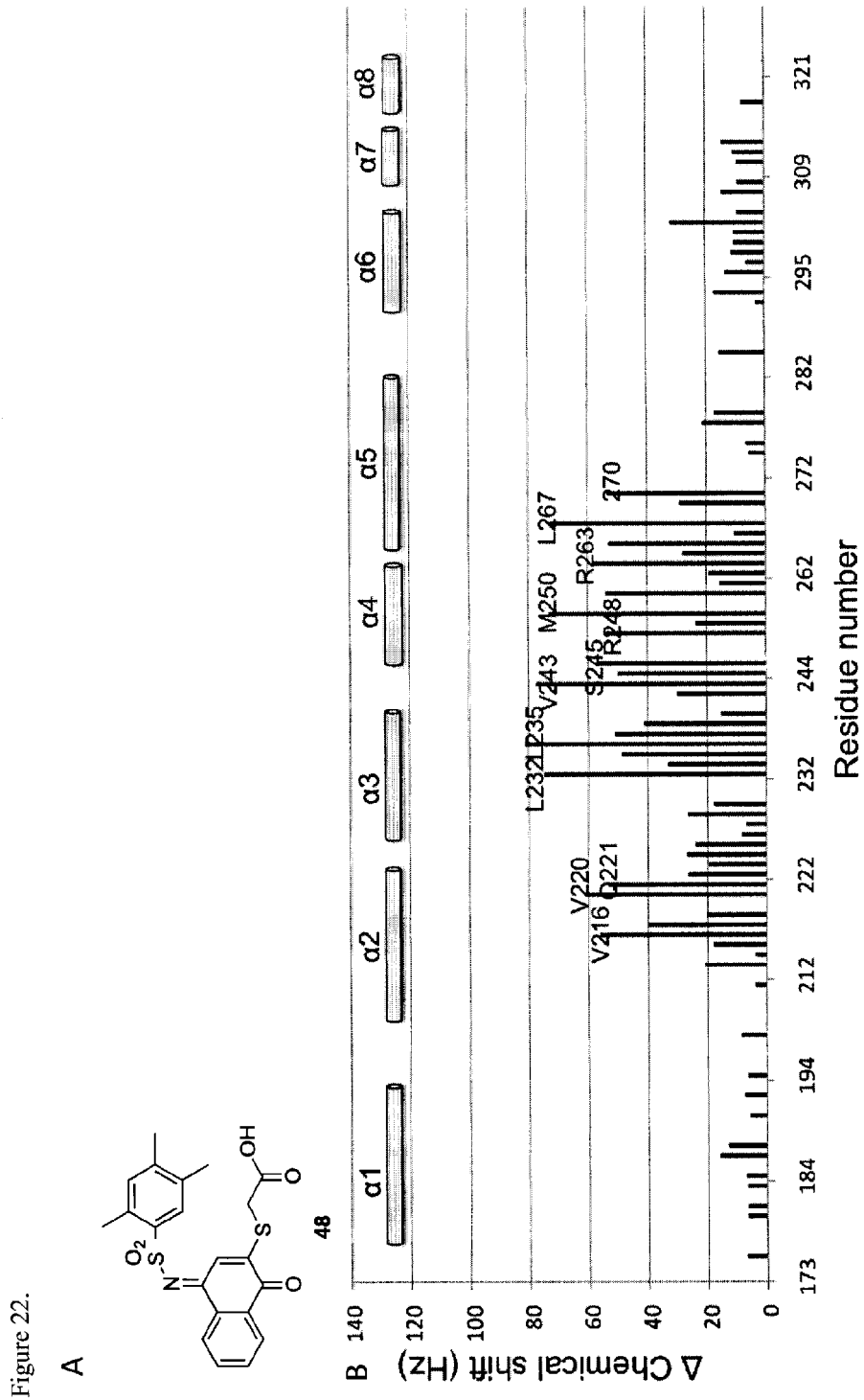

FIG. 22 (A) The structure of oxidized compound 48. (B) Plot of chemical shift changes calculated as $((\Delta^1 H\ Hz)^2+(\Delta^{15}N\ Hz)^2)^{0.5}$ of Mcl-1 amide upon addition of 48 (Mcl-1:48 ratio of 1 to 2) as a function of Mcl-1 residue numbers.

Figure 23:
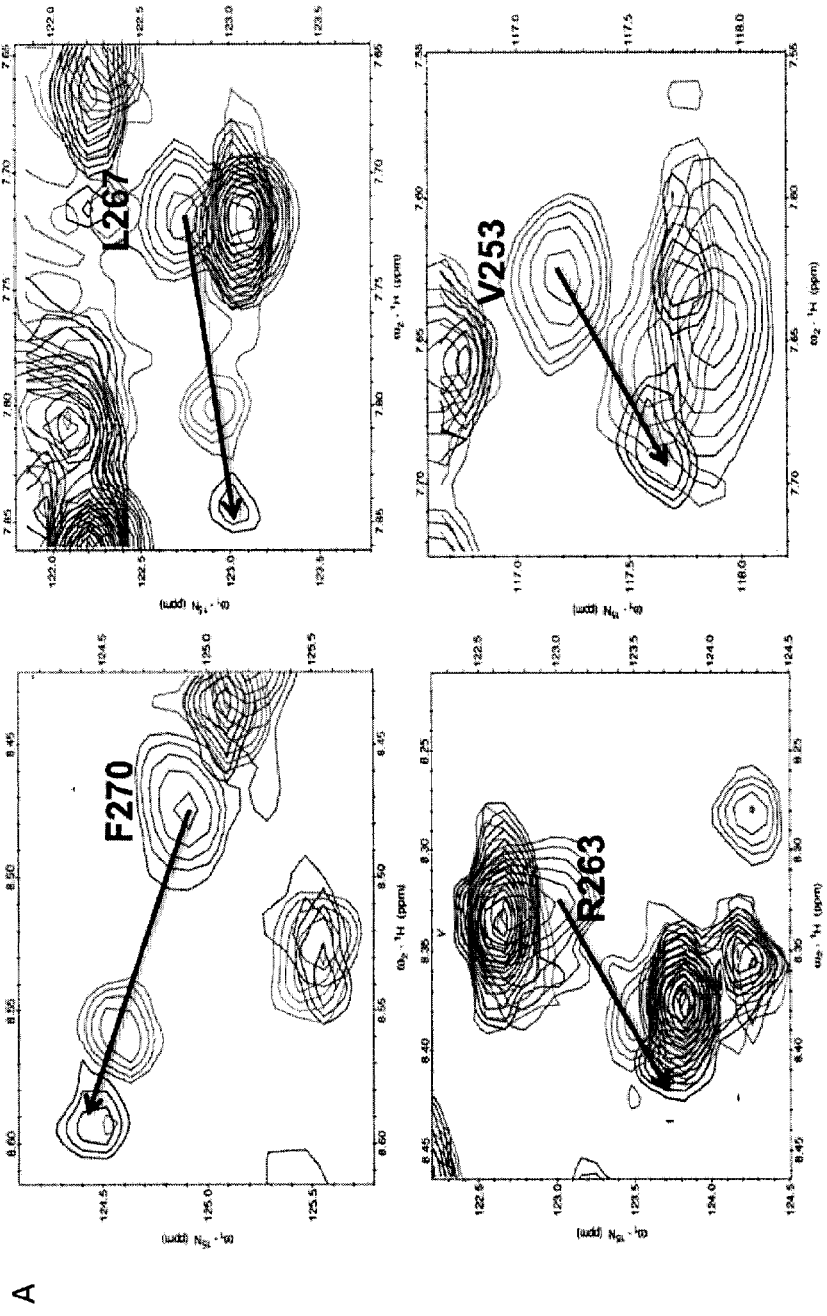
Figure 23:
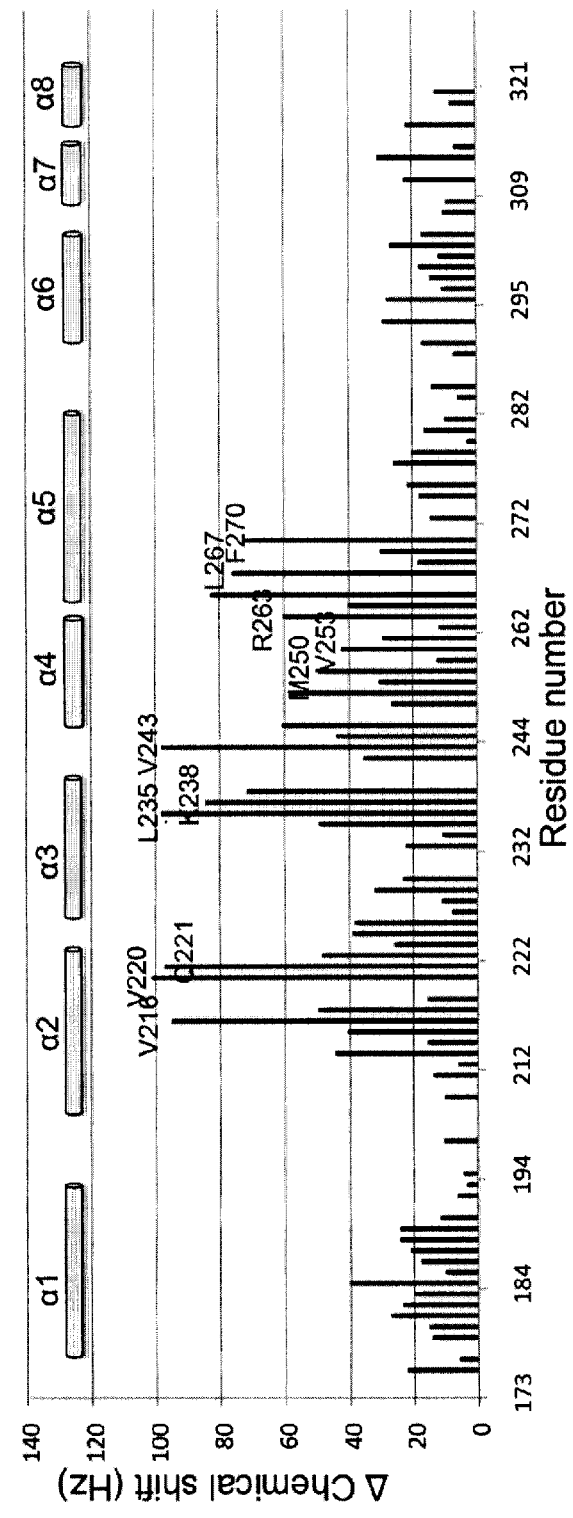

FIG. 23 shows (A) Slices of overlaid $^{15}$N—$^1$H HSQC spectra of Mcl-1 (greyish-red), and in presence of 18 (Mcl-1:18 ratio of 1 to 2) (black), (Mcl-1:1 ratio of 1 to 1) (greyish-purple). The arrows show the direction of chemical shift changes upon binding of 18. (B) Plot of chemical shift changes calculated as $((\Delta^1 H\ Hz)^2+(\Delta^{15}N\ Hz)^2)^{0.5}$ of Mcl-1 amide upon addition of 18 (Mcl-1:18 ratio of 1 to 2) as a function of Mcl-1 residue numbers.

Figure 24:
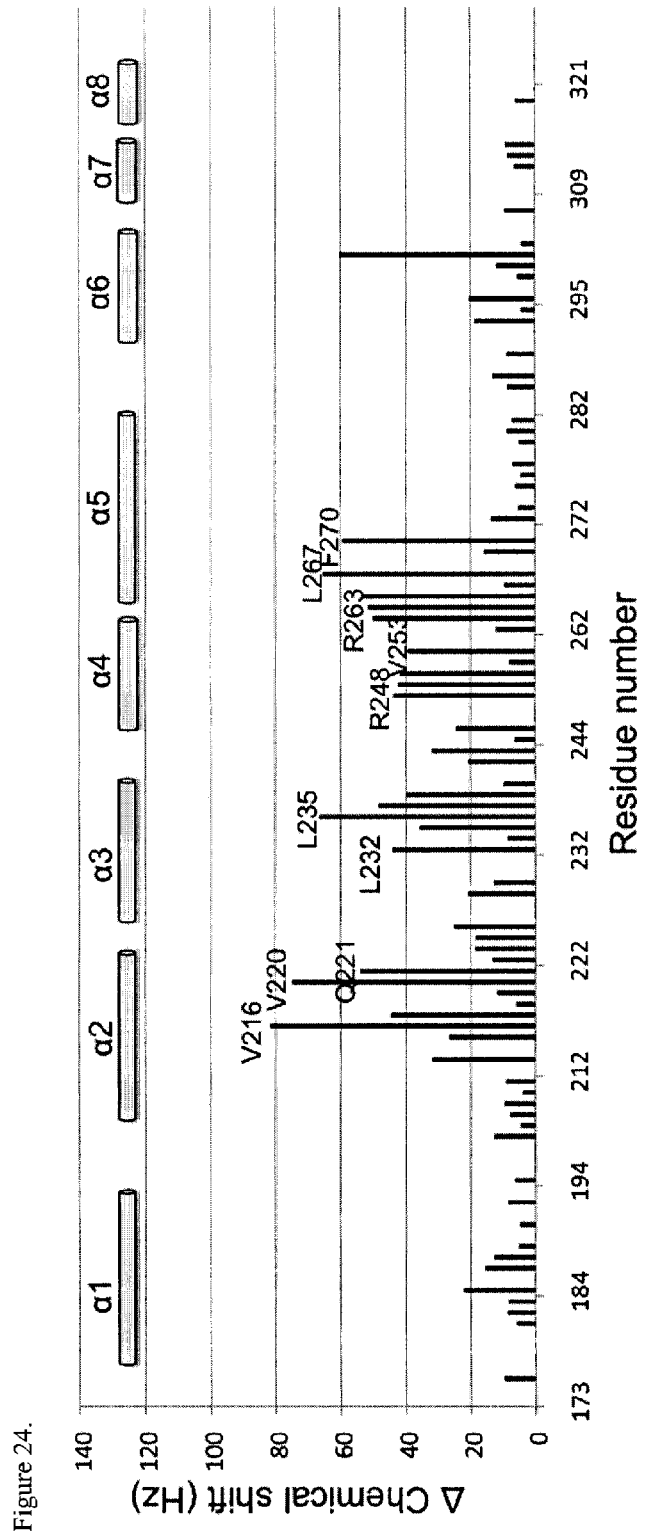

FIG. 24 shows plot of chemical shift changes calculated as $((\Delta^1\text{H Hz})^2+(\Delta^{15}\text{N Hz})^2)^{0.5}$ of Mcl-1 amide upon addition of 17 (Mcl-1:17 ratio of 1 to 2).

Figure 25:
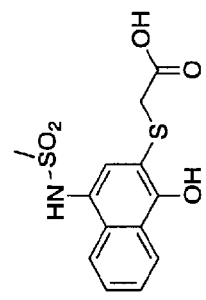
Figure 25:
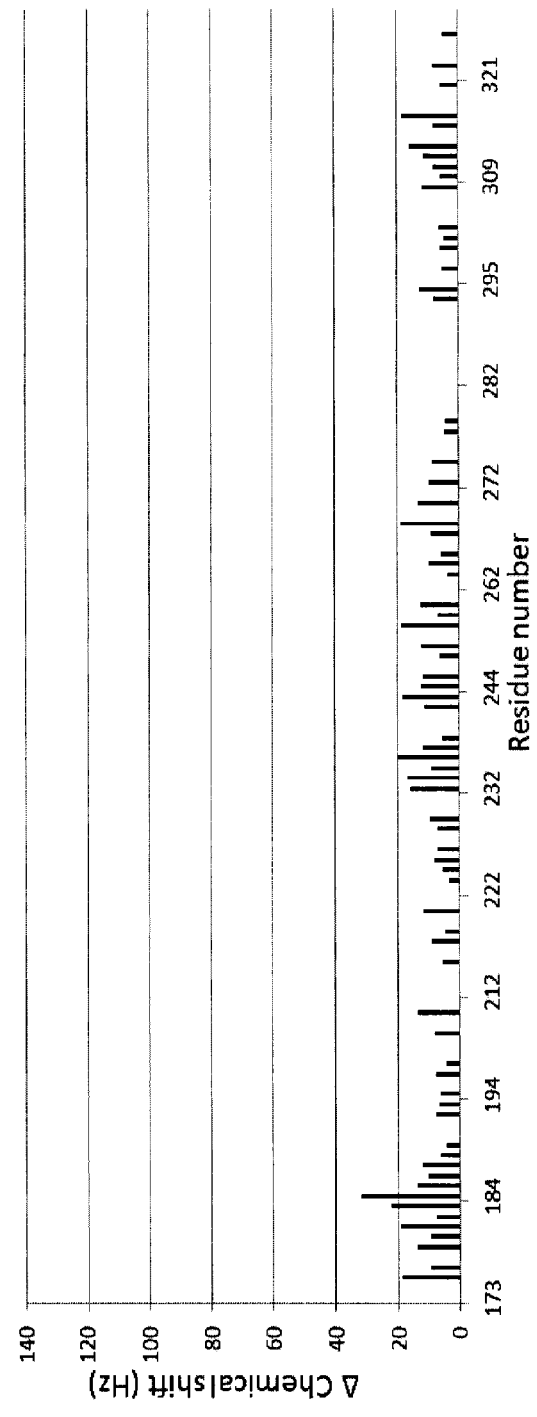

FIG. 25 shows a plot of chemical shift changes calculated as $((\Delta^1\text{H Hz})^2+(\Delta^{15}\text{N Hz})^2)^{0.5}$ of Mcl-1 amide upon addition of 21 (Mcl-1:21 ratio of 1 to 2).

Figure 26:
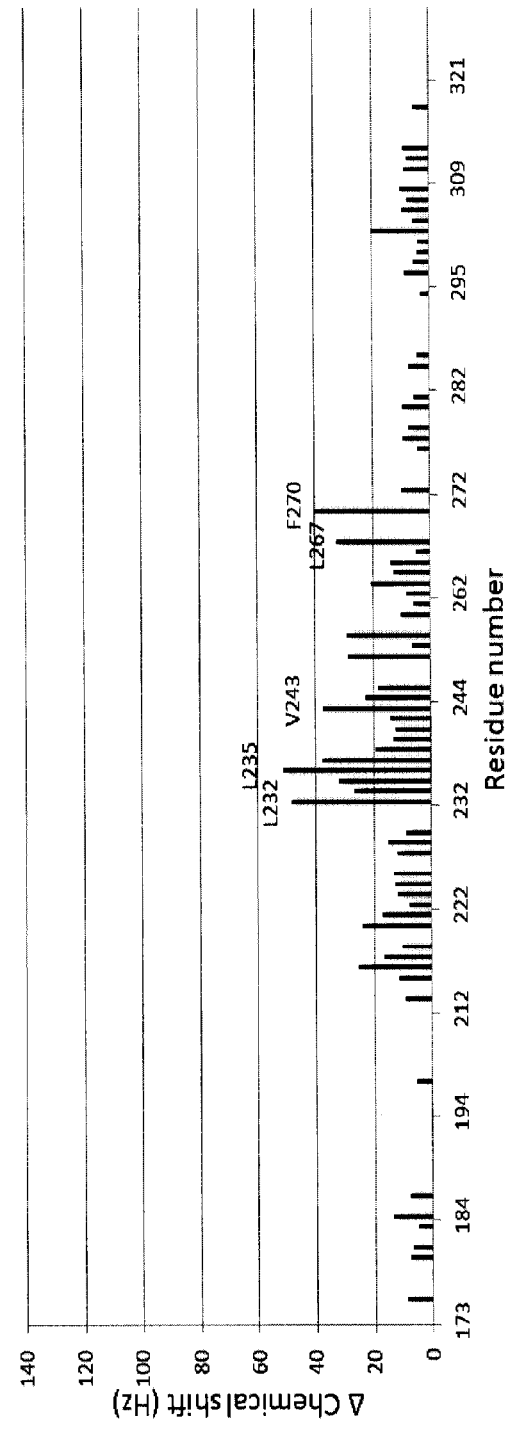

FIG. 26 shows a plot of chemical shift changes calculated as $((\Delta^1\text{H Hz})^2+(\Delta^{15}\text{N Hz})^2)^{0.5}$ of Mcl-1 amide upon addition of 22 (Mcl-1:22 ratio of 1 to 2).

Figure 27:
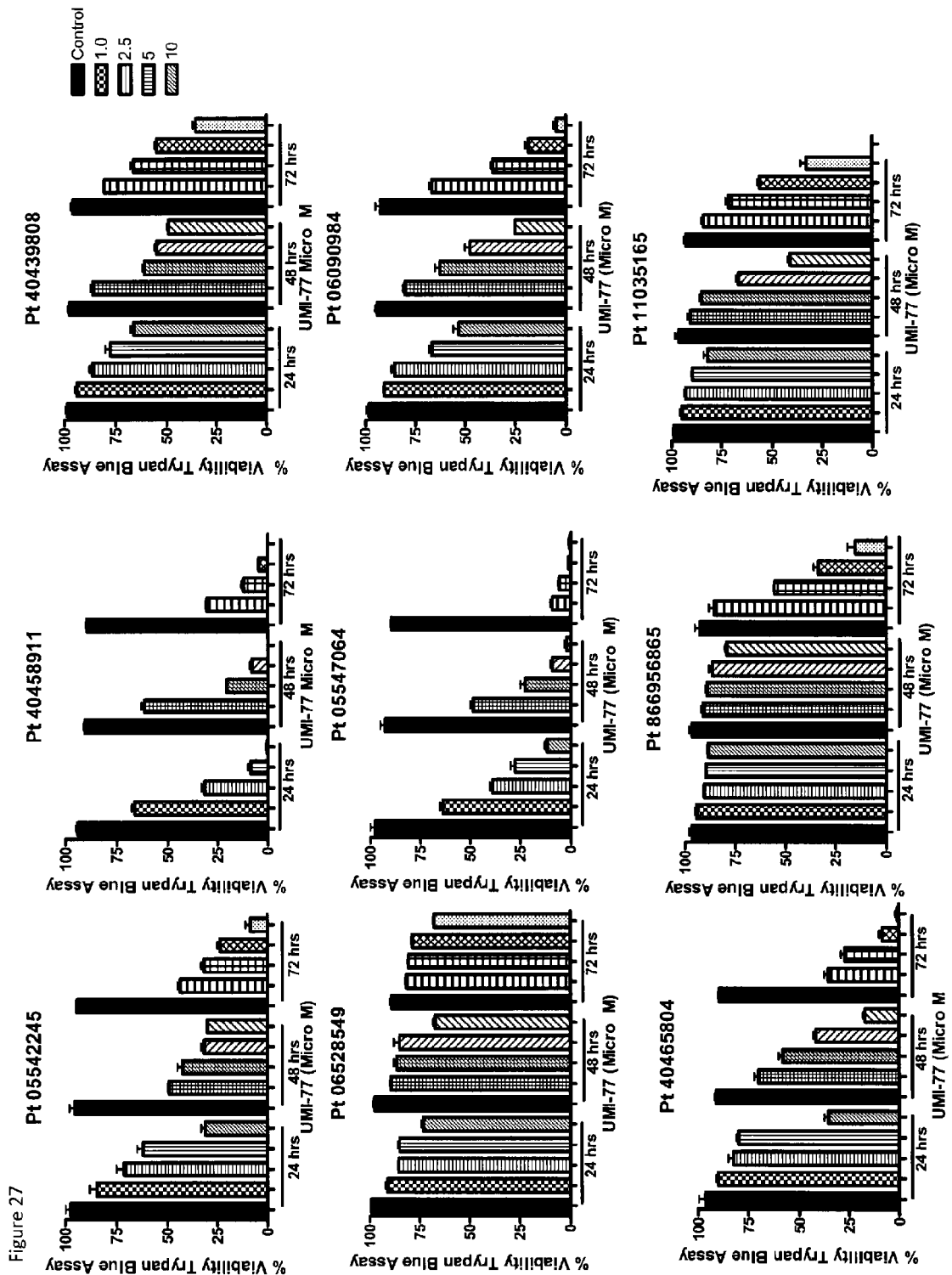

FIG. 27: UMI-77 effect on the viability of bone marrow derived cells from patients with multiple myeloma.

Figure 28:
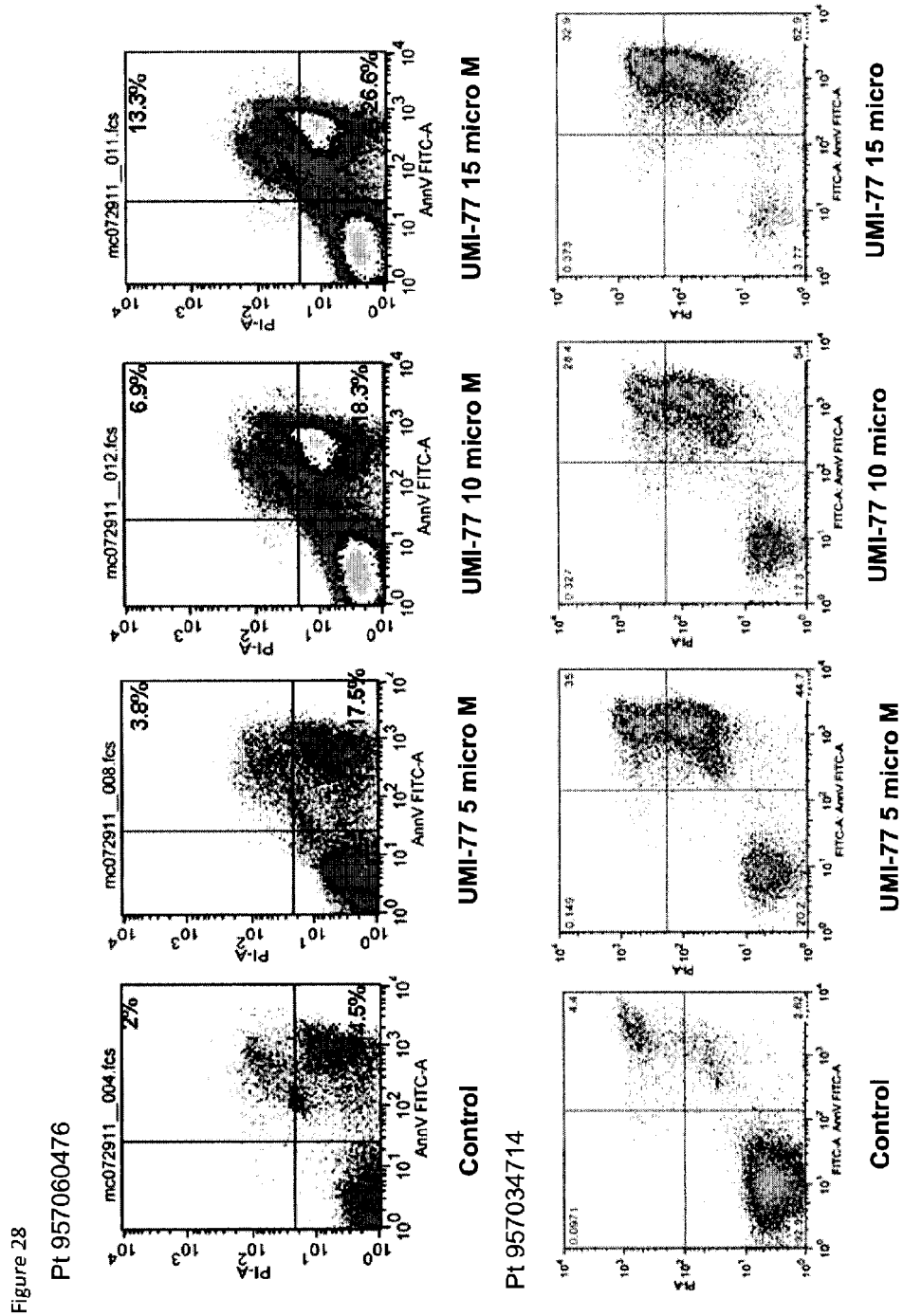
Figure 28:
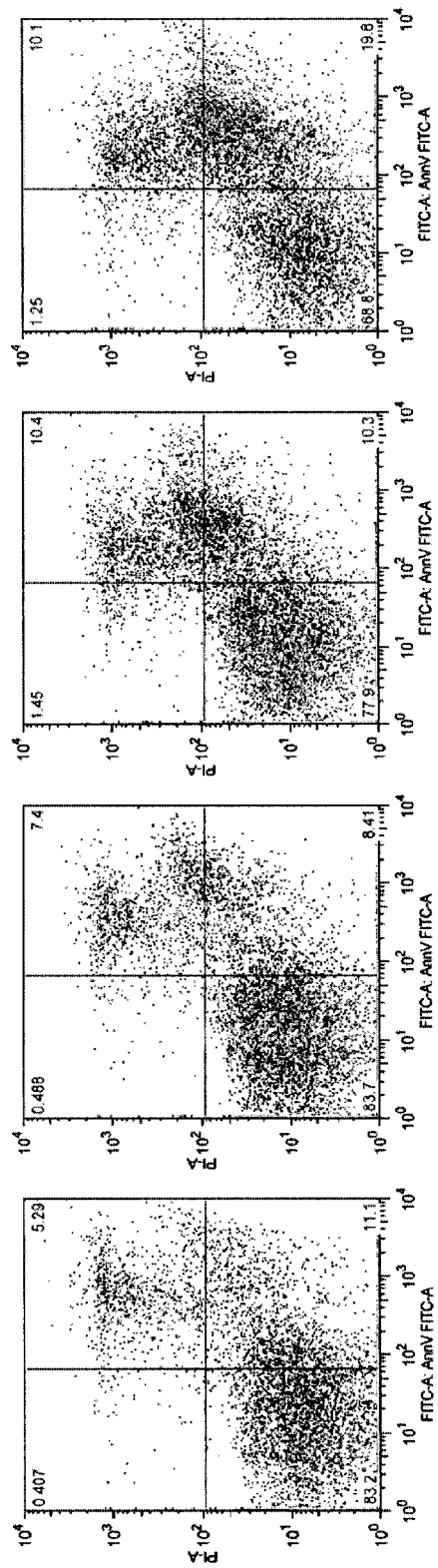

FIG. 28: Dose-dependent induction of apoptosis in bone marrow derived cells from three patients with multiple myeloma after treatment with UMI-77.

DEFINITIONS

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a sulfonamido-1-hydroxynaphthalen compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "functional Mcl-1," as used herein, refers to wild-type Mcl-1 expressed at normal, high, or low levels and mutant Mcl-1 that retains at least about 5% of the activity of wild-type Mcl-1, e.g., at least about 10%, about 20%, about 30%, about 40%, about 50%, or more of wild-type activity.

The term "Mcl-1-related protein," as used herein, refers to proteins that have partial sequence homology (e.g., at least 5%, 10%, 25%, 50%, 75%, 85%, 95%, 99%, 99.999%) with Mcl-1, have tumor suppressor activity, and are inhibited by interaction with a compound of the present invention (e.g UMI-77).

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Myeloid cell leukemia-1 (Mcl-1) is a potent anti-apoptotic protein, belonging to the prosurvival Bcl-2 subfamily and its role is emerging as a critical survival factor in a broad range of human cancers, including PC (see, e.g., Day C L, et al., J Biol. Chem. 2005; 280:4738-44; Day C L, et al., J Mol. Biol. 2008; 380:958-71; each herein incorporated by reference in its entirety). Functional studies have confirmed that Mcl-1 is capable of blocking apoptosis induced by various apoptotic stimuli, including chemotherapy and radiation (see, e.g., Zhou P, et al., Blood. 1997; 89:630-43; herein incorporated by reference in its entirety). Mcl-1 is highly up-regulated in PC cells and is associated with resistance to chemotherapeutic agents (see, e.g., Miyamoto Y, et al., Oncology. 1999; 56:73-82; Schniewind B, et al., Int J Cancer. 2004; 109:182-8; Ren L N, et al., Biochem Biophys Res Commun. 2009; 386:35-9; Wei S H, et al., Cancer Chemother Pharmacol. 2008; 62:1055-64; Guoan X, et al., Surgery. 2010; 147:553-61; Huang S, et al., Cancer Res. 2008; 68:2944-51; each herein incorporated by reference in its entirety). In addition, Mcl-1 is an important survival factor for PC cells and down-regulation of Mcl-1 enhances the induction of apoptosis and chemosensitivity to Gemcitabine, radiation and ABT-737 (see, e.g., Wei S H, et al., Cancer Chemother Pharmacol. 2008; 62:1055-64; Guoan X, et al., Surgery. 2010; 147:553-61; Huang S, et al., Cancer Res. 2008; 68:2944-51; each herein incorporated by reference in its entirety). Thus, Mcl-1 represents a very attractive molecular target for developing a new class of cancer therapy for treatment of PC by overcoming resistance to chemotherapeutic agents.

Potent small molecule inhibitors of Bcl-2 subfamily include the Bad-like BH3 mimetics (see, e.g., Oltersdorf T, et al., Nature. 2005; 435:677-81; Tse C, et al., Cancer Res. 2008; 68:3421-8; each herein incorporated by reference in its entirety). ABT-737, one of these mimetics, binds with high affinity ($K_i \leq 1$ nM) to Bcl-2, Bcl-$x_L$ and Bcl-w but fails to bind to Mcl-1 (see, e.g., Oltersdorf T, et al., Nature. 2005; 435:677-81; herein incorporated by reference in its entirety). Several studies have shown that resistance to ABT-737 is linked to high expression levels of Mcl-1 and in many instances this resistance can be overcome by treatment with agents that down-regulate, destabilize, or inactivate Mcl-1 (see, e.g., van Delft M F, et al., Cancer Cell. 2006; 10:389-99; Chen S, et al., Cancer Res. 2007; 67:782-91; each herein incorporated by reference in its entirety). It was recently shown that knockdown of Mcl-1 sensitizes human PC cancer cells to ABT-737-induced apoptosis, indicating that Mcl-1 is a relevant therapeutic target in these cancer cells (see, e.g., Huang S, et al., Cancer Res. 2008; 68:2944-51; herein incorporated by reference in its entirety).

Applying a high throughput screening (HTS) approach, experiments conducted during the course of developing embodiments for the present invention identified and validated a new class of small-molecules having sulfonamido-1-hydroxynaphthalene structure which function as inhibitors of Mcl-1 protein. Tables 2, 3, 4 and 5 show various sulfonamido-1-hydroxynaphthalene compounds and $IC_{50}$ values for binding with Mcl-1. In addition, such experiments identified a novel selective small molecule Mcl-1 inhibitor, labeled as UMI-77, an analogue of one of the identified lead compounds and illustrate its potency, specificity and ability to induce Bax/Bak dependent apoptosis through targeting Mcl-1 in PC cells. UMI-77 was shown to exhibit single-agent antitumor activity in BxPC3 xenograft model thereby indicating UMI-77 and Mcl-1 inhibitors as a new strategy for the treatment of human PC. Furthermore, these findings provide the basis and rational of combining UMI-77 with chemotherapy and radiation whose activity in pancreatic cancer is restrained by Mcl-1. Moreover, as described in Example 9, bone marrow derived cells from patients having multiple myeloma showed loss in viability post Mcl-1 (e.g., UMI-77) treatment.

The experiments further identified

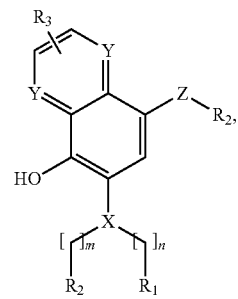

(compound 17) as a potent Mcl-1 inhibitor.

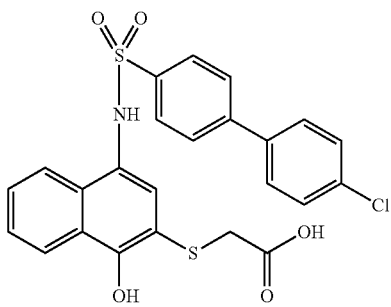 [SMILES: O=C(O)CSc1cc(NS(=O)(=O)c2ccc(-c3ccc(Cl)cc3)cc2)c2ccccc2c1O]

(compound 17) showed an $IC_{50}$ of 0.68±0.14 µM and a $K_i$ of 0.17±0.04 µM against Mcl-1 and selectively inhibited Mcl-1 over other anti-apoptotic Bcl-2 family proteins.

Accordingly, the present invention relates to compounds which function as inhibitors of Mcl-1 proteins. By inhibiting the activity of Mcl-1, these compounds sensitize cells to inducers of apoptosis and/or cell cycle arrest and, in some instances, themselves induce apoptosis and/or cell cycle arrest. Therefore, the invention relates to methods of sensitizing cells to inducers of apoptosis and/or cell cycle arrest and to methods of inducing apoptosis and/or cell cycle arrest in cells, comprising contacting the cells with a compound of the invention alone or in combination with additional agent(s), e.g., an inducer of apoptosis or a cell cycle disrupter.

The invention further relates to methods of treating, ameliorating, or preventing disorders in a patient, such as those that are responsive to induction of apoptosis, comprising administering to the patient a compound of the invention and additional agent(s), e.g., an inducer of apoptosis. Such disorders include those characterized by a dysregulation of apoptosis and those characterized by the proliferation of cells expressing functional Mcl-1 proteins (e.g., pancreatic cancer).

In a particular embodiment, sulfonamido-1-hydroxynaphthalene compounds have Formula I:

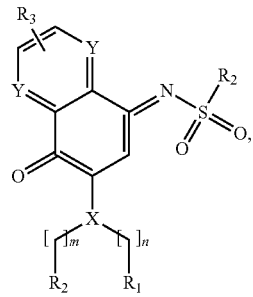

Formula II:

or Formula III:

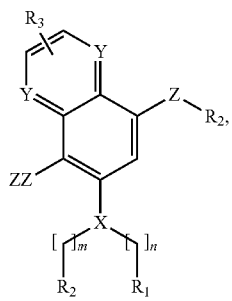

including pharmaceutically acceptable salts, solvates, and/or prodrugs thereof.

Formulas I, II and/or III are not limited to a particular chemical moiety for R1, R2, R3, m, n, X, Y, Z and ZZ. In some embodiments, R1, R2, R3, m, n, X, Y, Z and ZZ is independently include any chemical moiety that permits the resulting compound to bind with an Mcl-1 protein.

In some embodiments, X is selected from O, S, N or C.
In some embodiments, Y is selected from C or N.
In some embodiments, Z is selected from

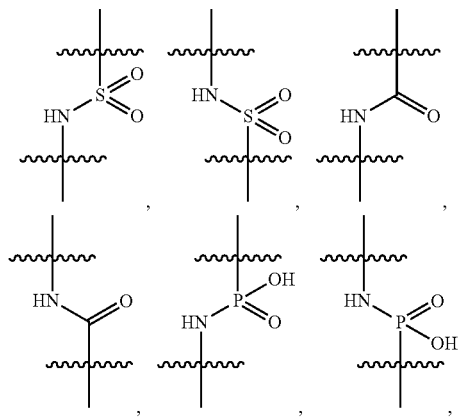

etc.

In some embodiments, ZZ is selected from the group consisting of OH, OCH$_3$, =O, and

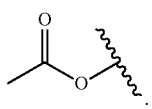 [SMILES: *OC(C)=O]

In some embodiments, m is between 0 and 6.
In some embodiments, n is between 0 and 4.
In some embodiments, R1 is selected from H, —COOH,

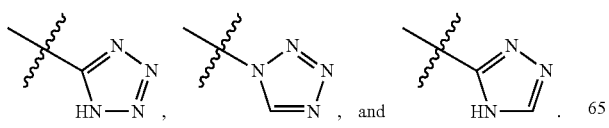

In some embodiments, R1 is any chemical moiety having hydrogen bond acceptors. In some embodiments, R1 is any negatively charged chemical moiety having hydrogen bond acceptors.

In some embodiments, R1 is absent.

In some embodiments, R2 is independently selected from —H,

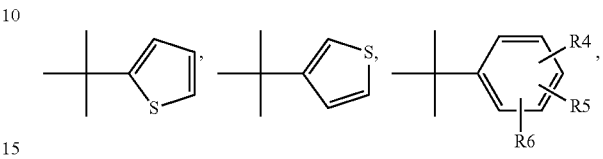

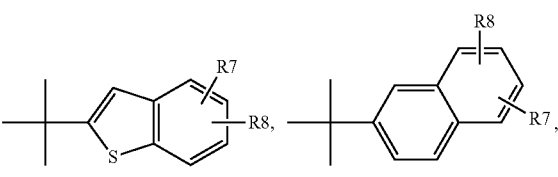

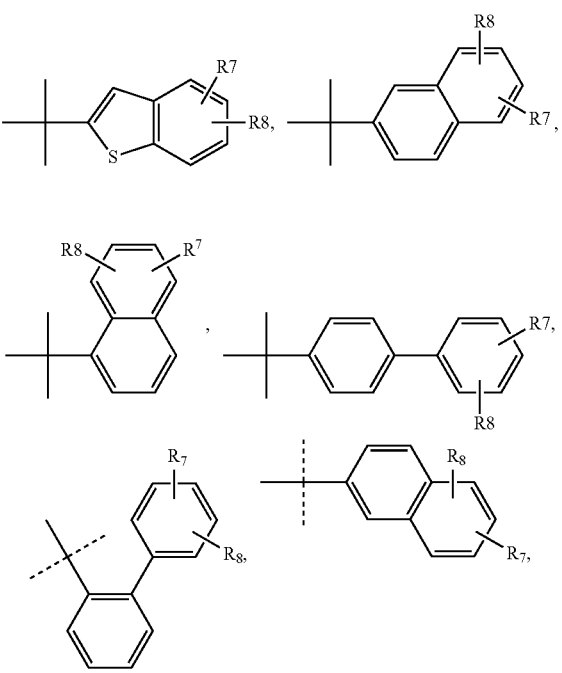

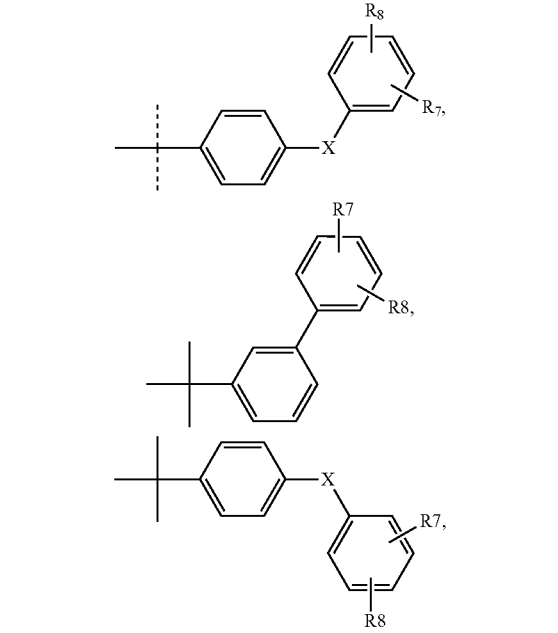

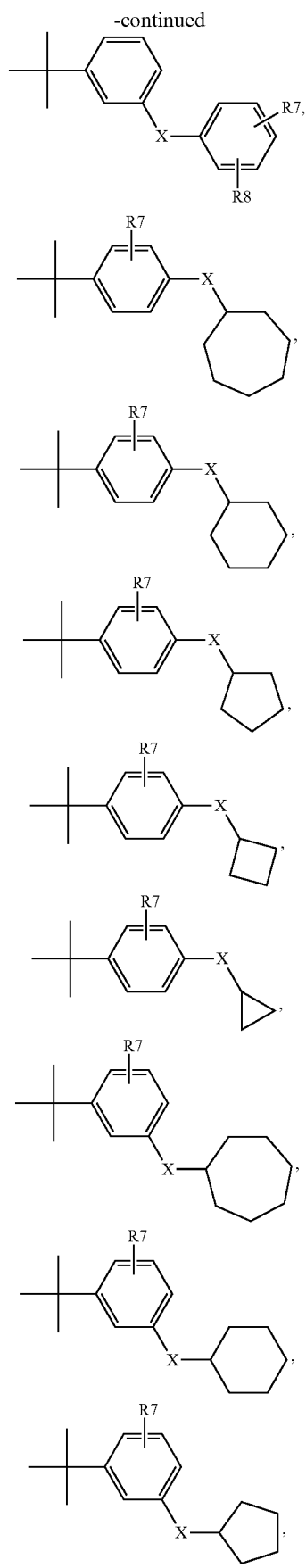
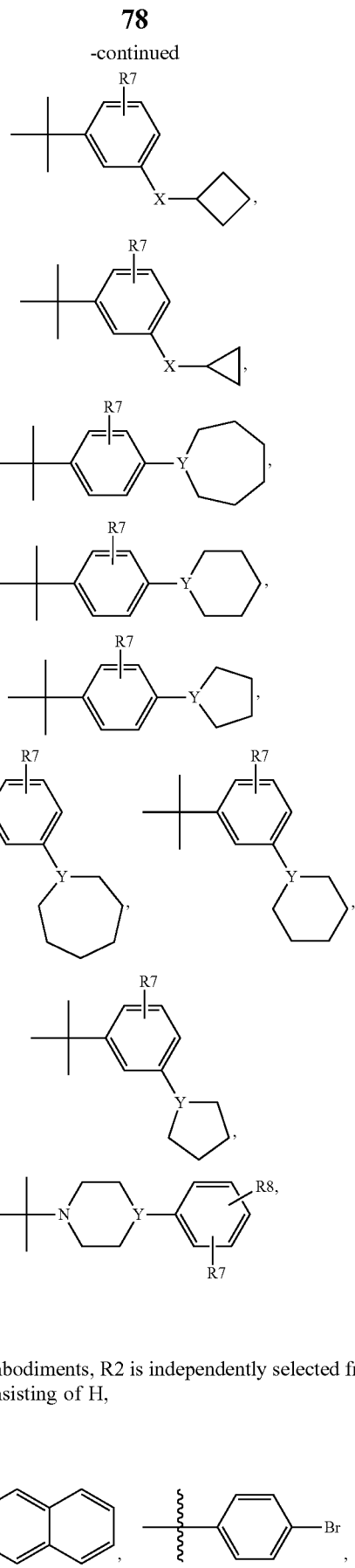
etc.
In some embodiments, R2 is independently selected from the group consisting of H, -continued
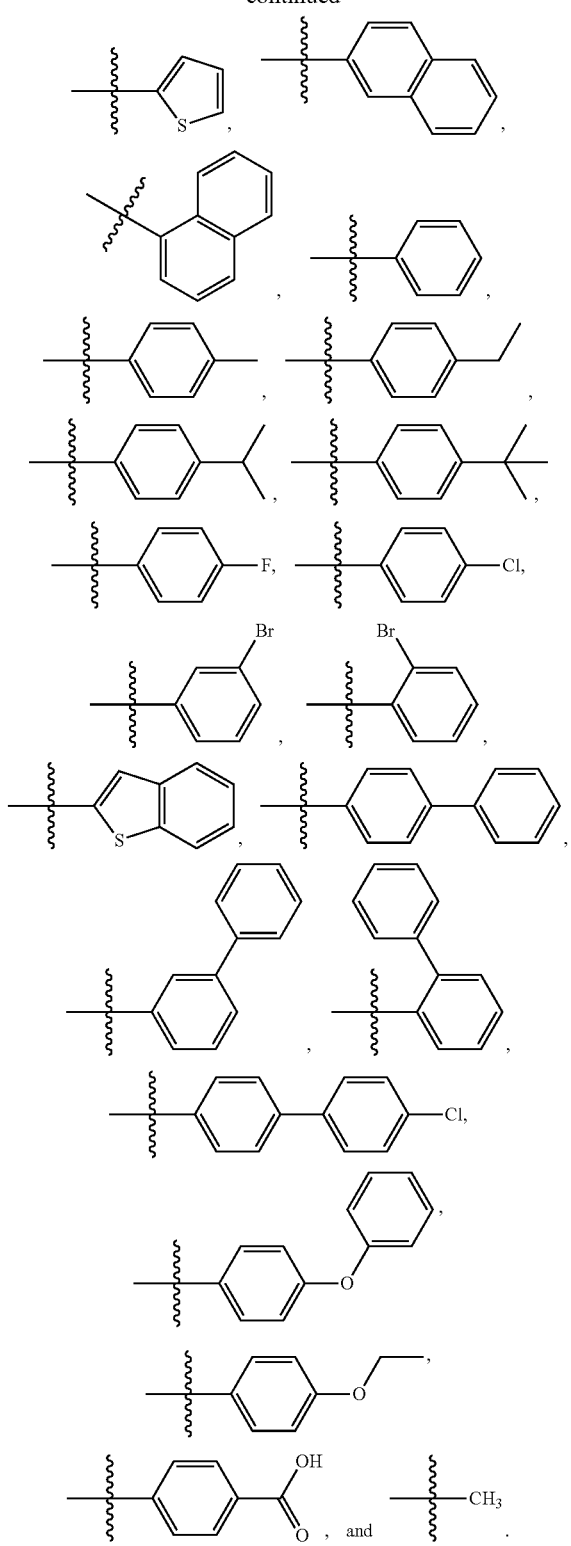
In some embodiments, R2 is absent.
In some embodiments, R3 is selected from —H, —F, —Cl, —Br, —CH$_3$, —CF$_3$, —OCH$_3$, etc.
In some embodiments, R3 is absent.
In some embodiments,
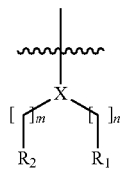
is selected from the group consisting of Cl, H,
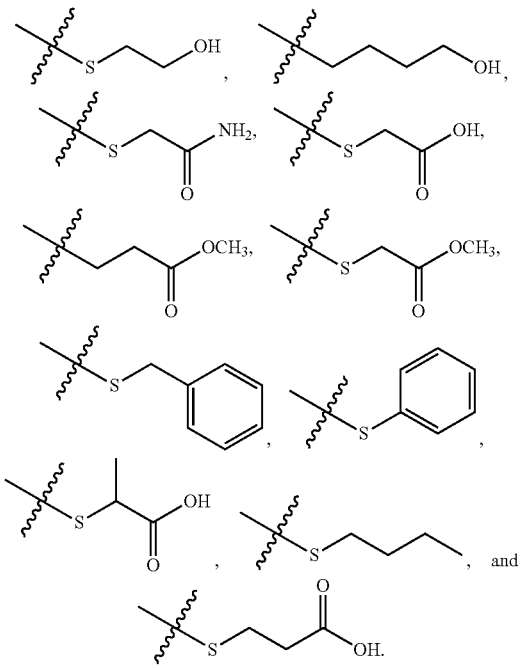
In some embodiments,
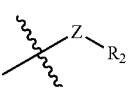
is selected from the group consisting of
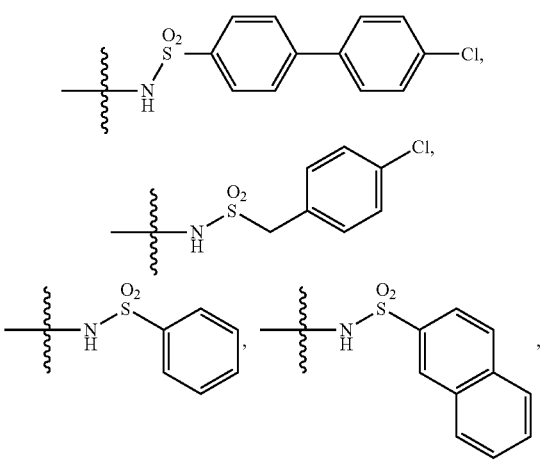

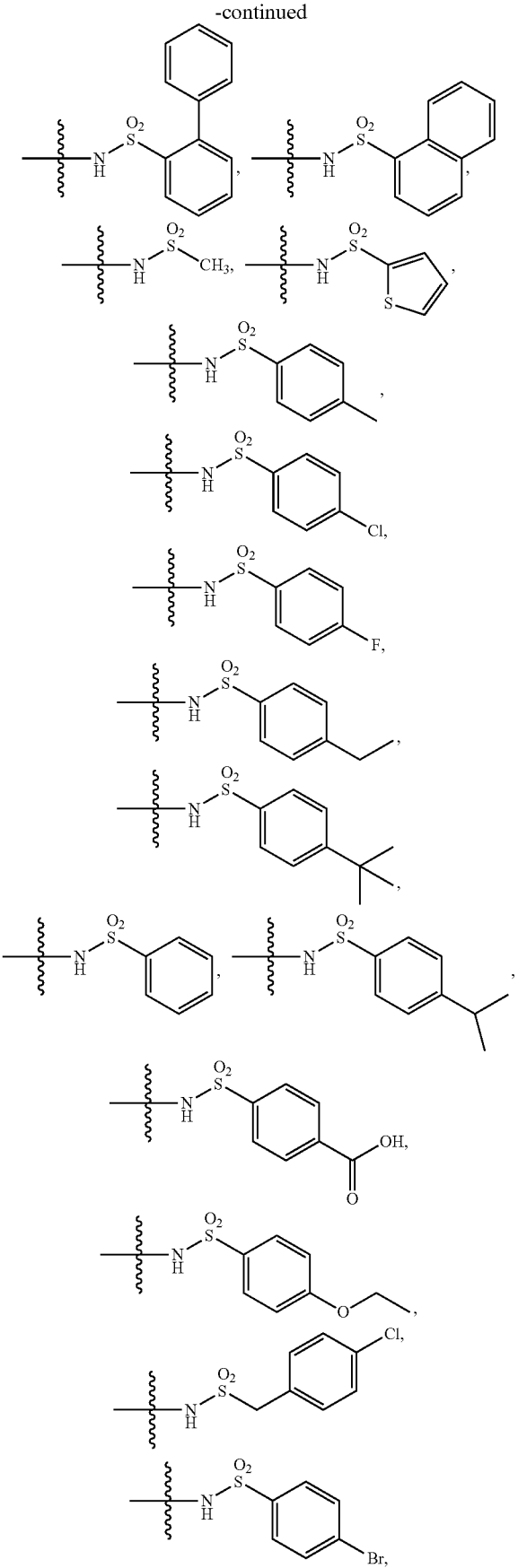

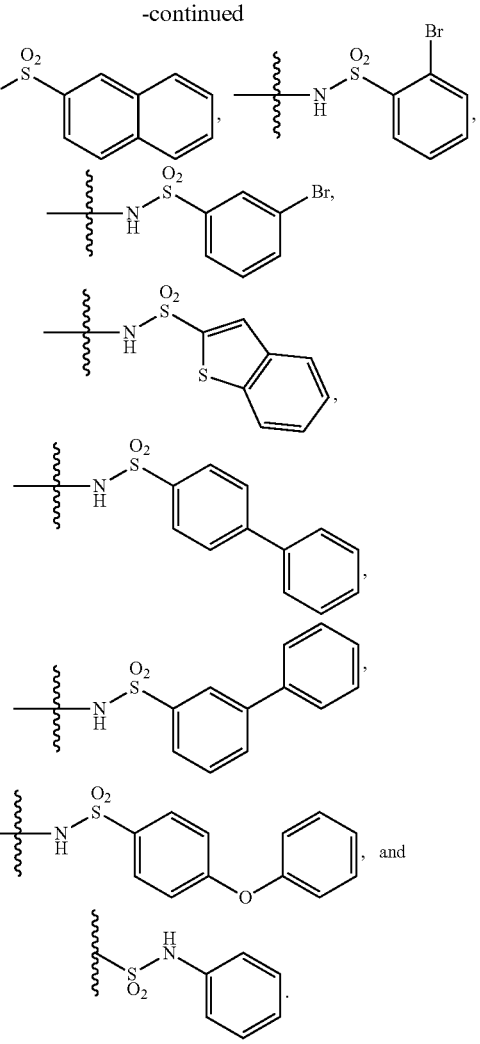

In some embodiments, R4, R5, and R6, are independently selected from H, —F, —Cl, —Br, —CH₃,

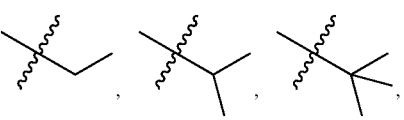

or any other alkyl groups (substituted or unsubstituted), —CF₃, —OH, —OCH₃, —OC₂H₅, —OCF₃, —NO₂, —COOH, etc.

In some embodiments, R7 and R8 are independently selected from —H, —F, —Cl, —Br, —CH₃,

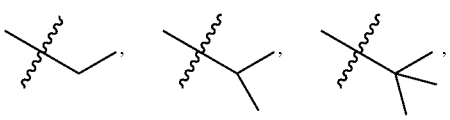

or any other alkyl groups (substituted or unsubstituted), —CF₃, —OH, —OCH₃, —OC₂H₅, etc.

Tables 2, 3, 4 and 5 shows binding affinities (IC$_{50}$ values were determined with fluorescence polarizing binding assay) for various compounds encompassed and inhibition against Mcl-1 within Formulas I, II and/or III.
In some embodiments, the following compounds are contemplated for Formula I, Formula II, and Formula III:
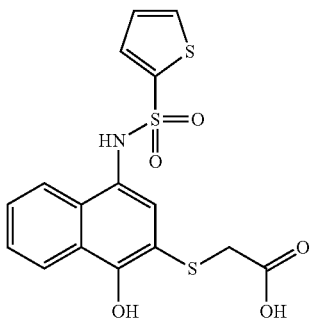
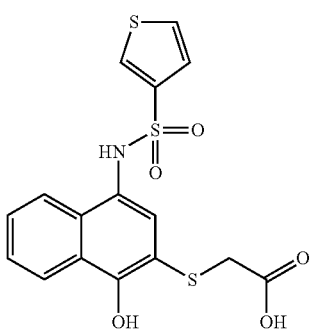
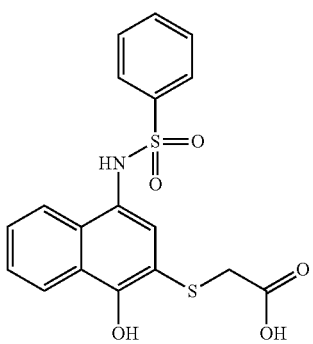
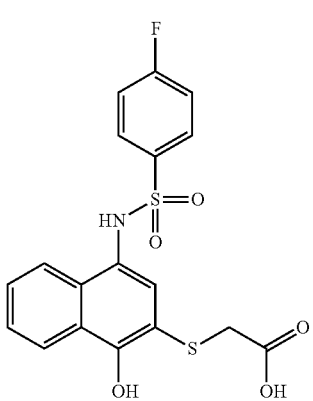
-continued
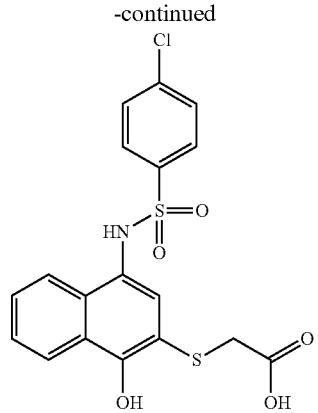
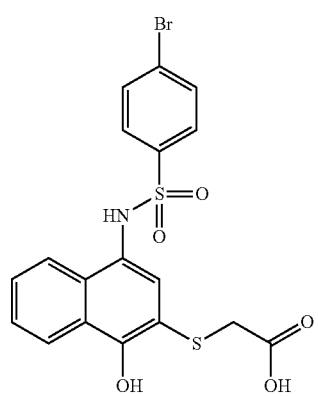
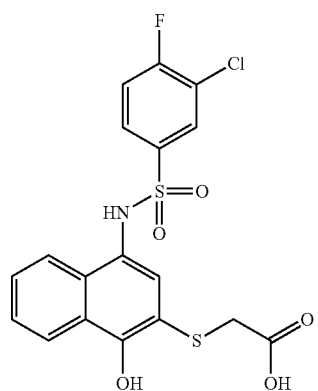
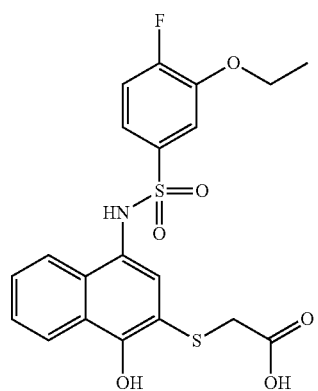

85
-continued
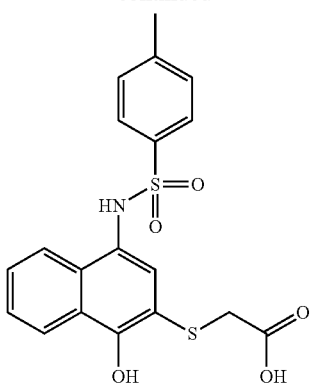
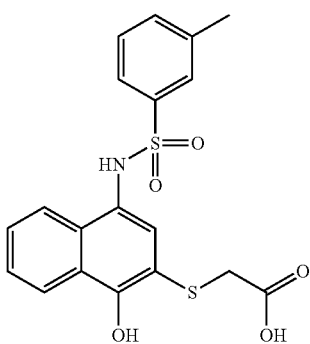
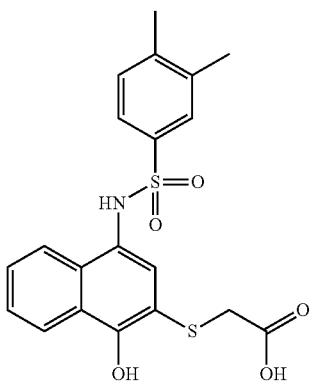
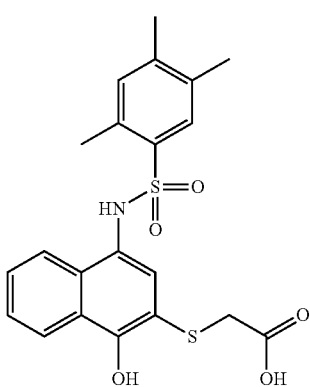
86
-continued
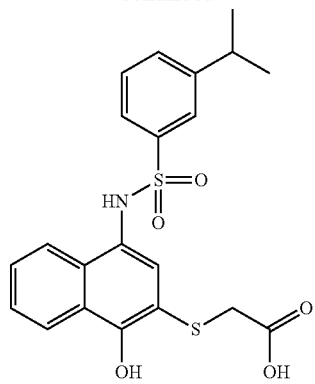
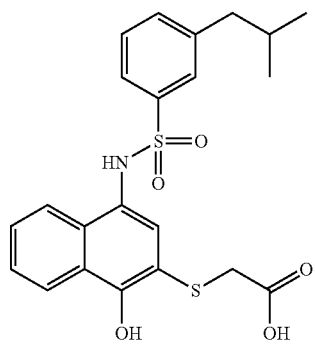
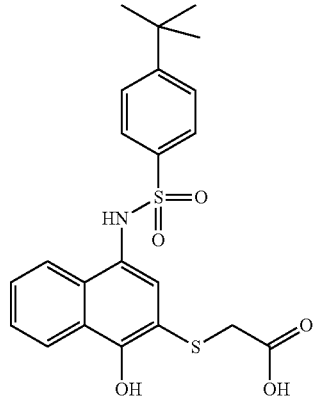
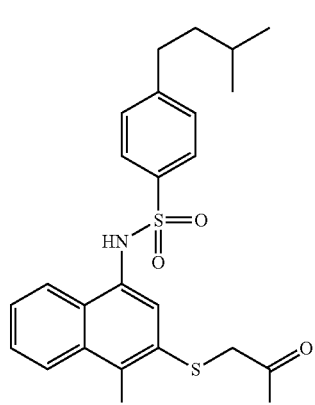

87
-continued
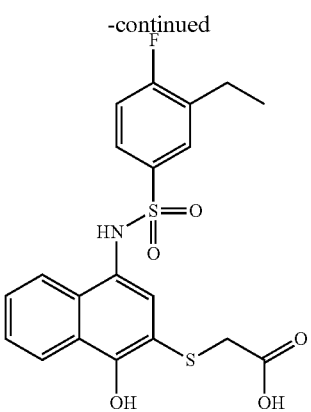
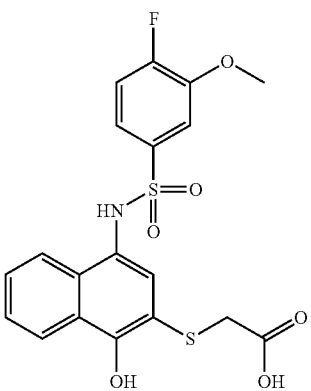
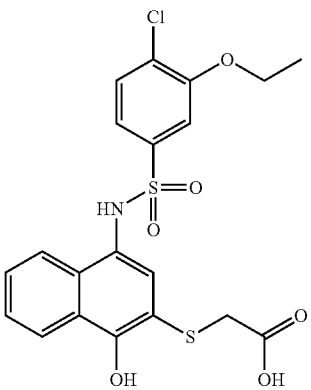
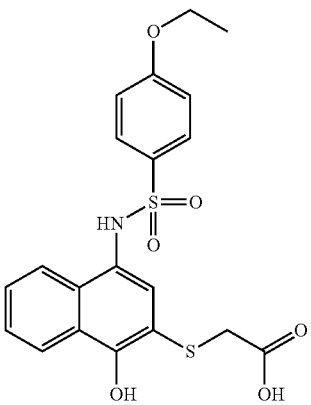
88
-continued
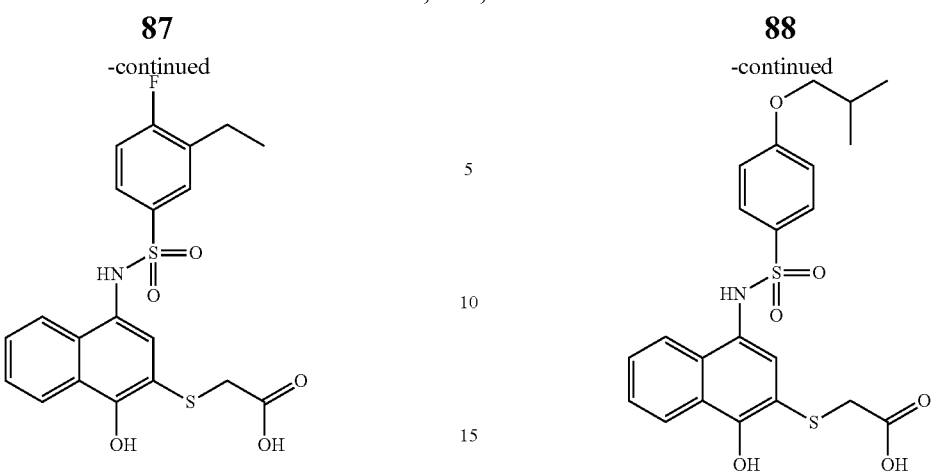
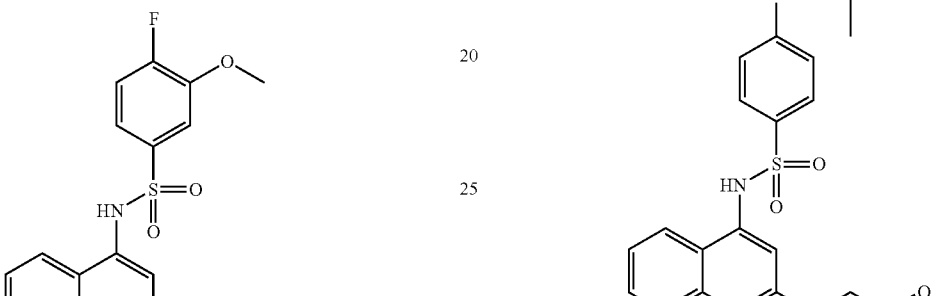
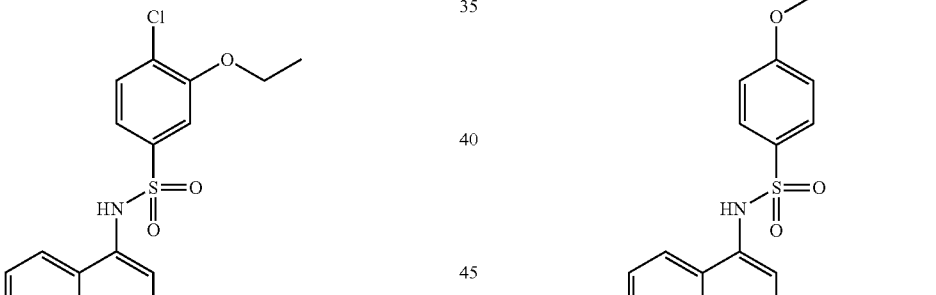
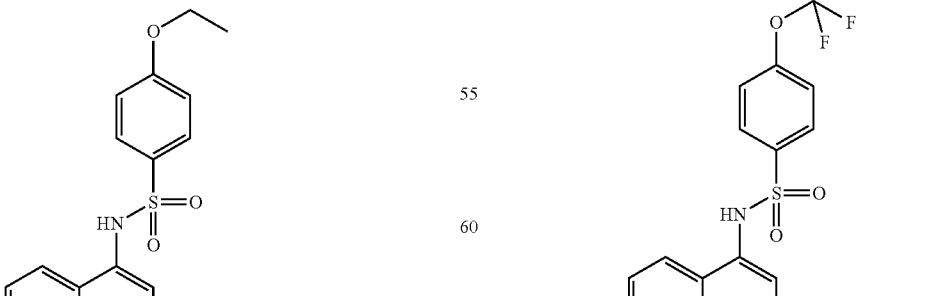

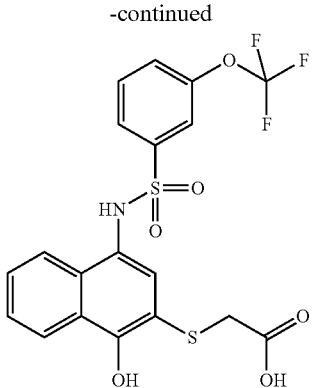
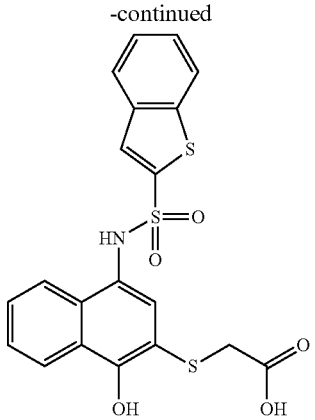

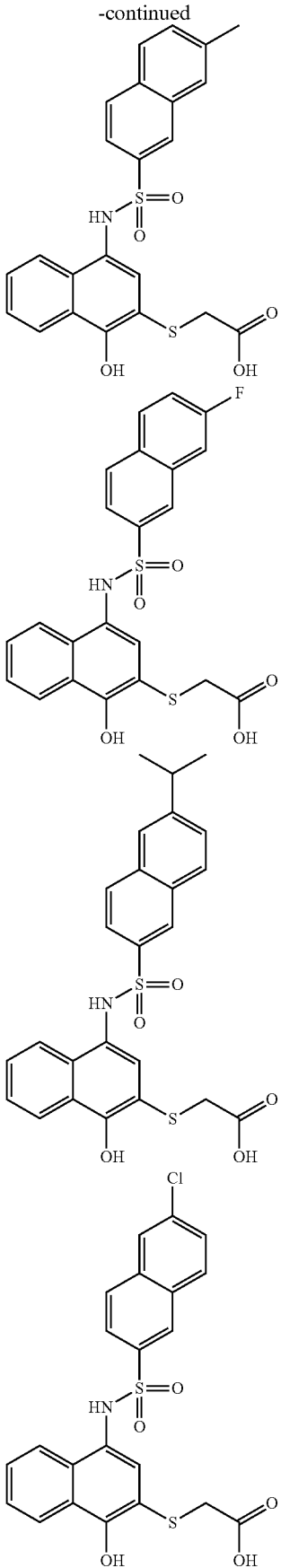
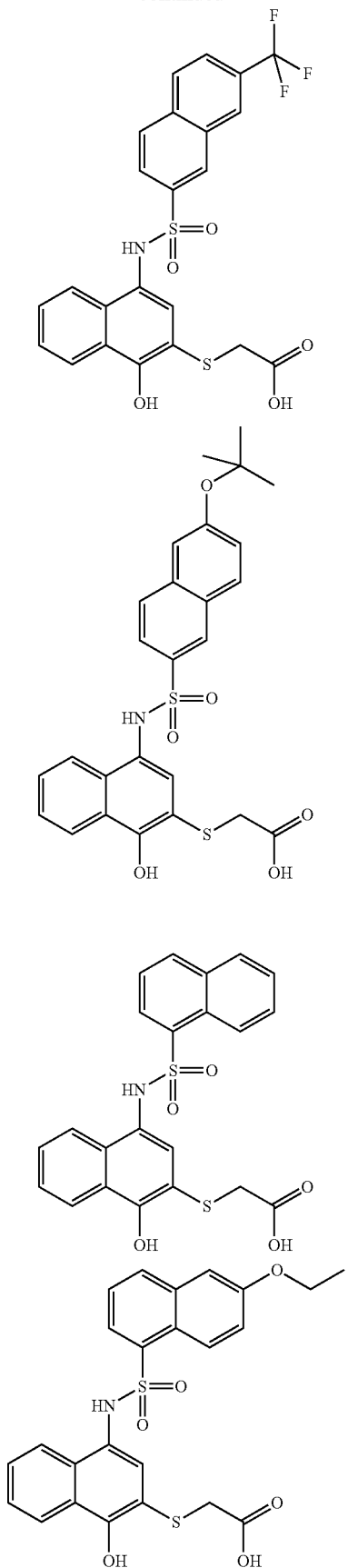

93
-continued
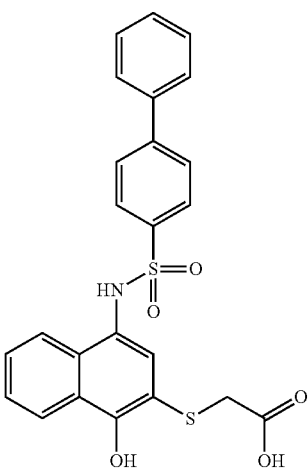
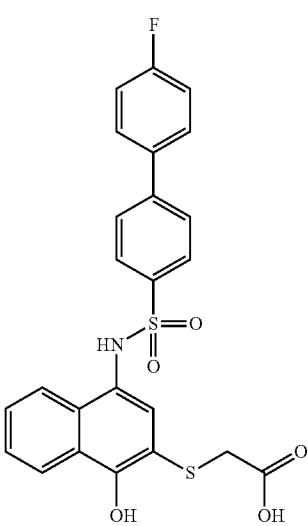
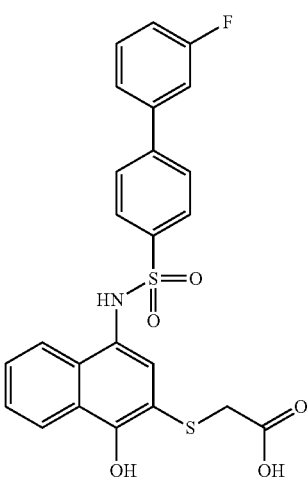
94
-continued
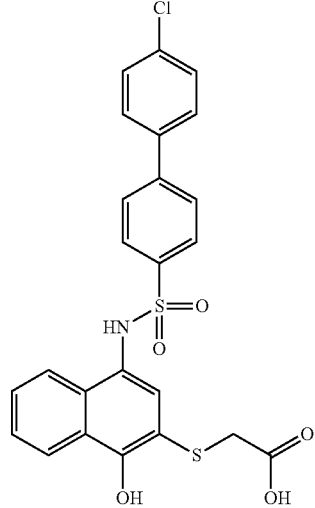
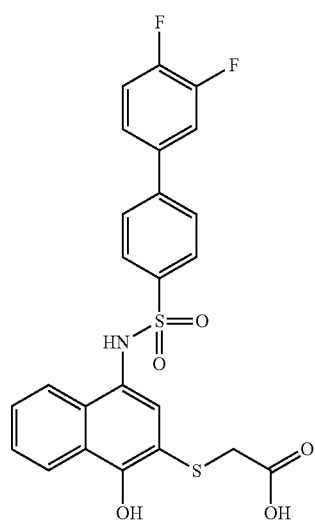
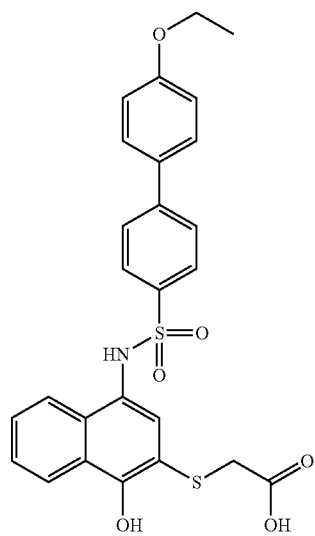

95
-continued
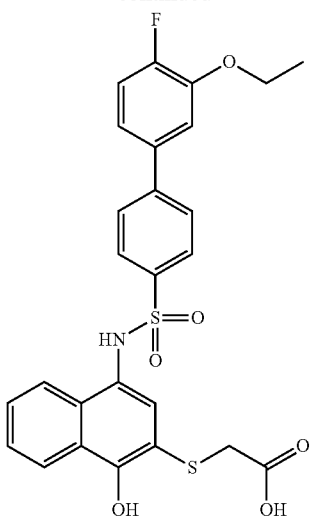
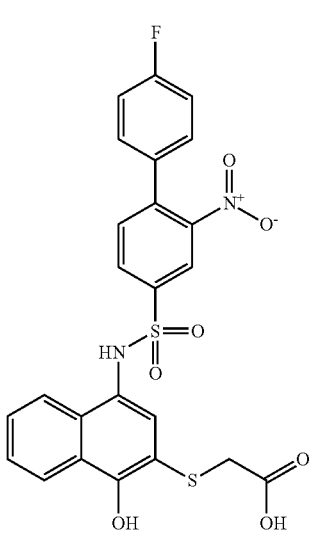
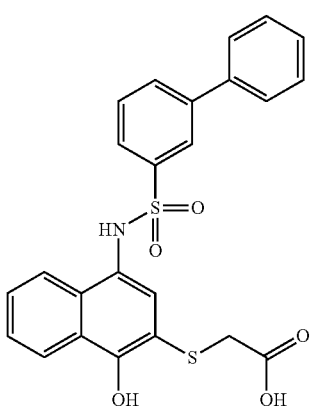
96
-continued
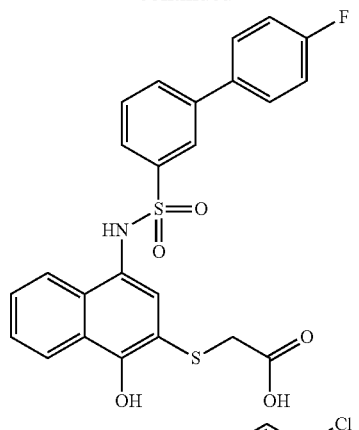
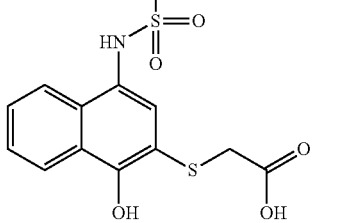
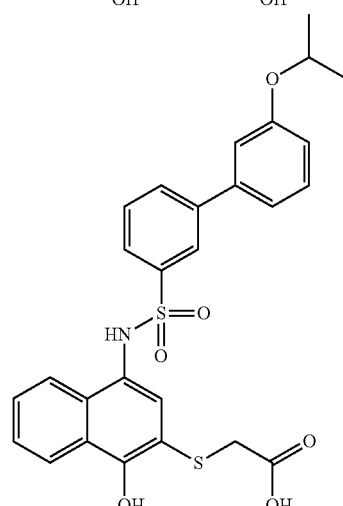
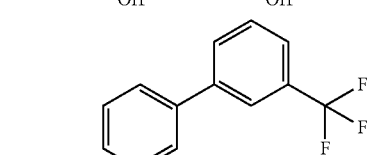
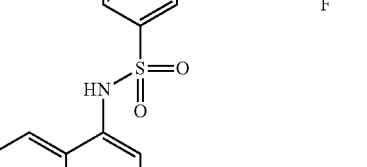
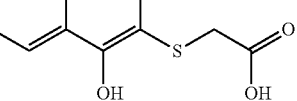

97
-continued
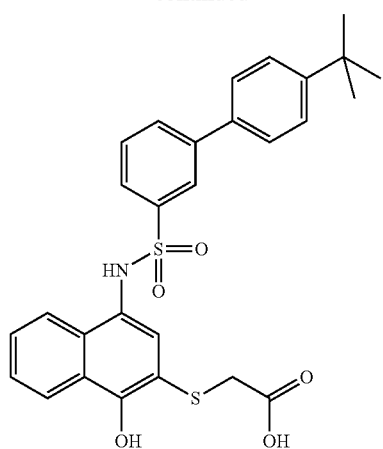
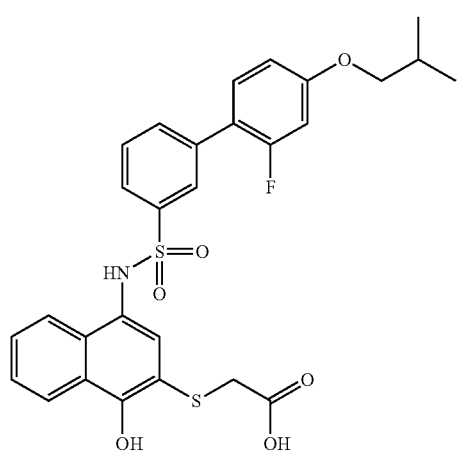
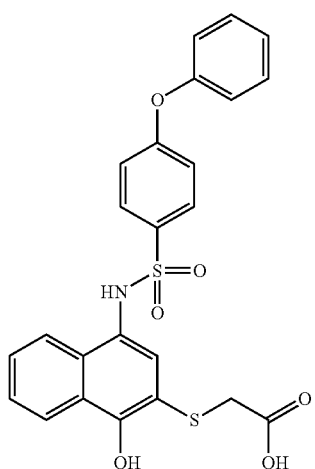
98
-continued
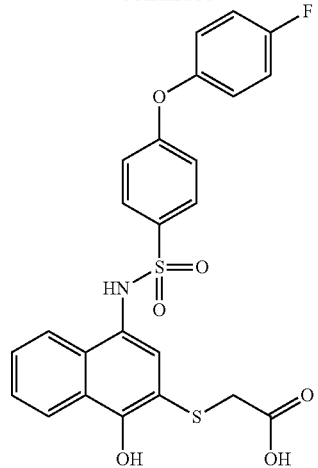
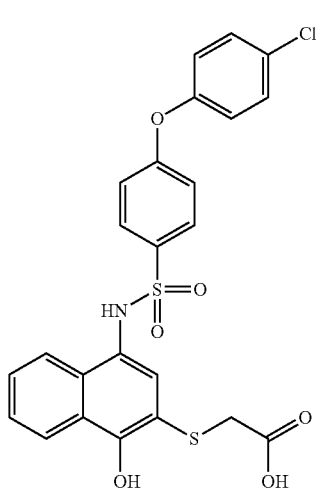
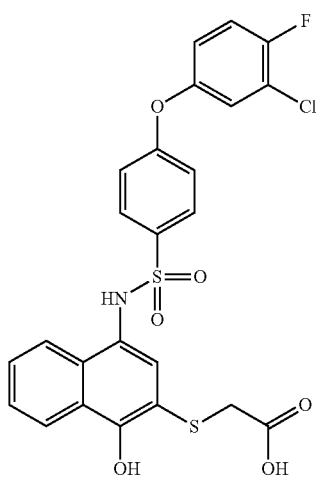

99
-continued
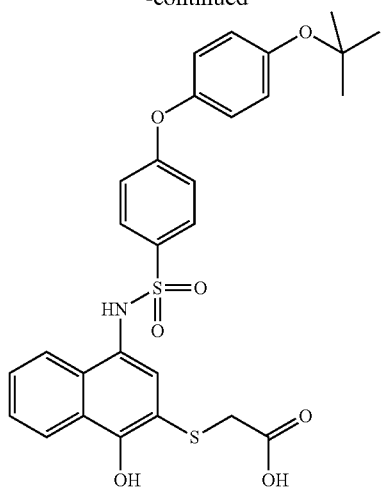
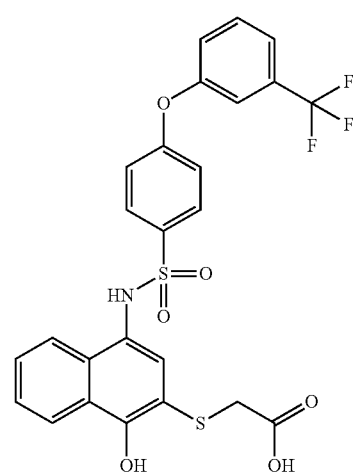
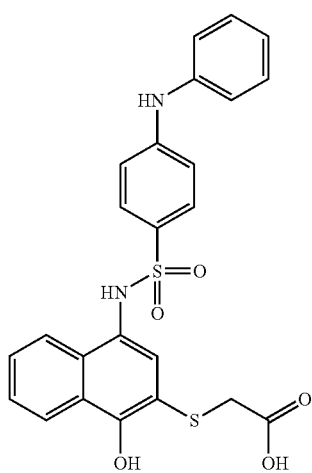
100
-continued
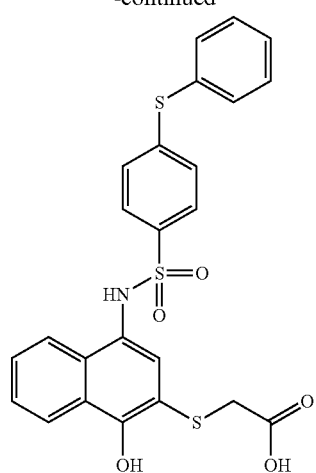
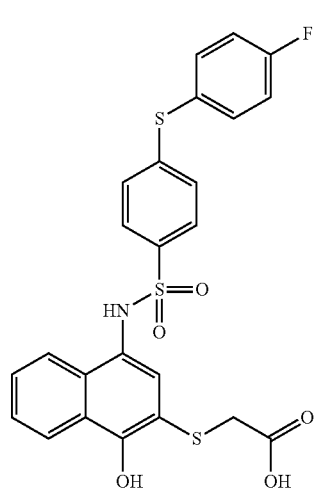
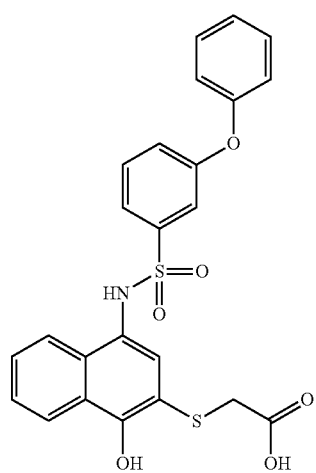

101
-continued
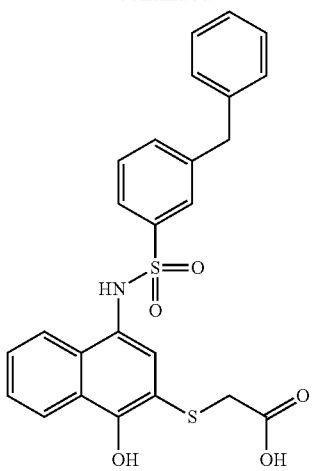
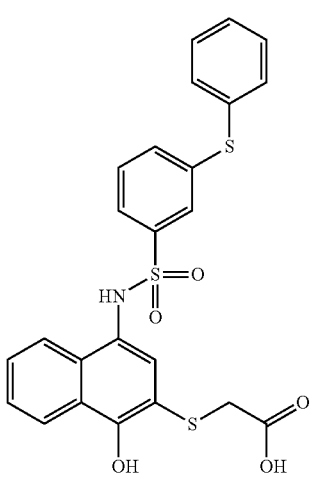
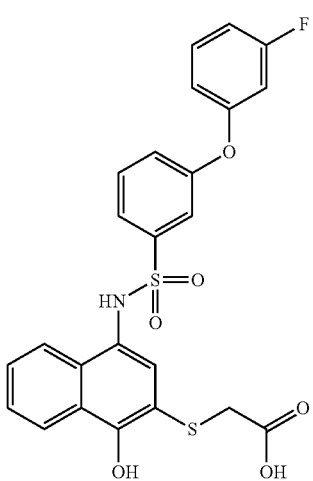
102
-continued
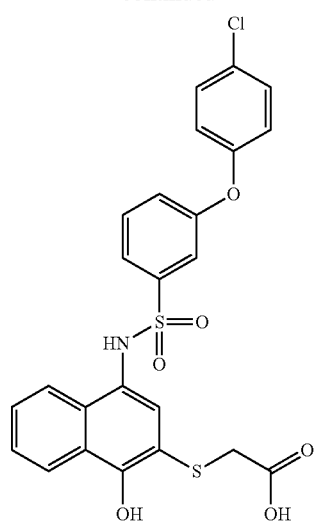
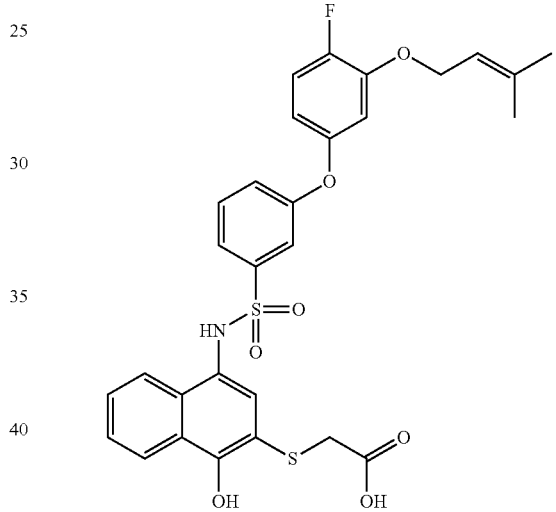
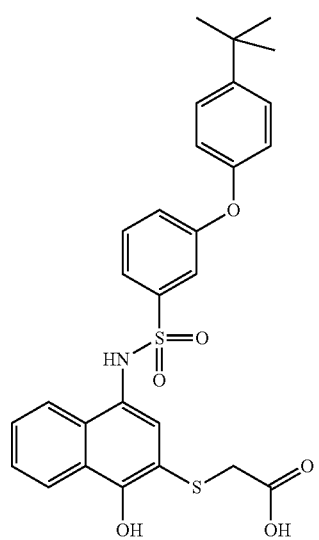

103
-continued
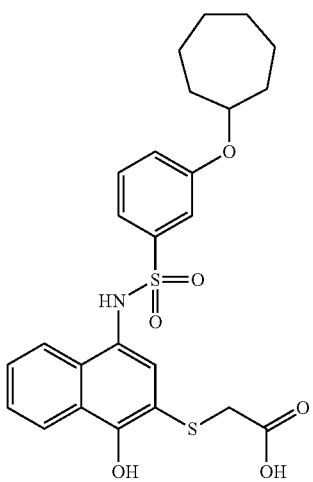
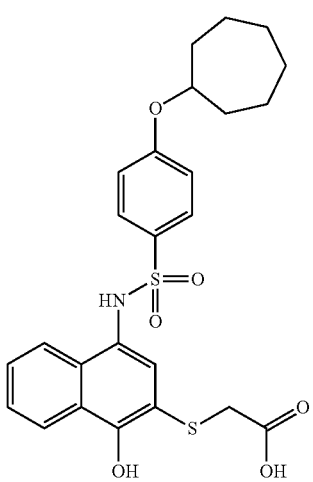
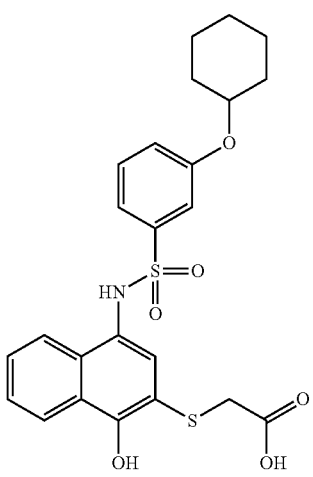
104
-continued
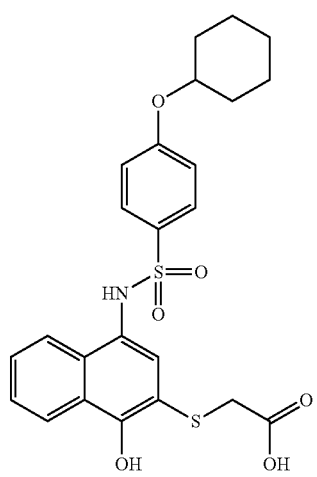
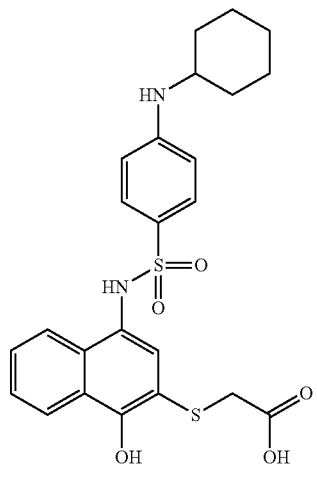
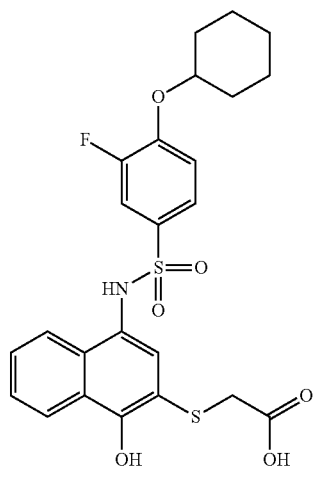

105
-continued
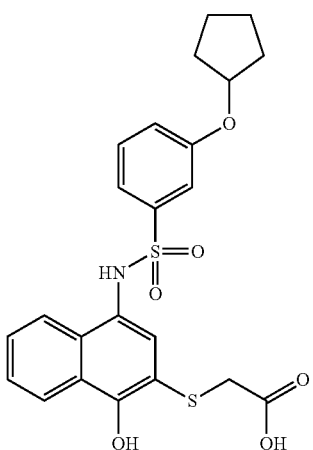
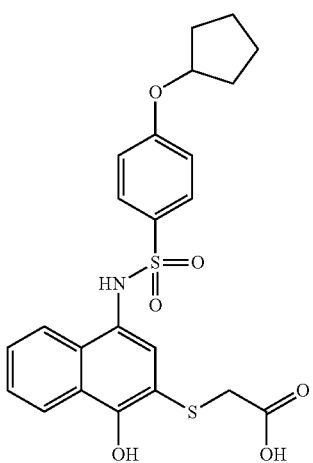
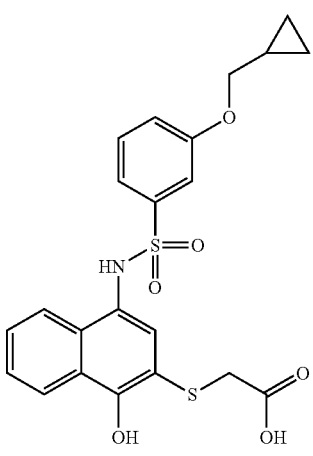
106
-continued
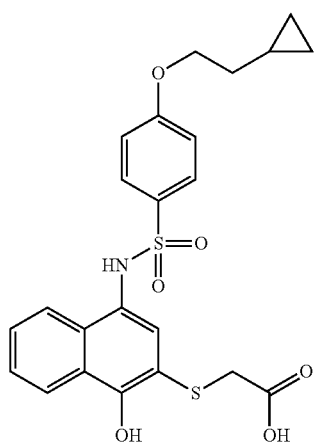
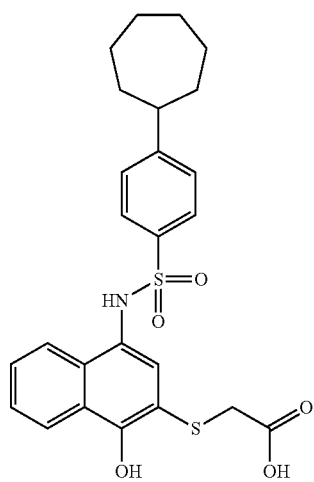
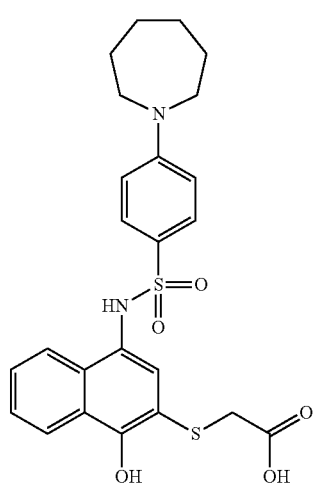

107 -continued
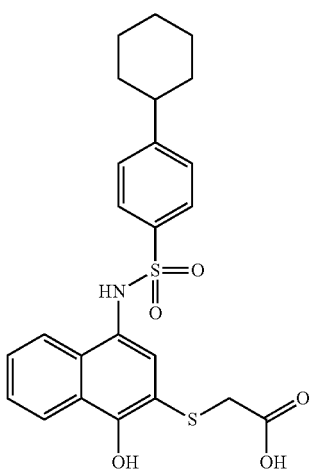
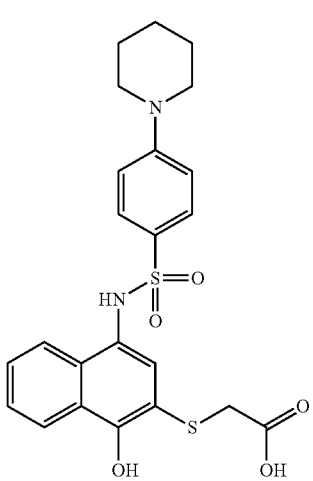
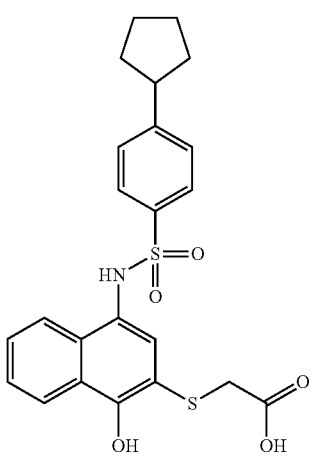
108 -continued
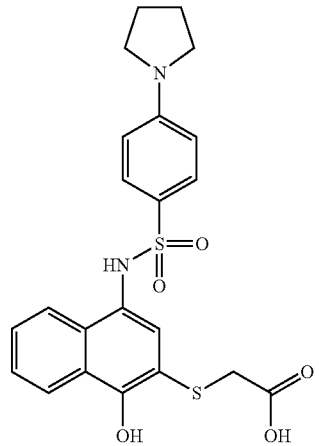
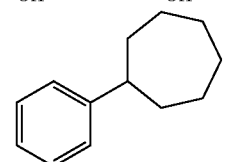
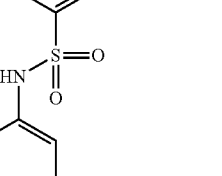
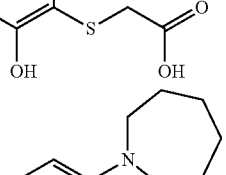
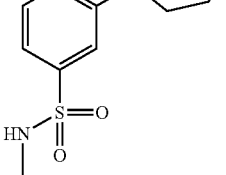
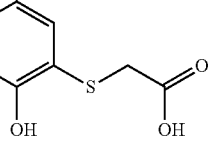

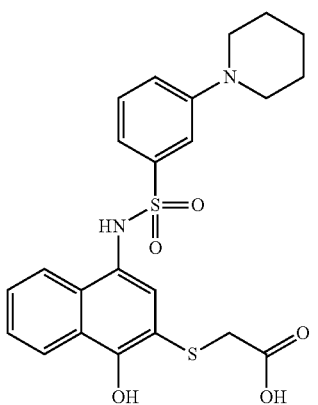
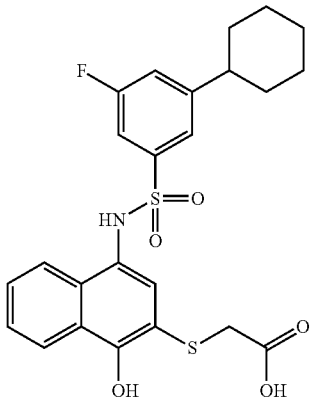
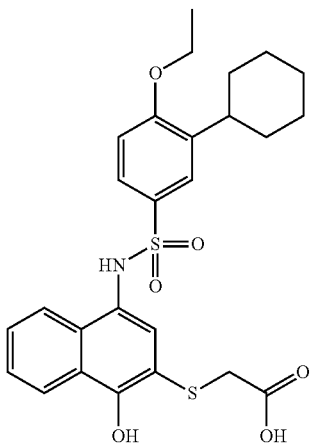
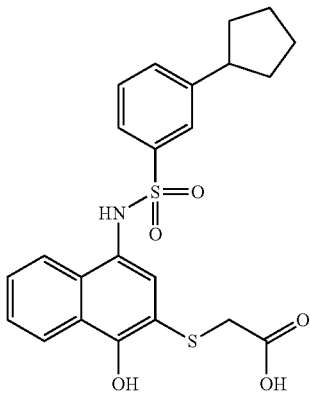
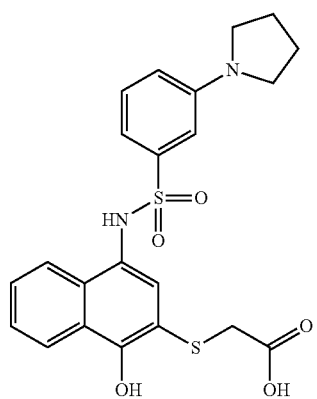
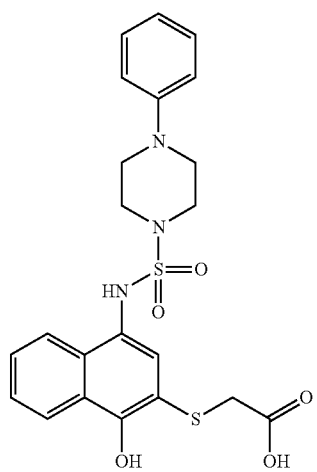
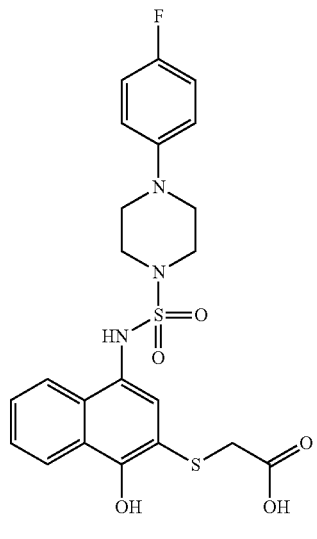

111
-continued
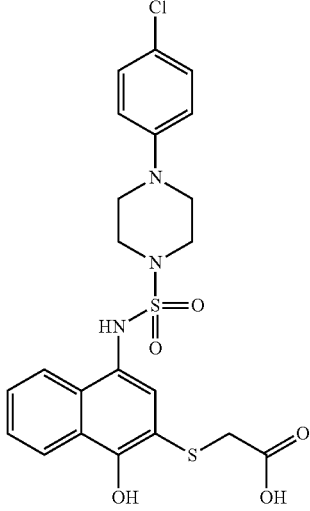
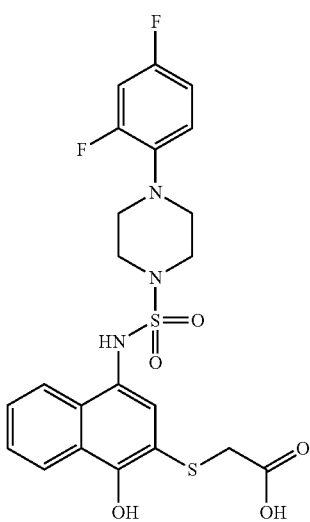
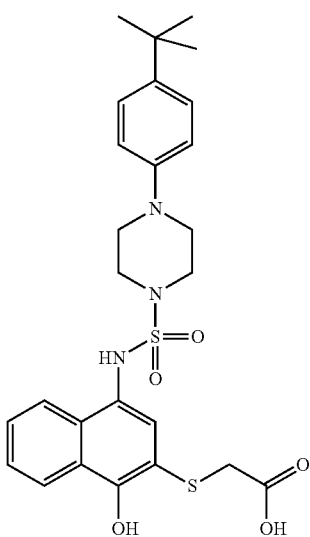
112
-continued
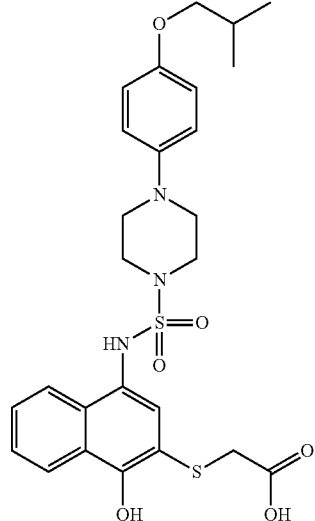
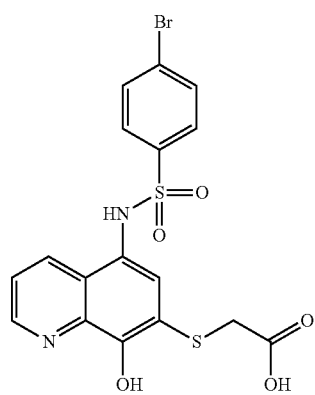

113
-continued
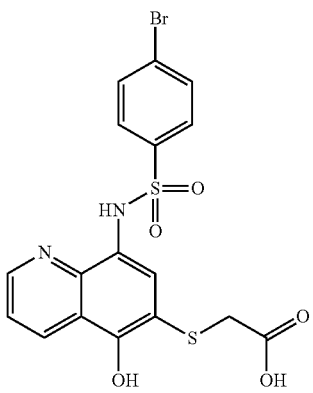
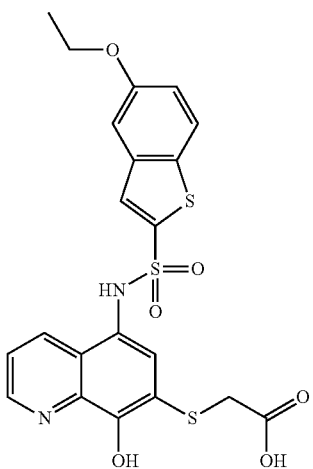
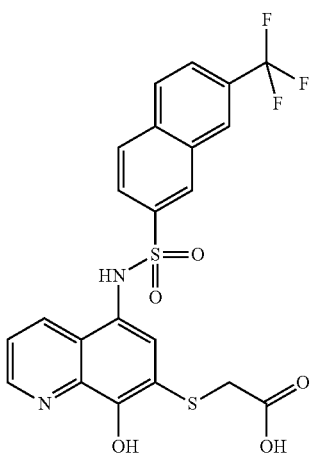
114
-continued
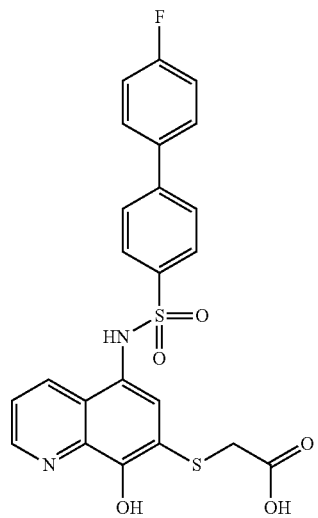
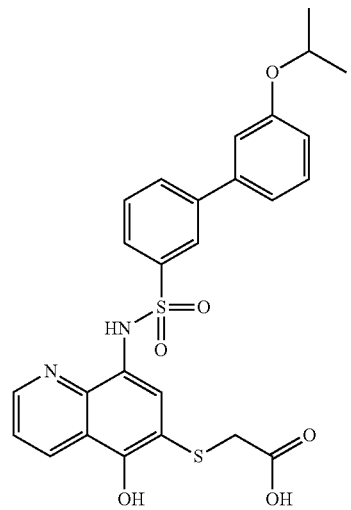
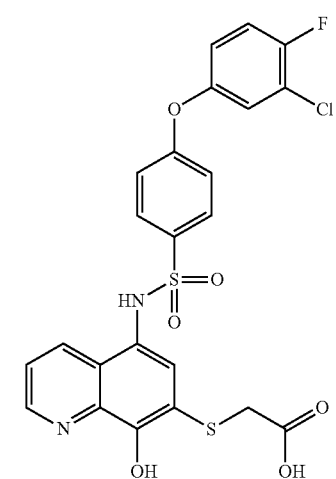

115
-continued
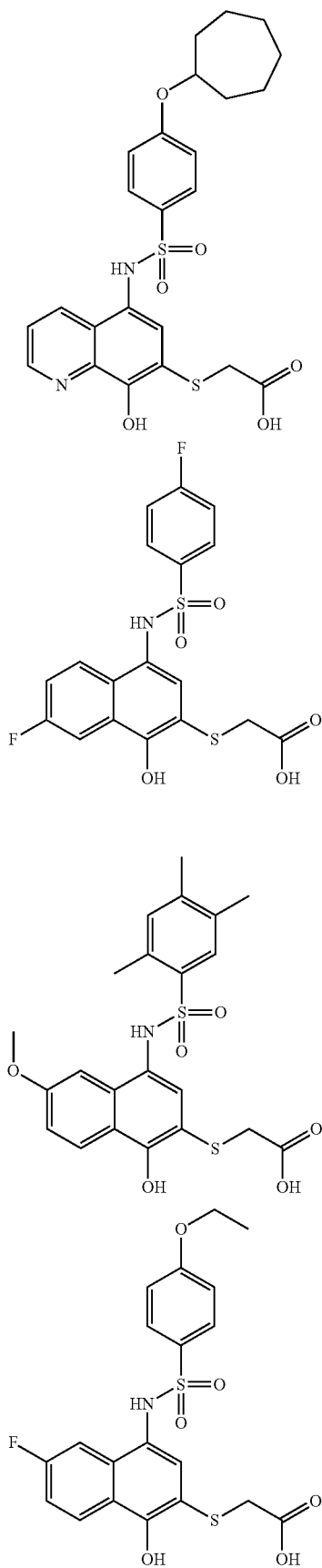
116
-continued
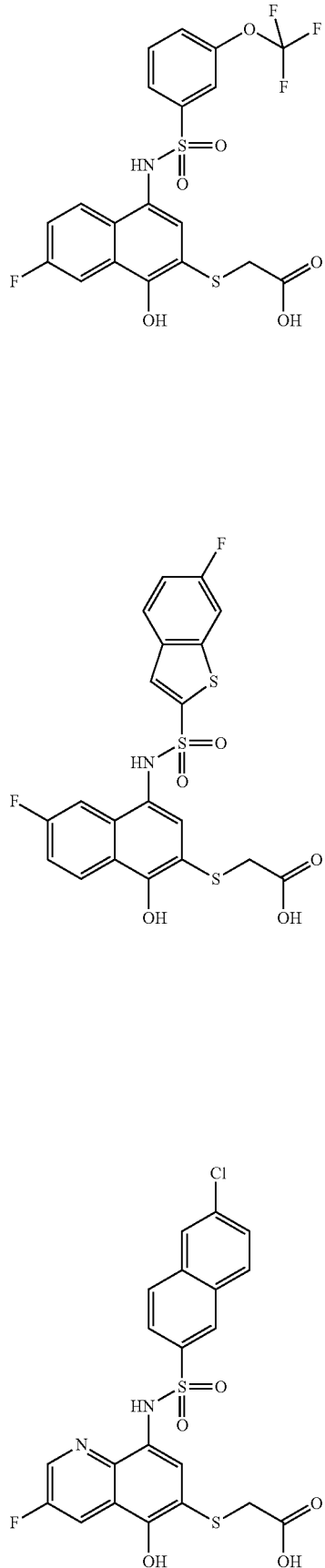

117
-continued
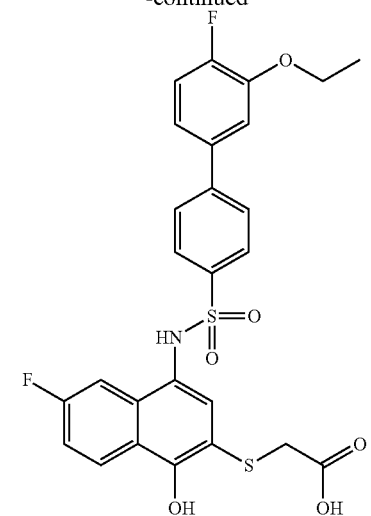
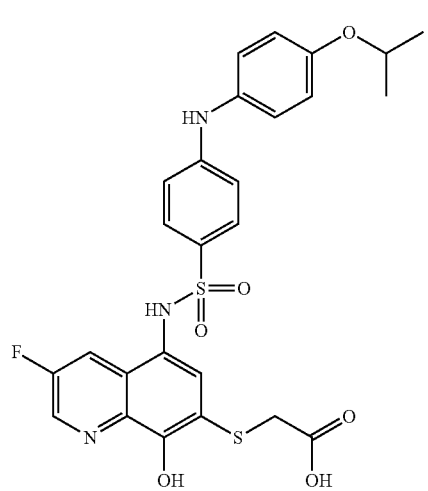
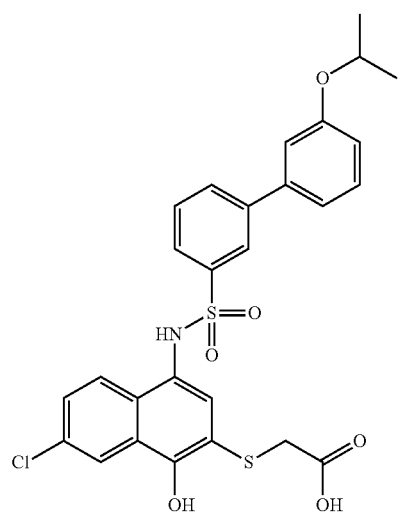
118
-continued
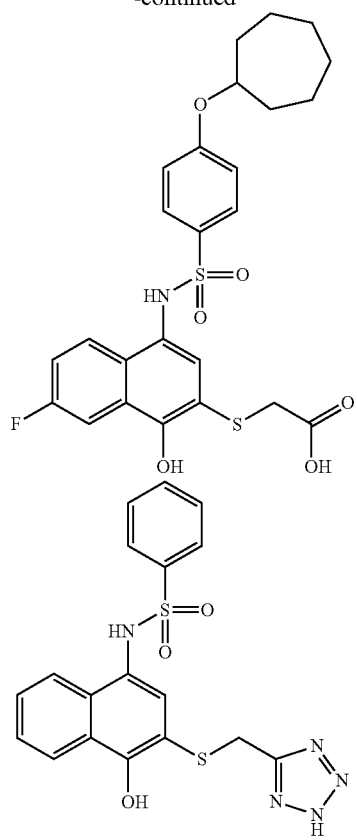
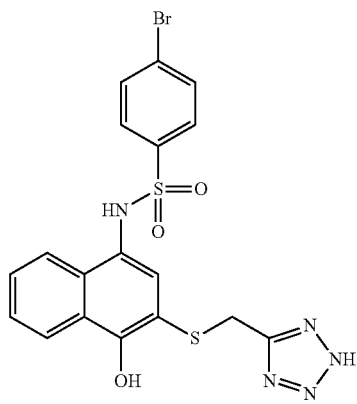
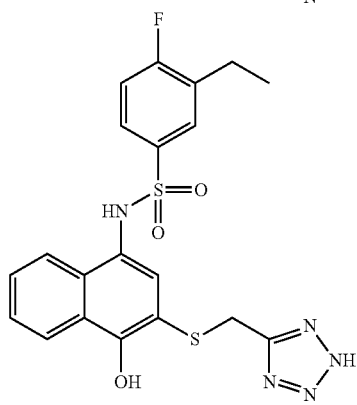

119
-continued
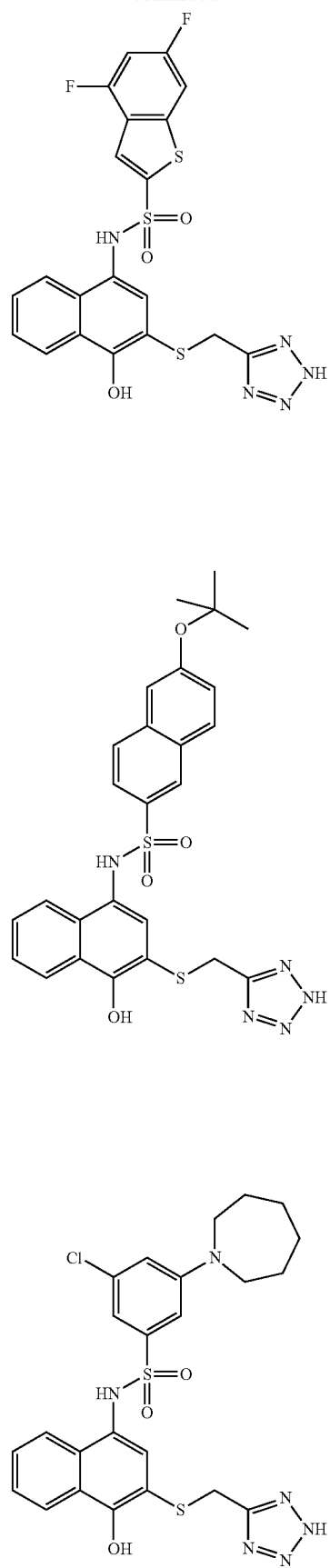
120
-continued
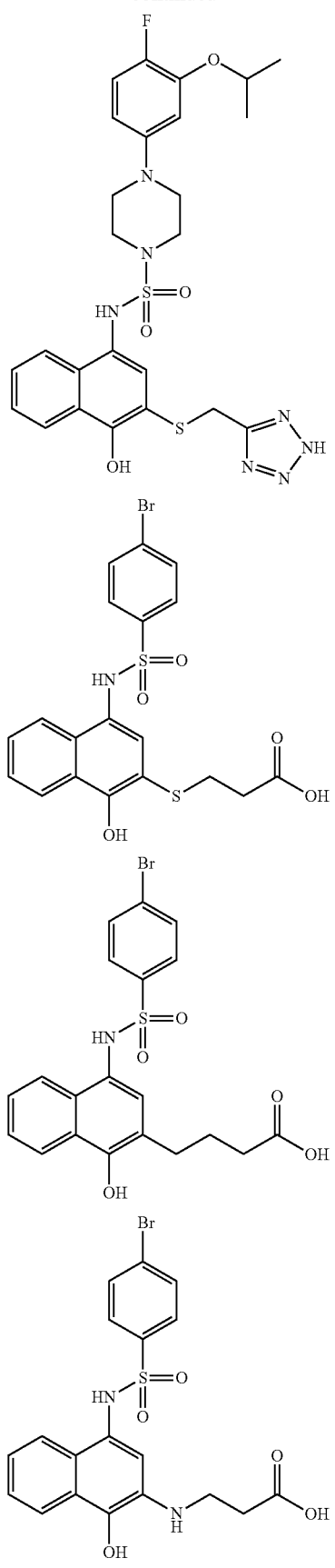

121
-continued
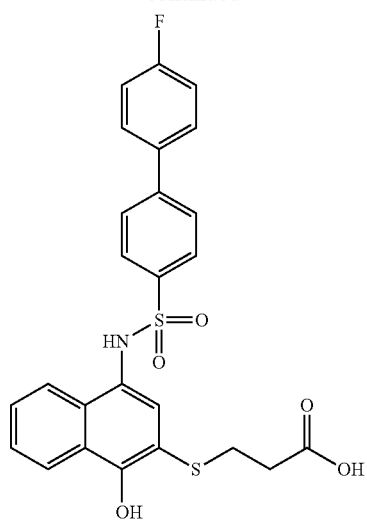
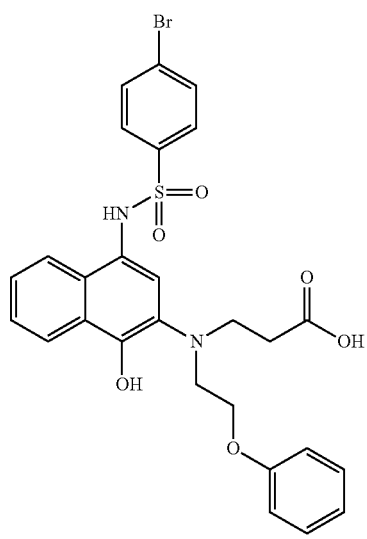
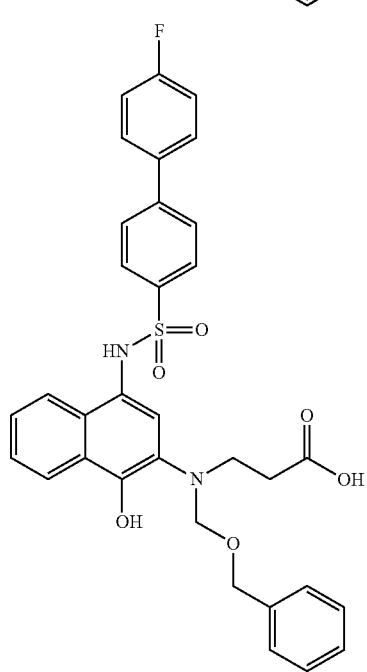
122
-continued
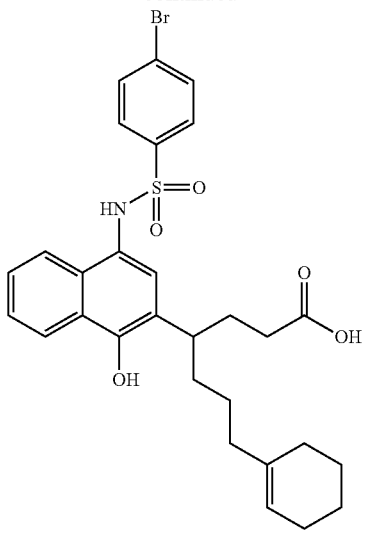
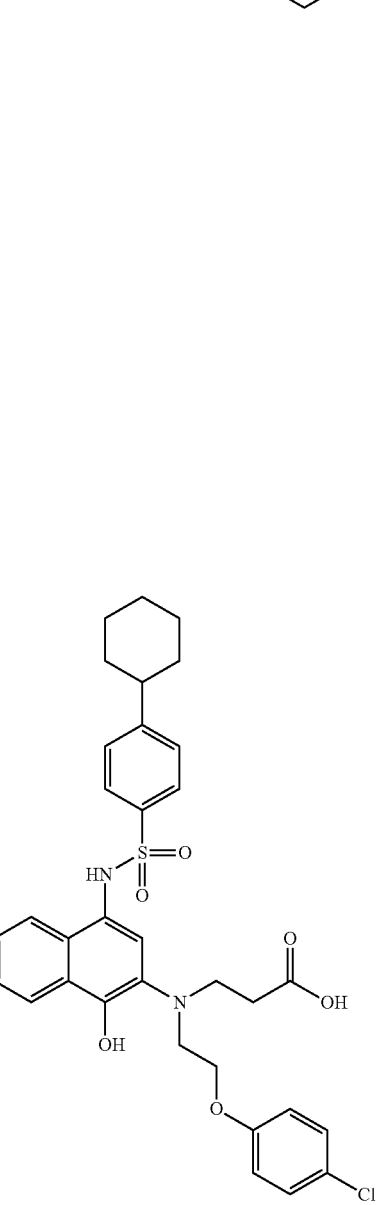

123
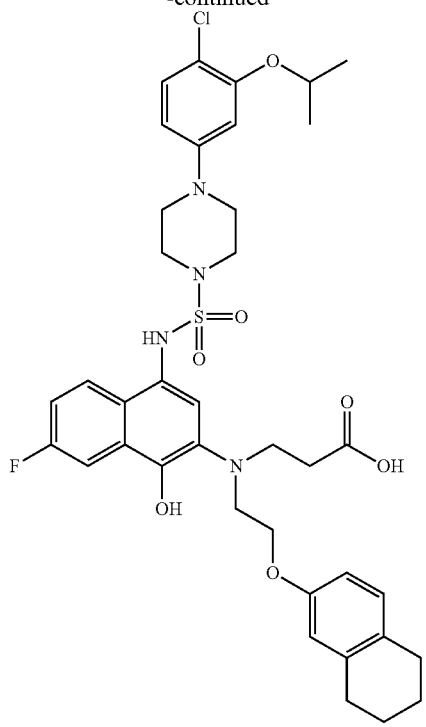
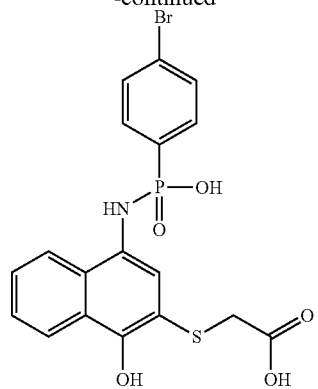
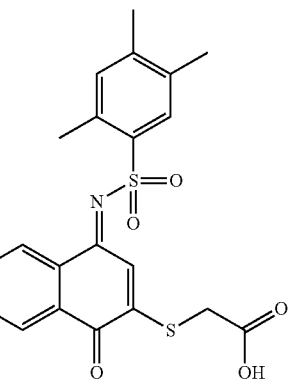
124
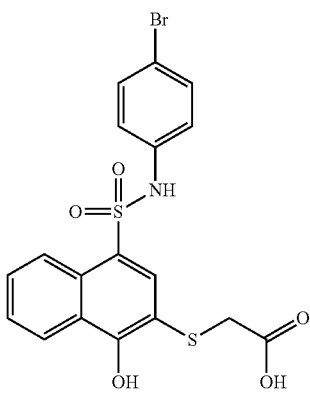
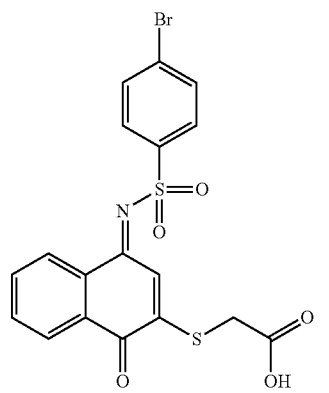
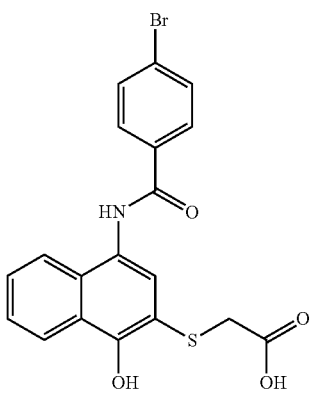
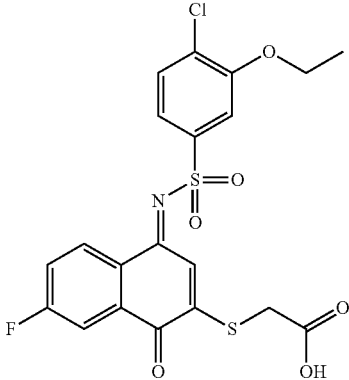

125
-continued
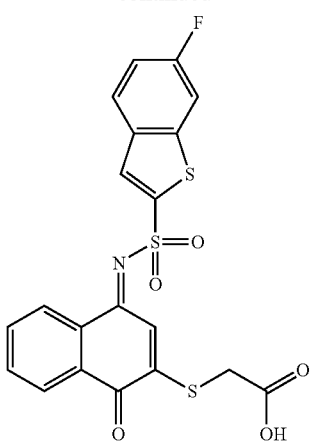
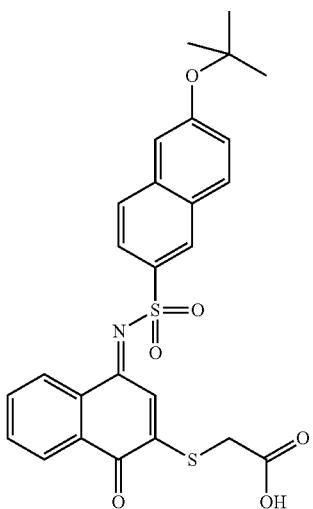
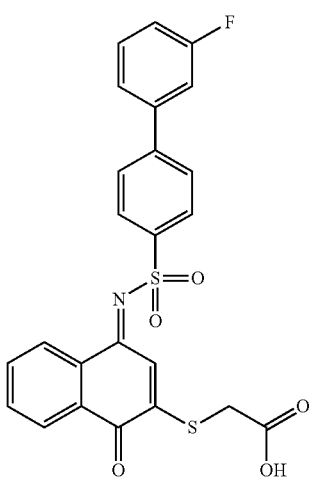
126
-continued
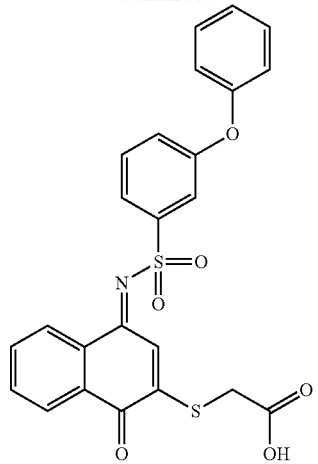
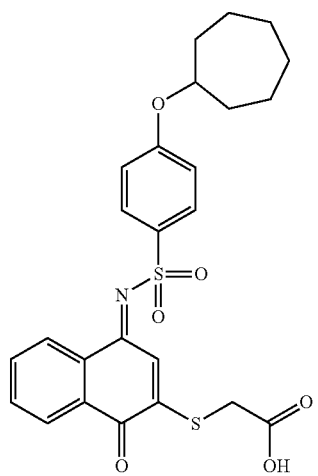
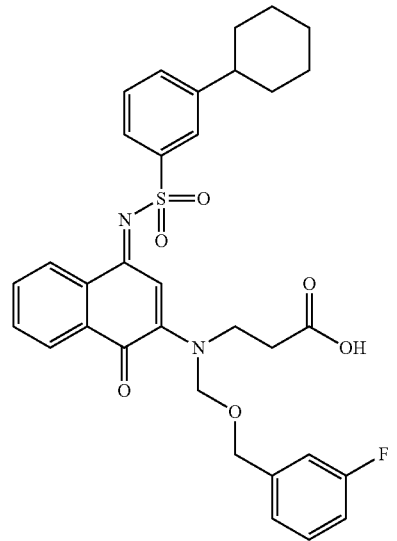

127
-continued
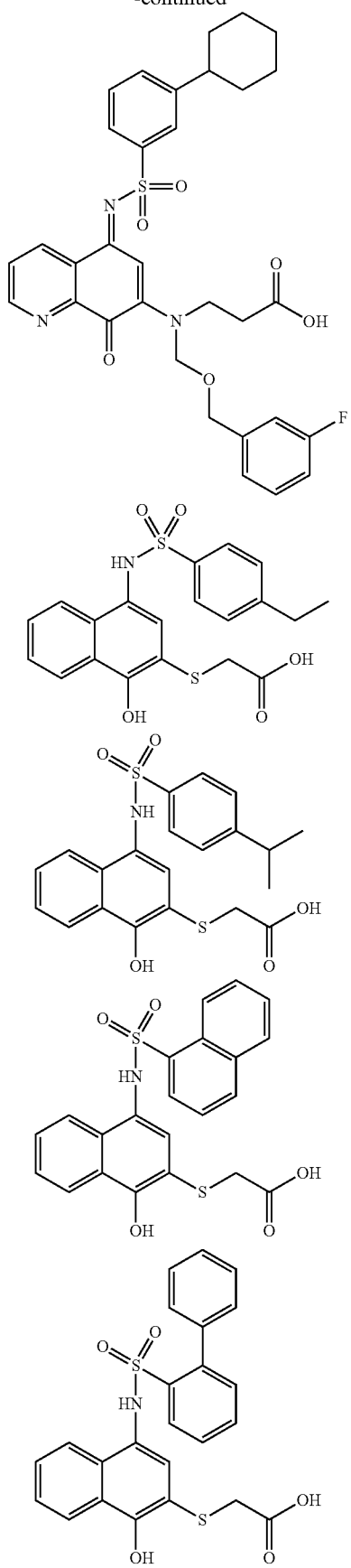
128
-continued
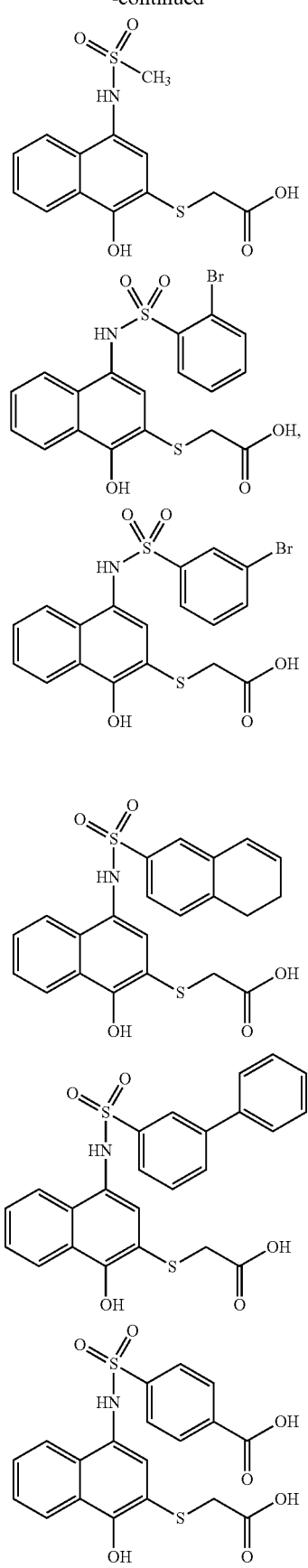

129
-continued
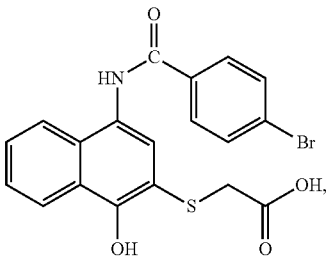
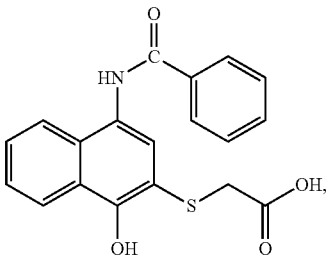
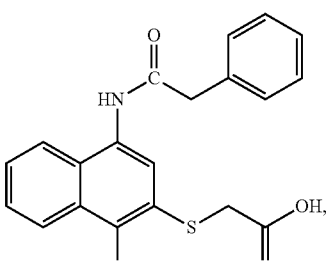
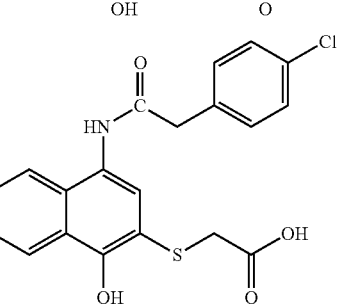
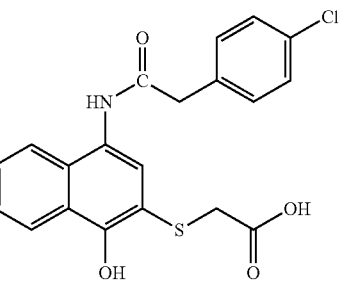
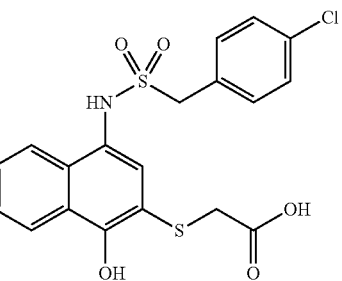
130
-continued
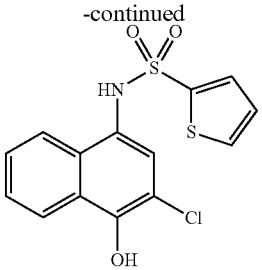
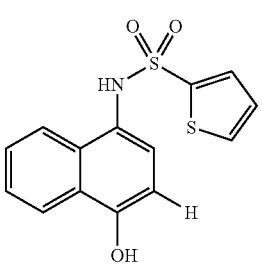
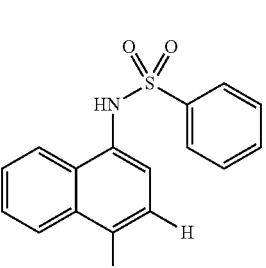
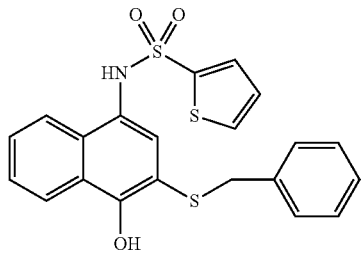
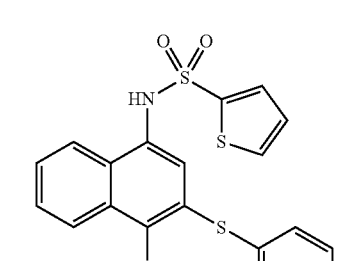
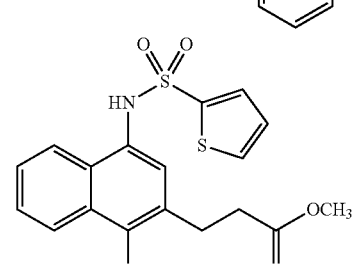

-continued
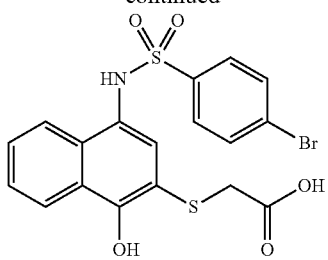
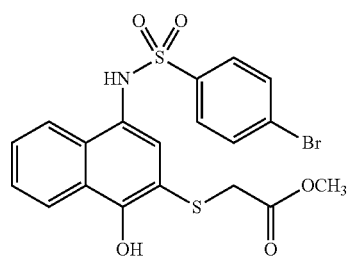
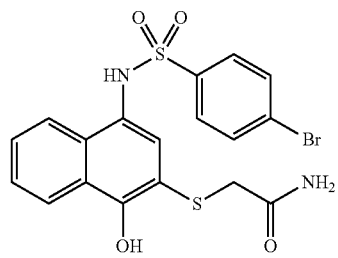
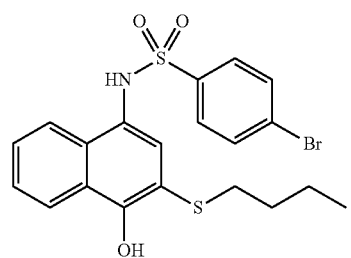
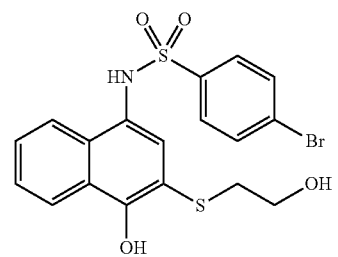
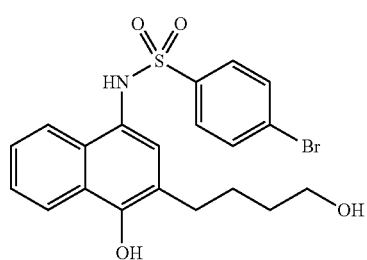
-continued
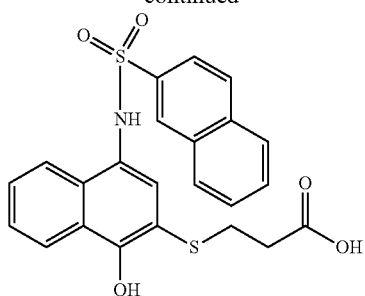
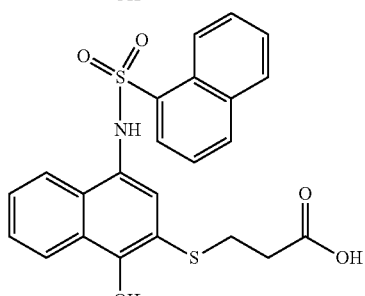
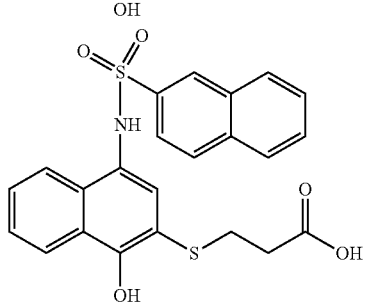
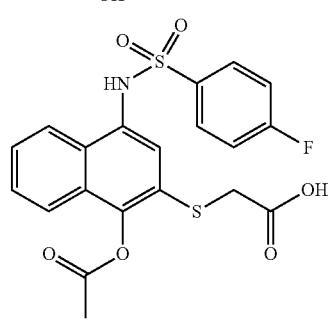
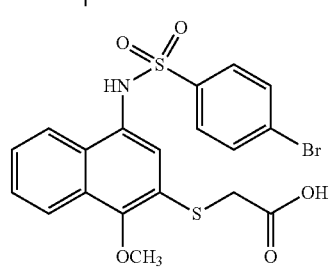
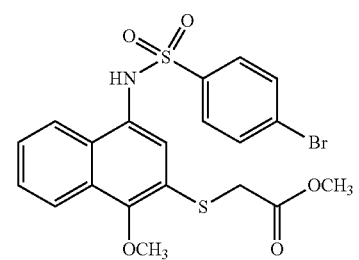

-continued

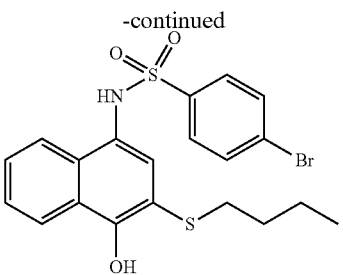

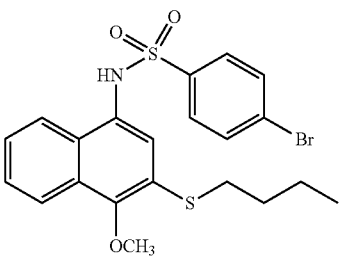

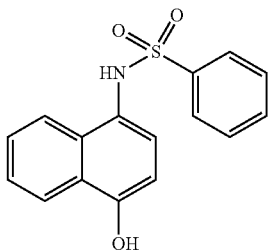

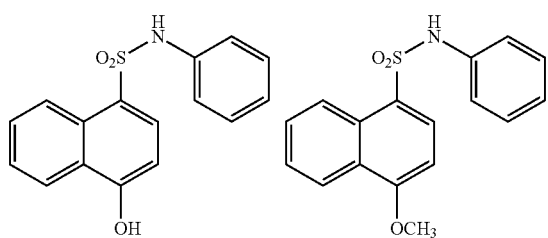

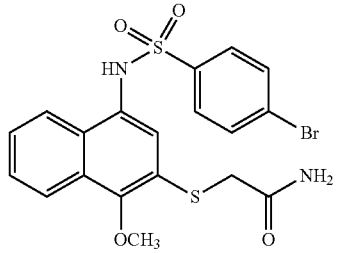

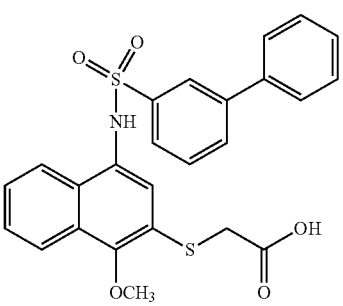

-continued

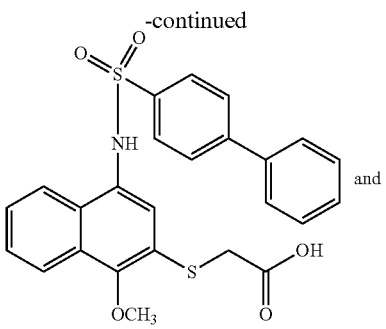

and

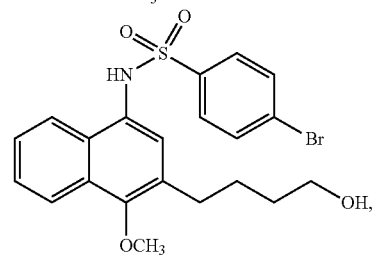

or a pharmaceutically acceptable salt, solvate, or prodrug thereof.

An important aspect of the present invention is that compounds of the invention induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The Mcl-1 inhibitors of the present invention (e.g., sulfonamido-1-hydroxynaphthalen compounds) can be used to induce apoptosis in any disorder that can be treated, ameliorated, or prevented by the induction of apoptosis. In one embodiment, the inhibitors can be used to induce apoptosis in cells comprising functional Mcl-1 and/or Mcl-1-related proteins.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents. In other embodiments, the disorder is any disorder having cells having Mcl-1 protein and/or Mcl-1-related protein expression.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is a anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF—KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTAS ONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol,2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |

TABLE 1-continued

| | | |
|---|---|---|
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |

TABLE 1-continued

| | | |
|---|---|---|
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino[1,2-b]quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \bullet HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |

TABLE 1-continued

| | | |
|---|---|---|
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |

TABLE 1-continued

| | | |
|---|---|---|
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R—(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petroleum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

This example describes the materials and methods for Examples 2-6.
Chemistry Information
Detailed information about the synthesis and characterization of compounds UMI-59 and UMI-77 are provided herein. Compound UMI-101 was purchased from Princeton BioMolecular Research.
Synthesis and Characterization of the Lead Compound UMI-59 and its Analog UMI-77

General: All reactions were performed under anhydrous conditions. Reagents were used as supplied without further purification. Purities of final compounds were assessed by analytical HPLC performed on a Shimadzu system with a Restek Ultra C18 (4.6×150 mm, 5 mm particle size) column and a gradient of acetonitrile with 0.1 vol % TFA (10-90%) in water with 0.1 vol % TFA. Semipreparative HPLC was performed on a Shimadzu system with a Restek Ultra C18 (21.2×150 mm, 5 mm particle size) column NMR spectra were obtained in DMSO-$d_6$ and results were recorded on a Varian 400 instrument. High resolution mass spectrometry (HRMS) analysis was performed on an Agilent Q-TOF system.

UMI-59 and UMI-77 were synthesized as shown in Scheme 1. Commercially available 1-methoxy-4-nitronaphthalene underwent electrophilic aromatic substitution with N-iodosuccinamide (see, e.g., Castanet A-S, Colobert F, Broutin P-E. Mild and regioselective iodination of electron-rich aromatics with N-iodosuccinimide and catalytic trifluoroacetic acid. Tetrahedron Letters. 2002; 43:5047-8; herein incorporated in its entirety) to provide the desired aryl iodide 4. Intermediate 4 was coupled with methyl thioglycolate using optimized palladium-catalyzed conditions (see, e.g., Eichman C C, Stambuli J P Zinc-mediated palladium-catalyzed formation of carbon-sulfur bonds. J Org. Chem. 2009; 74:4005-8; Itoh T, Mase T. A general palladium-catalyzed coupling of aryl bromides/triflates and thiols. Org. Lett. 2004; 6:4587-90; each herein incorporated by reference in its entirety). The nitro group of the intermediate was subsequently reduced to amine using iron powder (see, e.g., Riesgo E C, Jin X, Thummel R P. Introduction of Benzo[h] quinoline and 1,10-Phenanthroline Subunits by Friedlander Methodology. J Org. Chem. 1996; 61:3017-22; herein incorporated by reference in its entirety) and the amine was reacted with 2-thiophenesulfonyl chloride or 4-bromobenezesulfonyl chloride in presence of pyridine to provide the desired sulfonamide intermediates 6 and 7. The last step involved one-pot demethylation/ester hydrolysis using BBr$_3$ followed by mildly acidic workup. The crudes from the last step were purified by either trituration or reverse phase semipreparative HPLC to afford the final compounds UMI-59 and UMI-77.

Scheme 1. Synthetic pathway to prepare UMI-59 (R = thiophene) and UMI-77 (R = 4-Bromophenyl).

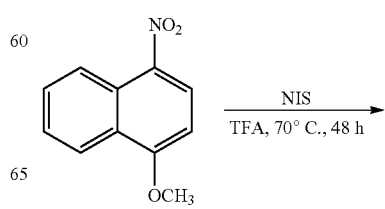

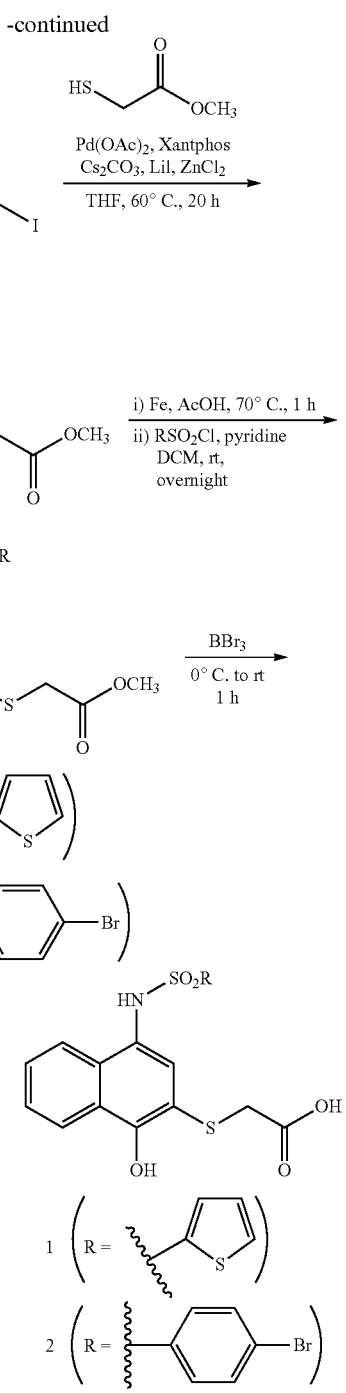

UMI-59: 2-((1-Hydroxy-4-(thiophene-2-sulfonamido)naphthalen-2-yl)thio)acetic acid The crude was purified on a semipreparative HPLC column with CH$_3$CN with 0.1 vol % TFA and H$_2$O with 0.1 vol % TFA as eluents to give 1 (59%) as a white/tan solid. 96% pure by HPLC. $^1$H NMR (400 MHz, DMSO-d$_6$) δ 10.10 (s, 1H), 8.17-8.14 (m, 1H), 7.89-7.84 (m, 2H), 7.52-7.40 (m, 2H), 7.36 (dd, J=1.32, 3.74 Hz, 1H), 7.09 (s, 1H), 7.07 (dd, J=3.74, 4.97 Hz, 1H), 3.56 (s, 2H); $^{13}$C NMR (100 MHz, DMSO-d$_6$) δ 171.54, 152.87, 140.58, 133.57, 132.80, 131.71, 129.80, 128.03, 127.20, 126.22, 125.46, 124.33, 123.61, 122.83, 113.36, 37.25; ESI HRMS: m/z 393.9870 (M−H).

UMI-77: 2-((4-(4-Bromophenylsulfonamido)-1-hydroxynaphthalen-2-yl)thio)acetic acid The crude was purified by trituration with a mixture of CH$_3$CN:H$_2$O 1:1 and cold CH$_2$Cl$_2$ and without a need for HPLC purification to give 2 (45%) as a white solid. 97% pure by HPLC. $^1$H NMR (400 MHz, DMSO-d$_6$) δ 12.80 (s, 1H), 10.05 (s, 1H), 9.87 (s, 1H), 8.14 (d, J=8.17 Hz, 1H), 7.84 (d, J=8.17 Hz, 1H), 7.71 (d, J=8.48 Hz, 2H), 7.54 (d, J=8.48 Hz, 2H), 7.48 (t, J=7.03 Hz, 1H), 7.43 (t, J=7.03 Hz, 1H), 7.04 (s, 1H), 3.53 (s, 2H); $^{13}$C NMR (100 MHz, DMSO-d$_6$) δ 171.52, 152.74, 139.45, 132.56, 131.45, 129.66, 129.28, 127.18, 126.92, 126.27, 125.48, 124.21, 123.63, 122.86, 113.38, 37.10; ESI HRMS: m/z 465.9418 (M−H)$^-$.

Protein Purification

Five recombinant anti-apoptotic Bcl-2 proteins were used in the binding studies: Mcl-1, Bcl-2, Bcl-xL, Bcl-w and A1/Bfl-1. His-tagged proteins containing Mcl-1 (residues 171-327), Bcl-2 (residues 1-202 with inserted Bcl-xL sequence from residues 35 to 50), Bcl-xL (residues 1-209 lacking its C-terminal transmembrane domain with a deletion of the flexible loop region 45-85), Bcl-w (residues 1-155), A1/Bfl-1 (residues 1-151), were expressed from the pHis-TEV vector (a modified pET vector) in E. coli BL21 (DE3) cells. Cells were grown at 37° C. in 2xYT containing antibiotics to an OD$_{600}$ density of 0.6. Protein expression was induced by 0.4 mM IPTG at 37° C. for 4 hours. Cells were lysed in 50 mM Tris pH 8.0 buffer containing 500 mM NaCl, 0.1% bME and 40 µl of Leupectin/Aprotin. All protein were purified from the soluble fraction using Ni-NTA resin (QIAGEN), following the manufacturer's instructions. Mcl-1 was further purified on a Source Q15 column (Amersham Biosciences) in 25 mM Tris pH 8.0 buffer, with NaCl gradient. Bcl-2 and Bcl-xL were purified on a Superdex75 column (Amersham Biosciences) in 25 mM Tris pH 8.0 buffers containing 150 mM NaCl and 2 mM DTT and at −80° C. in presence of 25% Glycerol.

The $^{15}$N labeled Mcl-1 protein for NMR studies was obtained from bacterial cells cultured in M9 medium containing $^{15}$NH$_4$Cl to label the protein uniformly with $^{15}$N and purified using the same protocol as for unlabeled protein.

Fluorescence Polarization (FP) Based Binding Assays

IC$_{50}$ and K$_i$ values of Mcl-1 inhibitors to anti-apoptotic proteins from Bcl-2 family were determined in FP-based competitive binding assays. The K$_i$ values were calculated using the equation described previously (see, e.g., Nikolovska-Coleska Z, Wang R, Fang X, Pan H, Tomita Y, Li P, et al. Development and optimization of a binding assay for the XIAP BIR3 domain using fluorescence polarization. Anal Biochem. 2004; 332:261-73; herein incorporated by reference in its entirety). Determination of the K$_d$ values of fluorescent probes to proteins and details of the competitive binding assays are provided.

Sensitive and quantitative FP-based binding assays were developed and optimized to determine the binding affinities of Bcl-2 family protein inhibitors to the recombinant Mcl-1, A1/Bfl-1, Bcl-w, Bcl-2, and Bcl-xL proteins.

1 Determine K$_d$ Values of Fluorescent Probes to Proteins

Fluorescein tagged BID BH3 (Bcl-2 Homology 3) peptide was used as a fluorescent probe in the FP-based binding assays. One fluorescein tagged BID peptide named as Flu-BID, labeled with fluorescein on the N-terminus of the BH3 peptide (79-99), while the second tracer was purchased from Abgent (Catalog #SP2121a), named as FAM-BID, where the BH3 peptide (80-99) is labeled with 5-FAM. Their $K_d$ values were determined to all members of the Bcl-2 family proteins with a fixed concentration of the tracer (2 nM of Flu-BID and FAM-BID) and different concentrations of the tested proteins, in a final volume of 125 µl in the assay buffer (100 mM potassium phosphate, pH 7.5, 100 µg/ml bovine γ-globulin, 0.02% sodium azide, Invitrogen, with 0.01% Triton X-100 and 4% DMSO). Plates were mixed and incubated at room temperature for 2 hours and the polarization values in millipolarization units (mP) were measured at an excitation wavelength of 485 nm and an emission wavelength of 530 nm. Equilibrium dissociation constants ($K_d$) were calculated by fitting the sigmoidal dose-dependent FP increases as a function of protein concentrations using Graphpad Prism 5.0 software (Graphpad Software). Based upon analysis of the dynamic ranges for the signals and their $K_d$ values, Flu-BID was selected as the tracer in the Mcl-1 and Bcl-2 competitive binding assays, while FAM-BID was selected as the tracer for the rest of the proteins, A1/Bfl-1, Bcl-w and Bcl-xL. The $K_d$ value of Flu-BID to Mcl-1 was 34±3.5 nM, and to Bcl-2 was 20±0.86 nM and the $K_d$ values of FAM-BID to A1/Bfl-1 was 0.83±0.06 nM, to Bcl-w was 5.5±1.6 nM, and to Bcl-xL was 10±4.0 nM respectively, in the saturation experiments.

2 Determine $IC_{50}$ Values of Mcl-1 Inhibitors

Based on the $K_d$ values, the concentrations of the proteins used in the competitive binding experiments were 90 nM for Mcl-1, 40 nM for Bcl-w, 50 nM for Bcl-xL, 60 nM for Bcl-2, and 4 nM for A1/Bfl-1. The fluorescent probes, Flu-BID and FAM-BID were fixed at 2 nM for all assays except for A1/Bfl-1 where FAM-BID was used at 1 nM. 5 µL of the tested compound in DMSO and 120 µL of protein/probe complex in the assay buffer (100 mM potassium phosphate, pH 7.5; 100 µg/ml bovine gamma globulin; 0.02% sodium azide, purchased from Invitrogen, Life Technologies) were added to assay plates (Microfluor 2Black, Thermo Scientific), incubated at room temperature for 3 h and the polarization values (mP) were measured at an excitation wavelength at 485 nm and an emission wavelength at 530 nm using the plate reader Synergy H1 Hybrid, BioTek. $IC_{50}$ values were determined by nonlinear regression fitting of the competition curves (GraphPad Software).

Surface Plasmon Resonance (SPR) Binding Assays

SPR experiments were performed using Biacore 2000 optical biosensors. Recombinant Bax, residues 1 to 100 (Novus Biologicals) and Mcl-1 proteins were used for competitive solution binding experiments. The details for immobilization of Bax protein, determination of the binding affinity of Mcl-1 to Bax, and conditions for testing Mcl-1 compounds are provided.

Recombinant Bax protein (residues 1-100) purchased from Novus Biologicals, Inc., was immobilized on a CM-5 sensor chip at different densities using standard EDC/NHS coupling chemistry followed by ethanolamine deactivation of the surfaces. The Fc1 surface was used as a control surface and was treated in the same manner as the Fc2 and Fc3 surfaces but in the absence of Bax. The binding affinity of recombinant Mcl-1 to immobilized Bax was determined by injecting Mcl-1 protein in concentration from 30 to 1,000 nM in HBS-EP buffer (10 mM HEPES pH 7.4, 150 mM NaCl, 3 mM EDTA, 0.005% v/v P20). Determination of $k_{on}$, $k_{off}$ and $K_d$ were calculated by simultaneous non-linear regression using BIAEvaluation software.

Using the same Bax immobilized CM5 chip, SPR competitive solution binding experiments were performed by pre-incubated Mcl-1 protein (300 nM) with tested small-molecule inhibitors for at least 30 minutes and then the reaction mixture was injected over the surfaces of the chip. Response units were measured at 60 seconds in the dissociation phase and the specific binding was calculated by subtracting the control surface (Fc1) signal from the surfaces with immobilized Bax. For maximum signal-to-noise ratio, the surface with the highest density of immobilized Bax protein was used for $IC_{50}$ determinations. $IC_{50}$ values were determined by non-linear least squares analysis using Graph Pad Prism 5.0 software.

Induced Fit Docking (IFD)

Crystal structure of Mcl-1 with mouse Noxa BH3 peptide (PDB entry 2NLA) was used to model the binding pose of 2 (UMI-77) with Mcl-1 (see, e.g., Czabotar P E, Lee E F, van Delft M F, Day C L, Smith B J, Huang D C, et al. Structural insights into the degradation of Mcl-1 induced by BH3 domains. Proc Natl Acad Sci USA. 2007; 104:6217-22; herein incorporated by reference in its entirety). Considering the significant degree of flexibility and adaptivity of the anti-apoptotic Bcl-2 family proteins (see, e.g., Arkin M R, Wells J A. Small-molecule inhibitors of protein-protein interactions: progressing towards the dream. Nat Rev Drug Discov. 2004; 3:301-17; herein incorporated by reference in its entirety), the Schrödinger's IFD protocol (see, e.g., Schrödinger Suite 2010 Induced Fit Docking protocol; Glide version 5.6, Schrödinger, LLC, New York, N.Y., 2009; Prime version 2.2, Schrödinger, LLC, New York, N.Y. 2010; herein incorporated by reference in its entirety) was employed for the docking studies. The docking pose was further refined with MC/SD, a molecular dynamic simulation program of Schrödinger's MacroModel (see, e.g., Macromodel 9.8, Schrodinger, LLC, New York, N.Y. 2010; herein incorporated by reference in its entirety).

Schrödinger's IFD predicts ligand binding modes and concomitant structural changes in the protein by combining Glide (the docking program of Schrödinger) and the refinement module in Prime (the protein structure prediction program of Schrödinger). Its main application is to generate an accurate complex structure for a ligand known to be active but that cannot be docked in a rigid structure of the receptor. IFD was used in the experiments conducted during the course of developing embodiments for the present invention because it incorporates the protein flexibility as well as the ligand flexibility, which is important for accurate docking, especially when the protein is too flexible. The protocol that was used for IFD studies is consisted of the following steps: (1) Constrained minimization of the protein with an RMSD cutoff of 0.18 Å. (2) Initial Glide docking of the ligand using a softened potential (Van der Waals radii scaling). (3) One round of Prime side-chain prediction for each protein/ligand complex, on residues within defined distance of any ligand pose. (4) Prime minimization of the same set of residues and the ligand for each protein/ligand complex pose. (5) Glide re-docking of each protein/ligand complex structure within a specified energy of the lowest energy structure. (6) Estimation of the binding energy (IFD-Score) for each output pose. In the experiments conducted, all docking calculations were run in the extra precision (XP) mode of Glide. The center of the grid box of the Mcl-1 was defined by the Val 249 (in h1), Phe 270 (in h2), Val 220 (in h3/h4) and Val 216 (in h4). The size of the grid box was set to 15 Å. Default values were used for all other parameters.

Schrödinger's MC/SD dynamic simulation performs constant temperature calculations that take advantage of the strengths of Monte Carlo methods for quickly introducing large changes in a few degree of freedom, and stochastic dynamics for its effective local sampling of collective motions. The MC/SD dynamic simulation time in the study was set to 100 ps by allowing movement of the docked ligand and the residues which is less than 6 Å to the ligand. The force field used was set to OPLS_2001. Default values were used for all other parameters.

Biotin-Streptavidin Pull-Down Experiment

Human breast cancer 2LMP cells, a subclone of the MDA-MB-231 cell line, were lysed in CHAPS buffer (10 mM HEPES (pH 7.4), 2.5 mM EDTA, 150 mM NaCl, 1.0% CHAP). Pre-cleared cell lysates were incubated with different concentrations of tested compounds, followed by incubation with biotinylated Noxa BH3 peptide (residues 18-43) and streptavidin-agarose beads to pull-down Mcl-1 protein bound to Noxa peptide. Beads were washed with CHAPS buffer, and Mcl-1 protein was eluted by boiling in SDS-PAGE sample buffer and analyzed by Western blotting using Mcl-1 antibody (Santa Cruz). DMSO alone was used as a control for nonspecific pull-down.

Cells and Growth Inhibition

Human PC cell lines AsPC-1, BxPC-3 and Capan-2 were cultured in RPMI 1640 medium, while Panc-1 and MiaPaCa were cultured in DMEM medium (Life Technologies), all supplemented with 10% fetal bovine serum (Thermo Scientific HyClone). The rate of cell growth inhibition after treatment with increasing concentrations of the tested compounds was determined by WST-8 assay as described in the manufacturers protocol (Dojindo Molecular Technologies Inc.).

Quantification of Apoptosis

An Annexin-V-FLUOS/Propidium iodide staining kit and ELISA detection kit (Roche Applied Science) were used to detect apoptosis in PC cells. Cells were treated with Mcl-1 inhibitors for different time points, harvested, washed with PBS and apoptosis was quantified according to manufacturer's protocol.

Immunofluorescence Microscopy

Cells ($3-4 \times 10^5$) were seeded on glass coverslips in six-well cell culture dishes and allowed to attach overnight, and then treated with UMI-77 for 24 hours. Cells mounted on glass slides were permeabilized with PBS containing 0.3% Triton X-100, and blocked with 1% bovine serum albumin in PBS for 30 min at room temperature, followed with overnight incubation with anti-Bak 6A7 (Calbiochem) at 4° C. After thorough washing of the sections in PBS, a secondary antibody labeled with DyLight 488 (Thermo Scientific) was added and incubated for 2 h at room temperature. Nuclei were visualized with DAPI. Samples were analyzed with a FluoView 500 Confocal Laser Scanning Microscope (Olympus).

RNA Interference

Human PC cells were transfected with Mcl-1 siRNA and control siRNA respectively (both from Santa Cruz), using Lipofectamine 2000 as described in the manufacturers protocol (Cell Signaling).

Western Blot Analysis

The cells were treated and harvested at the indicated time points after treatment. Total cell lysates were subjected to electrophoresis onto SDS-containing 4-20% polyacrylamide gels (Invitrogen), and transferred to polyvinylidene difluoride (PVDF) membranes (Thermo Scientific). Following blocking in 5% milk, membranes were incubated with a specific primary antibody, washed, and incubated with horseradish peroxidase linked secondary antibody (Santa Cruz). The signals were visualized with the chemiluminescent horseradish peroxidase antibody detection reagent (Roche Molecular Biochemicals). Primary antibodies included: caspase-3 (Enzo Life Sciences), Mcl-1 and actin (Santa Cruz), Bcl-xL (BD Transduction Laboratories); Bcl-2, Bax, pro-PARP and cytochrome-c (Cell Signaling), Bak (Calbiochem), and Smac (Abgent).

Immunoprecipitation

Cell lysate (500 µg) were subjected to immunoprecipitation by adding 2.5-5 µg of anti-Mcl-1 antibody and incubation overnight at 4° C. After adding 30 µl of Protein G-agarose (Immunoprecipitation Kit, Sigma) and incubation for 4 h, the samples were centrifuged. The agarose pellet was then washed 7 times, resuspended in Laemmli buffer (Santa Cruz), and boiled for 5 min. Boiled samples were centrifuged, and supernatant was used for Western blot analysis.

Metabolic Stability Assay

Metabolic stability of UMI-77 was determined using the pooled mice liver microsomes (XenoTech, LLC). The conditions of the assay and quantification of UMI-77 in different time points are provided.

The β-NADPH (Sigma-Aldrich) was dissolved in 0.1 M phosphate buffer containing 3.3 mM $MgCl_2$ right before use. The pooled mice liver microsomes (XenoTech, LLC) were diluted with 0.1 M phosphate buffer containing 3.3 mM $MgCl_2$, followed by adding the reduced β-NADPH solution. After initiating the enzymes by adding β-NADPH, the mixture was incubated at 37° C. for 30 mM The tested compound UMI-77 was added into the mixture and incubated at 37° C. The final concentrations of the compound, microsomes, β-NADPH, phosphate buffer and $MgCl_2$ were 1 µM, 1.2 mg/ml, 1 mM, 0.1 M, and 3.3 mM, respectively. An aliquot of 40 µl of mixture was collected at 0, 5, 10, 15, 30, 45 and 60 min and the reaction was stopped immediately by adding 120 µl of ice-cold acetonitrile containing an internal standard (100 mg/mL). The incubation solution was centrifuged at 14000 rpm for 5 minutes to precipitate protein. The UMI-77 concentration was determined by LC/MS/MS (Agilent 1200 HPLC system, Agilent Technologies and QTRAP 3200 mass spectrometer, Applied Biosystems/MDS Sciex). UMI-77 was detected under negative ionization mode and the multiple reaction monitoring (MRM) ion transition was m/z 468.1→221.0.

Animal Preclinical Efficacy Trail Design

For BxPC-3 subcutaneous model, $10 \times 10^6$ cells were subcutaneously injected into the flanks of 4-5 week old female severe combined immune deficient mice (ICR-SCID) (Taconic Farms) using 26 G ½ Precision Glide needles (Becton Dickinson). Palpable tumors started to appear in 3-5 weeks (see, e.g., Banerjee S, Kaseb A O, Wang Z, Kong D, Mohammad M, Padhye S, et al. Antitumor activity of gemcitabine and oxaliplatin is augmented by thymoquinone in pancreatic cancer. Cancer Res. 2009; 69:5575-83; herein incorporated by reference in its entirety). Tumors were measured twice weekly using a caliper and expressed in mg. To prevent any pain or discomfort, mice were euthanized and their tumors removed once they reached ~1800 mg burden. Tumors were then dissected into 50 mg pieces and re-transplanted into naïve ICR-SCID for serial propagation. Animals were treated with either vehicle or UMI-77 given i.v. (60 mg/kg) on day three post BxPC-3 transplantation for two weeks (5 days a week). Tumor weight was recorded throughout the treatment period using previously described methods. At the end of the treatment period, animals were euthanized and their tumors harvested for protein isolation and western blot analysis for apoptotic markers such as Bax, Bak, survivin and Mcl-1.

Statistical Analysis

Statistics was evaluated using GraphPad StatMate software (GraphPad Software, Inc.). Comparisons were made between control and treated groups and transfections. P<0.05 or P<0.01 was used to indicate statistical significance.

Example 2

This example shows that compound UMI-77 selectively binds Mcl-1 and blocks interactions between pro-apoptotic BH3 peptides and proteins.

Applying a HTS approach a library of 53,000 synthetic small molecules available at the Center for Chemical Genomics, University of Michigan, were screened using a FP based binding assay. Several lead compounds as Mcl-1 inhibitors were identified and extensively characterized using biochemical, biophysical, functional and cell based assays. Compound UMI-59 (FIG. 1A) is one of the validated hits, which was re-synthesized, confirmed its binding affinity to Mcl-1 protein and initiated further chemical modification and development of novel analogs (Scheme 1). Experiments conducted during the course of developing embodiments for the present invention present compound UMI-77, an analog of the lead compound UMI-59 with improved binding affinity to Mcl-1.

Figure 1:
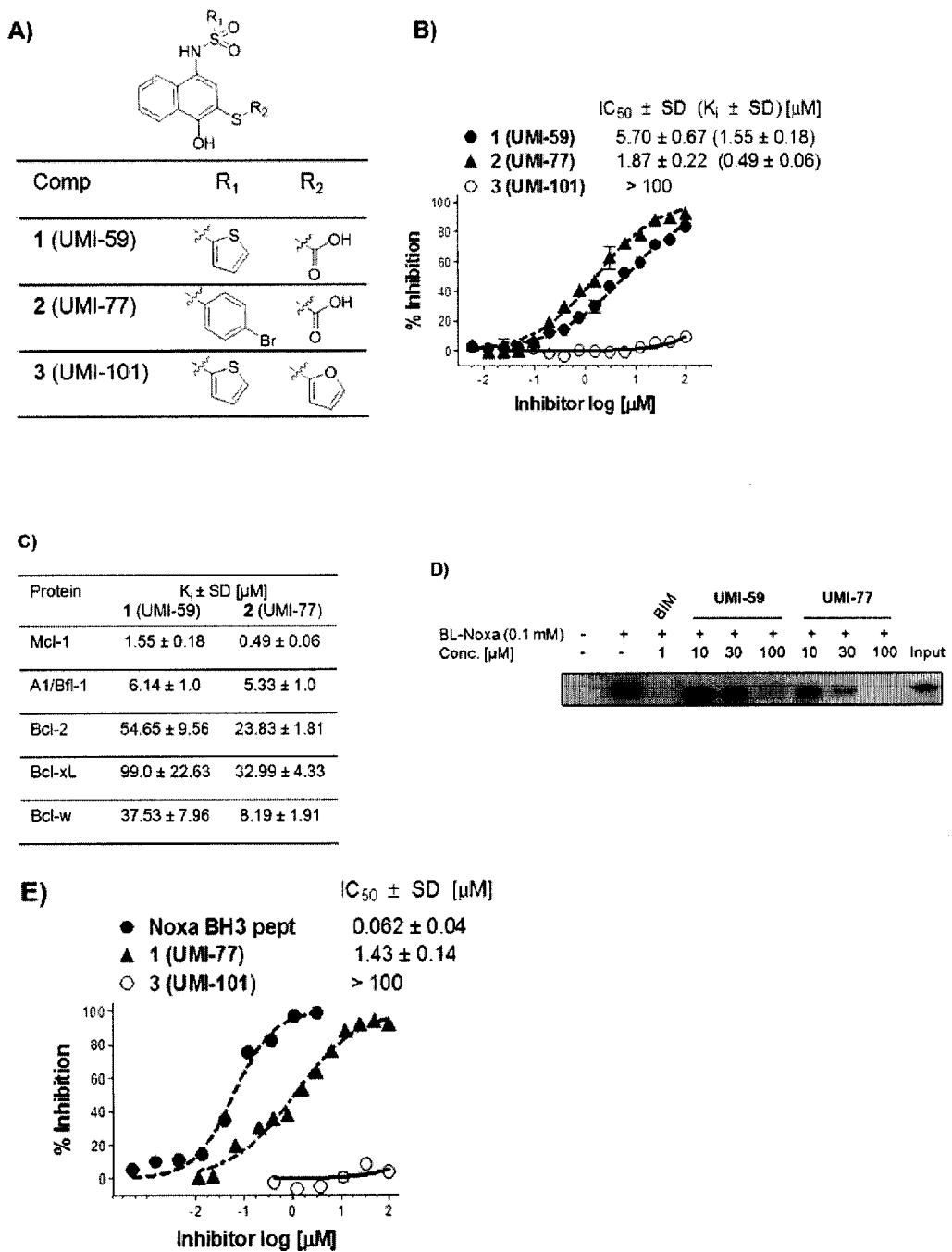
FIG. 1 shows biochemical characterization of UMI-77 binding to Mcl-1. A) Chemical structures of the lead compound UMI-59 and its two analogs UMI-77 and UMI-101. B) Competitive binding curves of small-molecule inhibitors against Mcl-1 obtained by FP based binding assay. C) Binding affinities of UMI-59 and UMI-77 for five members of Bcl-2 family of proteins in FP assay. D) Probing the interaction of UMI-77 to cellular Mcl-1 by a pull-down assay using biotin labeled Noxa. E) Solution competitive SPR based binding assay. Recombinant Bax protein (residues 1-100) was immobilized on the CM5 chip and increasing concentrations of UMI-77 pre-incubated with Mcl-1 were injected over the surface.

The binding affinity and selectivity of UMI-77 against five members of Bcl-2 family of proteins was determined using FP-based binding assays (FIGS. 1B and 1C). The obtained results showed that UMI-77 selectively and potently displaced fluorescent labeled BID-BH3 peptide from Mcl-1 protein with a $K_i=0.49\pm0.06$ μM, showing three times higher potency for binding to Mcl-1 than UMI-59 ($K_i=1.55\pm0.18$ μM). Compound UMI-101, an analog of UMI-77, did not show binding to Mcl-1 up to 100 μM and therefore was used as a negative control in cell based assays. The binding profile studies showed that UMI-77 displayed significantly decreased binding affinities to the rest of the anti-apoptotic proteins and its binding specificity was consistent with the structural similarities between Mcl-1 and the anti-apoptotic members of Bcl-2 family. UMI-77 bound to A1/Bfl-1 with 11 fold lower affinity than to Mcl-1 ($K_i=5.33\pm1.0$ μM), followed by Bcl-w with $K_i=8.19\pm1.9$ μM (17 fold decreased), and more than 50-fold reduced binding to Bcl-2 ($K_i=23.83\pm1.81$ μM) and Bcl-xL ($K_i=32.99\pm4.33$ μM). These binding results demonstrated that UMI-77 binds selectively to Mcl-1 over the rest anti-apoptotic proteins.

To extend these findings to a cellular context, a biotin-streptavidin pull-down assay using a biotin-labeled Noxa BH3 peptide (BL-Noxa) was employed to probe whether UMI-77 interacts with cellular Mcl-1 protein. BL-Noxa selectively pulls down cellular Mcl-1 from 2LMP cell lysate and this interaction can be blocked by Bim BH3 peptide which binds with high affinity to Mcl-1 protein (FIG. 1D). Both tested compounds, UMI-59 and UMI-77 effectively disrupted the interactions between BL-Noxa and cellular Mcl-1 in a dose dependent manner. Consistent with FP binding results, UMI-77 is more potent than UMI-59 and blocks this interaction starting from 10 μM. These data demonstrate that UMI-77 binds the endogenous, cellular Mcl-1 protein and blocks the binding of BL-Noxa to Mcl-1.

Figure 2:
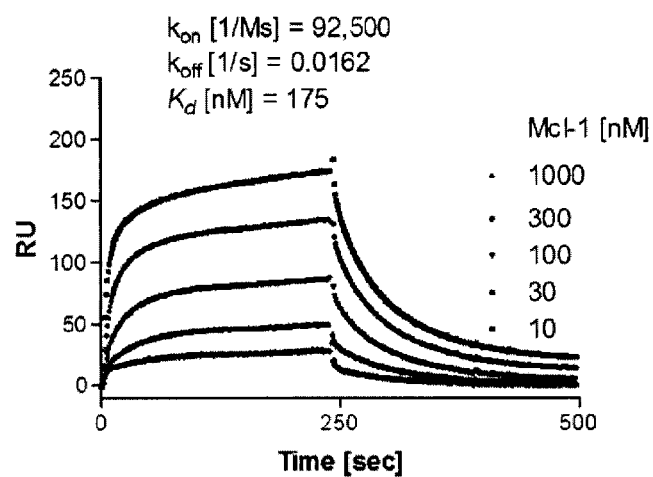
FIG. 2 shows determination of kinetic and steady state parameters for Mcl-1 binding to immobilized BAX protein. The $k_{on}$, $k_{off}$ and $K_d$ were calculated by simultaneous kinetics fit.

Current evidence suggests that Mcl-1 regulates pro-apoptotic multidomain proteins Bax and Bak, through binding their BH3-exposed conformers and preventing their activation, which are critical cell death mediators (see, e.g., Adams J M, Cory S. The Bcl-2 apoptotic switch in cancer development and therapy. Oncogene. 2007; 26:1324-37; Willis S N, Chen L, Dewson G, Wei A, Naik E, Fletcher J I, et al. Proapoptotic Bak is sequestered by Mcl-1 and Bcl-xL, but not Bcl-2, until displaced by BH3-only proteins. Genes Dev. 2005; 19:1294-305; each herein incorporated by reference in its entirety). Accordingly, an SPR based binding assay was developed which tests the ability of Mcl-1 inhibitors to interfere with the Mcl-1/Bax protein-protein interactions. For this SPR-based assay, recombinant Bax protein (residues 1-100) was immobilized on the surface of the SPR sensor chip using standard EDC/NHS amide coupling chemistry. To confirm that immobilized Bax was able to bind to Mcl-1 the binding of recombinant Mcl-1 protein was evaluated and determined that Mcl-1 binds to immobilized Bax with a $K_d$ value of 175 nM (FIG. 2). Pre-incubation of the Mcl-1 protein with increasing concentrations of UMI-77 blocked the binding of Mcl-1 to Bax in a dose-dependent manner with an $IC_{50}=1.43\pm0.14$ μM (FIG. 1E). Noxa BH3 peptide, which specifically binds Mcl-1 protein, inhibits the binding of Mcl-1 to Bax with an $IC_{50}=0.062\pm0.04$ μM, 23 fold more potent than UMI-77. Consistent with the results obtained from the FP based assay, UMI-101 failed to disrupt the Mcl-1/Bax protein-protein interactions. These results confirmed that UMI-77 specifically binds to the Mcl-1 protein and is capable of disrupting Mcl-1/Bax protein-protein interactions.

Example 3

This example shows that UMI-77 binds to the BH3 binding pocket of Mcl-1 protein.

To confirm the binding of UMI-77 to the BH3 groove of Mcl-1 protein and to further explore the interaction between the UMI-77 and Mcl-1, in silico docking analysis and heteronuclear single quantum correlation (HSQC) NMR spectroscopy studies were performed.

Figure 3:
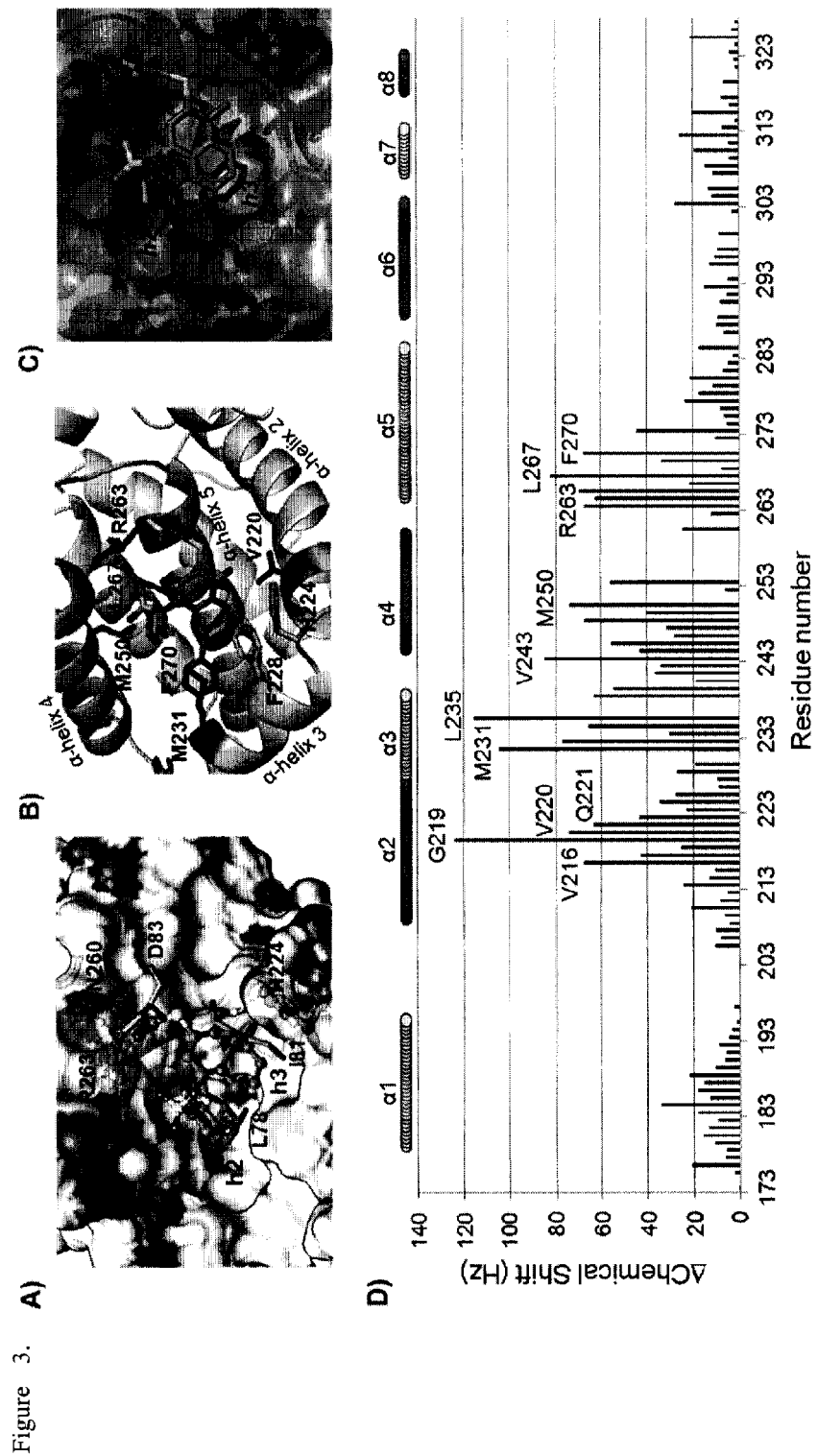
FIG. 3 shows computational and structural binding studies of UMI-77 with Mcl-1. A) Computational predicted binding pose of UMI-77 with Mcl-1 using the mNoxa BH3 peptide-bound Mcl-1 structure (PDB ID 2NLA). Superposition of the predicted binding pose of UMI-77 onto the crystal structure of mNoxa BH3 peptide with Mcl-1 (conserved residues from mNoxa, L78, I81 and D83, are presented). Hydrogen bonds with R263 and H224 are shown. B) Chemical shift mapping on the predicted binding model of UMI-77 to Mcl-1. The side chains of the residues involved in the interactions with UMI-77 and confirmed with the HSQC NMR studies are shown and labeled. C) Chemical shift mapping on the surface of the free Mcl-1 structure (chemical shifts >60 Hz are labeled in greyish-red, shifts between 30 and 60 Hz are labeled in greyish-pink). D) Chemical shift differences for Mcl-1 in presence of UMI-77 (2 equivalents) against residue number.
Figure 4:
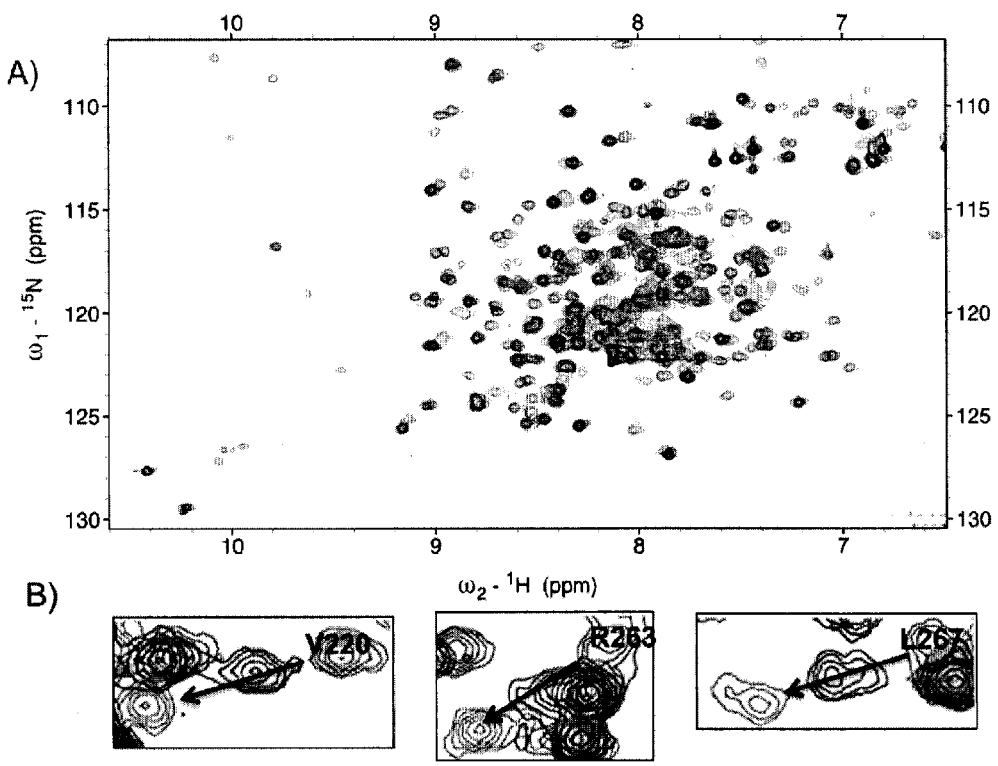
FIG. 4 shows A) Overlay of the $N^{15}$—HSQC spectra of only Mcl-1 protein (greyish-red), Mcl-1 in complex with UMI-77 (greyish-blue, 1 to 2 ratio) and Mcl-1 in complex with Bim BH3 peptide (greyish-magenta, 1 to 1 ratio). B) Zoom in of the spectra and presenting chemical shifts of several residues.

The predicted binding model of UMI-77 in the complex with Mcl-1 revealed that UMI-77 occupies two hydrophobic pockets in Mcl-1 protein, h2 and h3, mimicking two conserved hydrophobic residues from Noxa, Leu78 and Ile81, respectively (FIG. 3A). Specifically, the p-bromophenyl group inserts into the h2 pocket and has hydrophobic interactions with Met231, Met250, Val253, Leu267 and Phe270. The proposed interactions were confirmed with the HSQC NMR experiments in which these four residues showed significant chemical shift perturbations (>60 Hz), attributing to the interaction with the 4-bromophenyl group (FIG. 3B-3D). The predicted binding model shows that the naphthalenyl ring of UMI-77 occupies the h3 pocket and makes hydrophobic interactions with Phe228, while the 4-hydroxyl group in this ring forms a hydrogen bond with His224 (FIG. 3A). The h3 pocket is mainly constituted by the residues of His 224, Phe228, Met231, which is on the rim of h2 and h3 pockets, and Val220, on the rim of h3 and h4 pockets. Consistent with the computational model, NMR experiments showed that Met231 and Val220 have significant chemical shift perturbations (>60 Hz), as well as His224 and Phe228 (between 30 Hz and 60 Hz), confirming the predicted interactions of the UMI-77 in this region of the Mcl-1 protein. Recent reported study about the conformational flexibility of Mcl-1 and its binding hotspots identified His224 as an acidic hotspot in the h3 site of Mcl-1, further supporting the predicted electrostatic interaction in this region of Mcl-1 (see, e.g., Yang C Y, Wang S. Analysis of Flexibility and Hotspots in Bcl-xL and Mcl-1 Proteins for the Design of Selective Small-Molecule Inhibitors. ASC Med Chem Lett 2012; 3:308-12; herein incorporated by reference in its entirety). The docking model of the UMI-77 revealed that the carboxylic group of UMI-77 forms a hydrogen bonding network with Arg263 and Asn260. This carboxylic group mimics the conserved aspartate in proapoptotic proteins, which is able to form a salt bridge with arginine in anti-apoptotic proteins. Indeed, NMR studies showed that UMI-77 interacts with Arg263 causing a significant chemical shift (FIG. 3B-3D). Overall analysis of the chemical shifts of the Mcl-1/UMI-77 and Mcl-1/Bim BH3 peptide complexes showed that UMI-77 affected the same residues as Bim BH3 peptide, providing additional evidence that UMI-77 binds to the same site in the BH3 binding site (FIG. 4). Taken together, the in vitro binding studies, in silico docking and HSQC NMR spectroscopy studies confirmed that UMI-77 binds to the BH3-binding groove of Mcl-1 protein.

Example IV

This example shows that UMI-77 inhibits growth of PC cells and induces apoptosis through intrinsic apoptotic pathway.

Figure 5:
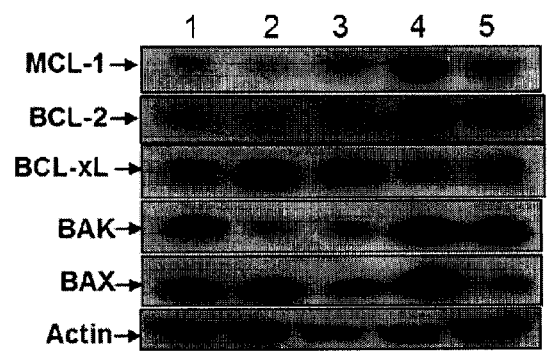
FIG. 5 shows protein expression profile in several pancreatic cancer cell lines: (1) MiaPaCa-2, (2) Capan-2, (3) AsPc1, (4) BxPC-3, and (5) Panc-1.
Figure 6:
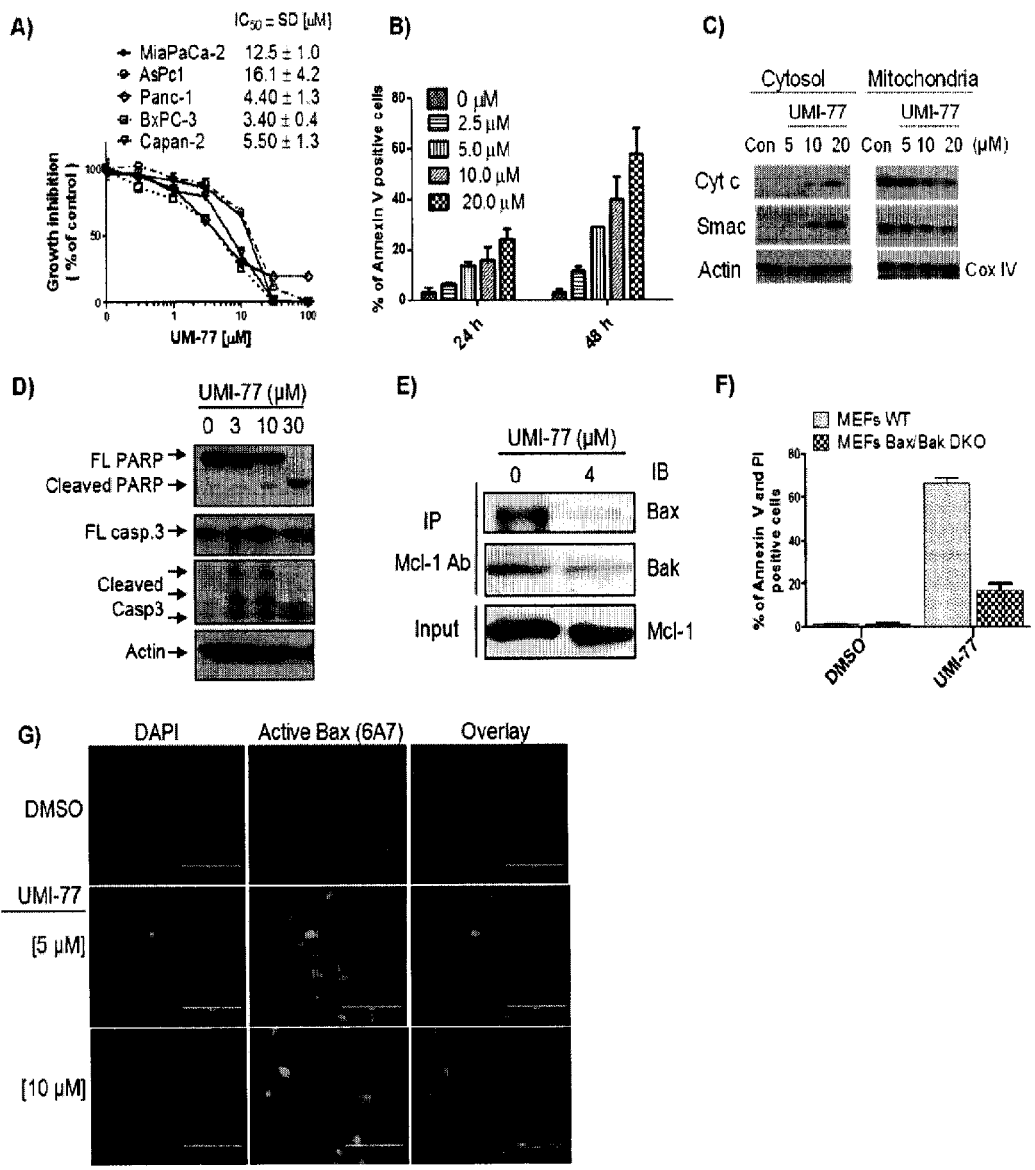
FIG. 6 shows UMI-77 effect on pancreatic cancer cell growth and induction of apoptosis. A) $IC_{50}$ values of cell growth inhibition of UMI-77 in panel of PC cell lines after 4 days treatment. B) Time and dose-dependent induction of apoptosis in Panc-1 cells after treatment with UMI-77. Cells were treated for different time points and apoptosis was determined with Annexin V/PI double staining. C) Release of cytochrome c and Smac from mitochondria in Panc-1 cells. Cells were treated for 24 h, mitochondria were isolated and cytochrome c and Smac were probed by Western blotting. D) Activation of caspases-3 and cleavage of PARP in BxPc-3 cells after 24 h treatment with UMI-77. Cells were treated for 24 h, and caspase-3 and PARP were probed by Western blotting. E) Immunoprecipitation on UMI-77 treated BxPC-3 cell lysate was performed using Mcl-1 antibody followed by western blot analysis with Bax or Bak.

Cytotoxic effect of UMI-77 was evaluated using a panel of five PC cell lines with different expression level of anti- and pro-apoptotic proteins (FIG. 5). A dose-response analysis revealed that UMI-77 most potently inhibits the cell growth of BxPC-3 and Panc-1 cell lines with $IC_{50}$ values of 3.4±0.4 and 4.4±1.3 µM respectively, and shows 3 to 5 times less potency in inhibition of the cell growth of two other tested cell lines MiaPaCa-2 (12.5±1.01 µM) and AsPc1 (16.1±4.2 µM) (FIG. 6A). The cell growth inhibition potency of UMI-77 correlates well with the Mcl-1 protein levels which have the highest expression in the sensitive cell lines, BxPC-3 and Panc-1. The specificity of cell growth inhibition by this compound was confirmed by experiments with compound UMI-101 which showed no binding to Mcl-1 at concentrations up to 100 µM and failed to show inhibition of the cell growth in an PC cell lines tested.

To gain insights into the underlying mechanism of action for the cell growth inhibition of UMI-77, BxPC-3 and Panc-1 cell lines were selected for further investigation. The cell growth inhibition is a combination of cell growth arrest and cell death induction, and to determine if apoptosis contributes to the antiproliferative effect of UMI-77, BxPC-3 and Panc-1 cells were treated with increasing concentrations of this compound for different times. Induction of apoptosis was monitored by flow cytometry using Annexin V and propium iodide (PI) double staining. As shown in FIG. 6B and FIG. 7, UMI-77 was very effective in induction of apoptosis in a time-dependent and dose-dependent manner in Panc-1 cells. Treatment of the Panc-1 cells with 5 and 10 µM concentrations of UMI-77 resulted in 15% and 21%, respectively, of early apoptotic cells after 24 hours treatment, and 21% and 49% after 48 hours treatment. Similar results were also obtained in BxPC-3 cells (FIG. 7). The inactive compound UMI-101 even at concentration of 100 µM failed to induce apoptosis in both tested PC cell lines. Next whether UMI-77 could directly induce apoptosis through activation of the intrinsic mitochondrial pathway was examined. Since cytochrome c release from mitochondria to the cytosol and subsequent activation of caspases represent key steps during intrinsic apoptosis, it was first determined whether UMI-77 could affect this process in Panc-1 cells. Treatment for 24 h of Panc-1 cells with UMI-77 resulted in dose-dependent release of cytochrome c and Smac from mitochondria, starting at a concentration of 10 µM (FIG. 6C) Similar results were obtained after treatment of BxPC-3 cells (FIG. 8). The induction of apoptosis and release of cytochrome c in BxPC-3 was accompanied by PARP cleavage and activation of caspase-3 (FIG. 6D). These results demonstrated that UMI-77 induced apoptosis in PC through activation of the intrinsic apoptotic pathway.

In the indirect activation model (see, e.g., Willis S N, Fletcher J I, Kaufmann T, van Delft M F, Chen L, Czabotar P E, et al. Apoptosis initiated when BH3 ligands engage multiple Bcl-2 homologs, not Bax or Bak. Science. 2007; 315:856-9; herein incorporated by reference in its entirety) the activity of the apoptosis effectors Bak and Bax can be suppressed by multidomain anti-apoptotic proteins such as Mcl-1. If cell death induction is specifically mediated by Mcl-1 protein, Bax or Bak would be required for release of cytochrome c and subsequent cell death. Therefore, to investigate if UMI-77-induced activation of the intrinsic apoptotic pathway involved the disruption of Mcl-1/Bax and/or Mcl-1/Bak complexes in PC, imminoprecipitation studies were performed. Treatment of BxPC-3 cells with UMI-77 at 4 µM for 24 h resulted in complete inhibition of the endogenous protein-protein interactions of Bax and Bak with Mcl-1 and their release, indicating that UMI-77 induced cell death and apoptosis by attenuating the ability of Mcl-1 to sequester pro-apoptotic proteins such as Bax and Bak (FIG. 6E). To further elucidate the role of Bak and Bax, wild type (WT) murine embryonic fibroblasts (MEF) and double knockout (DKO) cells, deficient in both Bax and Bak, were used. It is expected that in cells deficient in both Bax and Bak, cell death arising from Mcl-1 inhibition should be decreased. Indeed, UMI-77 at a concentration of 10 µM induced more than 60% apoptosis in the MEF WT cells, while at the same concentration the induction of apoptosis in MEF DKO cells was significantly reduced showing only 16% apoptotic cells (FIG. 6F). These results further confirmed that UMI-77 induced apoptosis in a Bax/Bak-dependent manner. To further interrogate the mechanism of action, the activation of Bax in Panc-1 and BxPC-3 cells was examined after treatment with UMI-77 using the 6A7 anti-Bax antibody, which specifically recognizes the conformationally active form of Bax (see, e.g., Takahashi Y, Karbowski M, Yamaguchi H, Kazi A, Wu J, Sebti S M, et al. Loss of Bif-1 suppresses Bax/Bak conformational change and mitochondrial apoptosis. Mol Cell Biol. 2005; 25:9369-82; herein incorporated by reference in its entirety). The immunostaining of the treated cells with UMI-77 was associated with a substantial increase in activated Bax in a dose dependent manner in both tested pancreatic cell lines starting from 5 µM (FIG. 6G and FIG. 9). These data suggest that UMI-77 treatment leads to Bax conformational change, consistent with the co-immunoprecipitation and fractionation studies, which demonstrated that UMI-77 can disrupt the Bax/Mcl-1 protein-protein interactions and release cytochrome c from mitochondria to the cytosol in PC cells. In summary, these experiments demonstrated that induction of apoptosis by UMI-77 depends on Bax and/or Bak, suggesting that UMI-77 functions as a BH3 mimetic and exhibits specific and mechanism-based cell growth inhibition.

Example V

This example demonstrates that knocking down Mcl-1 expression abrogates growth inhibition and apoptosis by UMI-77.

To further confirm the functional role of Mcl-1 in UMI-77-mediated apoptosis, RNA interference was employed to knock-down Mcl-1 in BxPC-3 cells in order to determine whether knocking down Mcl-1 expression would affect the sensitivity to UMI-77 in BxPC-3 cells. UMI-77 alone induced effective cell growth inhibition and induction of apoptosis in BxPC-3 cells. However, when BxPC-3 cells were treated with UMI-77 in the presence of Mcl-1 siRNA, blocking of Mcl-1 expression by siMcl-1 significantly decreased induction of apoptosis (P<0.05) and protected cells from killing induced by UMI-77 (FIGS. 10A and 10B), while control siRNA had no effect. This confirms the ability of UMI-77 to functionally inhibit Mcl-1 in a cellular context and the observed decrease in induction of apoptosis, as well as abrogation of cell growth is Mcl-1 dependent. Immunoblot analysis indicated that siMcl-1 completely and specifically inhibits Mcl-1 protein expression under the treatment condition and not in control siRNA samples, confirming efficient silencing (FIG. 10C).

Example VI

This example demonstrated that UMI-77 exhibits single-agent antitumor activity in BxPC-3 xenograft model.

The in vitro data described earlier prompted us to extend these observations and test the in vivo efficacy of UMI-77 in a BxPC-3 xenograft model in SCID mice. First, its in vitro microsomal stability was tested by incubating UMI-77 with pooled mice liver microsomes. UMI-77 exhibited moderate metabolic stability with a half-life of 45 minutes (FIG. 11A). This result was promising for continuation with in vivo efficacy studies in view of the fact that in vitro microsomal stability correlates with the in vivo plasma clearance. Second, the maximum tolerated dose (MTD) of UMI-77 in SCID mice was determined. UMI-77 delivered at 60 mg/kg i.v. for 5 consecutive days per week for two weeks did not cause any loss in the body weight in the experimental animals and there was no obvious sign of toxicity during the course of the treatment (FIG. 11B). However, increasing the dose to 80 mg/kg showed severe animal weight loss (>20%). Based on these results 60 mg/kg was used as a therapeutic dose for the in vivo efficacy studies. Daily treatment with UMI-77 for 5 consecutive days a week for two weeks (60 mg/kg) resulted in statistically significant tumor growth inhibition by 65% and 56% in comparison with the controls in day 19 (p<0.0001) and day 22 (p<0.003) respectively (FIGS. 11C and 11D). To further elucidate the molecular mechanism of UMI-77 mediated tumor growth inhibition, western blot and immunohistochemistry on tumor tissue were performed. The western blots of the tumor tissue lysates showed elevated levels of pro-apoptotic proteins, Bax and Bak, consistent with co-immunoprecipitation results revealing that UMI-77 can displace Bax and Bak from their complexes with Mcl-1 in BxPC-3 cells. The western blots also showed significant decrease of survivin, one of the Inhibitors of Apoptosis Proteins (IAPs) which potently inhibits apoptosis by antagonizing caspase activity (FIG. 11E). However, at this point the mechanism by which UMI-77 treatment leads to survivin down-regulation is unclear. Apoptotic cells in tumor tissue by TUNEL-based in situ method was further determined and the obtained results showed that positive apoptotic cells of tumor sections were significantly increased in UMI-77-treated BxPC-3 xenograft mice as compared with the control group (FIG. 11F). The toxicity of UMI-77 on normal tissues by H&E analyses was next determined (FIG. 12). Histopathology revealed that treatment of mice with UMI-77 for a total of 10 days at 60 mg/kg i.v. did not cause damage to tested tissues from kidney, liver and pancreas. Specifically, livers contained no morphological evidence of portal or central-zone injury, no hepatocyte swelling, cholestasis or steatosis, and no fibrosis or inflammation. Renal glomeruli and tubules were morphologically intact and non-inflamed, as were the structures of the endocrine and exocrine pancreas in all specimens. There was no histological evidence of vasculitis, ductitis, necrosis, increased apoptotic activity or other injury in any of the tissues studied and parenchymal mitotic activity was not increased. These results demonstrate that UMI-77 is not toxic to normal mouse tissues. These findings are consistent with in vitro results and provide in vivo support of the involvement of Mcl-1 regulated pathway in PC, implicating the potential of Mcl-1 inhibitors as novel antitumor agents for treatment of PC.

Example 8

Mcl-1, an anti-apoptotic member of Bcl-2 family proteins, is a validated and attractive target for cancer therapy. Overexpression of Mcl-1 in many cancers results in disease progression and resistance to current therapeutics. Through high throughput screening (HTS) approach, compound I (UMI-59) was identified as a selective Mcl-1 inhibitor, and its binding to the BH3 binding groove of Mcl-1 was confirmed by several different, but complementary biochemical and biophysical assays. Guided by structure-based drug design and supported by NMR experiments, comprehensive structure-activity relationship (SAR) studies were undertaken to develop potent Mcl-1 inhibitors. The most potent inhibitor, compound 17, showed an $IC_{50}$ of 0.68±0.14 µM and a $K_i$ of 0.17±0.04 µM against Mcl-1 and selectively inhibited Mcl-1 over other anti-apoptotic Bcl-2 family proteins.

Evasion of apoptosis or programmed cell death, a key regulator of physiological growth control and regulation of tissue homeostasis, is a hallmark of cancer and a cause of resistance of cancer cells to current chemotherapies (see, e.g., Hanahan, D.; Weinberg, R. A. The hallmarks of cancer. Cell 2000, 100, 57-70; Fulda, S.; Debatin, K. M. Extrinsic versus intrinsic apoptosis pathways in anticancer chemotherapy. Oncogene 2006, 25, 4798-811; each herein incorporated by reference in its entirety). The B-cell lumphoma-2 (Bcl-2) family proteins regulate the intrinsic (mitochondrial) pathway of apoptosis through a network of protein-protein interactions between pro- and anti-apoptotic members (see, e.g., Castanet, A.-S.; Colobert, F.; Broutin, P.-E. Mild and regioselective iodination of electron-rich aromatics with N-iodosuccinimide and catalytic trifluoroacetic acid. Tetrahedron Letters 2002, 43, 5047-5048; Youle, R. J.; Strasser, A. The BCL-2 protein family: opposing activities that mediate cell death. Nat Rev Mol Cell Biol 2008, 9, 47-59; each herein incorporated by reference in its entirety). Twenty five known members of the Bcl-2 protein family can be grouped functionally according to their pro- and anti-apoptotic effects, as well as structurally according to the Bcl-2 homology (BH) regions they contain. The Bcl-2 anti-apoptotic proteins consisting of Bcl-2, Bcl-$x_L$, Bcl-b, Bcl-w, Mcl-1, and A1, share up to four BH domains which form the hydrophobic BH3-binding groove for binding their cognate partners. The pro-apoptotic proteins are divided into two groups: (a) multidomain proteins including Bax and Bak with BH1-BH4 domains and (b) BH3-only proteins including Bad, Bid, Bim, Noxa and Puma, among others, sharing homology only in the BH3 α-helical domain. The BH3 domain possesses four conserved hydrophobic residues involved in the interaction with the ligand-BH3-binding groove of the pro-survival Bcl-2 family members, resulting in sequestering and blocking the function of the pro-death members.

Overexpression of Bcl-2 survival members is observed in different types of human tumor samples and cancer cell lines, and much effort has been focused to develop therapeutics against this family of proteins for the treatment of cancers (see, e.g., Bajwa, N.; Liao, C. Z.; Nikolovska-Coleska, Z. Inhibitors of the anti-apoptotic Bcl-2 proteins: a patent review. Expert Opinion on Therapeutic Patents 2012, 22, 37-55; Lessene, G.; Czabotar, P. E.; Colman, P. M. BCL-2 family antagonists for cancer therapy. Nat Rev Drug Discov 2008, 7, 989-1000; Vogler, M.; Dinsdale, D.; Dyer, M. J.; Cohen, G. M. Bcl-2 inhibitors: small molecules with a big impact on cancer therapy. Cell Death Differ 2009, 16, 360-7; each herein incorporated by reference in its entirety). Selective and potent small molecule inhibitors have been successfully developed against Bcl-2/Bcl-xL (see, e.g., Tse, C.; Shoemaker, A. R.; Adickes, J.; Anderson, M. G.; Chen, J.; Jin, S.; Johnson, E. F.; Marsh, K. C.; Mitten, M. J.; Nimmer, P.; Roberts, L.; Tahir, S. K.; Xiao, Y.; Yang, X.; Zhang, H.; Fesik, S.; Rosenberg, S. H.; Elmore, S. W. ABT-263: a potent and orally bioavailable Bcl-2 family inhibitor. Cancer Res 2008, 68, 3421-8; Zhou, H. B.; Chen, J. F.; Meagher, J. L.; Yang, C. Y.; Aguilar, A.; Liu, L.; Bai, L. C.; Gong, X.; Cai, Q.; Fang, X. L.; Stuckey, J. A.; Wang, S. M. Design of Bcl-2 and Bcl-xL Inhibitors with Subnanomolar Binding Affinities Based upon a New Scaffold. Journal of Medicinal Chemistry 2012, 55, 4664-4682; each herein incorporated by reference in its entirety) with Navitoclax (ABT-263) showing promising results in phase I clinical trials (see, e.g., Roberts, A. W.; Seymour, J. F.; Brown, J. R.; Wierda, W. G.; Kipps, T. J.; Khaw, S. L.; Carney, D. A.; He, S. Z.; Huang, D. C. S.; Xiong, H.; Cui, Y.; Busman, T. A.; McKeegan, E. M.; Krivoshik, A. P.; Enschede, S. H.; Humerickhouse, R. Substantial Susceptibility of Chronic Lymphocytic Leukemia to BCL2 Inhibition: Results of a Phase I Study of Navitoclax in Patients With Relapsed or Refractory Disease. Journal of Clinical Oncology 2012, 30, 488-496; herein incorporated by reference in its entirety). However, progress has been much slower in targeting Mcl-1 which has been proven to be a challenging target. Mcl-1 is highly upregulated in many human cancers, and has been linked to acquired resistance of cancer cells upon treatment with Navitoclax (see, e.g., Yecies, D.; Carlson, N. E.; Deng, J.; Letai, A. Acquired resistance to ABT-737 in lymphoma cells that up-regulate MCL-1 and BFL-1. Blood 2010, 115, 3304-13; herein incorporated by reference in its entirety). Combination of Navitoclax with Obatoclax, a pan inhibitor of anti-apoptotic proteins, showed effective cell growth inhibition of cancers that rely on Mcl-1 (see, e.g., Nguyen, M.; Marcellus, R. C.; Roulston, A.; Watson, M.; Serfass, L.; Madiraju, S. R. M.; Goulet, D.; Viallet, J.; Belec, L.; Billot, X.; Acoca, S.; Purisima, E.; Wiegmans, A.; Cluse, L.; Johnstone, R. W.; Beauparlant, P.; Shore, G. C. Small molecule obatoclax (GX15-070) antagonizes MCL-1 and overcomes MCL-1-mediated resistance to apoptosis. Proceedings of the National Academy of Sciences of the United States of America 2007, 104, 19512-19517; herein incorporated by reference in its entirety), highlighting the importance of targeting Mcl-1 as an anticancer target. Experiments conducted during the course of developing embodiments for the present invention report the structure-based design, synthesis and biological evaluation of selective small molecule Mcl-1 inhibitors starting from an HTS hit 1 (UMI-59) (FIG. 13A). Two-dimensional $^1$H,$^{15}$N heteronuclear single quantum coherence spectroscopy (HSQC) NMR studies were employed to demonstrate compound 1's binding mode and provided information for the design of additional analogues.

Lead Discovery.

HTS of 53,300 small molecule library was performed using fluorescence polarization (FP) binding assay based on the interaction between recombinant human Mcl-1 and fluorescent labeled Bid BH3 peptide (Flu-Bid). Several lead compounds as Mcl-1 inhibitors were identified and extensively characterized using biochemical, biophysical, functional and cell based assays. Compound 1 (UMI-59) is one of the validated hits, which was re-synthesized and its binding affinity to Mcl-1 protein was confirmed exhibiting an $IC_{50}$ of 5.70±0.67 µM and $K_i$=1.55±0.18 µM. To explore the possible binding models of 1 with Mcl-1, in silico induced fit docking (see, e.g., Schrödinger Suite 2010 Induced Fit Docking protocol; Glide version 5.6, Schrödinger, LLC, New York, N.Y., 2009; Prime version 2.2, Schrödinger, LLC, New York, N.Y. 2010; herein incorporated by reference in its entirety) studies were performed using the crystal structure of Mcl-1 in complex with the mNOXA BH3 peptide (PDB ID: 2NLA). The predicted binding model of 1 in the complex with Mcl-1 revealed that the thiophene ring and the naphthalene ring of 1 occupy two hydrophobic pockets in Mcl-1 protein, h2 and h3, mimicking two conserved hydrophobic residues from Noxa, Leu78 and Ile81, respectively (FIG. 13D). The obtained results from the predicted binding models are consistent with reported binding and structural studies of Bims2A, a highly selective Mcl-1 BH3-like peptide derived from Bim peptide, which demonstrated that residue Ile65 (position h3 in Bim BH3 peptide) is the most critical for the selective binding of Bims2A to Mcl-1 and it is required for a high affinity interaction with Mcl-1. The carboxylic acid group forms a network of hydrogen bonds with Arg 263 and Asn 260 of Mcl-1 mimicking the conserved Asp 83 of Noxa. The predicted binding model also suggests that the phenolic group forms a hydrogen bond with His 224, which is one of the residues composing the h3 pocket of Mcl-1.

To further experimentally validate the computational docking studies and confirm the binding of 1 to the BH3 groove of Mcl-1 protein, the heteronuclear single quantum correlation (HSQC) NMR spectroscopy studies were performed. For this purpose the backbone amides of apo human Mcl-1 were assigned based on the work by Liu et al. (see, e.g., Liu, Q.; Moldoveanu, T.; Sprules, T.; Matta-Camacho, E.; Mansur-Azzam, N.; Gehring, K. Apoptotic Regulation by MCL-1 through Heterodimerization. Journal of Biological Chemistry 2010, 285, 19615-19624; herein incorporated by reference in its entirety), and a series of $^1$H,$^{15}$N—HSQC studies were carried out. The HSQC spectra were of good quality with well-dispersed peaks, and concentration-dependent shifts of residues were observed indicating that 1 (UMI-59) binds Mcl-1 specifically and causes dose-dependent perturbations of backbone amides. The chemical shifts in presence of a 2-fold excess of 1 (UMI-59) were mapped and plotted against Mcl-1 residues (FIGS. 13B and 13C). Compound 1 (UMI-59) caused moderate to significant chemical shift perturbations for residues forming h2 and h3 pockets (Met 231, Met 250, Leu 267, Phe 270), predicted to be occupied with thiophene and naphthalene rings of 1, respectively. Moderate chemical shifts of Arg 263 and His 224 were also observed which were predicted to form hydrogen bond with the thioacidic acid and phenolic moieties of 1, respectively. Additionally, the residues in the vicinity of the predicted binding pose (Leu 232, Val 243, Arg 248), and the ones located on an unstructured loop connecting α3 to α4 (Lys 234, Leu 235, Lys 238, Asn 239) were also perturbed. Overall analysis of the chemical shifts of the compound 1 in complex with Mcl-1/1 showed that 1 affects the residues forming the BH3-binding groove, providing conclusive evidence that 1 binds to Mcl-1 protein at the same site where the Noxa BH3 peptide interacts with Mcl-1 protein. Therefore, based on the modeling and NMR results the substituted sulfonamido-1-hydroxynaphthalene scaffold represents a promising scaffold for further chemical optimization. A structure-based design approach supported by NMR studies was undertaken and a focused library of analogues of 1 (59FA) was designed and synthesized to understand the structural basis of binding to Mcl-1 toward improving the potency of this series of inhibitors.

Synthesis.

The synthesis of 1 and the majority of its analogues is outlined in Scheme 2. It starts with the electrophilic aromatic substitution of commercially available 1-methoxy-4-nitronaphthalene with N-iodosuccinamide to provide the desired aryl iodide (38) (see, e.g., Castanet, A.-S.; Colobert, F.; Broutin, P.-E. Mild and regioselective iodination of electron-rich aromatics with N-iodosuccinimide and catalytic trifluoroacetic acid. Tetrahedron Letters 2002, 43, 5047-5048; herein incorporated by reference in its entirety). This was subjected to Pd-catalyzed C—S or C—C cross-coupling using conditions previously reported (see, e.g., Ciattini, P. G.; Morera, E.; Ortar, G. Tetrahedron Letters 1995, 36, 4133-4136; Thansandote, P.; Gouliaras, C.; Turcotte-Savard, M. O.; Lautens, M. A rapid approach to the synthesis of highly functionalized tetrahydroisoquinolines. J Org Chem 2009, 74, 1791-3; Dai, W.; Petersen, J. L.; Wang, K. K. Synthesis of the Parent and Substituted Tetracyclic ABCD Ring Cores of Camptothecins via 1-(3-Aryl-2-propynyl)-1,6-dihydro-6-oxo-2-pyridinecarbonitriles. Organic Letters 2006, 8, 4665-4667; Eichman, C. C.; Stambuli, J P Zinc-Mediated Palladium-Catalyzed Formation of Carbon-Sulfur Bonds. Journal of Organic Chemistry 2009, 74, 4005-4008; Itoh, T.; Mase, T. A general palladium-catalyzed coupling of aryl bromides/triflates and thiols. Organic Letters 2004, 6, 4587-4590; Mispelaere-Canivet, C.; Spindler, J.-F.; Perrio, S.; Beslin, P. Pd2(dba)3/Xantphos-catalyzed cross-coupling of thiols and aryl bromides/triflates. Tetrahedron 2005, 61, 5253-5259; each herein incorporated by reference in its entirety) to provide the desired intermediates (39a-e). These were reduced with iron (see, e.g., Riesgo, E. C.; Jin, X.; Thummel, R. P. Introduction of Benzo[h]quinoline and 1,10-Phenanthroline Subunits by Friedlander Methodology. The Journal of Organic Chemistry 1996, 61, 3017-3022; herein incorporated by reference in its entirety^) or via catalytic hydrogenation (see, e.g., Ortar, G.; Cascio, M. G.; De Petrocellis, L.; Morera, E.; Rossi, F.; Schiano-Moriello, A.; Nalli, M.; de Novellis, V.; Woodward, D. F.; Maione, S.; Di Marzo, V. New N-arachidonoylserotonin analogues with potential "dual" mechanism of action against pain. J Med Chem 2007, 50, 6554-69; herein incorporated by reference in its entirety^) to provide the desired amines. Reaction of the amines with appropriate $R_1$ sulfonyl or acyl chlorides provided the penultimate compounds (40a-t), which were demethylated with $BBr_3$ followed by purification by trituration or reverse-phase HPLC to afford the target compounds (1-2, 8-12, 14-18, 21, 23-26, 30-34) of >95% purity (see, Tables 2-5). In the case of analogues with an ester side chain, the $BBr_3$ step provided a convenient way to concomitantly hydrolyze the ester in a single pot. The variations at $R_1$ were mainly achieved with commercially available sulfonyl or acyl chlorides. However, in case of 40u, the appropriate intermediate underwent Suzuki-Miyaura coupling (see, e.g., Greig, I. R.; Idris, A. I.; Ralston, S. H.; van't H of, R. J. Development and Characterization of Biphenyl-sulfonamides as Novel Inhibitors of Bone Resorption. Journal of Medicinal Chemistry 2006, 49, 7487-7492; Li, X.; Chu, S.; Feher, V. A.; Khalili, M.; Nie, Z.; Margosiak, S.; Nikulin, V.; Levin, J.; Sprankle, K. G.; Tedder, M. E.; Almassy, R.; Appelt, K.; Yager, K. M. Structure-Based Design, Synthesis, and Antimicrobial Activity of Indazole-Derived SAH/MTA Nucleosidase Inhibitors. Journal of Medicinal Chemistry 2003, 46, 5663-5673; each herein incorporated by reference in its entirety) with phenyl boronic acid to provide the desired compound which was subjected to $BBr_3$ ether and ester demethylation to provide 15. For analogue 16, the desired sulfonyl chloride was not commercially available thus it was synthesized as described previously (see, e.g., Hoffman, R. V. m-Trifluoromethylbenzenesulfonyl chloride. Org. Synth. 1981, 60, 121-6; Murugesan, N.; Hunt, J. T.; Stein, P. D. Preparation of phenylsulfonamidooxazole and -isoxazole endothelin antagonists. U.S. Pat. No. 5,514,696A, 1996; each herein incorporated by reference in its entirety). Methyl ester analogue 29 was synthesized by subjecting 40d to $BBr_3$ conditions followed by quench with MeOH at cold temperature. Aminolysis of 40d using aqueous $NH_4OH$ (see, e.g., Wagner, J.; von Matt, P.; Faller, B.; Cooke, N. G.; Albert, R.; Sedrani, R.; Wiegand, H.; Jean, C.; Beerli, C.; Weckbecker, G.; Evenou, J. P.; Zenke, G.; Cottens, S. Structure-activity relationship and pharmacokinetic studies of sotrastaurin (AEB071), a promising novel medicine for prevention of graft rejection and treatment of psoriasis. J Med Chem 2011, 54, 6028-39; herein incorporated by reference in its entirety^) provided 40v which was subjected to $BBr_3$ demethylation to provide 33. The thioacidic acid analogue 36 was obtained via LiOH ester hydrolysis of 40d. Acetylation of 9 (UMI-77) with acetyl chloride provided 37 (see, e.g., England, D. B.; Ken, M. A. Synthesis and Cross-Coupling Reactions of Substituted 5-Triflyloxyindoles. The Journal of Organic Chemistry 2005, 70, 6519-6522; herein incorporated by reference in its entirety^). Analogue 22 with a phenyl scaffold was synthesized using conditions similar to those described for 9 (UMI-77) starting from commercially available 2-iodoanisole (Scheme 3). The Synthesis of compound 27 without the thioacetic acid side chain at $R_2$ was achieved as shown in Scheme 4. 1-Nitronaphthalene was hydroxylated using cumene hydroperoxide as described before (see, e.g., Zhu, L.; Zhang, L. H. Specific para-hydroxylation of nitronaphthalenes with cumene hydroperoxide in basic aqueous media. Tetrahedron Letters 2000, 41, 3519-3522; herein incorporated by reference in its entirety^). Phenolic protection with the benzyl group (see, e.g., Motoyama, Y.; Kamo, K.; Nagashima, H. Catalysis in Polysiloxane Gels: Platinum-Catalyzed Hydrosilylation of Polymethylhydrosiloxane Leading to Reusable Catalysts for Reduction of Nitroarenes. Organic Letters 2009, 11, 1345-1348; herein incorporated by reference in its entirety^) followed by nitro reduction and sulfonamide formation provided 42, which was unmasked to 27 via benzyl hydrogenolysis.

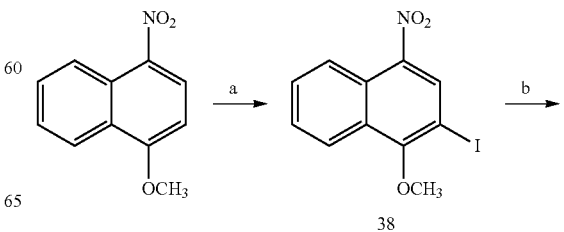

Scheme 2. <sup>a</sup>Synthetic route for 1 and analogs

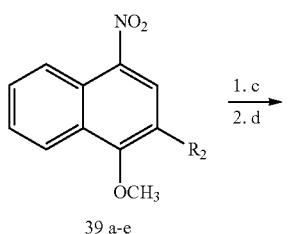

39 a-e

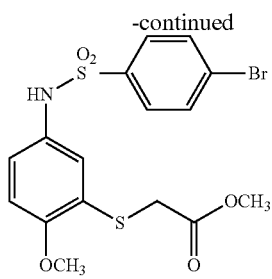

47

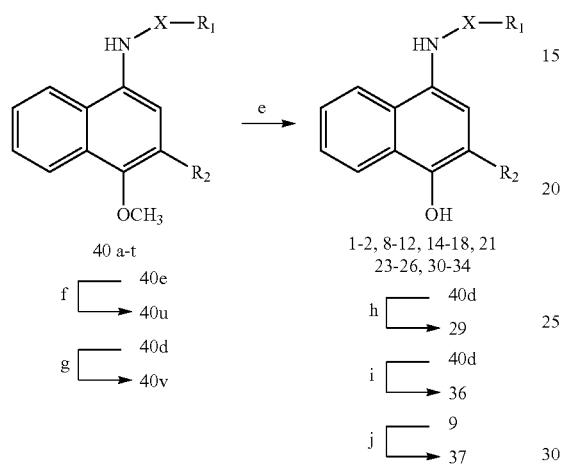

40 a-t f: 40e → 40u
g: 40d → 40v 1-2, 8-12, 14-18, 21
23-26, 30-34 h: 40d → 29
i: 40d → 36
j: 9 → 37

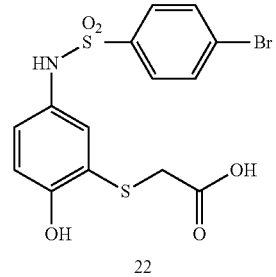

22

*Reagents and conditions:
(a) HNO$_3$, AcOH, 0° C. to 50° C., 1 h;
(b) HSCH$_2$COOH, Pd(OAc)$_2$, Xantphos, Cs$_2$CO$_3$, LiI, ZnCl$_2$, THF, 60° C., 6 h;
(c) Fe, AcOH, 70° C., 1 h;
(d) 4-bromobenzene sulfonyl chloride, pyridine, CH$_2$Cl$_2$, rt, overnight;
(e) BBr$_3$, CH$_2$Cl$_2$, 0° C. to rt, 1 h.

*Reagents and conditions:
(a) NIS, TFA, reflux, 24 h;
(b) HS(CH$_2$)$_n$COOH (n = 1,2), Pd(OAc)$_2$, Xantphos, Cs$_2$CO$_3$, LiI, ZnCl$_2$, THF, 60° C., overnight, or HS(CH$_2$)$_3$CH$_3$ or HS(CH$_2$)$_2$OH, Pd$_2$(dba)$_3$, Dppf, Et$_3$N, NMP, 80° C., 2-3 h, or HCC(CH$_2$)$_2$OH, Pd(PPh$_3$)$_2$Cl$_2$, CuI, Et$_3$N/THF (4:1), 60° C., 2 h;
(c) Fe, AcOH, 70° C., 1 h, or Pd/C, H$_2$ 30 psi, EtOH/EtOAc (6:1), rt, overnight;
(d) RSO$_2$Cl, pyridine, CH$_2$Cl$_2$, rt, overnight, or RCOCl, Et$_3$N, CH$_2$Cl$_2$, rt, overnight;
(e) BBr$_3$, CH$_2$Cl$_2$, 0° C. to rt, 1 h;
(f) phenyl boronic acid, Pd(PPh$_3$)$_4$, Na$_2$CO$_3$, THF/H$_2$O, 60° C., 2 h;
(g) NH$_4$OH, rt, 1 h;
(h) BBr$_3$, CH$_2$Cl$_2$, 0° C. to rt, 1 h, quench with MeOH at 0° C.;
(i) LiOH, THF, rt, 1 h;
(j) H$_3$CCOCl, Et$_3$N, 0° C. to rt, 30 min.

Scheme 4.*

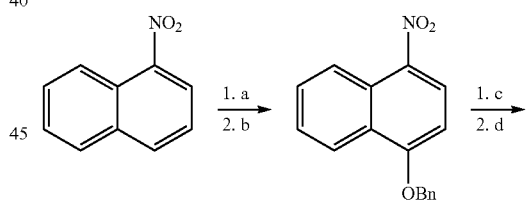

41

Scheme 3.*

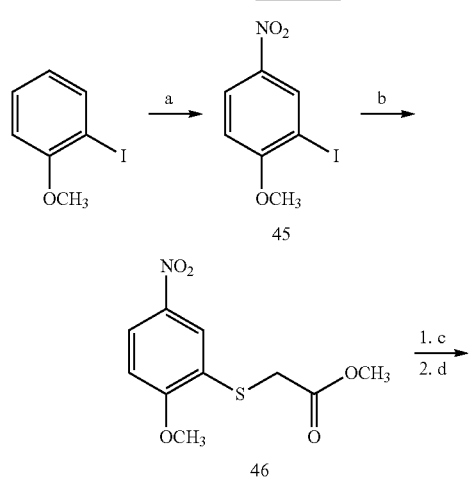

45

46

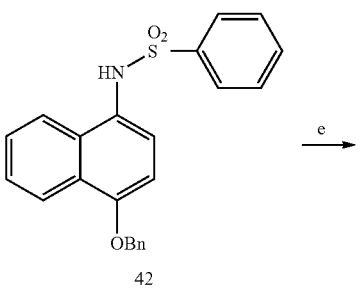

42

-continued

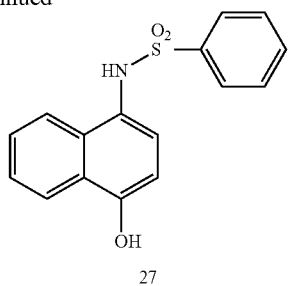

27

*Reagents and conditions:
(a) cumene hydroperoxide, KOH, DMSO/H₂O (3:1), 0° C. to rt, 2 h;
(b) benzyl bromide, NaH, DMF/THF (2:1), 0° C. to rt, 2-3 h;
(c) Fe, AcOH, 70° C., 1 h;
(d) benzenesulfonyl chloride, pyridine, CH₂Cl₂, rt, overnight;
(e) Pd/C, H₂ 30 psi, MeOH, rt, overnight.

TABLE 2

Binding Affinities of analogs with variations at R2.

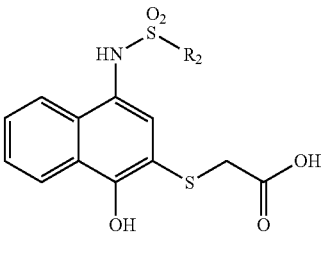

| Compound | R₂ | Mcl-1 IC$_{50}$ ± SD (µM) | K$_i$ ± SD (µM) |
|---|---|---|---|
| 1 (UMI-59) | 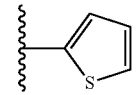 | 5.70 ± 0.67 | 1.55 ± 0.18 |
| 2 | 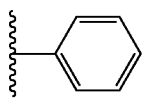 | 13.02 ± 1.62 | 3.56 ± 0.45 |
| 3 | 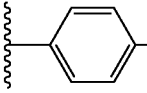 | 11.46 ± 0.78 | 3.13 ± 0.22 |
| 4 |  | 5.73 ± 1.34 | 1.55 ± 0.37 |
| 5 |  | 3.92 ± 0.63 | 1.06 ± 0.17 |
| 6 | 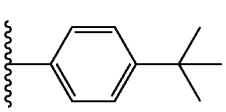 | 3.03 ± 0.17 | 0.81 ± 0.04 |
| 7 | 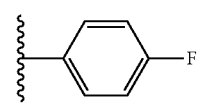 | 15.47 ± 3.38 | 4.23 ± 0.93 |

TABLE 2-continued

Binding Affinities of analogs with variations at R2.

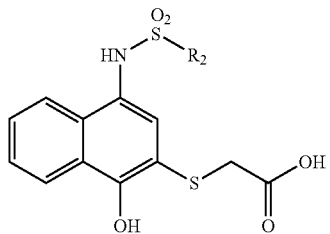

| Compound | R₂ | Mcl-1 IC$_{50}$ ± SD (µM) | K$_i$ ± SD (µM) |
|---|---|---|---|
| 8 | 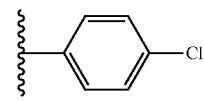 | 3.08 ± 0.35 | 0.82 ± 0.10 |
| 9 (UMI-77) | 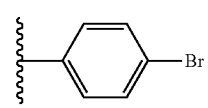 | 1.87 ± 0.22 | 0.49 ± 0.06 |
| 10 | 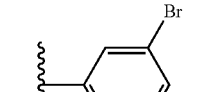 | 8.64 ± 0.69 | 2.35 ± 0.19 |
| 11 | 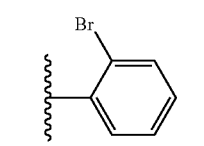 [SMILES: *c1ccccc1Br] | 16.18 ± 3.12 | 4.42 ± 0.86 |
| 12 | 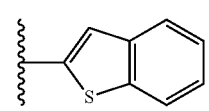 [SMILES: *c1cc2ccccc2s1] | 5.66 ± 1.15 | 1.54 ± 0.32 |
| 13 | 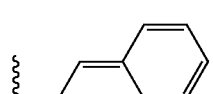 | 2.74 ± 0.18 | 0.73 ± 0.05 |
| 14 | 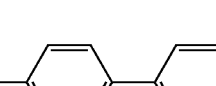 | 1.40 ± 0.36 | 0.37 ± 0.10 |
| 15 | 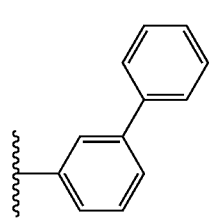 [SMILES: *c1cccc(-c2ccccc2)c1] | 1.41 ± 0.17 | 0.38 ± 0.03 |

TABLE 2-continued

Binding Affinities of analogs with variations at R2.

[Structure: naphthalene with HN-SO2-R2 at 4-position, OH at 1-position, and S-CH2-COOH at 2-position]

| Compound | R2 | Mcl-1 IC₅₀ ± SD (μM) | K$_i$ ± SD (μM) |
|---|---|---|---|
| 16 | 2-biphenyl | 7.47 ± 1.47 | 2.03 ± 0.41 |
| 17 | 4'-chloro-4-biphenyl | 0.68 ± 0.14 | 0.17 ± 0.04 |
| 18 | 4-phenoxyphenyl | 0.74 ± 0.20 | 0.18 ± 0.05 |
| 19 | 4-ethoxyphenyl | 50.09 ± 4.15 | 13.74 ± 1.14 |
| 20 | 4-carboxyphenyl | 17.42 | 4.76 |
| 21 | CH₃ | >200 | >50 |
| 22 | 4-bromophenyl | >800 | >200 |

[a]22 has the core of sulfonamido-1-hydroxybenzene instead of sulfonamido-1-hydroxynaphthalene.

TABLE 3

Binding Affinities of analogs with variations at the linker.

[Structure: naphthalene with Linker-R2 at 4-position, OH at 1-position, *** at 2-position]

| Compound | Z—R2 | *** | Mcl-1 IC₅₀ ± SD (μM) | K$_i$ ± SD (μM) |
|---|---|---|---|---|
| 23 | —NH-C(O)-C₆H₄-Br | —S-CH₂-COOH | >100 | >25 |
| 24 | —NH-C(O)-CH₂-C₆H₅ | —S-CH₂-COOH | 154.4 ± 40.19 | 42.37 ± 11.04 |

TABLE 3-continued

Binding Affinities of analogs with variations at the linker.

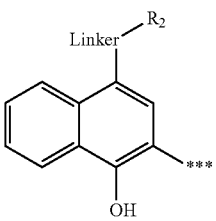

| Com-pound | Z—R$_2$ | *** | Mcl-1 IC$_{50}$ ± SD (µM) | K$_i$ ± SD (µM) |
|---|---|---|---|---|
| 25 | NHS(O$_2$)CH$_2$-C$_6$H$_4$-Cl | S-CH$_2$-COOH | 19.12 ± 1.31 | 5.23 ± 0.36 |
| 26 | NHC(O)CH$_2$-C$_6$H$_4$-Cl | S-CH$_2$-COOH | 45.70 ± 4.50 | 12.53 ± 1.24 |

TABLE 4

Binding Affinities of analogs with variations at *** and R$_2$.

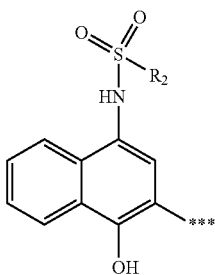

| Com-pound | R$_2$ | *** | Mcl-1 IC$_{50}$ ± SD (µM) | K$_i$ ± SD (µM) |
|---|---|---|---|---|
| 27 | phenyl | —H | >100 | >25 |
| 29 | 4-Br-C$_6$H$_4$ | S-CH$_2$-C(O)-OCH$_3$ | 18.58 ± 4.93 | 5.08 ± 1.35 |
| 30 | 4-Br-C$_6$H$_4$ | S-butyl | >100 | >25 |
| 32 | 4-Br-C$_6$H$_4$ | (CH$_2$)$_4$-OH | 8.01 ± 3.31 | 2.18 ± 0.91 |

TABLE 4-continued

Binding Affinities of analogs with variations at *** and R₂.

| Compound | R₂ | *** | Mcl-1 IC₅₀ ± SD (μM) | K$_i$ ± SD (μM) |
|---|---|---|---|---|
| 33 | 4-Br-phenyl | -S-CH₂-C(=O)-NH₂ | 6.27 ± 1.28 | 1.71 ± 0.35 |
| 34 | 2-naphthyl | -S-CH₂CH₂-C(=O)-OH | 4.20 ± 1.25 | 1.13 ± 0.34 |
| 35 | 1-naphthyl | -S-CH₂CH₂-C(=O)-OH | >50 | >12.5 |

TABLE 5

Binding Affinities of analogs with variations at ZZ, R2 and ***.

| Compound | R2 | *** | ZZ | Mcl-1 IC₅₀ ± SD (μM) | K$_i$ ± SD (μM) |
|---|---|---|---|---|---|
| 40d | 4-Br-phenyl | -S-CH₂-C(=O)-OCH₃ | —OCH₃ | >800 | >200 |
| 36 | 4-Br-phenyl | -S-CH₂-C(=O)-OH | —OCH₃ | 316.88 ± 55.90 | 86.98 ± 15.35 |

TABLE 5-continued

Binding Affinities of analogs with variations at ZZ, R2 and ***.

| Compound | R2 | *** | ZZ | Mcl-1 IC$_{50}$ ± SD (µM) | K$_i$ ± SD (µM) |
|---|---|---|---|---|---|
| 40p | -C$_6$H$_4$-Br (para) | -S-butyl | —OCH$_3$ | >800 | >200 |
| 4v | -C$_6$H$_4$-Br (para) | -S-CH$_2$-C(=O)-NH$_2$ | —OCH$_3$ | >100 | >25 |

TABLE 6

Selectivity of selected analogs against all Bcl-2 anti-apoptotic proteins

| Compound | Mcl-1 K$_i$ ± SD (µM) | A1/Bfl-1 K$_i$ ± SD (µM) | Bcl-2 K$_i$ ± SD (µM) | Bcl-w K$_i$ ± SD (µM) | Bcl-x$_L$ K$_i$ ± SD (µM) |
|---|---|---|---|---|---|
| 1 (UMI-59) | 1.55 ± 0.18 | 6.14 ± 1.0 | 54.65 ± 9.56 | 37.53 ± 7.96 | 99.0 ± 22.63 |
| 9 (UMI-79) | 0.49 ± 0.06 | 5.33 ± 1.0 | 23.83 ± 1.81 | 8.19 ± 1.91 | 32.99 ± 4.33 |
| 14 | 0.37 ± 0.1 | 2.34 ± 0.37 | 8.82 ± 0.65 | 1.92 ± 0.37 | 8.05 ± 0.5 |
| 15 | 0.38 ± 0.03 | 3.18 ± 0.41 | 7.85 ± 0.65 | 2.19 ± 0.45 | 15.14 ± 1.11 |
| 18 | 0.18 ± 0.05 | 3.36 ± 0.56 | 7.56 ± 1.08 | 1.58 ± 0.35 | 10.58 ± 1.53 |
| 17 | 0.17 ± 0.04 | 1.11 ± 0.19 | 6.11 ± 0.65 | 1.36 ± 0.51 | 9.59 ± 1.28 |
| 16 | 2.03 ± 0.41 | 17.26 ± 0.56 | 23.84 ± 3.16 | 4.41 ± 0.39 | 48.15 ± 3.28 |
| 29 | 5.08 ± 1.35 | >140 | 23.77 ± 5.08 | >90 | >130 |
| 22 | >200 | >140 | >200 | >90 | >130 |

Structure-Activity Relationship.

Structure-based design of analogues based on 1 (UMI-59) yielded a focused library of compounds for which SAR was established using the FP based assay. The binding of new compounds to Mcl-1 protein were further evaluated using $^1$H,$^{15}$N—HSQC NMR studies. Modeling showed that the thiophene ring of 1 (UMI-59) projects into the h2 pocket, which is the biggest and deepest pocket among the four hydrophobic pockets of Mcl-1 (see, e.g., Czabotar, P. E.; Lee, E. F.; van Delft, M. F.; Day, C. L.; Smith, B. J.; Huang, D. C.; Fairlie, W. D.; Hinds, M. G.; Colman, P. M. Structural insights into the degradation of Mcl-1 induced by BH3 domains. Proc Natl Acad Sci USA 2007, 104, 6217-22; herein incorporated by reference in its entirety^) and should be able to accommodate bulkier hydrophobic groups. To take advantage of further hydrophobic interactions and increase the binding affinity of 1, a series of analogues was synthesized to replace the thiophene ring with larger hydrophobic groups. Their structures and inhibition against Mcl-1 are shown in Table 2. When R$_1$ is changed to a larger phenyl ring 2, the binding affinity was similar Alkyl and halogen substituents of various sizes at the para-position of the phenyl ring were tolerated, and the binding affinity to Mcl-1 was improved with increasing the size of the alkyl or halogen group. Analogue 6 with the para-tert-butyl phenyl exhibited 4-fold and 9 (UMI-77) with para-bromo phenyl 7-fold improved binding over 2. Substitution of bromine at the meta- and the ortho-positions of the phenyl ring was also explored and the binding results indicated that para-bromo substitution is best exhibiting the highest binding affinity to Mcl-1 amongst these three isomers. To improve the quality and the accuracy of the identified chemical shifts by NMR studies, 3D experiments using $^{13}$C,$^{15}$N-Mcl-1 labeled protein in the presence of 2-fold excess of 9 (UMI-77) were performed. Consistent with the predicted binding model, the HSQC NMR experiments of the complex between 9 and Mcl-1 showed significant chemical shift perturbations of Met 231, Met 250, Val 253, Leu 267 and Phe 270, attributing to the predicted hydrophobic interaction with the 4-bromophenyl group which inserts into the h2 pocket. The h3 pocket is mainly constituted by the residues of His 224, Phe 228, Met 231, which are on the rim of h2 and h3 pockets, and Val220, on the rim of h3 and h4 pockets. NMR studies showed that Met 231, Val 220 and Phe 228 have significant chemical shift perturbations, as well as His 224 confirming the predicted hydrophobic and electrostatic interactions of 9 in the h3 pocket of the Mcl-1 protein. Recent reported study about the conformational flexibility of Mcl-1 and its binding hotspots identified His 224 as an acidic hotspot in the h3 site of Mcl-1, further supporting the findings that 4-hydroxyl group in the naphthalenyl ring forms a hydrogen bond with His 224. Chemical shift plots derived from $^1H,^{15}N$—HSQC experiments of the other two bromophenyl isomers showed a similar perturbation pattern as 9 (FIG. 14 A-F). However, consistent with the binding data, the strongest perturbation is observed for 9 (UMI-77) followed by 10 and 11. In addition, significant perturbation of residues located toward the C-terminus of the helix α2, which compose the h3 pocket and its neighboring residues, was observed for 9 (UMI-77) and 10 suggesting Mcl-1 conformational flexibility as it accommodates larger $R_1$ substituent into the h2 pocket.

Analogue 13, with fused rings at $R_1$ which model well into the h2 pocket, displayed 5-fold better binding than the corresponding monocyclic analogue, 2, reflecting the large and hydrophobic nature of the h2 pocket.

To further extent into the h2 pocket and gain additional interaction, analogues with biphenyl substituents were synthesized because biphenyl is considered to be a privileged moiety in targeting protein-protein interactions (see, e.g., Hajduk, P. J.; Bures, M.; Praestgaard, J.; Fesik, S. W. Privileged molecules for protein binding identified from NMR-based screening. Journal of Medicinal Chemistry 2000, 43, 3443-3447; herein incorporated by reference in its entirety^). Analogues 14, and 15, with para-, and meta-biphenyl substituents showed similar 9-fold improvement in binding compared to 2, while the ortho-biphenyl analogue, 16 showed only 2-fold increase in binding. The predicted binding models of these compounds showed that the second phenyl ring of 14 and 15 inserts and fits deeper into the h2 pocket (FIGS. 15D and 15E). For 16, this phenyl ring is partially solvent exposed (FIG. 15F) which might explain its lower affinity compared to 14 and 15. In agreement with their binding affinities, $^1H,^{15}N$—HSQC studies of 14 and 15 show stronger perturbation of residues involved in the binding site compared to 16 (FIG. 15A-C). In addition, different direction of the chemical shifts of the residues forming h2 pocket (Phe 270, Met 250) or in its vicinity (Phe 228) as well as residues located on α-helix 4, which forms the upper rim of the h2 pocket, (Val 249, Val 253), were identified by these three analogues (FIG. 16A-D). These results further confirm that the projection of $R_1$ group being toward the h2 pocket and highlight the flexibility of this pocket in accommodating these large biphenyl moieties at $R_1$. The results are consistent with a recently published report (see, e.g., Yang, C.-Y.; Wang, S. Analysis of Flexibility and Hotspots in Bcl-xL and Mcl-1 Proteins for the Design of Selective Small-Molecule Inhibitors. ACS Medicinal Chemistry Letters 2012; herein incorporated by reference in its entirety^) which identifies α-helix 4 as the most flexible helix of Mcl-1. Analogues 17 and 18 with para-chlorobiphenyl and para-phenoxyphenyl substituents at $R_1$ showed an overall improved binding of around 19-fold compared to 2, being the most potent analogues in the series with an $IC_{50}$ of 680 nM and 740 nM, respectively. HSQC spectra of 17 and 18 showed a similar shift pattern to 14 suggesting a similar binding conformation. Additionally compound 20 with para-benzoic acid showed similar binding affinity as 2 ($IC_{50}$=17.42 μM) demonstrating that the h2 pocket of Mcl-1 is also tolerant of polar groups.

FIG. 23 shows (A) Slices of overlaid $^{15}N$—$^1H$ HSQC spectra of Mcl-1 (greyish-red), and in presence of 18 (Mcl-1:18 ratio of 1 to 2) (black), (Mcl-1:1 ratio of 1 to 1) (greyish-purple). The arrows show the direction of chemical shift changes upon binding of 18. (B) Plot of chemical shift changes calculated as $((\Delta^1H\ Hz)^2+(\Delta^{15}N\ Hz)^2)^{0.5}$ of Mcl-1 amide upon addition of 18 (Mcl-1:18 ratio of 1 to 2) as a function of Mcl-1 residue numbers.

FIG. 24 shows plot of chemical shift changes calculated as $((\Delta^1H\ Hz)^2+(\Delta^{15}N\ Hz)^2)^{0.5}$ of Mcl-1 amide upon addition of 17 (Mcl-1:17 ratio of 1 to 2).

It has been demonstrated that the conserved hydrophobic interactions between BH3-domain of the pro-apoptotic proteins are critical for their interactions with the anti-apoptotic proteins. The binding and NMR studies clearly demonstrate that sulfonamido-1-hydroxynaphthalene scaffold substituted with hydrophobic bulky moieties mimic two critical hydrophobic interactions. To further confirm these findings compounds 21 and 22 were synthesized. Changing $R_1$ to a methyl group in 21 or contracting the naphthalene core of 1 to phenyl as in 22 showed to be detrimental to binding Mcl-1. A lack of observed binding up to 200 μM which was confirmed with NMR studies where the chemical shifts of Mcl-1 protein were not detected in the presence of these two compounds. These results confirmed the importance of hydrophobic interactions at h2 and h3 pockets to the overall Mcl-1 binding.

FIG. 25 shows a plot of chemical shift changes calculated as $((\Delta^1H\ Hz)^2+(\Delta^{15}N\ HZ)^2)^{0.5}$ of Mcl-1 amide upon addition of 21 (Mcl-1:21 ratio of 1 to 2).

FIG. 26 shows a plot of chemical shift changes calculated as $((\Delta^1H\ Hz)^2+(\Delta^{15}N\ HZ)^2)^{0.5}$ of Mcl-1 amide upon addition of 22 (Mcl-1:22 ratio of 1 to 2).

Modeling suggested that the sulfonamide linker in this class of compounds lacks any specific interactions with Mcl-1. It was hypothesized that this group is important for proper directions of the $R_1$ substituent toward h2 pocket. Several compounds were synthesized in order to probe the importance of the linker (Table 3). When sulfonamide linker was replaced with amide in 23 and 24, the binding to Mcl-1 was abolished, which was also confirmed by NMR studies (FIG. 17). This result suggested that the amide linker orients the scaffold in a conformation not favorable in binding to Mcl-1. To explore the impact of the flexibility of the linker, compound 25 was synthesized where a methylene linker was inserted between the sulfonamide and 4-chlorophenyl ring. 25 showed 6-fold decreased in the binding in comparison with the corresponding compound 8. Replacement of sulfonamide (25 with amide 26) decreased the binding as was expected based on previous results, but not to the same extent as 9 (UMI-77) vs 23 possibly due to the higher conformational mobility of the $R_1$ substituent of 26.

To further explore the thioacetic acid side chain at $R_2$, analogues with different substituents at this position were synthesized (Table 4). Removal of the acid side chain in 27 abolished binding as expected since modeling has predicted that the acid mimics the conserved Asp residue of BH3-only peptides. Evaluation of this compound in HSQC NMR (FIG. 18) further confirmed the results in which little to no shift of Mcl-1 residues were present at a 2:1 ratio (27:Mcl-1) and only flexible residues were moderately shifted. Therefore, to further explore this site, analogues with different substituents at $R_2$ were synthesized. Modeling has shown that the thioacetic acid moiety mimics the conserved Asp of BH3-only peptides and is able to form hydrogen bonds with Asn 260 and Arg 263 of Mcl-1. Replacement of thioacetic acid with thiobutyl in compound 30 abolished the binding to Mcl-1 protein. Replacing the carboxylic acid function of 9 (UMI-77) with a methyl ester 29, or an amide 33 resulted in decreased binding by 3 to 10-fold (Table 4), consistent with each of these forming a weaker hydrogen bond with Arg 263 compared to the carboxylic acid. Chemical shift plots of 29 (FIG. 19) and 33 (FIG. 20) showed only moderate perturbation of residues in the binding site. When the thioacetic acid of 9 was replaced by butan-1-ol in 32, the binding was only 4-fold decreased indicating that butan-1-ol side chain can form the necessary interaction. Extending the thioacetic acid (34) to thiopropanoic acid 13 had no detrimental effect on binding and even slightly improved it. This can be attributed to the flexibility of both the thiopropanoic acid and Arg 263 moieties. However, changing the point of fusion of the naphthalene ring of 34 substantially affected the binding with 1-naphthyl analogue (35) showing no binding up to 50 μM. Docking studies suggest that this can be attributed to a clash with the residues in h2 pocket of Mcl-1.

Modeling showed that the phenolic group at $R_3$ forms a hydrogen bond with His 224 of Mcl-1. This prediction is consistent with a report identifying an acidic hotspot close to His 224 through cosolvent simulations (see, e.g., Yang, C.-Y.; Wang, S. Analysis of Flexibility and Hotspots in Bcl-xL and Mcl-1 Proteins for the Design of Selective Small-Molecule Inhibitors. ACS Medicinal Chemistry Letters 2012; herein incorporated by reference in its entirety^). Table 5 focuses on the contribution of this group to the binding to Mcl-1. Analogues 40d and 40p where $R_2$ is methyl thioacetate or thiobutane and $R_3$ is a methoxy group showed no binding to Mcl-1 even at 800 μM. These results were confirmed with HSQC studies of 40d which showed no binding to Mcl-1 (FIG. 21). When $R_2$ was changed to the thioacetic acid group in 36, the binding improved compared to 40d; however, it is still a significant 170-fold decrease compared to phenolic 9 (UMI=77). The same loss of binding is apparent in 4v compared to its corresponding phenolic analogue (33).

The core scaffold of this class of analogues is prone to oxidation over time to a quinone imine-type structure. While differences in the binding/NMR data was not observed using old or freshly prepared stocks, identification of a few compounds represented by 48 (FIG. 22) as Mcl-1 inhibitors in an HTS performed were detected. Fresh powder of 48 was purchased and tested in an FP-based assay, and it's binding to Mcl-1 was confirmed. HSQC studies of this compound in 2:1 ratio (48:Mcl-1) (FIG. 22) showed very similar shift patterns to other analogues with a substituted phenyl ring at $R_1$ further confining its binding to Mcl-1.

Selectivity Profile Against Anti-Apoptotic Members of Bcl-2 Family.

To determine the selectivity of this class of compounds against the other four Bcl-2 anti-apoptotic proteins (Bcl-2, Bcl-$x_L$, Bcl-w, A1), the most potent analogues were tested in competitive FP based assays optimized for each protein and $K_i$ values were calculated using equations developed previously (Table 6). In general, all the analogues inhibit Mcl-1 most potently and the order of the shown selectively was A1>Bcl-w>Bcl-2>Bcl-$x_L$. Inhibition of A1 with less selectivity is expected as this protein shares a high percentage sequence similarity with Mcl-1. The most potent analogue in this series, 17, showed a selective profile inhibiting Mcl-1 with 7-fold selectivity against A1, 8-fold against Bcl-w, 36-fold against Bcl-2, and 56-fold against Bcl-$x_L$.

Experimental Section

1. Chemistry Materials and Methods.

All reagents were commercially available and used without further purification. Thin-layer chromatography (TLC) was conducted with silica gel UV254 pre-coated plates (0.25 mm), and visualized using UV lamps. Silica gel (particle size 40-63 μm) was used for flash chromatography. $^1$H and $^{13}$C NMR spectra were obtained on Bruker 500 MHz spectrometers with CDCl$_3$ or d$_6$-DMSO as solvent and chemical shifts are reported relative to the residual solvent peak in δ (ppm). Mass spectrometry analysis was performed using a Waters LCT time-of-flight mass spectrometry instrument. High resolution mass spectrum etry (HRMS) analysis was performed on an Agilent Q-TOF system. Purities of final compounds were assessed by analytical HPLC performed on a Shimadzu system with a Restek Ultra C18 (4.6×150 mm, 5 mm particle size) column and a gradient of acetonitrile with 0.1 vol % TFA (10-90%) in water with 0.1 vol % TFA. Semipreparative HPLC was performed on a Shimadzu system with a Restek Ultra C18 (21.2×150 mm, 5 mm particle size) column.

2-Iodo-1-methoxy-4-nitronaphthalene (38)

A mixture of commercially available 1-methoxy-4-nitronaphthalene (2.1 g, 10.4 mmol), N-iodosuccinimide (2.7 g, 12 mmol) in TFA (40 mL) was heated to reflux and stirred for 20 h under a N$_2$ atmosphere. The reaction mixture was diluted with EtOAc (40 mL), washed with saturated aqueous Na$_2$S$_2$O$_3$ solution (30 mL), saturated aqueous NaHCO$_3$ (30 mL×2), and brine (30 mL). The organic layer was dried (MgSO$_4$), filtered and silica was added to filtrate and the solvent was removed under reduced pressure. The adsorbed crude residue was purified by flash column chromatography (100% hexane) on silica gel to give 38 (2.4 g, 70%) as a light yellow solid. $^1$H NMR (400 MHz, CDCl$_3$) δ 8.59 (s, 1H), 8.58 (s, 1H), 8.21 (d, J=8.42 Hz, 1H), 7.74 (t, J=7.53 Hz, 1H), 7.65 (t, J=7.53 Hz, 1H), 4.03 (s, 3H); $^{13}$C NMR (100 MHz, CDCl$_3$) δ 161.69, 142.85, 134.07, 129.99, 128.55, 128.08, 126.55, 123.92, 123.02, 83.35, 62.20; ESI MS: m/z 330.0 (M+H)$^+$. Note: R$_f$ of starting material and product are very close and a good separation is achieved with a relatively long silica gel column and 100% hexane gradient. >95% pure product is needed for pd-catalyzed coupling step.

2-Iodo-1-methoxy-4-nitrobenzene (45)

To a stirred solution of commercially available iodoanisole (1 mL, 7.7 mmol) in AcOH (2 mL) was added fuming nitric acid (0.8 mL, 17 mmol) dropwise at 0° C. The mixture was let to warm up to rt and then heated up to 50° C. and stirred for 1 h under a N$_2$ atmosphere when the color of the mixture became dark red/orange. Solid precipitate formed on cooling which was collected by filtration. Solid was washed with a 4:1 mixture of EtOH:H$_2$O (10 mL) and dried on high vacuum to give 45 (1.2 g, 56%) as a light orange solid. $^1$H NMR (400 MHz, CDCl$_3$) δ 8.66 (s, 1H), 8.24 (d, J=8.88 Hz, 1H), 6.85 (d, J=8.88 Hz, 1H), 3.98 (s, 3H); $^{13}$C NMR (100 MHz, CDCl$_3$) δ 163.01, 141.88, 135.10, 125.69, 109.56, 85.13, 57.13; ESI MS: m/z 279.8 (M+H)$^+$.

Methyl 2-((1-methoxy-4-nitronaphthalen-2-yl)thio) acetate (39a)

To a solution of Cs$_2$CO$_3$ (1.5 g, 4.5 mmol) in dry THF (7 mL) under a N$_2$ atmosphere was added methylthioglycolate (277 mL, 2.9 mmol). The mixture was stirred at rt for 10 min. At this time, a solution of ZnCl$_2$ (288 mg, 2.1 mmol) in dry THF (3 mL) was added and the mixture was stirred at rt for an additional 10 min. In a separate flask Pd(OAc)$_2$ (36 mg, 0.16 mmol) and xantphos (90 mg, 0.15 mmol) were premixed in dry THF (5 mL) under a N$_2$ atmosphere and stirred at rt for about 30 min. To the solution of thiol, Cs$_2$CO$_3$, and ZnCl$_2$ was added 38 (1.0 g, 3.1 mmol), LiI (200 mg, 1.5 mmol) and premixed solution of the catalyst and ligand. The mixture was stirred at 60° C. under a N$_2$ atmosphere for 20 h. The reaction mixture was filtered to remove Cs$_2$CO$_3$ and silica was added to the mixture and the solvent was removed under reduced pressure. The adsorbed crude residue was purified by column chromatography (hexane/EtOAc 4:1) on silica gel to give 39a (606 mg, 66%) as a yellow oil which solidified. $^1$H NMR (400 MHz, CDCl$_3$) δ 8.59 (d, J=8.50 Hz, 1H), 8.37 (s, 1H), 8.19 (d, J=8.50 Hz, 1H), 7.70 (t, J=7.57 Hz, 1H), 7.64 (t, J=7.57 Hz, 1H), 4.07 (s, 3H), 3.77 (s, 2H), 3.70 (s, 3H); $^{13}$C NMR (100 MHz, CDCl$_3$) δ 169.48, 159.95, 142.50, 129.73, 128.88, 127.85, 127.22, 125.94, 123.71, 122.93, 122.68, 61.92, 52.72, 35.10; ESI MS: m/z 308.1 (M+H)$^+$.

Butyl(1-methoxy-4-nitronaphthalen-2-yl)sulfane (39b)

A stirred mixture of 38 (300 mg, 0.91 mmol), Pd$_2$(dba)$_3$ (42 mg, 0.05 mmol), dppf (104 mg, 0.18 mmol) and Et$_3$N (0.2 mL) in dry NMP (7 mL) was flushed with N$_2$ for 15 min at rt. Butanethiol (83 μL, 0.77 mmol) was then added and the reaction mixture was heated to 80° C. and stirred for 2-3 h. The mixture was diluted with EtOAC (10 mL) and washed with H$_2$O (10 mL×4) and brine (10 mL). The organic layer was dried (MgSO$_4$), filtered and silica was added to the filtrate and the solvent was removed under reduced pressure. The adsorbed crude residue was purified by flash column chromatography (100% hexane) on silica gel to give 39b (189 mg, 71%) as a yellow oil. $^1$H NMR (400 MHz, CDCl$_3$) δ 8.58 (ddd, J=0.72, 1.50, 8.36 Hz, 1H), 8.26 (s, 1H), 8.16 (ddd, J=0.72, 1.50, 8.36 Hz, 1H), 7.68-7.59 (m, 2H), 4.03 (s, 3H), 3.03 (t, J=7.36 Hz, 2H), 1.67 (p, J=7.36 Hz, 2H), 1.48 (h, J=7.36 Hz, 2H), 0.93 (t, J=7.36 Hz, 3H); $^{13}$C NMR (100 MHz, CDCl$_3$) δ 158.48, 142.53, 129.05, 128.81, 127.69, 125.69, 125.57, 125.03, 123.62, 122.34, 61.31, 32.23, 31.10, 21.92, 13.60; ESI MS: m/z 292.0 (M+H)$^+$.

2-((1-Methoxy-4-nitronaphthalen-2-yl)thio)ethanol (39c)

Synthesized using a similar procedure used to prepare 39b except using 2-mercaptoethanol. Crude was subjected to flash column chromatography (hexane/EtOAc 85:15) on silica gel to afford 39c (195 mg, 58%) as a yellow oil. $^1$H NMR (400 MHz, CDCl$_3$) δ 8.57 (d, J=8.64 Hz, 1H), 8.34 (s, 1H), 8.18 (d, J=8.64 Hz, 1H), 7.72-7.66 (m, 1H), 7.66-7.61 (m, 1H), 4.07 (s, 3H), 3.75 (t, J=5.85 Hz, 2H), 3.19 (t, J=5.85 Hz, 2H); $^{13}$C NMR (100 MHz, CDCl$_3$) δ 160.42, 142.63, 129.69, 128.87, 127.92, 127.72, 125.82, 123.67, 123.09, 122.65, 62.15, 60.50, 36.81. ESI MS: m/z 279.9 (M+H)$^+$, 301.9 (M+Na)$^+$.

4-(1-Methoxy-4-nitronaphthalen-2-yl)but-3-yn-1-ol (39d)

A mixture of 38 (504 mg, 1.5 mmol), Pd(PPh$_3$)$_2$Cl2 (55 mg, 0.08 mmol), and copper(I) iodide (28 mg, 0.15 mmol) in Et$_3$N (9 mL) and dry THF (3 mL) was added dropwise to a solution of 3-butyn-1-ol (0.22 mL, 2.9 mmol) in Et$_3$N (3 mL) under a N$_2$ atmosphere at rt. Reaction mixture was heated to 60° C. and stirred for 1-2 h then diluted with EtOAc (10 mL) and washed with saturated aqueous NH$_4$Cl (15 mL×2) and brine (15 mL). The organic layer was dried (MgSO$_4$), filtered, concentrated under reduced pressure. The crude was purified by flash column chromatography (hexane/EtOAc 3:2) on silica gel to give 39d (338 mg, 83%) as a yellow solid. $^1$H NMR (400 MHz, CDCl$_3$) δ 8.53 (d, J=8.56 Hz, 1H), 8.23 (s, 1H), 8.19 (d, J=8.56 Hz, 1H), 7.63 (t, J=7.59 Hz, 1H), 7.53 (t, J=7.59 Hz, 1H), 4.23 (s, 3H), 3.87 (t, J=6.14 Hz, 2H), 2.76 (t, J=6.14 Hz, 2H), 2.45 (s, 1H); $^{13}$C NMR (100 MHz, CDCl$_3$) δ 162.29, 141.11, 130.19, 129.91, 128.36, 127.48, 126.03, 123.43, 123.10, 109.99, 108.73, 93.90, 61.77, 60.96, 24.07; ESI MS: m/z 272.1 (M+H)$^+$.

Methyl 3-((1-methoxy-4-nitronaphthalen-2-yl)thio) propanoate (39e)

Synthesized using a similar procedure used to prepare 39a except using methyl 3-mercaptopropionate. The mixture was stirred at 60° C. under a N$_2$ atmosphere for 5 h. Crude was purified using flash column chromatography (hexane/EtOAc 4:1) on silica gel to give 39e (194 mg, 66%) as a yellow oil. $^1$H NMR (400 MHz, CDCl$_3$) δ 8.56 (d, J=8.48 Hz, 1H), 8.27 (s, 1H), 8.16 (d, J=8.48 Hz, 1H), 7.70-7.64 (m, 1H), 7.64-7.58 (m, 1H), 4.03 (s, 3H), 3.65 (s, 3H), 3.28 (t, J=7.24 Hz, 2H), 2.65 (t, J=7.24 Hz, 2H); $^{13}$C NMR (100 MHz, CDCl$_3$) δ 171.64, 159.79, 142.48, 129.51, 128.93, 127.81, 126.94, 125.60, 123.62, 123.45, 122.57, 61.59, 51.90, 34.11, 28.11; ESI MS: m/z 322.0 (M+H)$^+$, 343.9 (M+Na)$^+$.

Methyl 2-((2-methoxy-5-nitrophenyl)thio)acetate (46)

Synthesized using a similar procedure used to prepare 39a except using 45 as the aryl iodide. The mixture was stirred at 60° C. under a N$_2$ atmosphere for 6 h. Crude was purified by flash column chromatography (hexane/EtOAc 85:15) on silica gel to give 46 (178 mg, 63%) as a light yellow solid. $^1$H NMR (400 MHz, CDCl$_3$) δ 8.20 (d, J=2.70 Hz, 1H), 8.12 (dd, J=2.70, 9.0 Hz, 1H), 6.90 (d, J=9.0 Hz, 1H), 3.98 (s, 3H), 3.72 (s, 3H), 3.69 (s, 2H); $^{13}$C NMR (100 MHz, CDCl$_3$) δ 169.36, 161.83, 141.62, 125.41, 124.74, 124.07, 109.73, 56.65, 52.71, 33.99; ESI MS: m/z 279.9 (M+Na)$^+$.

A Representative Procedure for Reduction of Nitro to Amine and Subsequent Sulfonamide Coupling Reaction of Aryl Amines with Sulfonyl Chlorides Methyl 2-((1-methoxy-4-(thiophene-2-sulfonamido) naphthalen-2-yl)thio)acetate (40a)

To a suspension of iron powder (538 mg, 9.6 mmol) in acetic acid (5 mL) was added 39a (195 mg, 0.63 mmol) dissolved in glacial acetic acid (5 mL). The mixture was stirred at 70° C. under a N$_2$ atmosphere for 1 h until the mixture turned milky. The mixture was then diluted with EtOAc (15 mL) and washed with saturated aqueous NaHCO$_3$ (20 mL×2) and brine (20 mL). Organic layer was dried (MgSO$_4$) and the solvent was removed under reduced pressure. Crude (a purple oil) was used in the next step without further purification. $^1$H NMR (400 MHz, CDCl$_3$) δ 8.03 (d, J=8.29 Hz, 1H), 7.76 (d, J=8.29 Hz, 1H), 7.50 (t, J=7.58 Hz, 1H), 7.43 (t, J=7.58 Hz, 1H), 6.78 (s, 1H), 3.91 (s, 3H), 3.73 (s, 2H), 3.68 (s, 3H); $^{13}$C NMR (100 MHz, CDCl₃) δ 170.48, 147.81, 138.68, 128.54, 126.54, 125.33, 124.24, 123.36, 122.45, 121.35, 111.08, 61.41, 52.53, 35.37; ESI MS: m/z 278.1 (M+H)⁺.

A solution of the crude amine dissolved in dry CH₂Cl₂ (4 mL) was added to 2-thiophenesulfonyl chloride (119 mg, 0.65 mmol). Addition of pyridine (0.08 mL, 0.99 mmol) was followed and the mixture was stirred at rt under a N₂ atmosphere overnight. The mixture was diluted with EtOAc (10 mL) and washed with H₂O (10 mL×3) and brine (10 mL). The organic layer was dried (MgSO₄), filtered and the solvent was removed under reduced pressure. Crude was purified by flash column chromatography (hexane/EtOAc 7:3) on silica gel to give 40a (176 mg, 66% over two steps) as a purple oil which solidified upon standing. ¹H NMR (400 MHz, CDCl₃) δ 8.01 (d, J=8.40 Hz, 1H), 7.82 (d, J=8.40 Hz, 1H), 7.49-7.43 (m, 2H), 7.42-7.39 (m, 1H), 7.39-7.34 (m, 2H), 6.92-6.88 (m, 1H), 3.95 (s, 3H), 3.68 (s, 3H), 3.65 (s, 2H); ¹³C NMR (100 MHz, CDCl₃) δ 169.91, 154.12, 139.48, 133.09, 132.51, 130.06, 128.60, 127.74, 127.39, 126.96, 125.74, 123.39, 122.29, 61.49, 52.68, 35.12; ESI MS: m/z 423.9 (M+H)⁺, 445.8 (M+Na)⁺.

Methyl 2-((1-methoxy-4-(phenylsulfonamido)naphthalen-2-yl)thio)acetate (40b)

Synthesized using the procedure for 40a except using benzenesulfonyl chloride, which afforded the title compound (119 mg, 64% over two steps) as a purple oil which solidified upon standing. ¹H NMR (400 MHz, CDCl₃) δ 8.01 (d, J=8.40 Hz, 1H), 7.74 (t, J=9.06 Hz, 3H), 7.47 (q, J=8.19, 8.80 Hz, 2H), 7.36 (t, J=7.61 Hz, 3H), 7.29 (s, 1H), 6.93 (s, 1H), 3.95 (s, 3H), 3.68 (s, 3H), 3.61 (s, 2H); ¹³C NMR (100 MHz, CDCl₃) δ 169.80, 154.02, 139.11, 132.95, 129.95, 128.98, 128.63, 127.82, 127.33, 126.95, 126.90, 125.67, 123.36, 122.31, 122.28, 61.49, 52.63, 35.06; ESI MS: m/z 417.9 (M+H)⁺, 439.9 (M+Na)⁺.

Methyl 2-((4-(4-chlorophenylsulfonamido)-1-methoxynaphthalen-2-yl)thio)acetate (40c)

Synthesized using the procedure for 40a except using 4-chlorobenzenesulfonyl chloride, which afforded the title compound (280 mg, 67% over two steps) as a light pink solid. ¹H NMR (400 MHz, CDCl₃) δ 8.02 (d, J=8.40 Hz, 1H), 7.74 (d, J=8.40 Hz, 1H), 7.66 (t, J=1.96 Hz, 1H), 7.65 (t, J=1.96 Hz, 1H), 7.47 (ddd, J=1.17, 6.86, 8.24 Hz, 1H), 7.38 (ddd, J=1.17, 6.86, 8.24 Hz, 1H), 7.35-7.33 (m, 2H), 7.32 (t, J=1.94 Hz, 1H), 7.07 (s, 1H), 3.95 (s, 3H), 3.69 (s, 3H), 3.63 (s, 2H); ¹³C NMR (100 MHz, CDCl₃) δ 169.84, 154.18, 139.50, 137.67, 129.86, 129.25, 128.78, 128.66, 127.49, 127.05, 125.81, 123.42, 122.41, 122.14, 61.50, 52.64, 35.02; ESI MS: m/z 451.9 (M+H)⁺, 473.8 (M+Na)⁺.

Methyl 2-((4-(4-bromophenylsulfonamido)-1-methoxynaphthalen-2-yl)thio)acetate (40d)

Synthesized using the procedure for 40a except using 4-bromobenzenesulfonyl chloride, which afforded the title compound (185 mg, 61% over two steps) as a pink/purple solid. 97% pure by HPLC. ¹H NMR (400 MHz, CDCl₃) δ 8.04 (d, J=8.38 Hz, 1H), 7.72 (d, J=8.38 Hz, 1H), 7.61-7.59 (m, 1H), 7.58 (t, J=2.04 Hz, 1H), 7.54-7.47 (m, 3H), 7.44-7.38 (m, 1H), 7.34 (s, 1H), 6.76 (s, 1H), 3.97 (s, 3H), 3.71 (s, 3H), 3.64 (s, 2H); ¹³C NMR (100 MHz, CDCl₃) δ 169.83, 154.25, 138.21, 132.29, 129.91, 128.89, 128.71, 128.07, 127.41, 127.12, 125.92, 123.47, 122.48, 122.17, 122.09, 61.56, 52.70, 35.03; ESI HRMS: m/z 493.9724 (M−H)⁻.

Methyl 2-((4-(3-bromophenylsulfonamido)-1-methoxynaphthalen-2-yl)thio)acetate (40e)

Synthesized using the procedure for 40a except using 3-bromobenzenesulfonyl chloride, which afforded the title compound (331 mg, 78%) as purple/pink solid. ¹H NMR (400 MHz, CDCl₃) δ 8.04 (d, J=8.40 Hz, 1H), 7.88 (s, 1H), 7.73 (d, J=8.40 Hz, 1H), 7.62 (t, J=9.41 Hz, 2H), 7.49 (t, J=7.59 Hz, 1H), 7.40 (t, J=7.59 Hz, 1H), 7.34 (s, 1H), 7.26-7.21 (m, 1H), 6.82 (s, 1H), 3.98 (s, 3H), 3.70 (s, 3H), 3.65 (s, 2H); ¹³C NMR (100 MHz, CDCl₃) δ 169.72, 154.55, 141.06, 135.89, 130.41, 130.24, 130.03, 128.75, 127.31, 127.04, 127.02, 126.33, 125.89, 123.45, 122.90, 122.48, 122.09, 61.48, 52.55, 35.16; ESI MS: m/z 495.8 (M+H)⁺, 417.8 (M+Na)⁺.

Methyl 2-((4-(2-bromophenylsulfonamido)-1-methoxynaphthalen-2-yl)thio)acetate (40f)

Synthesized using the procedure for 40a except using 2-bromobenzenesulfonyl chloride, which afforded the title compound (314 mg, 74% over two steps) as a purple oil. ¹H NMR (400 MHz, CDCl₃) δ 8.16-8.11 (m, 1H), 8.05-8.00 (m, 1H), 7.93 (d, J=7.72 Hz, 1H), 7.78 (d, J=7.72 Hz, 1H), 7.54-7.48 (m, 3H), 7.42-7.32 (m, 2H), 7.19 (s, 1H), 7.13 (s, 1H), 3.94 (s, 3H), 3.68 (s, 3H), 3.49 (s, 2H); ¹³C NMR (100 MHz, CDCl₃) δ 169.52, 154.35, 138.58, 135.17, 133.92, 132.04, 130.52, 128.75, 127.83, 127.55, 127.11, 127.07, 125.00, 123.16, 122.90, 122.26, 119.94, 61.40, 52.50, 35.13; ESI MS: m/z 495.8 (M+H)⁺, 417.8 (M+Na)⁺.

Methyl 2-((4-(benzo[b]thiophene-2-sulfonamido)-1-methoxynaphthalen-2-yl)thio)acetate (40 g)

Synthesized using the procedure for 40a except using 1-benzothiophene-2-sulfonyl chloride, which afforded the title compound (132 mg, 57% over two steps) as a purple oil which solidified upon standing. ¹H NMR (400 MHz, CDCl₃) δ 8.02 (d, J=8.40 Hz, 1H), 7.90 (d, J=8.40 Hz, 1H), 7.79 (d, J=7.99 Hz, 1H), 7.74 (d, J=7.99 Hz, 1H), 7.69 (s, 1H), 7.48-7.42 (m, 2H), 7.41 (s, 1H), 7.40-7.35 (m, 2H), 7.01 (s, 1H), 3.96 (s, 3H), 3.64 (s, 3H), 3.51 (s, 2H); ¹³C NMR (100 MHz, CDCl₃) δ 169.77, 154.23, 141.85, 139.53, 137.38, 130.61, 130.05, 128.66, 127.47, 127.37, 127.06, 125.72, 125.47, 125.44, 123.47, 122.62, 122.34, 122.25, 61.51, 52.58, 34.95; ESI MS: m/z 473.9 (M+H)⁺, 495.8 (M+Na)⁺.

Methyl 2-((4-([1,1'-biphenyl]-4-ylsulfonamido)-1-methoxynaphthalen-2-yl)thio)acetate (40h)

Synthesized using the procedure for 40a except using 4-biphenylsulfonyl chloride, which afforded the title compound (152 mg, 71% over two steps) as a purple oil which solidified upon standing. ¹H NMR (400 MHz, CDCl₃) δ 8.02 (d, J=8.34 Hz, 1H), 7.83-7.76 (m, 3H), 7.58 (d, J=8.31 Hz, 2H), 7.51 (d, J=7.14 Hz, 2H), 7.49-7.42 (m, 2H), 7.42-7.35 (m, 3H), 7.33 (s, 1H), 6.90 (s, 1H), 3.96 (s, 3H), 3.65 (s, 3H), 3.60 (s, 2H); ¹³C NMR (100 MHz, CDCl₃) δ 169.75, 153.99, 145.89, 139.09, 137.68, 129.97, 128.98, 128.66, 128.50, 127.90, 127.86, 127.56, 127.23, 126.98, 126.93, 125.58, 123.43, 122.35, 122.33, 61.49, 52.58, 35.02; ESI MS: m/z 494.1 (M+H)⁺, 516.1 (M+Na)⁺.

Methyl 2-((4-([1,1'-biphenyl]-2-ylsulfonamido)-1-methoxynaphthalen-2-yl)thio)acetate (40i)

Synthesized using the procedure for 40a except using 2-biphenylsulfonyl chloride which was synthesized as previously reported. The title compound (57 mg, 58% over two steps) was obtained as a pink oil. $^1$H NMR (400 MHz, CDCl$_3$) δ 8.16 (d, J=8.20 Hz, 1H), 8.00 (d, J=8.20 Hz, 1H), 7.62 (t, J=7.54 Hz, 1H), 7.51 (q, J=7.13, 7.54 Hz, 3H), 7.44-7.37 (m, 2H), 7.37-7.29 (m, 5H), 6.93 (s, 1H), 5.86 (s, 1H), 3.91 (s, 3H), 3.67 (s, 3H), 3.44 (s, 2H); $^{13}$C NMR (100 MHz, CDCl$_3$) δ 169.66, 152.79, 140.89, 138.72, 138.15, 132.77, 132.73, 129.66, 129.43, 128.59, 128.52, 128.39, 128.20, 128.11, 127.94, 127.07, 126.69, 123.16, 122.20, 122.04, 120.40, 61.44, 52.62, 34.96; ESI MS: m/z 492.1 (M−H)$^−$.

Methyl 2-((4-(4'-chloro-[1,1'-biphenyl]-4-ylsulfonamido)-1-methoxynaphthalen-2-yl)thio)acetate (40j)

Synthesized using the procedure for 40a except using 4'-chlorobiphenyl-4-sulfonyl chloride, which afforded the title compound (284 mg, 80% over two steps) as a pink oil which solidified upon standing. $^1$H NMR (400 MHz, CDCl$_3$) δ 8.02 (d, J=7.14 Hz, 1H), 7.80 (d, J=7.14 Hz, 1H), 7.78 (d, J=7.54 Hz, 2H), 7.54 (d, J=7.54 Hz, 2H), 7.49-7.44 (m, 2H), 7.44-7.40 (m, 3H), 7.40-7.35 (m, 1H), 7.33 (s, 1H), 6.97 (s, 1H), 3.96 (s, 3H), 3.65 (s, 3H), 3.61 (s, 2H); $^{13}$C NMR (100 MHz, CDCl$_3$) δ 169.73, 154.05, 144.56, 138.08, 137.53, 134.79, 129.97, 129.19, 128.67, 128.48, 128.01, 127.80, 127.40, 126.98, 126.93, 125.64, 123.40, 122.35, 122.33, 61.50, 52.60, 35.03; ESI MS: m/z 528.1 (M+H)$^+$, 550.1 (M+Na)$^+$.

Methyl 2-((1-methoxy-4-(4-phenoxyphenylsulfonamido)naphthalen-2-yl)thio)acetate (40k)

Synthesized using the procedure for 40a except using 4-phenoxybenzenesulfonyl chloride, which afforded the title compound (244 mg, 72% over two steps) as a pink/purple oil. $^1$H NMR (400 MHz, CDCl$_3$) δ 8.02 (d, J=8.43 Hz, 1H), 7.80 (d, J=8.43 Hz, 1H), 7.66 (d, J=8.14 Hz, 2H), 7.52-7.46 (m, 1H), 7.42-7.32 (m, 4H), 7.23 (s, 1H), 7.17 (t, J=7.38 Hz, 1H), 6.94 (d, J=8.52 Hz, 2H), 6.87 (d, J=8.52 Hz, 2H), 3.95 (s, 3H), 3.69 (s, 3H), 3.66 (s, 2H); $^{13}$C NMR (100 MHz, CDCl$_3$) δ 169.85, 161.65, 155.11, 153.85, 132.59, 130.09, 129.85, 129.59, 128.60, 128.03, 126.90, 126.85, 125.50, 124.81, 123.42, 122.38, 122.31, 120.02, 117.64, 61.50, 52.67, 35.05; ESI MS: m/z 509.8 (M+H)$^+$.

Methyl 2-((1-methoxy-4-(methylsulfonamido)naphthalen-2-yl)thio)acetate (40l)

Synthesized using the procedure for 40a except using methanesulfonyl chloride, which afforded the title compound (61 mg, 34% over two steps) as a light pink solid. $^1$H NMR (400 MHz, CDCl$_3$) δ 8.13-8.08 (m, 1H), 8.05-8.00 (m, 1H), 7.65 (s, 1H), 7.60-7.54 (m, 2H), 6.80 (s, 1H), 3.99 (s, 3H), 3.75 (s, 2H), 3.69 (s, 3H), 3.04 (s, 3H); $^{13}$C NMR (100 MHz, CDCl$_3$) δ 169.98, 154.06, 129.61, 128.85, 127.84, 127.36, 127.19, 125.15, 123.67, 122.67, 122.07, 61.50, 52.64, 39.91, 35.00; ESI MS: m/z 355.9 (M+H)$^+$, 377.9 (M+Na)$^+$.

Methyl 2-((4-(4-bromobenzamido)-1-methoxynaphthalen-2-yl)thio)acetate (40m)

Synthesized using the procedure for 40a except using 4-bromobenzoyl chloride and Et$_3$N as the base, which afforded the title compound (245 mg, 66%) as a pink solid. $^1$H NMR (400 MHz, CDCl$_3$) δ 8.14 (s, 1H), 8.09 (d, J=8.38 Hz, 1H), 7.88 (s, 1H), 7.82-7.73 (m, 3H), 7.63-7.56 (m, 2H), 7.56-7.43 (m, 2H), 3.98 (s, 3H), 3.74 (s, 2H), 3.68 (s, 3H); $^{13}$C NMR (100 MHz, CDCl$_3$) δ 170.08, 165.42, 153.22, 133.17, 132.01, 131.74, 131.53, 128.82, 128.59, 128.43, 126.80, 126.77, 123.92, 123.50, 122.67, 121.57, 61.45, 52.57, 35.18; ESI MS: m/z 460.0 (M+H)$^+$, 482.0 (M+Na)$^+$.

Methyl 2-((4-((4-chlorophenyl)methylsulfonamido)-1-methoxynaphthalen-2-yl)thio)acetate (40n)

Synthesized using the procedure for 40a except using 4-chlorobenzylsulfonyl chloride, which afforded the title compound (110 mg, 41% over two steps) as a light pink solid. $^1$H NMR (400 MHz, CDCl$_3$) δ 8.10 (d, J=8.31 Hz, 1H), 7.75 (d, J=8.31 Hz, 1H), 7.65 (s, 1H), 7.57 (t, J=7.54 Hz, 1H), 7.50 (t, J=7.54 Hz, 1H), 7.22-7.16 (m, 4H), 6.73 (s, 1H), 4.37 (s, 2H), 4.00 (s, 3H), 3.75 (s, 2H), 3.70 (s, 3H); $^{13}$C NMR (100 MHz, CDCl$_3$) δ 170.00, 153.34, 135.04, 132.09, 128.91, 128.74, 128.31, 127.98, 127.18, 127.08, 126.88, 123.66, 122.67, 122.59, 121.65, 61.55, 57.41, 52.66, 34.96; ESI MS: m/z 465.8 (M+H)$^+$, 487.8 (M+Na)$^+$.

Methyl 2-((4-(2-(4-chlorophenyl)acetamido)-1-methoxynaphthalen-2-yl)thio)acetate (40o)

Synthesized using the procedure for 40a except using 4-chlorophenylacetyl chloride and Et$_3$N as the base, which afforded the title compound (208 mg, 69% over two steps) a light yellow solid. $^1$H NMR (400 MHz, CDCl$_3$) δ 8.05 (d, J=8.34 Hz, 1H), 7.82 (s, 1H), 7.49 (m, 1H), 7.45-7.38 (m, 3H), 7.38-7.32 (m, 3H), 3.94 (s, 3H), 3.82 (s, 2H), 3.73 (s, 2H), 3.67 (s, 3H); $^{13}$C NMR (100 MHz, CDCl$_3$) δ 170.16, 169.79, 153.07, 133.95, 132.72, 130.93, 129.52, 128.47, 128.24, 127.90, 126.80, 126.72, 123.43, 123.32, 122.67, 120.80, 61.41, 52.59, 43.65, 35.14; ESI MS: m/z 429.9 (M+H)$^+$, 451.8 (M+Na)$^+$.

4-Bromo-N-(3-(butylthio)-4-methoxynaphthalen-1-yl)benzenesulfonamide (40p)

Nitro 39b was first converted to the desired amine using the iron reduction procedure described for 39a and the crude was used in the next step without further purification. $^1$H NMR (400 MHz, CDCl$_3$) δ 8.03 (d, J=8.30 Hz, 1H), 7.75 (d, J=8.30 Hz, 1H), 7.49 (t, J=7.42 Hz, 1H), 7.40 (t, J=7.42 Hz, 1H), 6.72 (s, 1H), 3.92 (s, 3H), 2.96 (t, J=7.33 Hz, 2H), 1.65 (p, J=7.33 Hz, 2H), 1.47 (h, J=7.33 Hz, 2H), 0.92 (t, J=7.33 Hz, 3H); $^{13}$C NMR (100 MHz, CDCl$_3$) δ 146.85, 138.46, 128.54, 126.42, 125.50, 124.73, 123.45, 122.20, 121.30, 110.24, 61.02, 32.29, 31.50, 22.02, 13.67; ESI MS: m/z 262.0 (M+H)$^+$.

The title compound was synthesized using the procedure for 40a except using the above amine, and 4-bromobenzenesulfonyl chloride, which afforded 40p (55 mg, 57% over two steps) as a light brown oil which solidified. 96% pure by HPLC. $^1$H NMR (400 MHz, CDCl$_3$) δ 8.01 (d, J=8.44 Hz, 1H), 7.77 (d, J=8.44 Hz, 1H), 7.59 (d, J=8.36 Hz, 2H), 7.49 (d, J=8.36 Hz, 2H), 7.46 (d, J=7.85 Hz, 1H), 7.35 (t, J=7.85 Hz, 1H), 7.21 (s, 1H), 7.16 (s, 1H), 3.94 (s, 3H), 2.81 (t, J=7.24 Hz, 2H), 1.58 (p, J=7.24 Hz, 2H), 1.45 (h, J=7.24 Hz, 2H), 0.92 (t, J=7.24 Hz, 3H); $^{13}$C NMR (100 MHz, CDCl$_3$) δ 152.71, 138.26, 132.23, 128.92, 128.88, 128.65, 127.99, 127.25, 126.93, 126.37, 125.79, 124.49, 122.19, 122.04, 61.01, 31.92, 31.20, 21.95, 13.67; ESI MS: m/z 479.8 (M+H)$^+$.

4-Bromo-N-(3-((2-hydroxyethyl)thio)-4-methoxynaphthalen-1-yl)benzenesulfonamide (40q)

Nitro 39c was first converted to the desired amine using the iron reduction procedure described for 39a and the crude was used in the next step without further purification. $^1$H NMR (400 MHz, CDCl$_3$) δ 8.05 (d, J=8.28 Hz, 1H), 7.76 (d, J=8.28 Hz, 1H), 7.54-7.48 (m, 2H), 7.48-7.42 (m, 2H), 6.80 (s, 1H), 3.95 (s, 3H), 3.65 (t, J=5.66 Hz, 2H), 3.09 (t, J=5.66 Hz, 2H); $^{13}$C NMR (100 MHz, CDCl$_3$) δ 149.23, 138.87, 128.56, 126.54, 125.49, 124.49, 122.63, 122.51, 121.30, 112.67, 61.93, 60.35, 37.39; ESI MS: m/z 250.1 (M+H)$^+$.

The title compound was synthesized using the procedure for 40a except using the above amine and 4-bromobenzenesulfonyl chloride, which afforded 40q (166 mg, 58% over two steps) as a light pink solid. $^1$H NMR (400 MHz, DMSO-d$_6$) δ 10.27 (s, 1H), 7.92 (d, J=8.84 Hz, 2H), 7.72 (d, J=8.56 Hz, 2H), 7.58 (d, J=8.56 Hz, 2H), 7.54-7.48 (m, 1H), 7.43-7.37 (m, 1H), 6.99 (s, 1H), 3.82 (s, 3H), 3.49 (t, J=6.62 Hz, 2H), 2.84 (t, J=6.62 Hz, 2H); $^{13}$C NMR (100 MHz, DMSO-d$_6$) δ 151.96, 139.44, 132.75, 129.62, 129.26, 129.07, 128.41, 127.51, 127.15, 126.35, 125.23, 124.32, 124.13, 121.73, 61.06, 60.24, 34.67; ESI MS: m/z 490.0 (M+Na)$^+$.

4-Bromo-N-(3-(4-hydroxybutyl)-4-methoxynaphthalen-1-yl)benzenesulfonamide (40r)

A stirred solution of 39d (270 mg, 1 mmol) in a mixture of EtOH (12 mL) and EtOAc (2 mL) was hydrogenated in the presence of 10% Pd/C (60 mg) at rt and under 30 psi of H$_2$ overnight. The suspension was filtered through a pad of celite and the filtrate was concentrated under reduced pressure. The crude was used in the next reaction without further purification. $^1$H NMR (400 MHz, CDCl$_3$) δ 7.99 (d, J=8.39 Hz, 1H), 7.72 (d, J=8.39 Hz, 1H), 7.43 (t, J=7.33 Hz, 1H), 7.34 (t, J=7.33 Hz, 1H), 6.52 (s, 1H), 3.79 (s, 3H), 3.56 (t, J=6.43 Hz, 2H), 2.67 (t, J=6.43 Hz, 2H), 1.65 (dt, J=6.60, 14.36 Hz, 2H), 1.56 (dt, J=6.60, 14.36 Hz, 2H). $^{13}$C NMR (100 MHz, CDCl$_3$) δ 145.98, 138.36, 130.77, 128.39, 125.85, 124.33, 123.72, 122.34, 121.36, 111.52, 62.32, 61.97, 32.45, 29.21, 26.89.

The title compound was synthesized using the procedure for 40a except using the above amine and 4-bromobenzenesulfonyl chloride, which afforded 40r (226 mg, 49% over two steps) as a light pink solid. $^1$H NMR (400 MHz, DMSO-d$_6$) δ 10.09 (s, 1H), 7.99-7.91 (m, 2H), 7.70 (d, J=8.43 Hz, 2H), 7.54 (d, J=8.43 Hz, 2H), 7.49 (t, J=7.34 Hz, 1H), 7.40 (t, J=7.34 Hz, 1H), 6.81 (s, 1H), 4.33 (t, J=5.42 Hz, 1H), 3.78 (s, 3H), 3.37 (q, J=5.42 Hz, 2H), 2.59 (t, J=7.01 Hz, 2H), 1.49-1.28 (m, 4H); $^{13}$C NMR (100 MHz, DMSO-d$_6$) δ 152.35, 139.45, 132.62, 130.46, 130.42, 129.33, 128.54, 128.24, 126.97, 126.82, 126.78, 126.02, 124.16, 122.21, 62.36, 60.92, 32.66, 28.85, 26.90; ESI MS: m/z 464.1 (M+H)$^+$, 486.1 (M+Na)$^+$.

Methyl 3-((1-methoxy-4-(naphthalene-2-sulfonamido)naphthalen-2-yl)thio)propanoate (40s)

Nitro 39e was first converted to the desired amine using the iron reduction procedure described for 39a and the crude was used in the next step without further purification. $^1$H NMR (400 MHz, CDCl$_3$) δ 8.02 (d, J=8.36 Hz, 1H), 7.75 (d, J=8.36 Hz, 1H), 7.49 (m, 1H), 7.42 (t, J=7.56 Hz, 1H), 6.72 (s, 1H), 6.26 (s, 2H), 3.89 (s, 3H), 3.65 (s, 3H), 3.22 (t, J=7.46 Hz, 2H), 2.64 (t, J=7.46 Hz, 2H); $^{13}$C NMR (100 MHz, CDCl$_3$) δ 172.38, 147.73, 138.77, 128.63, 126.51, 125.12, 123.92, 123.56, 122.36, 121.35, 110.85, 61.21, 51.78, 34.48, 27.90; ESI MS: m/z 292.0 (M+H)$^+$.

The title compound was synthesized using the procedure for 40a except using the above amine and 2-naphthalenesulfonyl chloride, which afforded 40s (180 mg, 59% over two steps) as a light pink solid. $^1$H NMR (400 MHz, CDCl$_3$) δ 8.30 (s, 1H), 7.98 (d, J=8.39 Hz, 1H), 7.90-7.85 (m, 2H), 7.85-7.80 (m, 2H), 7.80-7.76 (m, 1H), 7.59 (t, J=7.36 Hz, 1H), 7.53 (t, J=7.36 Hz, 1H), 7.43 (t, J=7.39 Hz, 1H), 7.34 (t, J=7.39 Hz, 1H), 7.19 (s, 1H), 6.98 (s, 1H), 3.89 (s, 3H), 3.64 (s, 3H), 2.94 (t, J=7.23 Hz, 2H), 2.40 (t, J=7.23 Hz, 2H); $^{13}$C NMR (100 MHz, CDCl$_3$) δ 171.84, 153.85, 135.99, 134.83, 131.94, 129.66, 129.43, 129.20, 129.02, 128.91, 128.75, 127.82, 127.78, 127.54, 126.95, 126.72, 125.21, 123.73, 122.39, 122.19, 109.99, 61.20, 51.79, 34.05, 27.65; ESI MS: m/z 481.9 (M+H)$^+$, 503.9 (M+Na)$^+$.

Methyl 2-((1-methoxy-4-(2-phenylacetamido)naphthalen-2-yl)thio)acetate (40t)

Synthesized using the procedure for 40m except using phenylacetyl chloride. Crude was triturated with cold CH$_2$Cl$_2$ to yield the title compound (154 mg, 49% over two steps) as a white solid. $^1$H NMR (400 MHz, CDCl$_3$) δ 8.06 (d, J=8.38 Hz, 1H), 7.94 (s, 1H), 7.53-7.44 (m, 4H), 7.40 (q, J=7.27 Hz, 2H), 7.33 (s, 1H), 7.29-7.24 (m, 1H), 3.96 (s, 3H), 3.89 (s, 2H), 3.78 (s, 2H), 3.71 (s, 3H); $^{13}$C NMR (100 MHz, CDCl$_3$) δ 170.10, 169.71, 152.55, 134.54, 129.69, 129.46, 128.70, 128.40, 127.92, 127.64, 126.59, 123.48, 122.57, 122.48, 120.78, 61.40, 52.61, 44.64, 35.16; ESI MS: m/z 396.1 (M+H)$^+$, 418.1 (M+Na)$^+$.

Methyl 2-((4-([1,1'-biphenyl]-3-ylsulfonamido)-1-methoxynaphthalen-2-yl)thio)acetate (40u)

Synthesized using reported literature with modifications. A stirred mixture of 40e (307 mg, 0.62 mmol), phenylboronic acid (113 mg, 0.91 mmol), 2M aqueous Na$_2$CO$_3$ (0.93 mL), Pd(PPh$_3$)$_4$ (72 mg, 0.06 mmol) in THF (6 mL)/H$_2$O (1 mL) was heated at 60° C. under a N$_2$ atmosphere for 2 h. Mixture was diluted with EtOAc (10 mL) and washed with H$_2$O (15 mL×2) and brine (15 mL). Organic layer was dried (MgSO4), filtered and concentrated under reduced pressure. The crude was purified by flash column chromatography on silica to give 40u (284 mg, 92%) as a light brown oil. $^1$H NMR (400 MHz, CDCl$_3$) δ 8.01 (d, J=8.42 Hz, 1H), 7.85 (s, 1H), 7.78-7.72 (m, 2H), 7.72-7.65 (m, 1H), 7.49-7.41 (m, 3H), 7.40-7.31 (m, 6H), 6.98 (s, 1H), 3.93 (s, 3H), 3.63 (s, 3H), 3.59 (s, 2H); $^{13}$C NMR (100 MHz, CDCl$_3$) δ 169.86, 154.00, 142.22, 139.49, 138.99, 133.60, 131.46, 131.02, 130.00, 129.44, 128.89, 128.63, 128.14, 127.89, 127.03, 126.98, 126.88, 125.92, 125.87, 125.80, 123.46, 122.38, 122.27, 61.43, 52.60, 34.97; ESI MS: m/z 494.1 (M+H)$^+$.

2-((4-(4-Bromophenylsulfonamido)-1-methoxynaphthalen-2-yl)thio)acetamide (40v)

Compound 40d (82 mg, 0.16 mmol) was suspended in aqueous NH$_4$OH (29%, 3 mL). The mixture was stirred at rt for 1 h. Workup included diluting the mixture with EtOAc (5 mL) and washing with H$_2$O (10 mL×2) and brine (10 mL). Organic layer was dried (MgSO$_4$), filtered and concentrated under reduced pressure to give 40v (69 mg, 90%) as a pink solid. Crude was used in the next step without further purification. $^1$H NMR (400 MHz, DMSO-d$_6$) δ 10.32 (s, 1H), 7.95 (d, J=8.50 Hz, 1H), 7.85 (d, J=8.50 Hz, 1H), 7.72 (d, J=8.20 Hz, 2H), 7.60 (d, J=8.20 Hz, 2H), 7.56-7.50

(m, 1H), 7.43-7.37 (m, 1H), 7.21 (s, 1H), 7.15 (s, 1H), 3.88 (s, 3H), 3.53 (s, 2H); $^{13}$C NMR (100 MHz, DMSO-d$_6$) δ 169.76, 151.88, 139.67, 132.70, 129.69, 129.18, 129.05, 128.23, 127.46, 127.03, 126.41, 125.24, 124.89, 123.95, 121.82, 61.27, 35.91; ESI MS: m/z 480.7 (M+H)$^+$, 502.7 (M+Na)$^+$.

Methyl 2-((5-(4-bromophenylsulfonamido)-2-methoxyphenyl)thio)acetate (47)

Nitro 46 was first converted to the desired amine using the iron reduction procedure described for reduction of 39a and the crude was used in the next step without further purification. $^1$H NMR (400 MHz, CDCl$_3$) δ 6.69 (d, J=2.60 Hz, 1H), 6.64 (d, J=8.58 Hz, 1H), 6.50 (dd, J=2.60, 8.58 Hz, 1H), 3.74 (s, 3H), 3.64 (s, 3H), 3.57 (s, 2H); $^{13}$C NMR (100 MHz, CDCl$_3$) δ 170.30, 150.99, 140.41, 123.27, 118.30, 115.00, 112.25, 56.34, 52.38, 34.91; ESI MS: m/z 228.0 (M+H)$^+$.

The title compound was synthesized using the procedure for 40a except using the above amine and 4-bromobenzenesulfonyl chloride, which afforded 47 (122 mg, 41% over two steps) as a white solid. $^1$H NMR (400 MHz, CDCl$_3$) δ 7.58-7.51 (m, 4H), 7.03 (d, J=2.50 Hz, 1H), 6.89 (dd, J=2.50, 8.70 Hz, 1H), 6.70 (d, J=8.70 Hz, 1H), 6.58 (s, 1H), 3.83 (s, 3H), 3.67 (s, 3H), 3.54 (s, 2H); $^{13}$C NMR (100 MHz, CDCl$_3$) δ 169.83, 156.05, 137.82, 132.26, 128.80, 128.72, 127.98, 126.06, 124.19, 123.85, 110.90, 56.04, 52.59, 34.33; ESI MS: m/z 443.9 (M−H)$^-$.

A Representative Procedure for a Single-Pot Ester Hydrolysis and Demethylation with BBr$_3$ 2-((1-Hydroxy-4-(thiophene-2-sulfonamido)naphthalen-2-yl)thio)acetic acid (1 (UMI-59))

To a stirred solution of 40a (48 mg, 0.12 mmol) suspended in dry CH$_2$Cl$_2$ (1.5 mL) was added BBr$_3$ in CH$_2$Cl$_2$ (1 M, 0.5 mL) dropwise at −78° C. (dry ice/acetone bath) under a N$_2$ atmosphere. The mixture was allowed to warm up to rt. The starting material was entirely consumed and the product formed as determined by TLC and MS (ESI) after 1 h. The mixture was slowly added to a stirred solution of saturated aqueous NH$_4$Cl (20 mL) at 0° C. The solution was extracted with EtOAc (15 mL×2). The combined organic extracts were washed with brine (15 mL), dried (MgSO$_4$), filtered, and the solvent was removed under reduced pressure. The crude was purified using a C$_{18}$ reverse phase semipreparative HPLC column with solvent A (0.1% of TFA in water) and solvent B (0.1% of TFA in CH$_3$CN) as eluents to give 1 (28 mg, 59%) as a white/tan solid. 96% pure by HPLC. $^1$H NMR (400 MHz, DMSO-d$_6$) δ 10.10 (s, 1H), 8.17-8.14 (m, 1H), 7.89-7.84 (m, 2H), 7.52-7.40 (m, 2H), 7.36 (dd, J=1.32, 3.74 Hz, 1H), 7.09 (s, 1H), 7.07 (dd, J=3.74, 4.97 Hz, 1H), 3.56 (s, 2H); $^{13}$C NMR (100 MHz, DMSO-d$_6$) δ 171.54, 152.87, 140.58, 133.57, 132.80, 131.71, 129.80, 128.03, 127.20, 126.22, 125.46, 124.33, 123.61, 122.83, 113.36, 37.25; ESI HRMS: m/z 393.9870 (M−H)$^-$.

2-((1-Hydroxy-4-(phenylsulfonamido)naphthalen-2-yl)thio)acetic acid (2)

Synthesized using the procedure for 1 except 40b was used as the starting material. The title compound was obtained (21 mg, 22%) as a white solid after HPLC purification. 97% pure by HPLC. $^1$H NMR (400 MHz, DMSO-d$_6$) δ 12.76 (s, 1H), 9.91 (s, 1H), 9.79 (s, 1H), 8.14 (d, J=8.22 Hz, 1H), 7.88 (d, J=8.22 Hz, 1H), 7.67-7.61 (m, 2H), 7.61-7.56 (m, 1H), 7.54-7.47 (m, 3H), 7.46-7.39 (m, 1H), 7.01 (s, 1H), 3.51 (s, 2H); $^{13}$C NMR (100 MHz, DMSO-d$_6$) δ 171.46, 152.56, 140.16, 133.03, 131.56, 129.53, 129.44, 127.25, 127.05, 126.17, 125.46, 124.56, 123.76, 122.75, 113.34, 37.16; ESI HRMS: m/z 388.0319 (M−H)$^-$.

2-((4-(4-Chlorophenylsulfonamido)-1-hydroxynaphthalen-2-yl)thio)acetic acid (8)

Synthesized using the procedure for 1 except 40c was used as the starting material. The title compound was obtained (48 mg, 20%) as a white solid after trituration with a mixture of CH$_3$CN:H$_2$O 1:1 and cold CH$_2$Cl$_2$ and without a need for HPLC purification. 95% pure by HPLC. $^1$H NMR (400 MHz, DMSO-d$_6$) δ 12.77 (s, 1H), 10.03 (s, 1H), 9.84 (s, 1H), 8.15 (d, J=8.12 Hz, 1H), 7.85 (d, J=8.12 Hz, 1H), 7.66-7.59 (m, 2H), 7.59-7.52 (m, 2H), 7.46 (dt, J=7.28, 14.85 Hz, 2H), 7.05 (s, 1H), 3.54 (s, 2H); $^{13}$C NMR (100 MHz, DMSO-d$_6$) δ 171.48, 152.72, 139.06, 137.95, 131.47, 129.66, 129.60, 129.19, 127.15, 126.25, 125.48, 124.24, 123.63, 122.84, 113.38, 37.11; ESI HRMS: m/z 421.9930 (M−H)$^-$.

2-((4-(4-Bromophenylsulfonamido)-1-hydroxynaphthalen-2-yl)thio)acetic acid (9 (UMI-77))

Synthesized using the procedure for 1 except 40d was used as the starting material. The title compound was obtained (134 mg, 45%) as a white solid after trituration with a mixture of CH$_3$CN:H$_2$O 1:1 and cold CH$_2$Cl$_2$ and without a need for HPLC purification. 97% pure by HPLC. $^1$H NMR (400 MHz, DMSO-d$_6$) δ 12.80 (s, 1H), 10.05 (s, 1H), 9.87 (s, 1H), 8.14 (d, J=8.17 Hz, 1H), 7.84 (d, J=8.17 Hz, 1H), 7.71 (d, J=8.48 Hz, 2H), 7.54 (d, J=8.48 Hz, 2H), 7.48 (t, J=7.03 Hz, 1H), 7.43 (t, J=7.03 Hz, 1H), 7.04 (s, 1H), 3.53 (s, 2H); $^{13}$C NMR (100 MHz, DMSO-d$_6$) δ 171.52, 152.74, 139.45, 132.56, 131.45, 129.66, 129.28, 127.18, 126.92, 126.27, 125.48, 124.21, 123.63, 122.86, 113.38, 37.10; ESI HRMS: m/z 465.9418 (M−H)$^-$ 2-((4-(3-Bromophenylsulfonamido)-1-hydroxynaphthalen-2-yl)thio)acetic acid (10)

Synthesized using the procedure for 1 except 40e was used as the starting material. The title compound was obtained (21 mg, 35%) as a white/tan solid after trituration with a mixture of CH$_3$CN:H$_2$O 1:1 and cold CH$_2$Cl$_2$ and without a need for HPLC purification. 88% pure by HPLC. $^1$H NMR (400 MHz, DMSO-d$_6$) δ 10.08 (s, 1H), 8.15 (d, J=7.56 Hz, 1H), 7.87-7.78 (m, 2H), 7.75 (t, J=1.78 Hz, 1H), 7.62-7.56 (m, 1H), 7.52-7.39 (m, 3H), 7.01 (s, 1H), 3.52 (s, 2H); $^{13}$C NMR (100 MHz, DMSO-d$_6$) δ 171.52, 152.92, 142.07, 135.93, 131.78, 131.49, 129.77, 129.59, 127.18, 126.34, 126.28, 125.53, 124.02, 123.58, 122.89, 122.35, 113.43, 37.24; ESI HRMS: m/z 465.9414 (M−H)$^-$ 2-((4-(2-Bromophenylsulfonamido)-1-hydroxynaphthalen-2-yl)thio)acetic acid (11)

Synthesized using the procedure for 1 except 40f was used as the starting material. The title compound was obtained (34 mg, 40%) as a white solid after HPLC purification. 90% pure by HPLC. $^1$H NMR (400 MHz, DMSO-d$_6$) δ 12.80 (s, 1H), 10.23 (s, 1H), 9.88 (s, 1H), 8.16-8.10 (m, 1H), 8.07-8.02 (m, 1H), 7.86 (dd, J=1.52, 7.83 Hz, 1H), 7.78 (dd, J=1.52, 7.83 Hz, 1H), 7.52-7.46 (m, 3H), 7.42 (td, J=1.33, 7.60 Hz, 1H), 7.05 (s, 1H), 3.46 (s, 2H); $^{13}$C NMR (100 MHz, DMSO-d$_6$) δ 171.42, 152.60, 139.23, 135.82, 134.64, 131.92, 131.77, 129.49, 128.52, 127.18, 126.32, 125.44, 123.98, 123.78, 122.78, 119.92, 113.54, 37.03; ESI HRMS: m/z 465.9408 (M−H)$^-$.

2-((4-(Benzo[b]thiophene-2-sulfonamido)-1-hydroxynaphthalen-2-yl)thio)acetic acid (12)

Synthesized using the procedure for 1 except 40g was used as the starting material. The title compound was obtained (13 mg, 22%) as an orange solid after HPLC purification. 98% pure by HPLC. $^1$H NMR (400 MHz, DMSO-d$_6$) δ 10.32 (s, 1H), 8.11 (d, J=8.14 Hz, 1H), 8.02 (d, J=8.14 Hz, 1H), 7.89 (t, J=8.09 Hz, 2H), 7.72 (s, 1H), 7.47 (t, J=7.56 Hz, 1H), 7.41 (t, J=7.35 Hz, 2H), 7.38-7.32 (m, 1H), 7.14 (s, 1H), 3.40 (s, 2H); $^{13}$C NMR (100 MHz, DMSO-d$_6$) δ 206.89, 171.57, 153.29, 141.31, 141.04, 137.80, 131.73, 129.99, 129.94, 127.65, 127.22, 126.21, 125.86, 125.54, 123.96, 123.54, 123.41, 122.92, 113.33, 31.12; ESI HRMS: m/z 444.0041 (M−H)$^-$.

2-((4-([1,1'-Biphenyl]-4-ylsulfonamido)-1-hydroxynaphthalen-2-yl)thio)acetic acid (14)

Synthesized using the procedure for 1 except 40h was used as the starting material. The title compound was obtained (29 mg, 45%) as a white/tan solid after HPLC purification. 99% pure by HPLC; $^1$H NMR (400 MHz, DMSO-d$_6$) δ 9.92 (s, 1H), 8.11 (d, J=7.93 Hz, 1H), 7.90 (d, J=7.93 Hz, 1H), 7.76 (d, J=7.47 Hz, 2H), 7.72-7.62 (m, 4H), 7.50-7.42 (m, 3H), 7.43-7.36 (m, 2H), 7.02 (s, 1H), 3.46 (s, 2H); $^{13}$C NMR (100 MHz, DMSO-d$_6$) δ 171.52, 152.74, 144.57, 139.00, 138.90, 131.65, 129.57, 129.52, 128.92, 128.00, 127.63, 127.46, 127.08, 126.18, 125.55, 124.53, 123.85, 122.81, 113.42, 37.27; ESI HRMS: m/z 464.0630 (M−H)$^-$.

2-((4-([1,1'-Biphenyl]-3-ylsulfonamido)-1-hydroxynaphthalen-2-yl)thio)acetic acid (15)

Synthesized using the procedure for 1 except 40u was used as the starting material. The title compound was obtained (48 mg, 34%) as a white/tan solid after HPLC purification. 99% pure by HPLC; $^1$H NMR (400 MHz, DMSO-d$_6$) δ 12.73 (s, 1H), 9.93 (s, 1H), 9.79 (s, 1H), 8.10 (d, J=8.25 Hz, 1H), 7.88-7.81 (m, 2H), 7.79 (s, 1H), 7.60-7.50 (m, 2H), 7.50-7.41 (m, 4H), 7.41-7.32 (m, 3H), 7.04 (s, 1H), 3.45 (s, 2H); $^{13}$C NMR (100 MHz, DMSO-d$_6$) δ 171.44, 152.66, 141.46, 140.82, 139.01, 131.50, 131.30, 130.18, 129.60, 129.55, 128.66, 127.17, 127.07, 126.23, 126.07, 125.51, 125.26, 124.59, 123.73, 122.81, 113.44, 37.16; ESI HRMS: m/z 464.0632 (M−H)$^-$ 2-((4-([1,1'-Biphenyl]-2-ylsulfonamido)-1-hydroxynaphthalen-2-yl)thio)acetic acid (16)

Synthesized using the procedure for 1 except 40i was used as the starting material. The title compound was obtained (20 mg, 43%) as a white/tan solid after HPLC purification. 84% pure by HPLC. $^1$H NMR (400 MHz, DMSO-d$_6$) δ 12.77 (s, 1H), 9.76 (s, 1H), 9.70 (s, 1H), 8.12 (d, J=8.03 Hz, 1H), 7.95 (d, J=8.03 Hz, 1H), 7.74 (d, J=8.30 Hz, 1H), 7.58 (t, J=7.46 Hz, 1H), 7.52 (t, J=7.46 Hz, 1H), 7.48-7.41 (m, 1H), 7.41-7.34 (m, 1H), 7.23 (q, J=4.82, 5.81 Hz, 2H), 7.17 (t, J=7.46 Hz, 3H), 7.01-6.95 (m, 1H), 6.93 (s, 1H), 6.91 (s, 1H), 3.43 (s, 2H); $^{13}$C NMR (100 MHz, DMSO-d$_6$) δ 171.57, 152.24, 141.36, 139.92, 138.75, 133.21, 132.68, 131.42, 129.62, 129.37, 128.85, 128.36, 127.55, 127.48, 126.97, 126.21, 125.49, 124.57, 123.79, 122.69, 113.65, 37.07; ESI HRMS: m/z 464.0636 (M−H)$^-$.

2-((4-(4'-Chloro-[1,1'-biphenyl]-4-ylsulfonamido)-1-hydroxynaphthalen-2-yl)thio)acetic acid (17)

Synthesized using the procedure for 1 except 40j was used as the starting material. The title compound (36 mg, 25%) as a white solid after HPLC purification. 99% pure by HPLC. $^1$H NMR (400 MHz, DMSO-d$_6$) δ 12.75 (s, 1H), 9.96 (s, 1H), 9.81 (s, 1H), 8.10 (d, J=8.09 Hz, 1H), 7.88 (d, J=8.09 Hz, 1H), 7.77 (d, J=8.24 Hz, 2H), 7.72-7.64 (m, 4H), 7.52 (d, J=8.24 Hz, 2H), 7.47-7.36 (m, 2H), 6.99 (s, 1H), 3.45 (s, 2H); $^{13}$C NMR (100 MHz, DMSO-d$_6$) δ 171.45, 152.51, 143.18, 139.25, 137.67, 133.88, 131.56, 129.50, 129.39, 129.27, 128.05, 127.65, 127.09, 126.24, 125.50, 124.54, 123.84, 122.78, 113.44, 37.04; ESI HRMS: m/z 498.0247 (M−H)$^-$.

2-((1-Hydroxy-4-(4-phenoxyphenylsulfonamido)naphthalen-2-yl)thio)acetic acid (18)

Synthesized using the procedure for 1 except 40k was used as the starting material. The title compound was obtained (18 mg, 13%) as a white solid after HPLC purification. 96% pure by HPLC. $^1$H NMR (400 MHz, DMSO-d$_6$) δ 12.81 (s, 1H), 9.87 (s, 1H), 9.83 (s, 1H), 8.14 (d, J=8.31 Hz, 1H), 7.86 (d, J=8.31 Hz, 1H), 7.59 (d, J=8.75 Hz, 2H), 7.50 (t, J=7.09 Hz, 1H), 7.44 (t, J=7.81 Hz, 3H), 7.23 (t, J=7.09 Hz, 1H), 7.05-6.98 (m, 5H), 3.55 (s, 2H); $^{13}$C NMR (100 MHz, DMSO-d$_6$) δ 171.53, 160.76, 155.60, 152.58, 134.17, 131.57, 130.75, 129.84, 129.76, 127.06, 126.16, 125.48, 125.07, 124.60, 123.78, 122.80, 120.03, 118.33, 113.38, 37.15; ESI HRMS: m/z 480.0579 (M−H)$^-$.

2-((1-Hydroxy-4-(methylsulfonamido)naphthalen-2-yl)thio)acetic acid (21)

Synthesized using the procedure for 1 except 40l was used as the starting material. The title compound (27 mg, 48%) as a white solid after HPLC purification. 95% pure by HPLC. $^1$H NMR (400 MHz, DMSO-d$_6$) δ 9.40 (s, 1H), 8.20 (d, J=8.09 Hz, 1H), 8.14 (d, J=8.09 Hz, 1H), 7.56 (p, J=6.86 Hz, 2H), 7.47 (s, 1H), 3.69 (s, 2H), 2.99 (s, 3H); $^{13}$C NMR (100 MHz, DMSO-d$_6$) δ 171.73, 152.58, 131.89, 129.38, 127.31, 126.30, 125.65, 125.18, 124.32, 122.82, 113.55, 39.79, 37.03; ESI HRMS: m/z 326.0164 (M−H)$^-$.

2-((5-(4-Bromophenylsulfonamido)-2-hydroxyphenyl)thio)acetic acid (22)

Synthesized using the procedure for 1 except 47 was used as the starting material. The title compound (22 mg, 29%) as a white solid after HPLC purification. 97% pure by HPLC. $^1$H NMR (400 MHz, DMSO-d$_6$) δ 12.65 (s, 1H), 9.89 (s, 2H), 7.75 (d, J=7.98 Hz, 2H), 7.58 (d, J=7.98 Hz, 2H), 6.93 (s, 1H), 6.69-6.66 (m, 2H), 3.58 (s, 2H); $^{13}$C NMR (100 MHz, DMSO-d$_6$) δ 170.87, 153.27, 139.08, 132.62, 129.15, 126.97, 124.00, 122.38, 122.13, 115.50, 109.99, 34.26; ESI HRMS: m/z 415.9273 (M−H)$^-$.

2-((4-(4-Bromobenzamido)-1-hydroxynaphthalen-2-yl)thio)acetic acid (23)

Synthesized using the procedure for 1 except 40m was used as the starting material. The title compound was obtained (18 mg, 13%) as a white/light yellow solid after HPLC purification. 98% pure by HPLC. $^1$H NMR (400 MHz, DMSO-$d_6$) δ 10.36 (s, 1H), 8.23 (d, J=5.36 Hz, 1H), 8.02 (d, J=8.05 Hz, 2H), 7.83 (d, J=5.36 Hz, 1H), 7.78 (d, J=8.05 Hz, 2H), 7.57-7.50 (m, 3H), 3.72 (s, 2H); $^{13}$C NMR (100 MHz, DMSO-$d_6$) δ 171.74, 165.71, 151.94, 133.90, 131.89, 130.66, 130.30, 128.64, 127.11, 126.17, 126.13, 125.80, 125.47, 123.80, 122.97, 113.65, 37.15; ESI HRMS: m/z 429.9747 (M−H)$^-$.

2-((1-Hydroxy-4-(2-phenylacetamido)naphthalen-2-yl)thio)acetic acid (24)

Synthesized using the procedure for 1 except 40t was used as the starting material. The title compound was obtained (50 mg, 61%) as a white solid after trituration with a mixture of CH$_3$CN:H$_2$O 1:1 and cold CH$_2$Cl$_2$ and without a need for HPLC purification. 95% pure by HPLC. $^1$H NMR (400 MHz, DMSO-$d_6$) δ 12.78 (s, 1H), 9.97 (s, 1H), 9.66 (s, 1H), 8.26-8.12 (m, 1H), 7.92-7.77 (m, 1H), 7.59-7.47 (m, 3H), 7.42 (d, J=7.64 Hz, 2H), 7.37 (t, J=7.40 Hz, 2H), 7.31-7.24 (m, 1H), 3.77 (s, 2H), 3.67 (s, 2H); $^{13}$C NMR (100 MHz, DMSO-$d_6$) δ 171.73, 170.25, 151.26, 136.74, 129.70, 129.58, 128.76, 127.10, 126.97, 126.92, 126.19, 126.06, 125.38, 123.22, 122.99, 113.49, 43.09, 37.13; ESI HRMS: m/z 366.0802 (M−H)$^-$.

2-((4-((4-Chlorophenyl)methylsulfonamido)-1-hydroxynaphthalen-2-yl)thio)acetic acid (25)

Synthesized using the procedure for 1 except 40n was used as the starting material. The title compound was obtained (15.5 mg, 20%) as a white solid after HPLC purification. 97% pure by HPLC. $^1$H NMR (400 MHz, DMSO-$d_6$) δ 12.86 (s, 1H), 9.84 (s, 1H), 9.55 (s, 1H), 8.20 (d, J=8.36 Hz, 1H), 8.07 (d, J=8.36 Hz, 1H), 7.60-7.51 (m, 2H), 7.44 (s, 1H), 7.43-7.38 (m, 4H), 4.49 (s, 2H), 3.71 (s, 2H); $^{13}$C NMR (100 MHz, DMSO-$d_6$) δ 171.81, 152.35, 133.45, 133.18, 131.79, 129.37, 128.93, 128.72, 127.23, 126.30, 125.63, 124.99, 124.28, 122.79, 113.67, 57.16, 36.96; ESI HRMS: m/z 436.0086 (M−H)$^-$.

2-((4-(2-(4-Chlorophenyl)acetamido)-1-hydroxynaphthalen-2-yl)thio)acetic acid (26)

Synthesized using the procedure for 1 except 40o was used as the starting material. The title compound was obtained (19 mg, 10%) as a white solid after trituration with a mixture of CH$_3$CN:H$_2$O 1:1 and cold CH$_2$Cl$_2$ and without a need for HPLC purification. 94% pure by HPLC. $^1$H NMR (400 MHz, DMSO-$d_6$) δ 9.96 (s, 1H), 8.23-8.17 (m, 1H), 7.89-7.83 (m, 1H), 7.57-7.50 (m, 3H), 7.47-7.39 (m, 4H), 3.78 (s, 2H), 3.66 (s, 2H); $^{13}$C NMR (100 MHz, DMSO-$d_6$) δ 171.72, 169.89, 151.36, 135.73, 131.66, 131.49, 129.70, 128.69, 127.15, 127.00, 126.11, 126.07, 125.40, 123.21, 123.02, 113.51, 42.24, 37.21; ESI HRMS: m/z 400.0417 (M−H)$^-$.

4-Bromo-N-(3-(butylthio)-4-hydroxynaphthalen-1-yl)benzenesulfonamide (30)

Synthesized using the procedure for 1 except 40p was used as the starting material. The title compound was obtained (10 mg, 8%) as a white solid after HPLC purification. 99% pure by HPLC. $^1$H NMR (400 MHz, CDCl$_3$) δ 8.23 (d, J=7.40 Hz, 1H), 7.79 (d, J=7.40 Hz, 1H), 7.59-7.50 (m, 4H), 7.50-7.45 (m, 1H), 7.37 (s, 1H), 7.26 (s, 1H), 6.60 (s, 1H), 3.49 (s, 1H), 2.65 (t, J=7.24 Hz, 2H), 1.52-1.45 (m, 2H), 1.45-1.35 (m, 2H), 0.90 (t, J=7.24 Hz, 3H); $^{13}$C NMR (100 MHz, CDCl$_3$) δ 154.04, 138.33, 132.18, 131.86, 131.23, 128.98, 128.09, 127.90, 126.29, 123.80, 123.47, 122.92, 122.16, 111.25, 36.61, 31.70, 21.74, 13.60; ESI HRMS: m/z 463.9998 (M−H)$^-$.

4-Bromo-N-(4-hydroxy-3-((2-hydroxyethyl)thio)naphthalen-1-yl)benzenesulfonamide (31)

Synthesized using the procedure for 1 except 40q was used as the starting material. The title compound (9 mg, 12%) as a white solid after HPLC purification. 99% pure by HPLC. $^1$H NMR (400 MHz, DMSO-$d_6$) δ 10.00 (s, 1H), 9.68 (s, 1H), 8.14 (d, J=8.00 Hz, 1H), 7.92 (d, J=8.00 Hz, 1H), 7.74 (d, J=8.48 Hz, 2H), 7.55 (d, J=8.48 Hz, 2H), 7.52-7.42 (m, 2H), 6.91 (s, 1H), 5.10 (s, 1H), 3.42 (t, J=6.46 Hz, 2H), 2.73 (t, J=6.46 Hz, 2H); $^{13}$C NMR (100 MHz, DMSO-$d_6$) δ 152.93, 139.30, 132.60, 131.50, 130.06, 129.35, 127.08, 126.97, 126.28, 125.44, 124.11, 123.81, 122.82, 113.47, 60.14, 37.72; ESI HRMS: m/z 451.9633 (M−H)$^-$.

4-Bromo-N-(4-hydroxy-3-(4-hydroxybutyl)naphthalen-1-yl)benzenesulfonamide (32)

Synthesized using the procedure for 1 except 40r was used as the starting material. the title compound (49 mg, 34%) as a white solid after HPLC purification. 98% pure by HPLC. $^1$H NMR (400 MHz, DMSO-$d_6$) δ 9.84 (s, 1H), 9.13 (s, 1H), 8.12 (d, J=8.17 Hz, 1H), 7.87 (d, J=8.17 Hz, 1H), 7.69 (d, J=8.49 Hz, 2H), 7.51 (d, J=8.49 Hz, 2H), 7.39 (t, J=7.31 Hz, 1H), 7.33 (t, J=7.31 Hz, 1H), 6.67 (s, 1H), 4.36 (s, 1H), 3.42-3.33 (m, 2H), 2.58 (t, J=5.70 Hz, 2H), 1.45-1.26 (m, 4H); $^{13}$C NMR (100 MHz, DMSO-$d_6$) δ 149.19, 139.58, 132.50, 130.54, 129.39, 128.16, 126.78, 126.20, 125.66, 125.39, 123.64, 123.61, 122.58, 122.46, 61.16, 32.47, 29.39, 26.67. ESI HRMS: m/z 448.0223 (M−H)$^-$.

2-((4-(4-Bromophenylsulfonamido)-1-hydroxynaphthalen-2-yl)thio)acetamide (33)

Synthesized using the procedure for 1 except 40v was used as the starting material. The title compound (24 mg, 42%) as a yellow solid after trituration with a mixture of CH$_3$CN:H$_2$O 1:1 and cold CH$_2$Cl$_2$ and without a need for HPLC purification. 95% pure by HPLC. $^1$H NMR (400 MHz, DMSO-$d_6$) δ 11.13 (s, 1H), 9.99 (s, 1H), 8.17 (d, J=7.98 Hz, 1H), 7.84 (d, J=7.98 Hz, 2H), 7.72 (d, J=8.04 Hz, 2H), 7.54 (d, J=8.04 Hz, 2H), 7.46 (p, J=6.51 Hz, 2H), 7.01 (s, 1H), 3.49 (s, 2H); $^{13}$C NMR (100 MHz, DMSO-$d_6$) δ 172.97, 154.81, 139.45, 132.53, 132.16, 131.48, 129.33, 127.52, 126.89, 126.19, 125.69, 123.60, 123.58, 123.22, 112.76, 31.12; ESI HRMS: m/z 464.9591 (M−H)$^-$.

3-((1-Hydroxy-4-(naphthalene-2-sulfonamido)naphthalen-2-yl)thio)propanoic acid (34)

Synthesized using the procedure for 1 except 40s was used as the starting material. The title compound was obtained (23 mg, 15%) as a white solid after HPLC purification. 96% pure by HPLC. $^1$H NMR (400 MHz, DMSO-$d_6$) δ 12.31 (s, 1H), 10.01 (s, 1H), 9.60 (s, 1H), 8.23 (s, 1H), 8.14-8.06 (m, 2H), 8.06-7.97 (m, 3H), 7.80 (d, J=8.52 Hz, 1H), 7.68 (t, J=7.36 Hz, 1H), 7.60 (t, J=7.36 Hz, 1H), 7.43 (p, J=6.84 Hz, 2H), 6.87 (s, 1H), 2.62 (t, J=6.83 Hz, 2H), 2.17 (t, J=6.83 Hz, 2H); $^{13}$C NMR (100 MHz, DMSO-$d_6$) δ

172.97, 137.07, 134.56, 131.90, 131.48, 129.68, 129.51, 129.23, 129.20, 128.33, 128.20, 128.00, 126.94, 126.22, 125.51, 124.61, 123.96, 122.93, 122.70, 113.33, 34.12, 31.10, 29.59; ESI HRMS: m/z 452.0630 (M−H)⁻.

Methyl 2-((4-(4-bromophenylsulfonamido)-1-hydroxynaphthalen-2-yl)thio)acetate (29)

To a stirred solution of 40d (122 mg, 0.25 mmol) suspended in dry $CH_2Cl_2$ (2 mL) was added 1M $BBr_3$ in $CH_2Cl_2$ (1 mL) dropwise at −78° C. (dry ice/acetone bath). The mixture was allowed to warm up to rt and stirred under a $N_2$ atmosphere. The starting material was entirely consumed as determined by TLC and analytical HPLC after 1 h. The mixture was again cooled down to −78° C. (dry ice/acetone bath) and MeOH (3 mL) was added. After addition, the mixture was allowed to warm up to rt and stirred at rt for 1-2 h till a new spot formed as monitored by TLC. The mixture was slowly added to a stirring solution of saturated aqueous $NH_4Cl$ (15 mL) at 0° C. The solution was extracted with EtOAc (15 mL×2). The combined organic extracts were washed with brine (15 mL), dried ($MgSO_4$), and filtered. The solvent was removed under reduced pressure. The crude was triturated with cold $CH_2Cl_2$ to give 29 (16 mg, 13%) as a light yellow solid. 96% pure by HPLC. $^1$H NMR (400 MHz, DMSO-$d_6$) δ 10.08 (s, 1H), 9.90 (s, 1H), 8.15 (d, J=8.22 Hz, 1H), 7.85 (d, J=8.22 Hz, 1H), 7.73 (d, J=8.58 Hz, 2H), 7.55 (d, J=8.58 Hz, 2H), 7.52-7.41 (m, 2H), 6.99 (s, 1H), 3.60 (s, 5H); $^{13}$C NMR (100 MHz, DMSO-$d_6$) δ 170.21, 152.67, 139.44, 132.58, 131.45, 129.39, 129.23, 127.20, 126.93, 126.30, 125.51, 124.25, 123.67, 122.85, 113.07, 52.64, 36.18; ESI HRMS: m/z 479.9588 (M−H)⁻.

2-((4-(4-Bromophenylsulfonamido)-1-methoxynaphthalen-2-yl)thio)acetic acid (36)

To a solution of 40d (425 mg, 0.85 mmol) in dry THF (2 mL) was added 1N aqueous LiOH (4 mL). The mixture was stirred at rt under a $N_2$ atmosphere for 1 h. Reaction mixture was diluted with water (10 mL) and washed with EtOAc (10 mL×2). Aqueous phase was acidified with 1N HCl and extracted with EtOAc (10 mL×3). Combined organic extracts were washed with brine, dried ($MgSO_4$) and filtered. The solvent was removed under reduced pressure. Crude was triturated with cold $CH_2Cl_2$ to give 36 (305 mg, 74%) as a white/tan solid. 99% pure by HPLC. $^1$H NMR (400 MHz, DMSO-$d_6$) δ 10.32 (s, 1H), 7.92 (d, J=8.38 Hz, 1H), 7.87 (d, J=8.38 Hz, 1H), 7.68 (d, J=8.08 Hz, 2H), 7.57 (d, J=8.08 Hz, 2H), 7.51 (t, J=7.56 Hz, 1H), 7.40 (t, J=7.56 Hz, 1H), 7.09 (s, 1H), 3.84 (s, 3H), 3.65 (s, 2H); $^{13}$C NMR (100 MHz, DMSO-$d_6$) δ 170.59, 152.07, 139.60, 132.69, 129.83, 129.18, 129.13, 128.28, 127.54, 127.09, 126.57, 124.60, 124.56, 124.01, 121.86, 61.30, 34.63; ESI HRMS: m/z 479.9578 (M−H)⁻.

2-((1-Acetoxy-4-(4-bromophenylsulfonamido)naphthalen-2-yl)thio)acetic acid (37)

A stirred solution of 9 (50 mg, 0.11 mmol) dissolved in dry THF (1.5 mL) was cooled to 0° C. $Et_3N$ (31 μL, 0.22 mmol) was added and the mixture was stirred for 5 min before acetylchloride (10 μL, 0.14 mmol) was added at 0° C. The mixture was stirred under a $N_2$ atmosphere for an additional 20 min then diluted with EtOAc (10 mL) and washed with $H_2O$ (10 mL×3). The organic layer was dried (MgSO4), filtered and concentrated under reduced pressure. The crude was subjected to flash column chromatography (hexane/EtOAc 4:1) on silica gel to afford 37 (34 mg, 61%) as a white solid. 99% pure by HPLC. $^1$H NMR (400 MHz, $CDCl_3$) δ 8.29 (d, J=8.10 Hz, 1H), 7.96 (d, J=8.48 Hz, 2H), 7.76 (d, J=8.10 Hz, 1H), 7.71 (d, J=8.48 Hz, 2H), 7.69-7.59 (m, 2H), 7.37 (s, 1H), 3.63 (s, 2H), 1.79 (s, 3H); $^{13}$C NMR (100 MHz, $CDCl_3$) δ 170.13, 161.35, 147.04, 137.50, 132.14, 131.33, 131.18, 129.73, 129.46, 128.87, 128.46, 126.94, 125.55, 122.76, 121.64, 114.58, 28.48, 24.29; ESI HRMS: m/z 507.9533 (M−H)

1-(Benzyloxy)-4-nitronaphthalene (41)

A stirred solution of commercially available 1-nitronaphthalene (1.5 g, 8 mmole) dissolved in DMSO (30 mL) was cooled down to 0° C. KOH (1.8 g, 32 mmole) dissolved in $H_2O$ (10 mL) was added dropwise. Color of the solution changed from yellow to dark green. Addition of cumene hydroperoxide (1.5 mL, 8 mmole, technical grade) dissolved in DMSO (4 mL) via syringe was followed at 0° C. to provide a dark brown solution which was stirred for 2 h at rt. Saturated aqueous $Na_2S_2O_3$ solution (10 mL) was added and the mixture was stirred for another 15 min at rt. The mixture was diluted with $H_2O$ (10 mL) and washed with EtOAc (30 mL×2). Aqueous phase was acidified with 1N HCl and extracted with EtOAc (30 mL×3). The organic extracts were washed with brine (30 mL), dried ($MgSO_4$) and filtered. The solvent was removed under reduced pressure to provide a black oil which was purified by flash column chromatography (hexane/EtOAc 3:2) on silica gel to give 4-nitronaphthalen-1-ol (1.03 g, 67%) as a yellow/brown solid. $^1$H NMR spectroscopic data were identical to those published previously. $^1$H NMR (400 MHz, DMSO-$d_6$) δ 11.89 (s, 1H), 8.64 (d, J=8.78 Hz, 1H), 8.38 (d, J=9.34 Hz, 1H), 8.30 (d, J=8.16 Hz, 1H), 7.77 (t, J=7.62 Hz, 1H), 7.61 (t, J=7.62 Hz, 1H), 6.95 (d, J=8.16 Hz, 1H); $^{13}$C NMR (100 MHz, DMSO-$d_6$) δ 160.80, 137.07, 130.79, 128.95, 127.23, 126.57, 124.70, 123.54, 123.26, 107.19; ESI MS: m/z 190.0 (M+H)⁺.

To a stirred solution of 4-nitronaphthalen-1-ol (505 mg, 2.7 mmol) in dry DMF (3 mL) was added NaH (60 wt %, 193 mg, 4.8 mmol) suspended in dry DMF (3 mL) at 0° C. Benzyl bromide (0.46 mL, 19 mmol) in dry THF (3 mL) was added next at 0° C. The mixture was warmed up to rt and stirred under a $N_2$ atmosphere for 2-3 h. Mixture was diluted with EtOAc (10 mL), washed with dH2O (10 mL×4) and brine (10 mL). The organic layer was dried (MgSO4), filtered, concentrated and purified by column chromatography on silica to give 41 (465 mg, 64%) as a light brown solid. $^1$H NMR (400 MHz, $CDCl_3$) δ 8.77 (d, J=9.40 Hz, 1H), 8.43 (d, J=7.70 Hz, 1H), 8.36 (d, J=7.70 Hz, 1H), 7.73 (t, J=7.70 Hz, 1H), 7.58 (t, J=7.70 Hz, 1H), 7.53-7.47 (m, 2H), 7.46-7.35 (m, 3H), 6.88 (d, J=9.40 Hz, 1H), 5.34 (s, 2H); $^{13}$C NMR (100 MHz, $CDCl_3$) δ 159.50, 139.36, 135.54, 130.06, 128.81, 128.50, 127.46, 127.01, 126.92, 126.60, 125.76, 123.47, 122.88, 103.15, 70.91; ESI MS: m/z 280.0 (M+H)⁺, 302.0 (M+Na)⁺.

N-(4-(Benzyloxy)naphthalen-1-yl)benzenesulfonamide (42)

Nitro compound 41 was reduced to 4-(benzyloxy)naphthalen-1-amine using the procedure for reduction of 39a. The crude amine was used in the next step without further purification. $^1$H NMR (400 MHz, $CDCl_3$) δ 8.40-8.35 (m, 1H), 7.87-7.80 (m, 1H), 7.55-7.49 (m, 4H), 7.42 (t, J=7.36 Hz, 2H), 7.39-7.31 (m, 5H), 6.78-6.69 (m, 2H), 5.18 (s, 2H);

$^{13}$C NMR (100 MHz, CDCl$_3$) δ 148.64, 137.56, 134.70, 128.53, 127.81, 127.38, 126.40, 125.83, 125.46, 125.39, 122.79, 120.98, 110.41, 106.12, 70.56; ESI MS: m/z 250.0 (M+H)$^+$.

Title compound was synthesized according to the procedure for 40a except using crude 4-(benzyloxy)naphthalen-1-amine and benzenesulfonyl chloride, which afforded 42 (236 mg, 55% over two steps) as a brown oil which solidified. $^1$H NMR (400 MHz, CDCl$_3$) δ 8.30 (d, J=7.94 Hz, 1H), 7.75-7.66 (m, 3H), 7.49 (t, J=6.20 Hz, 3H), 7.46-7.39 (m, 4H), 7.38-7.32 (m, 3H), 7.20 (d, J=8.22 Hz, 1H), 6.75 (d, J=8.22 Hz, 1H), 6.60 (s, 1H), 5.21 (s, 2H); $^{13}$C NMR (100 MHz, CDCl$_3$) δ 154.17, 139.41, 136.59, 132.70, 131.08, 128.83, 128.60, 128.07, 127.38, 127.30, 127.14, 126.13, 125.68, 125.61, 123.75, 122.58, 121.75, 104.42, 70.24; ESI MS: m/z 389.9 (M+H)$^+$, 411.9 (M+Na)$^+$.

N-(4-Hydroxynaphthalen-1-yl)benzenesulfonamide (27)

Compound 27 was synthesized according to the procedure used for reduction of 39d except using 42 and MeOH as the solvent, which afforded the title compound (32 mg, 21%) as a white solid after HPLC purification. 99% pure by HPLC. $^1$H NMR (400 MHz, DMSO-d$_6$) δ 8.07 (d, J=7.83 Hz, 1H), 7.86 (d, J=7.83 Hz, 1H), 7.63 (d, J=7.58 Hz, 2H), 7.60-7.53 (m, 1H), 7.48 (t, J=7.37 Hz, 2H), 7.38 (p, J=6.69 Hz, 2H), 6.85 (d, J=7.98 Hz, 1H), 6.71 (d, J=7.98 Hz, 1H); $^{13}$C NMR (100 MHz, DMSO-d$_6$) δ 151.24, 139.13, 131.28, 130.38, 127.80, 125.58, 124.92, 124.39, 123.71, 123.55, 122.05, 122.01, 120.89, 106.09; ESI HRMS: m/z 298.0547 (M−H)$^-$.

4-(Benzyloxy)naphthalene-1-sulfonyl chloride (43)

To a stirred solution of commercially available 4-hydroxy-1-naphthalenesulfonic acid sodium salt (1.0 g, 2.8 mmol, technical grade) in H$_2$O (7 mL) was added sodium hydroxide (297 mg, 7.4 mmol). The flask was then charged with benzyl bromide (0.33 mL, 2.8 mmol) in EtOH (7 mL) and the mixture was heated to reflux under a N$_2$ atmosphere for 20 h, cooled and filtered. The collected solid was washed with cold ethanol (10 mL) and dried to give sodium 4-(benzyloxy)naphthalene-1-sulfonate (352 mg, 37%) as white crystals which was used in the next step without further purification. $^1$H NMR (400 MHz, DMSO-d$_6$) δ 8.77 (d, J=7.90 Hz, 1H), 8.18 (d, J=7.90 Hz, 1H), 7.84 (d, J=8.02 Hz, 1H), 7.57-7.37 (m, 6H), 7.36-7.29 (m, 1H), 6.95 (d, J=8.02 Hz, 1H), 5.29 (s, 2H); $^{13}$C NMR (100 MHz, DMSO-d$_6$) δ 154.69, 137.45, 137.20, 130.55, 128.94, 128.28, 128.04, 127.92, 126.42, 125.64, 125.47, 125.43, 121.68, 104.16, 69.91; ESI MS: m/z 336.9 (M+H)$^+$, 358.9 (M+Na)$^+$.

To a stirred solution of sodium 4-(benzyloxy)naphthalene-1-sulfonate (347 mg, 1 mmol) in dry DMF (4 mL) at it was added thionyl chloride dropwise. The reaction mixture was stirred at rt for 10 min then poured onto ice, stirred for additional 5 min and the precipitate was filtered. The collected solid was dissolved in CH$_2$Cl$_2$ (10 mL) and washed with water (10 mL×2). The organic layer was dried (MgSO$_4$), filtered and concentrated under reduced pressure to afford 43 (286 mg, 86%) as a white/tan solid which was used directly in the next step without further purification. $^1$H NMR (400 MHz, CDCl$_3$) δ 8.72 (d, J=8.29 Hz, 1H), 8.47 (d, J=8.29 Hz, 1H), 8.31 (d, J=8.29 Hz, 1H), 7.79 (t, J=7.36 Hz, 1H), 7.64 (t, J=7.36 Hz, 1H), 7.54-7.47 (m, 2H), 7.47-7.34 (m, 3H), 6.92 (d, J=8.22 Hz, 1H), 5.35 (s, 2H); $^{13}$C NMR (100 MHz, CDCl$_3$) δ 160.89, 135.27, 131.85, 131.52, 129.84, 128.89, 128.85, 128.60, 127.50, 126.97, 126.21, 123.97, 123.38, 102.93, 71.04.

4-(Benzyloxy)-N-phenylnaphthalene-1-sulfonamide (44)

Compound 44 was synthesized according to the procedure for 40a except using 43 and aniline as the amine, which afforded the title compound (269 mg, 82%) as a white solid. $^1$H NMR (400 MHz, CDCl$_3$) δ 8.60 (d, J=8.10 Hz, 1H), 8.38 (d, J=8.10 Hz, 1H), 8.11 (d, J=8.10 Hz, 1H), 7.69-7.60 (m, 1H), 7.58-7.50 (m, 1H), 7.46 (d, J=7.48 Hz, 2H), 7.43-7.32 (m, 2H), 7.09 (t, J=7.68 Hz, 2H), 7.04-6.94 (m, 2H), 6.91 (d, J=8.28 Hz, 2H), 6.79 (d, J=8.16 Hz, 1H), 5.23 (s, 2H); $^{13}$C NMR (100 MHz, CDCl$_3$) δ 158.98, 136.48, 135.76, 132.39, 129.43, 129.10, 128.95, 128.72, 128.37, 127.49, 126.19, 126.14, 125.54, 125.18, 123.88, 123.32, 121.63, 103.02, 70.58; ESI MS: m/z 389.9 (M+H)$^+$.

4-Hydroxy-N-phenylnaphthalene-1-sulfonamide (28)

Compound 28 was synthesized according to the procedure for reduction of 39d except using 44 and MeOH as the solvent, which afforded the title compound (122 mg, 71%) as a white solid. >99% pure by HPLC. $^1$H NMR (400 MHz, DMSO-d$_6$) δ 11.30 (s, 1H), 10.43 (s, 1H), 8.63 (d, J=8.43 Hz, 1H), 8.23 (d, J=8.43 Hz, 1H), 8.08 (d, J=8.43 Hz, 1H), 7.69 (t, J=7.71 Hz, 1H), 7.57 (t, J=7.71 Hz, 1H), 7.11 (t, J=7.77 Hz, 2H), 6.99 (d, J=8.01 Hz, 2H), 6.93-6.84 (m, 2H); $^{13}$C NMR (100 MHz, DMSO-d$_6$) δ 158.86, 138.35, 132.94, 129.74, 129.36, 128.71, 126.00, 125.20, 124.59, 124.19, 123.50, 123.36, 118.99, 106.56; ESI HRMS: m/z 298.0547 (M−H)$^-$.

Example 9

Experiments were conducted to study the in vitro efficacy and mechanism of action of myeloid cell leukemia 1 (MCL 1) inhibitors in bone marrow samples of multiple myeloma patients. More specifically, experiments were conducted to estimate the half maximal inhibitory concentration (IC50) of the Mcl-1 inhibitor in bone marrow derived plasma cells of multiple myeloma patients.

High expression of Myeloid cell leukemia 1 (Mcl-1), an anti-apoptotic member of the B-cell lymphoma 2 (Bcl-2) family, in Multiple Myeloma (MM), exemplifies its role in the observed resistance to traditional apoptosis inducing drugs. Preliminary studies from suggested that the observed resistance to Bcl-2 family small molecule inhibitors (SMI's) in some cell lines could be attributed to the variable status of basal Mcl-1. This apoptotic protein is emerging to be an important player in the observed resistance towards both standard chemotherapy and SMI's of the apoptotic machinery. The human Mcl-1 gene is located on chromosome 1q21 and comprises three exons with alternative splicing giving rise to two distinct Mcl-1 mRNAs either containing or lacking exon 2 and encoding the Mcl-1L and Mcl-1S isoforms, respectively. Mcl-1 is primarily localized to the outer mitochondrial membrane and promotes cell survival by suppressing cytochrome c release from mitochondria via heterodimerization and neutralization of effector proapoptotic Bcl-2 family members including Bak.

MCL-1 expression is essential for multiple myeloma cells survival trough JAK/STAT pathway, and specifically, understanding the mode of action of MCL-1 inhibitors in patient derived samples will build a strong case and provide solid platform for their application in a clinical setting.

Blood or bone marrow samples from multiple myeloma patients was obtained from treated or untreated patients after informed consent. Plasma cells were obtained after gradient density centrifugation using Ficoll Hypaque. Some samples were purified for C138+ population using flow cytometry. In all cases, purity of the plasma cells was higher than 90%, as assessed by morphology.

Cellular Viability Assays:

Isolated MM cells were maintained in RPMI 1640 medium supplemented with 10% fetal bovine serum (Hyclone Laboratories, Logan, Utah) and 1% Penicillin-Streptomycin (Invitrogen, Carlsbad, Calif.), at 37° C. in a humidified incubator with 5% $CO_2$. MM cells ($1 \times 10^6$ cells per well) were incubated in flat-bottomed 24-well culture plates in the absence or presence of Mcl-1 inhibitor (e.g., UMI-77) (0-10 µM) for 0-72 hrs (see, e.g., Figure %%%). The number of viable cells was determined by trypan blue exclusion test with trypan blue (0.4%) purchased from Sigma Chemical Co. (St. Louis, Mo.). All experiments are performed in triplicate and statistical analysis was done using the t test (two tailed) with 95% confidence intervals between treated and untreated samples. P<0.05 was used to indicate statistical significance.

Measurement of Apoptosis in MM Cells:

MM cell lines were cultured in six-well plates and treated as described above. At the end of the treatment the cells were washed and resuspended in annexin binding buffer (10 mM 4-(2-hydroxyethyl)-1-piperazineethanesulfonic acid pH 7.4, 140 mM NaCl, 2.5 mM $CaCl_2$) after which Annexin V-FITC and Propodium Iodide solution was added (5 micro L each) according to manufactures protocol (BD Bioscences). Flow cytometry was performed using a FACSCanto (BD Biosciences, San Jose, Calif., USA).

As presented in FIG. 27 bone marrow derived cells from multiple patients showed loss in viability post drug treatment. Most of the patient samples showed drastic loss in viability while some were resistant. However, in general the IC50s were found to be between 2.5 and 5 µM. As presented in FIG. 28. Mcl-1 treatment resulted in dose dependent induction of apoptosis in patient bone marrow derived plasma cells. For example in Pt 957060476 untreated control showed minimal apoptotic cells (both early 2% and late events 14.5%). However on exposure to increasing concentrations of Mcl-1 inhibitor enhancement in the apoptotic cell fraction was observed (early events 13.3% and late events 26.6%). For Pt 957034714 untreated control showed minimal apoptosis (early events 4.4% and late events 2.62%) while in treated group the apoptosis was significantly enhanced (early events 32.9% and late events 62.9%). A third patient Pt 90620372 showed enhancement in apoptosis with an increase from early event 5% and late event 11.1% (in untreated control) to early event 10.1% to late event 19.8% (in treated group).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

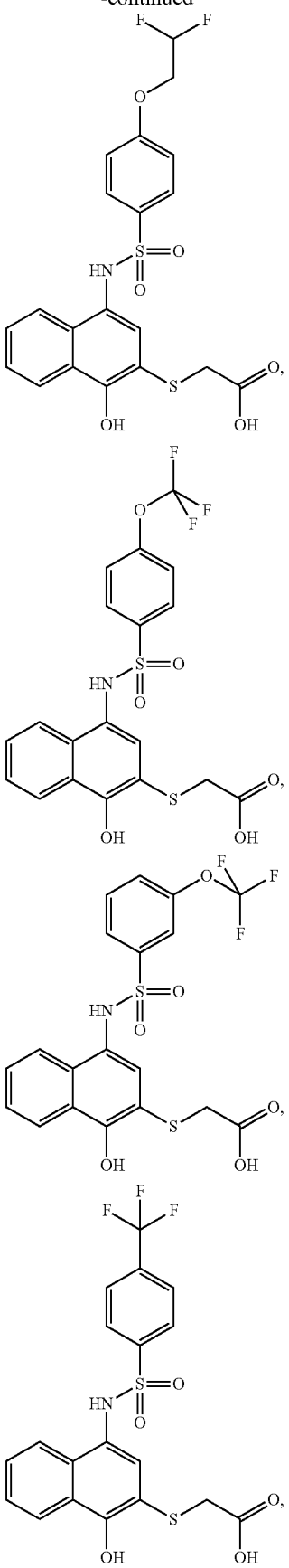
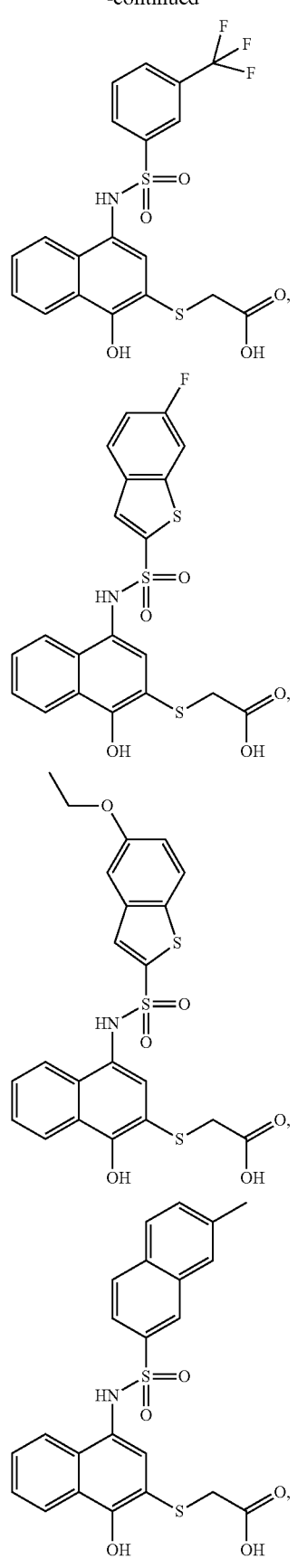

245
-continued
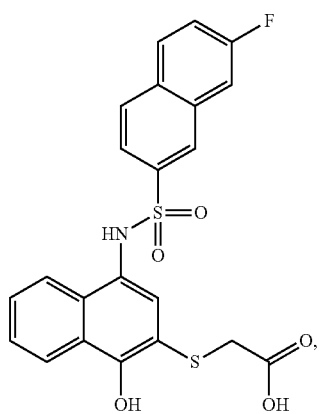
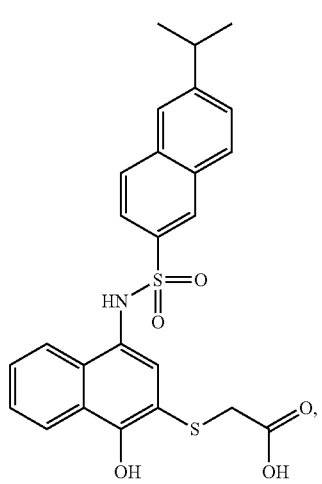
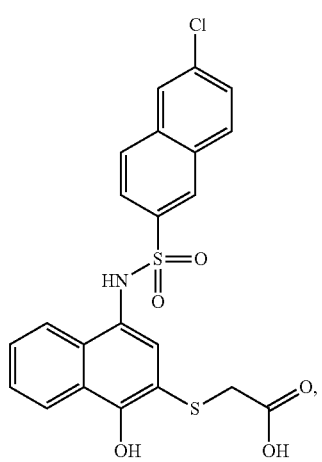
246
-continued
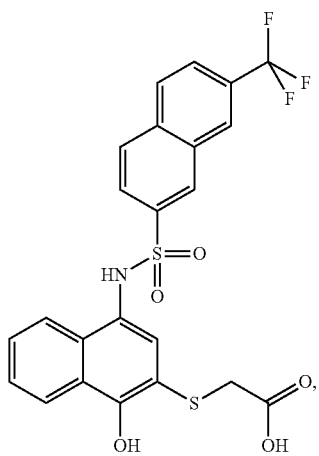
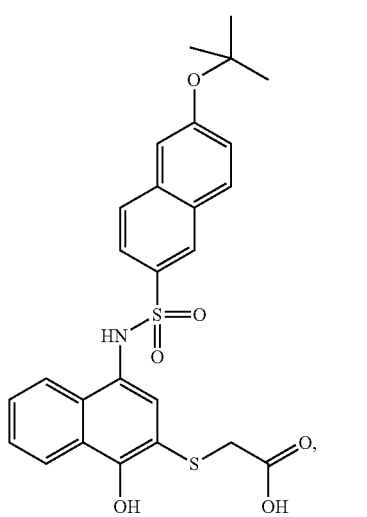
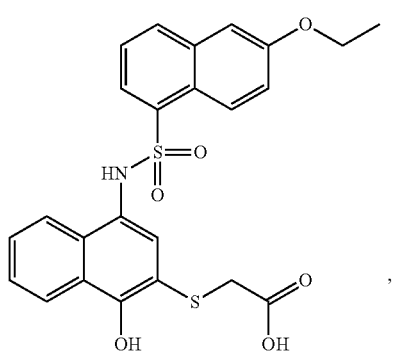

247
-continued
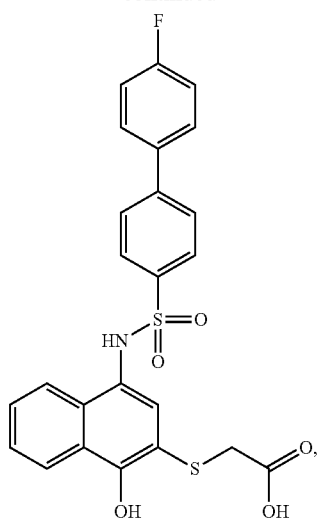
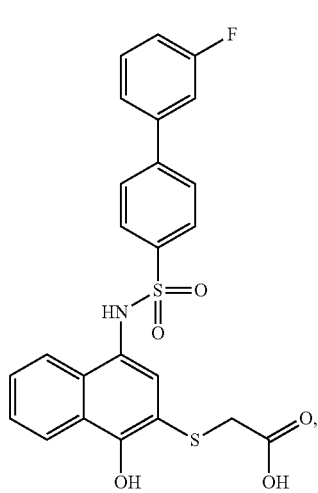
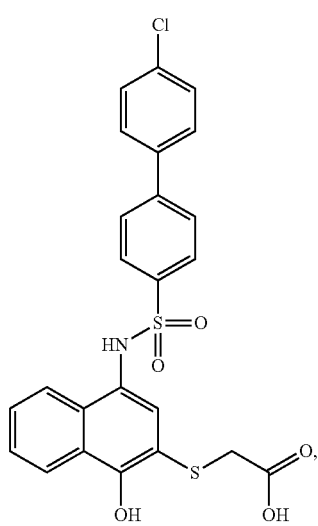
248
-continued
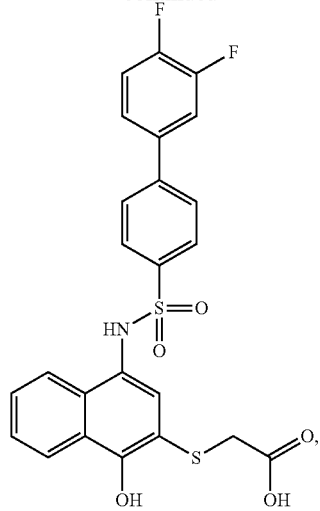
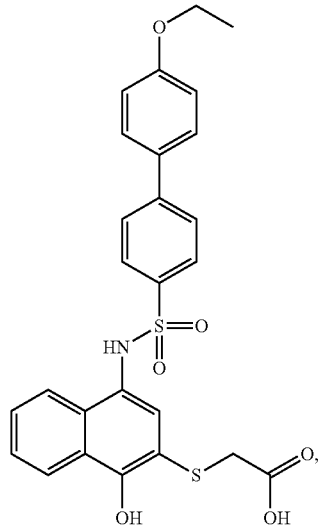
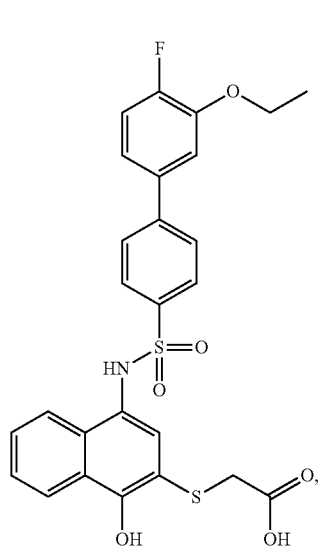

249
-continued
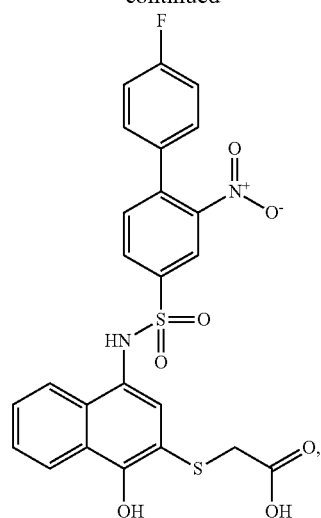
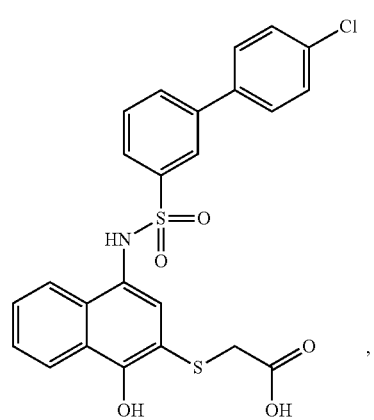
250
-continued
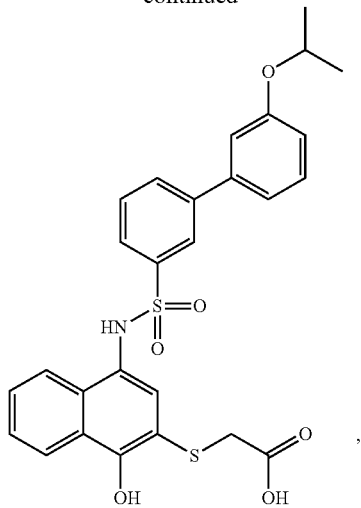
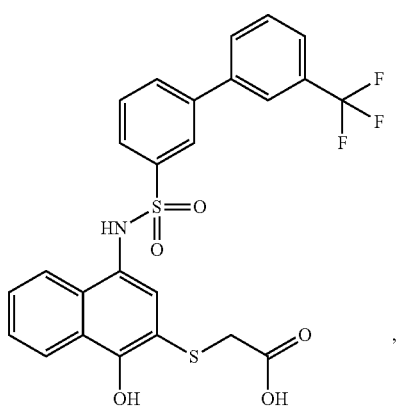
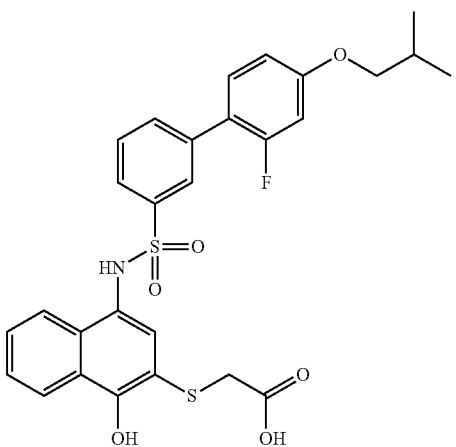

251
-continued
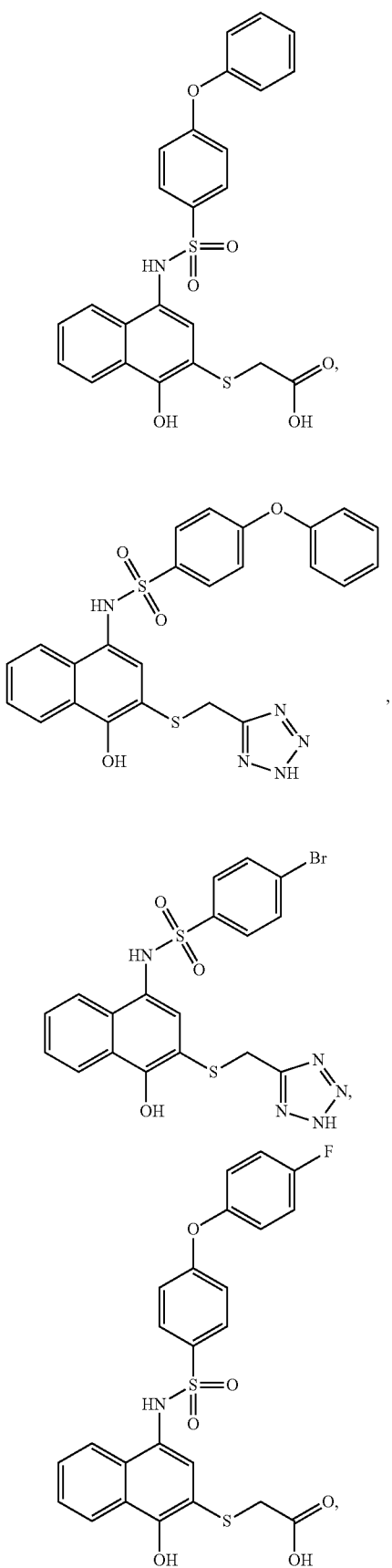
252
-continued
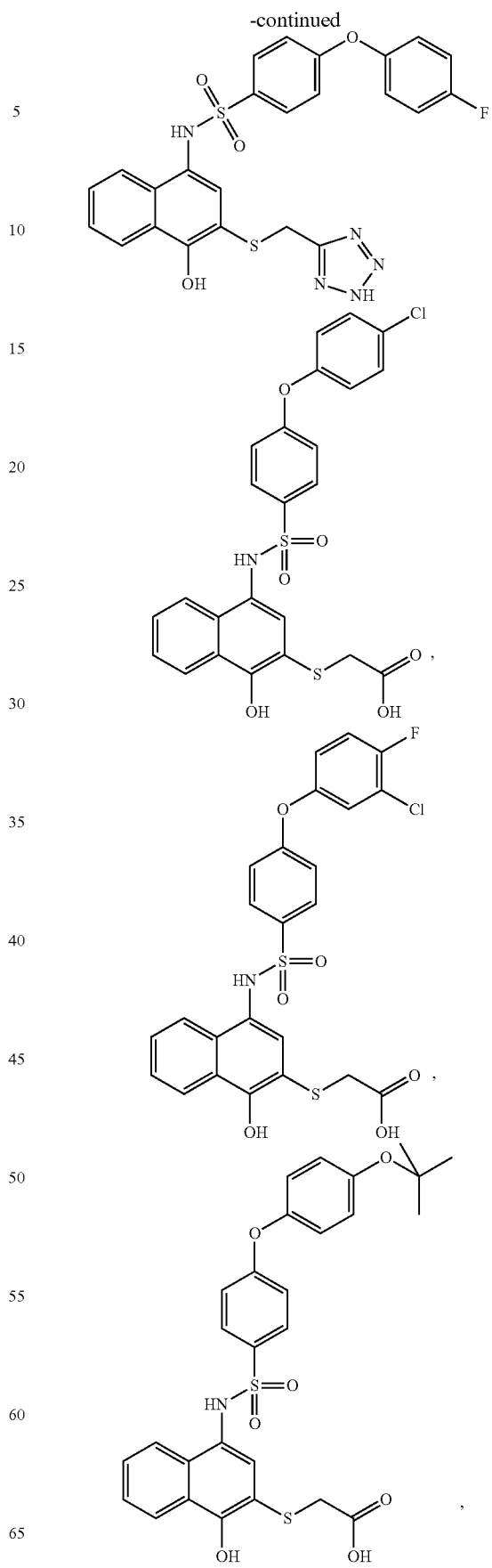

253
-continued
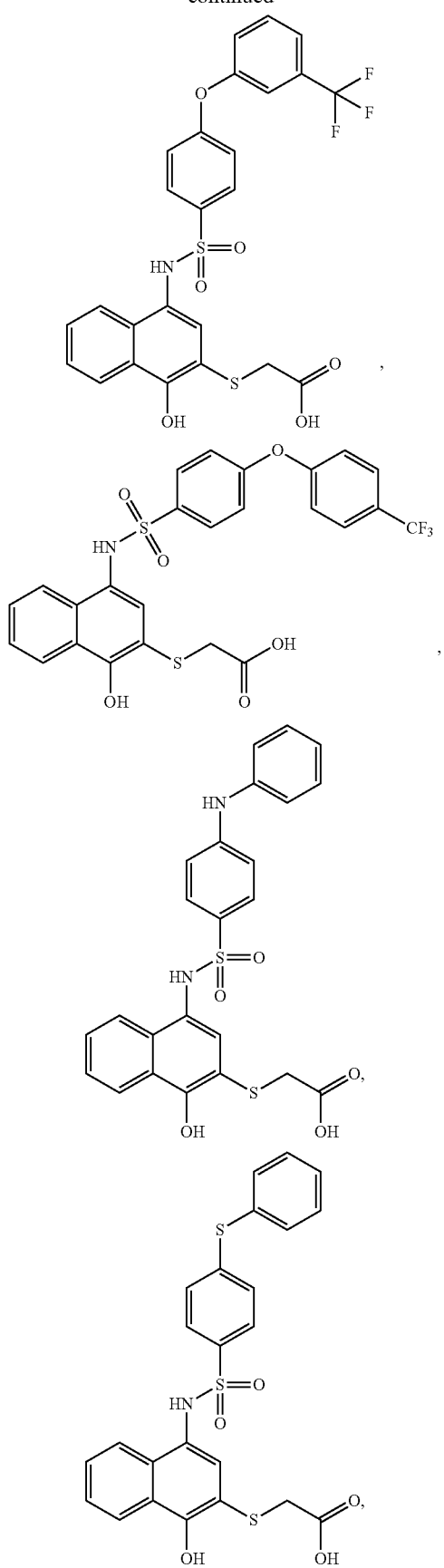
254
-continued
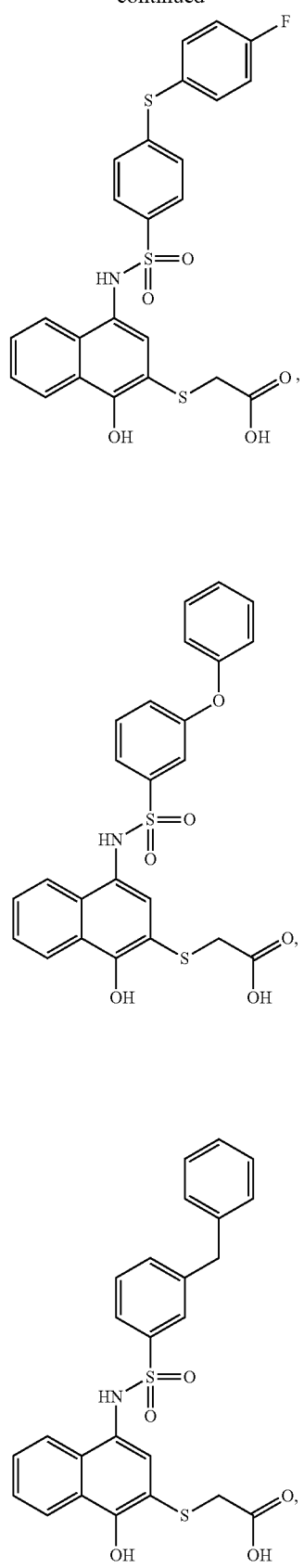

255
-continued
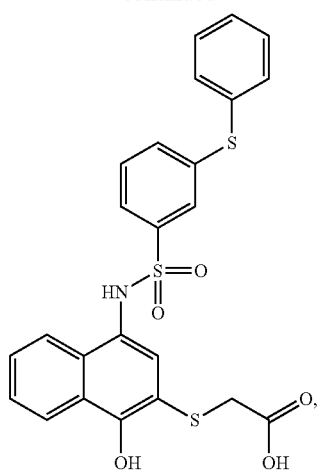
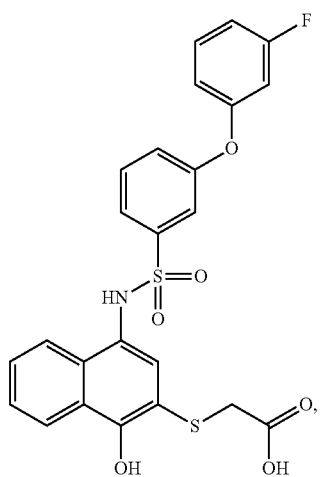
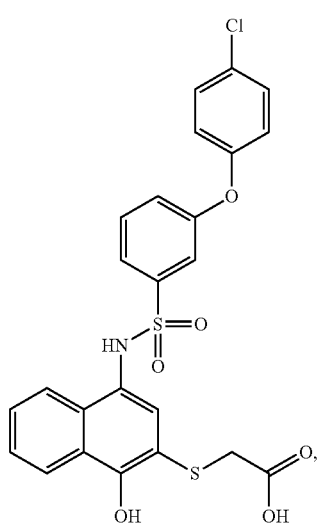
256
-continued
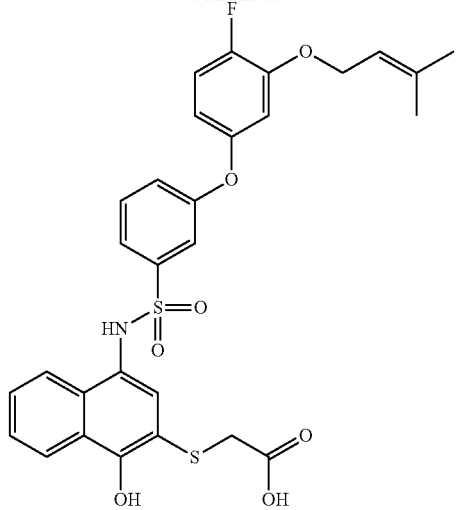
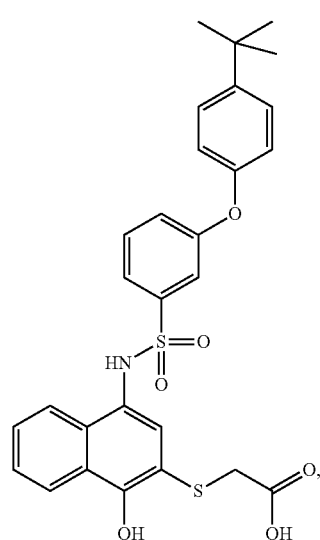
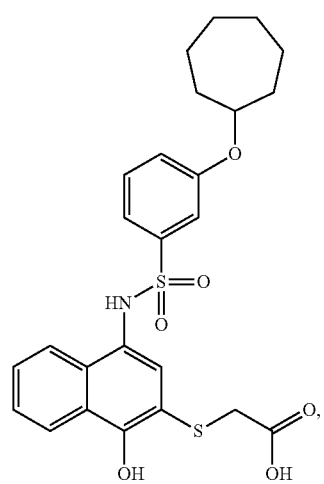

257
-continued
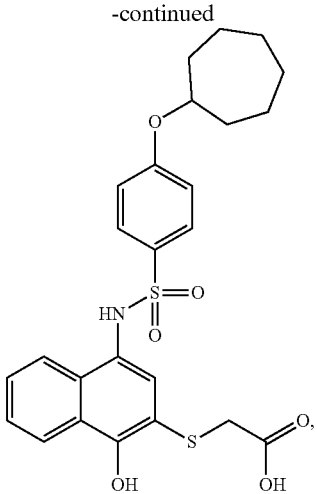
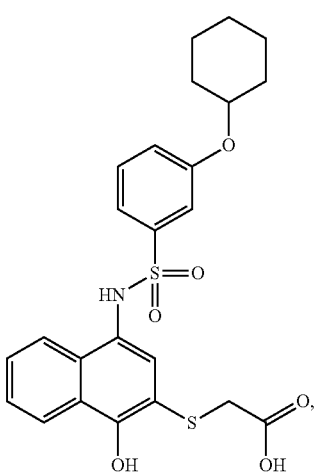
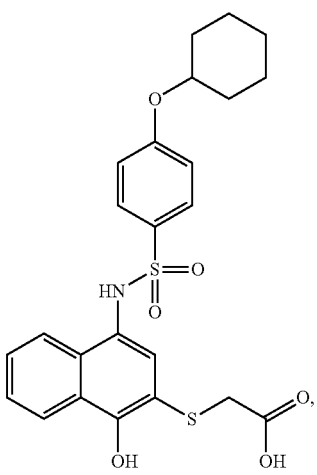
258
-continued
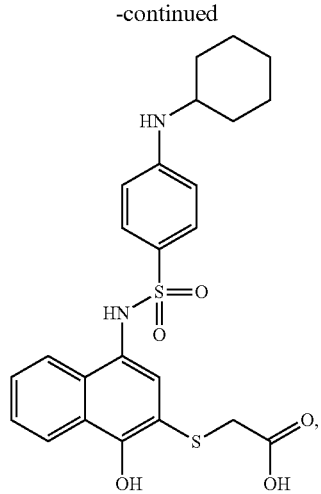
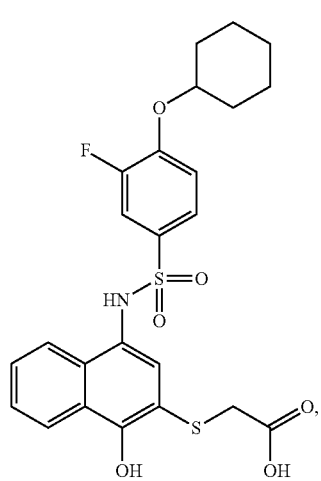
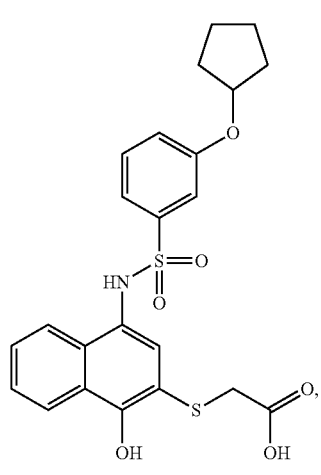

259
-continued
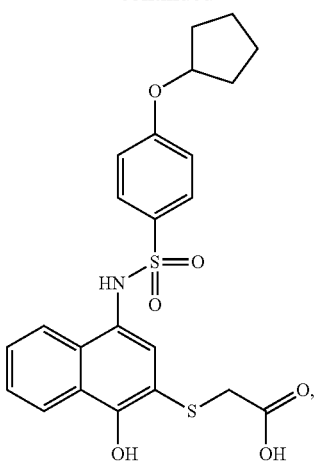
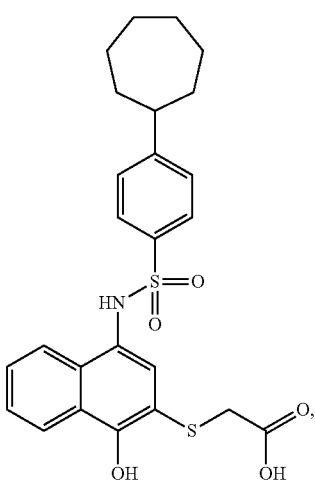
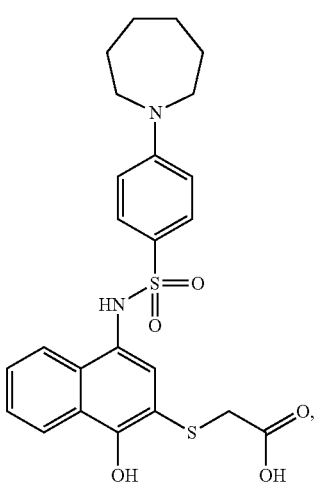
260
-continued
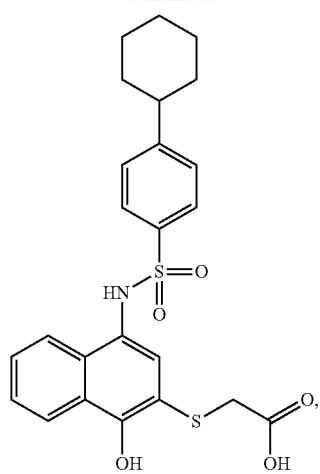
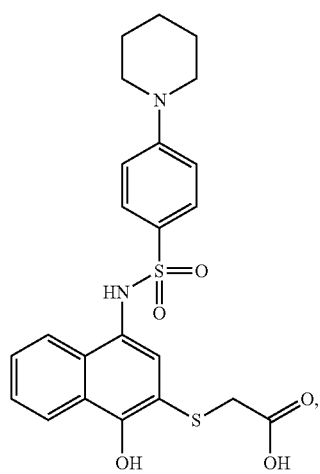
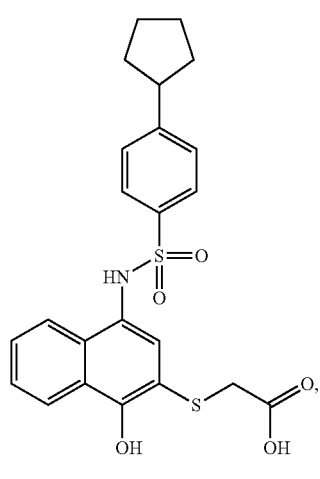

261
-continued
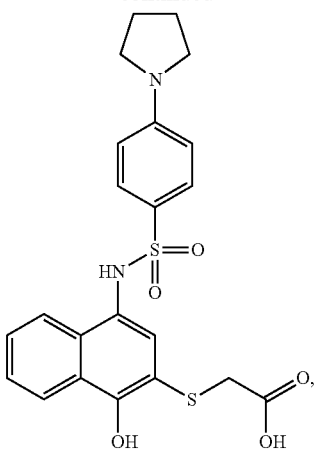
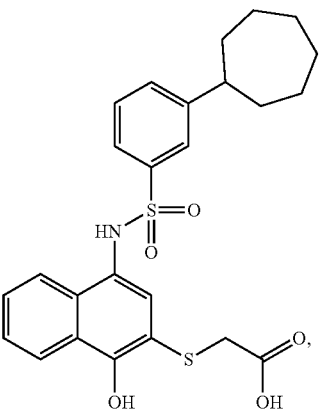
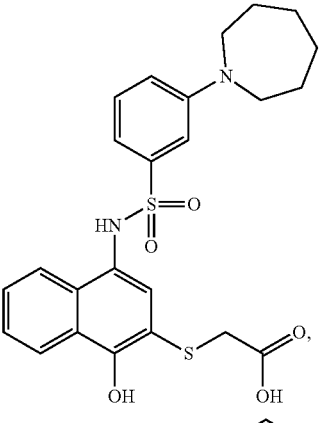
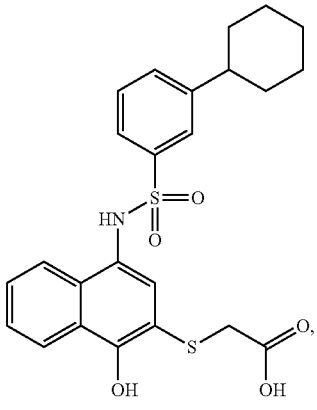
262
-continued
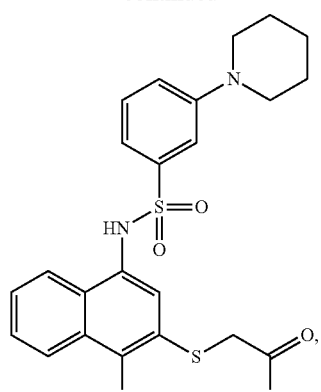
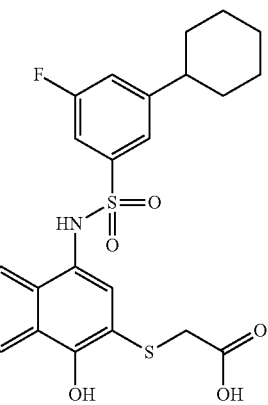
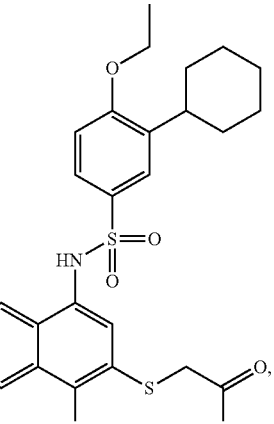
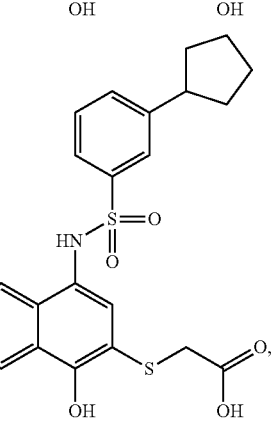

263
-continued
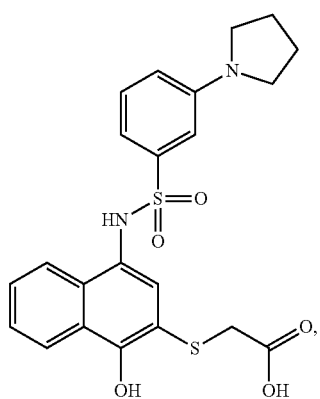
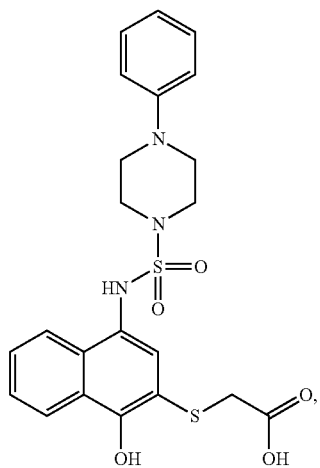
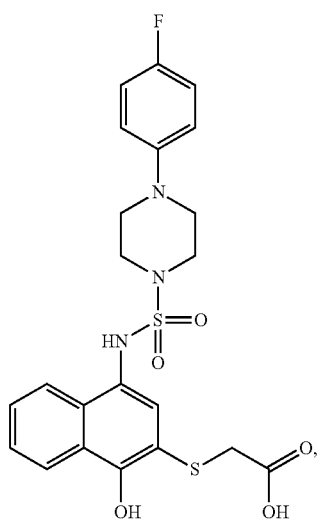
264
-continued
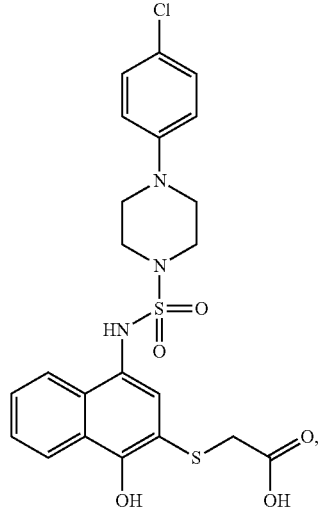
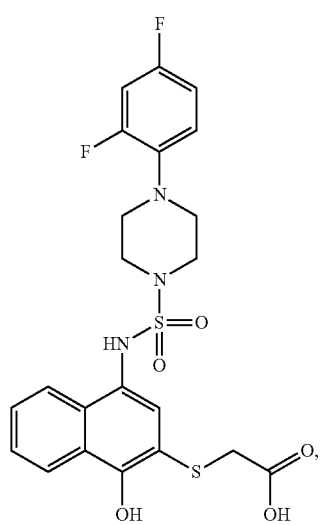
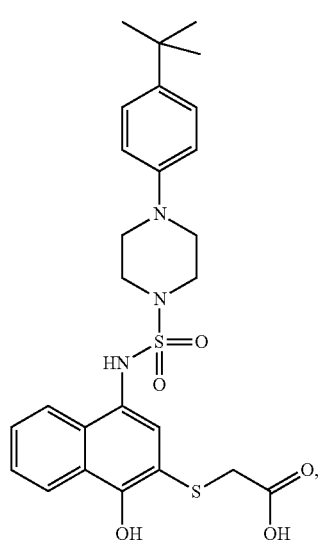

265
-continued
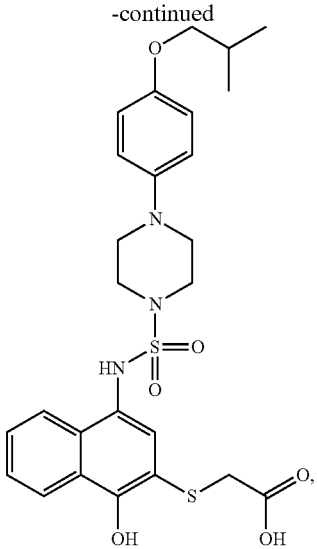
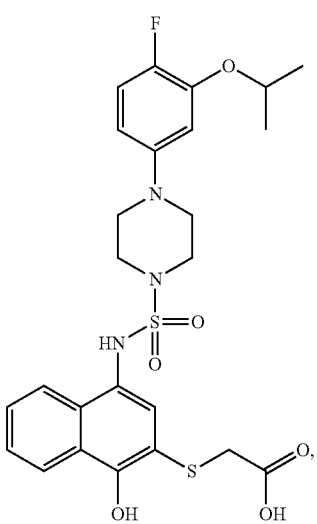
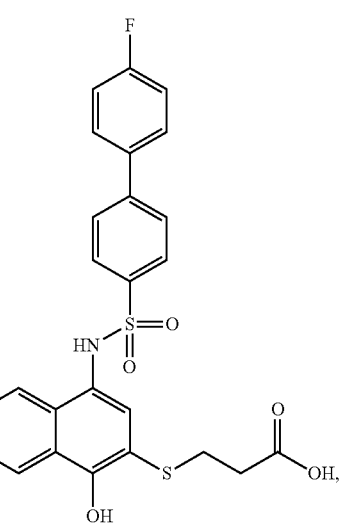
266
-continued
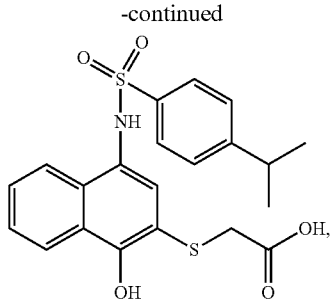
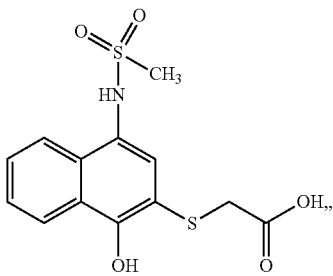
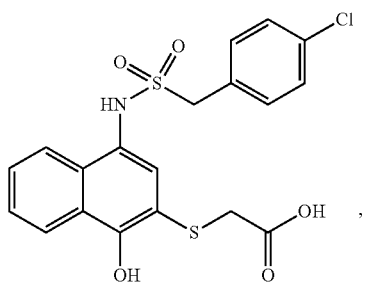
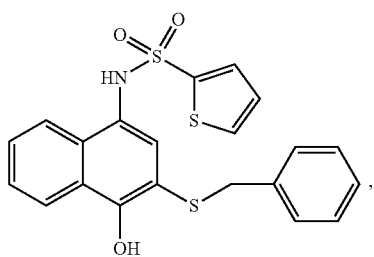
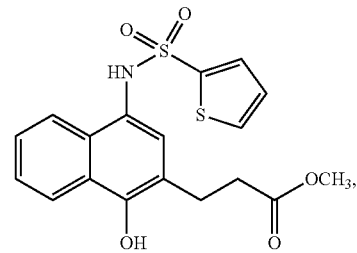
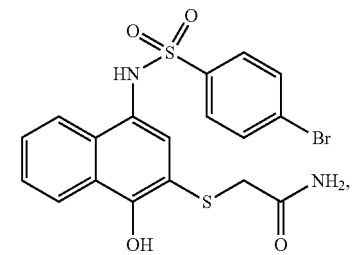

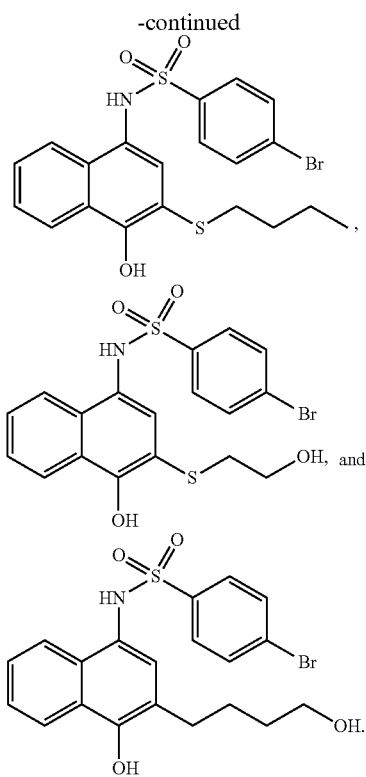

What is claimed is:

1. A compound having the following formula;

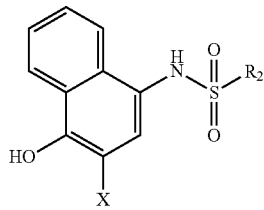

and
wherein X is selected from the group consisting of

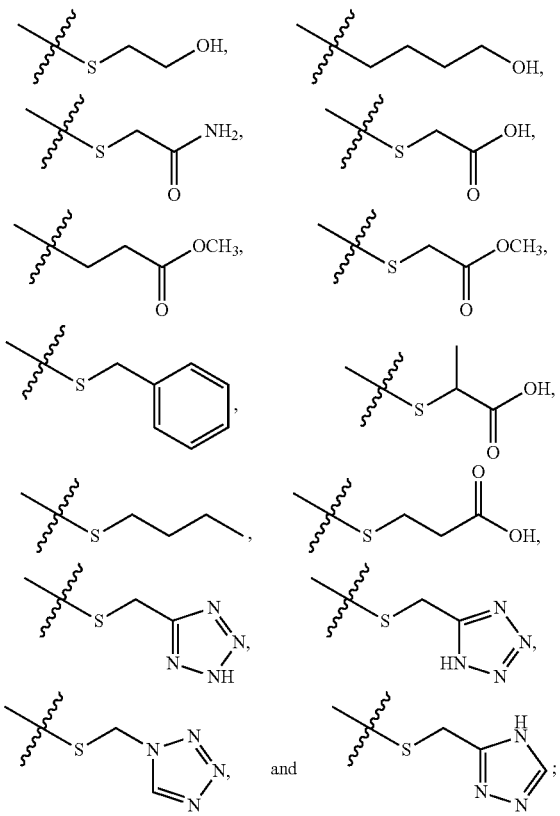

wherein R2 is selected from the group consisting of —H, CH₃,
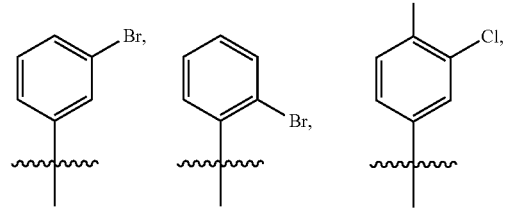
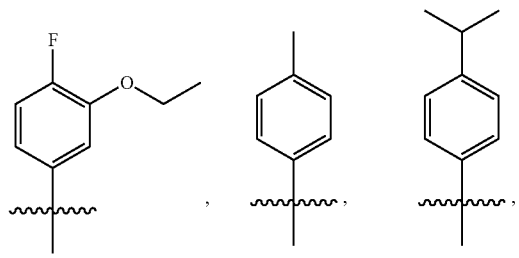
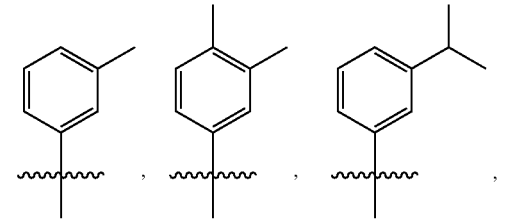
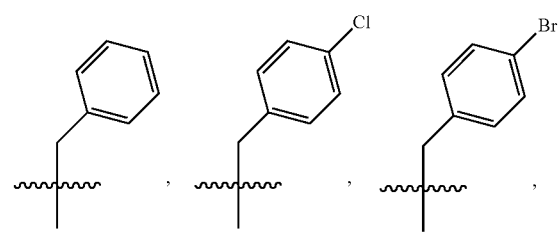
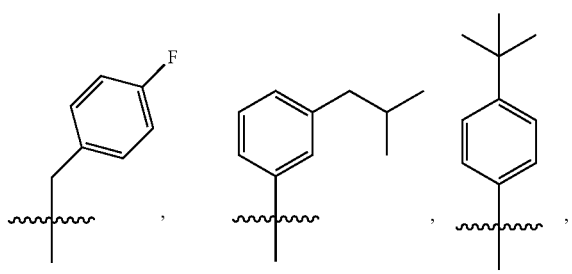
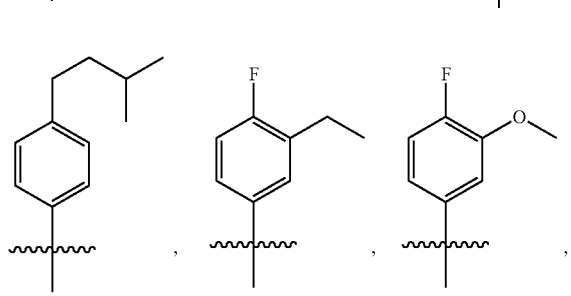
-continued
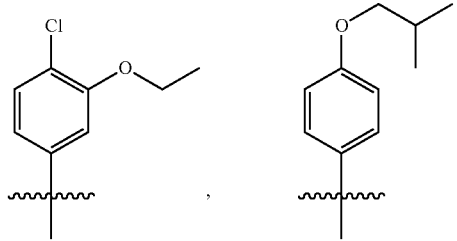
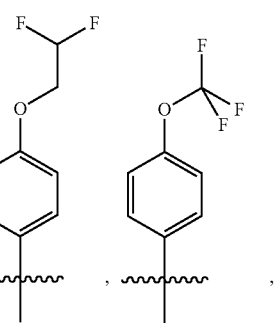
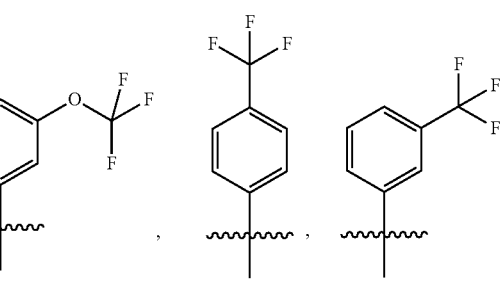
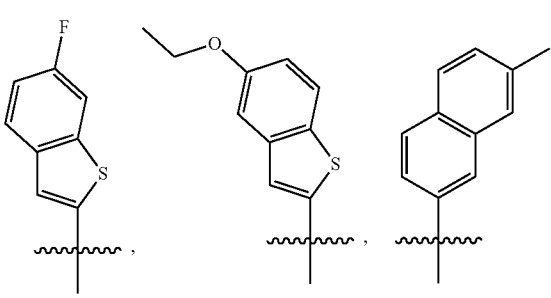
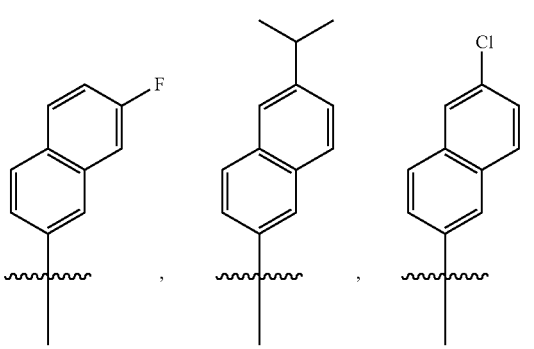

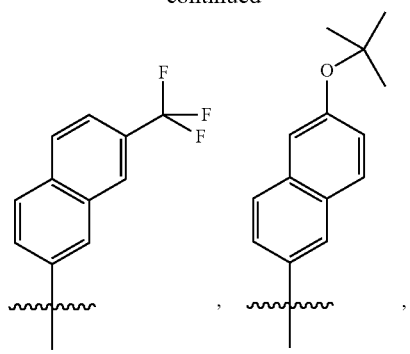
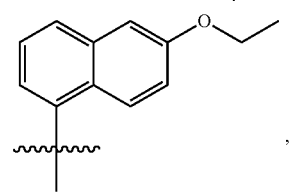
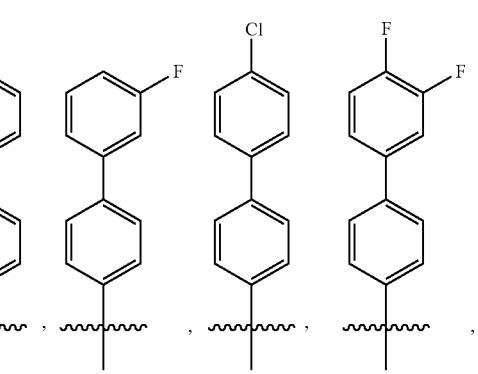
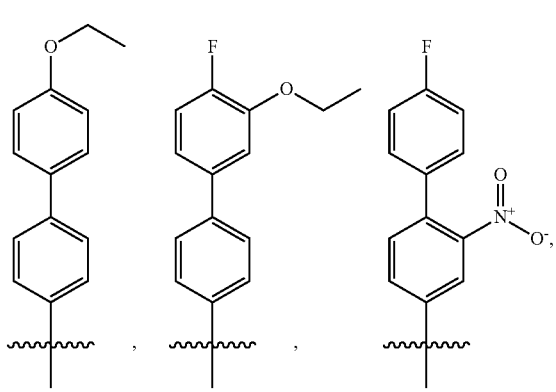
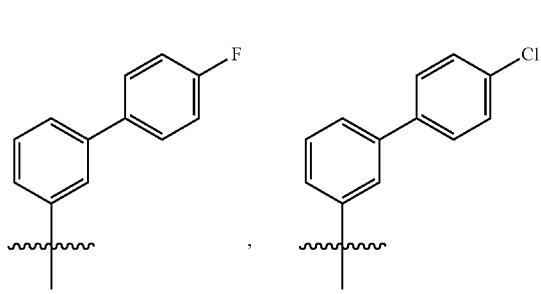
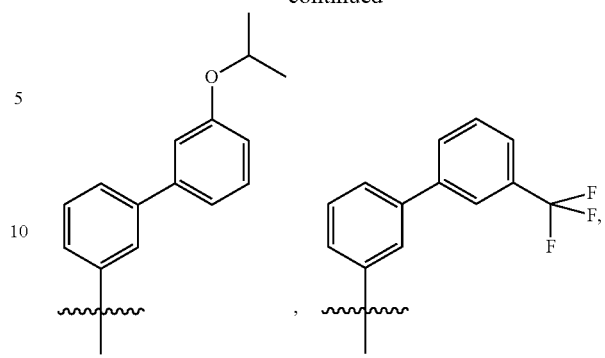
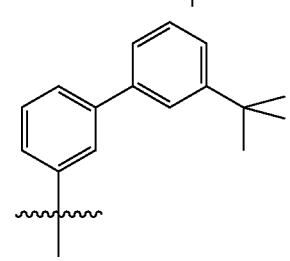
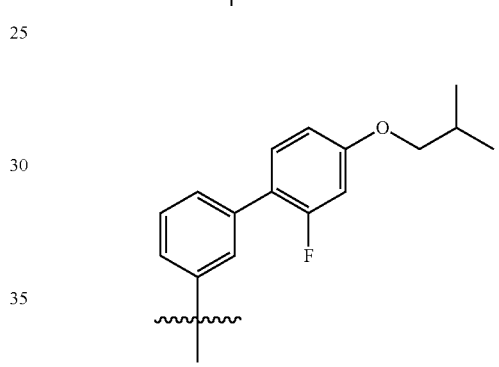
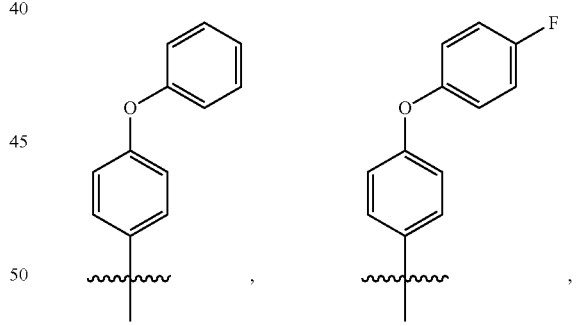
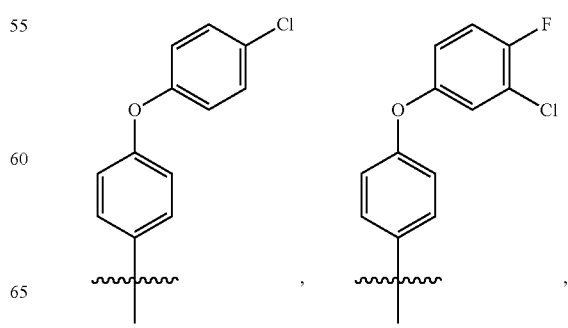

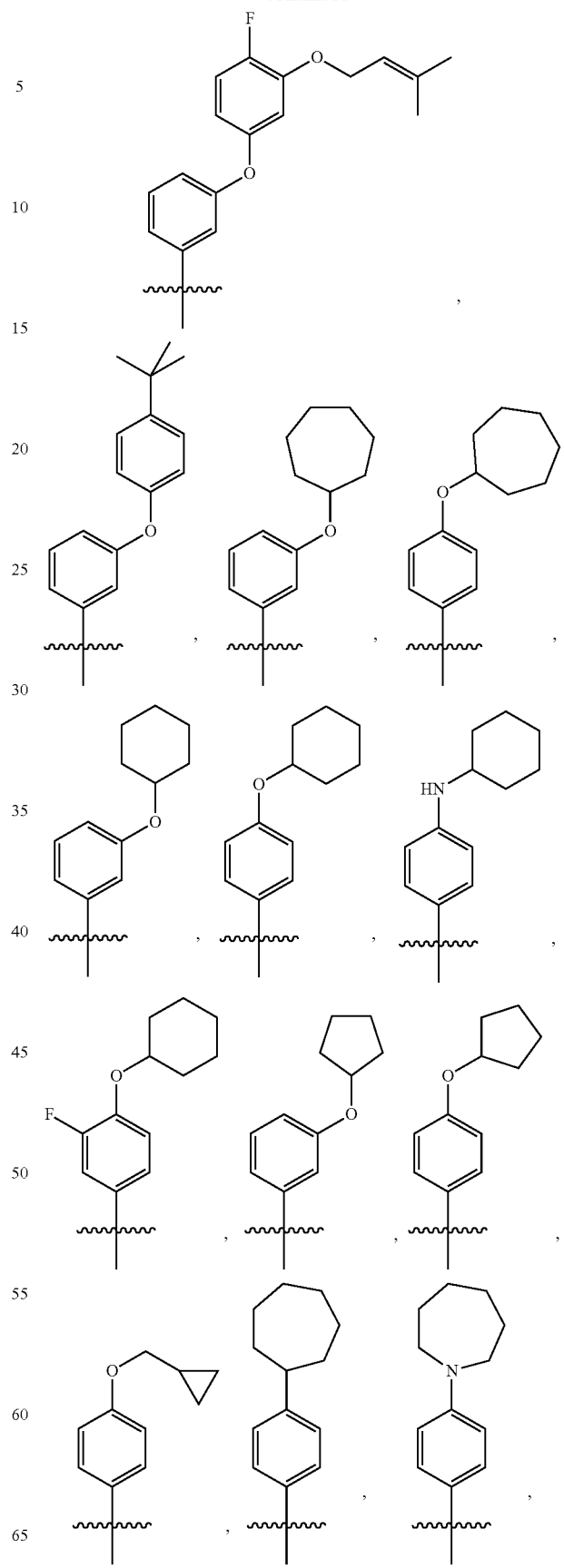
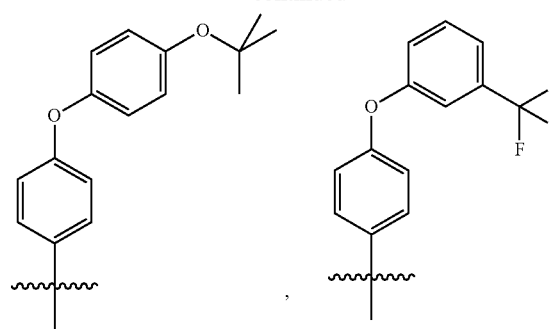

-continued
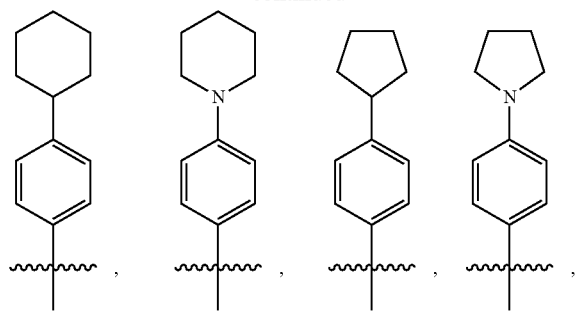
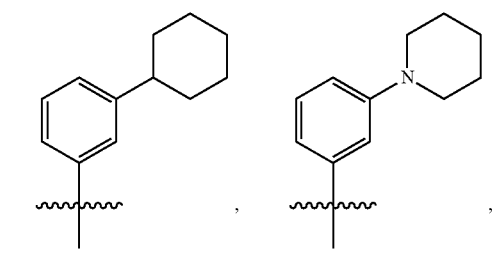
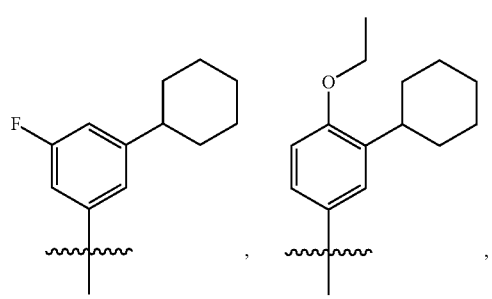
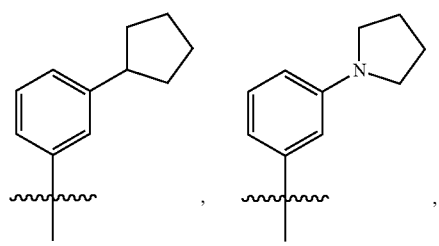
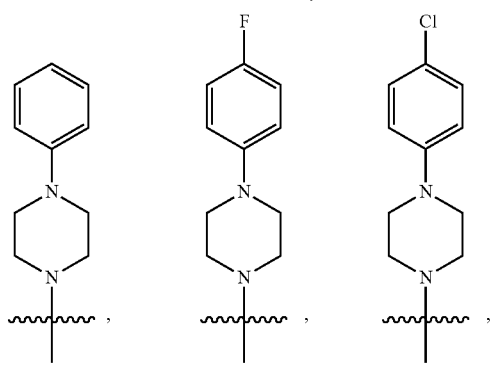
-continued
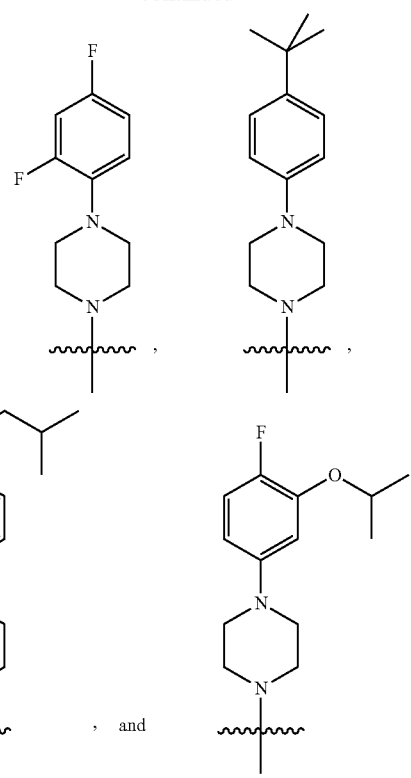
2. The compound of claim 1, wherein said compound is selected from the group consisting of:
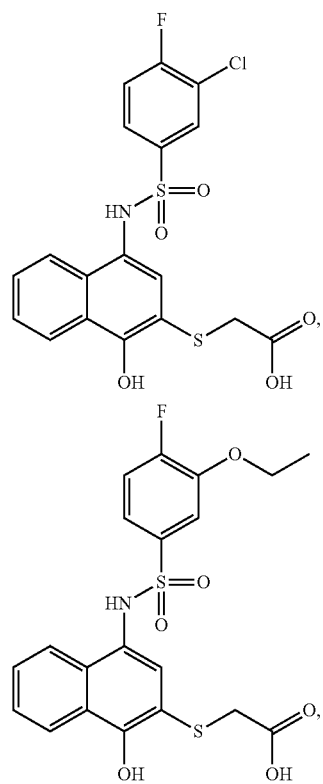

213
-continued
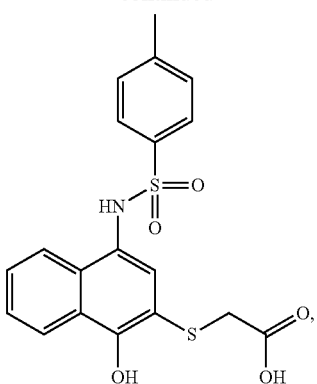
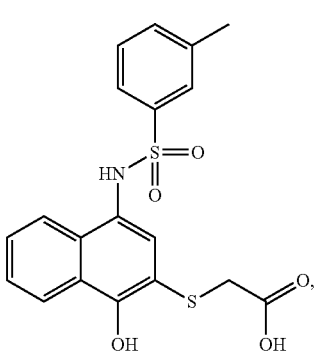
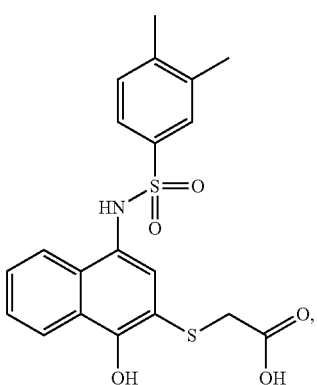
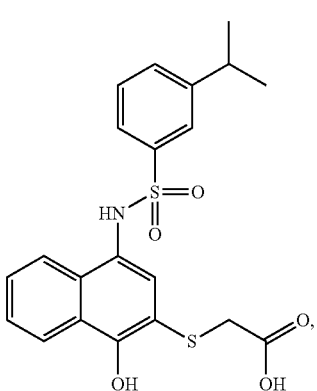
214
-continued
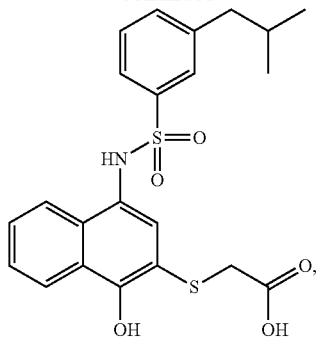
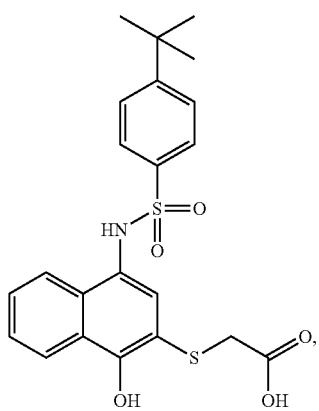
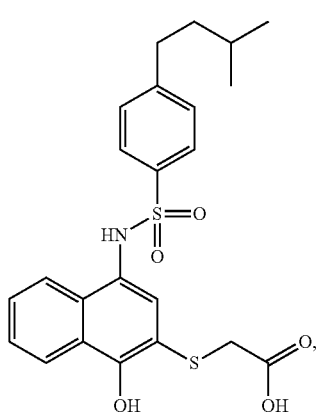
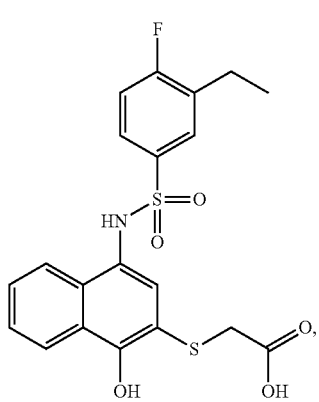

215
-continued
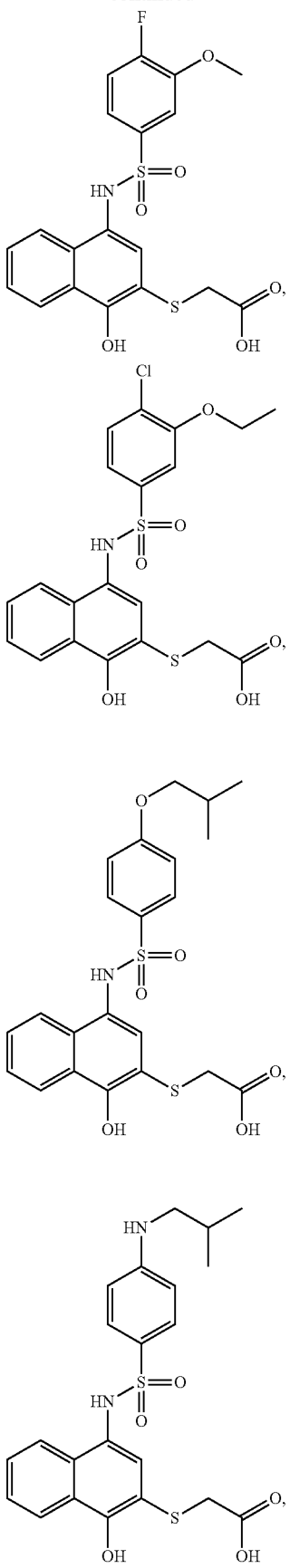
216
-continued
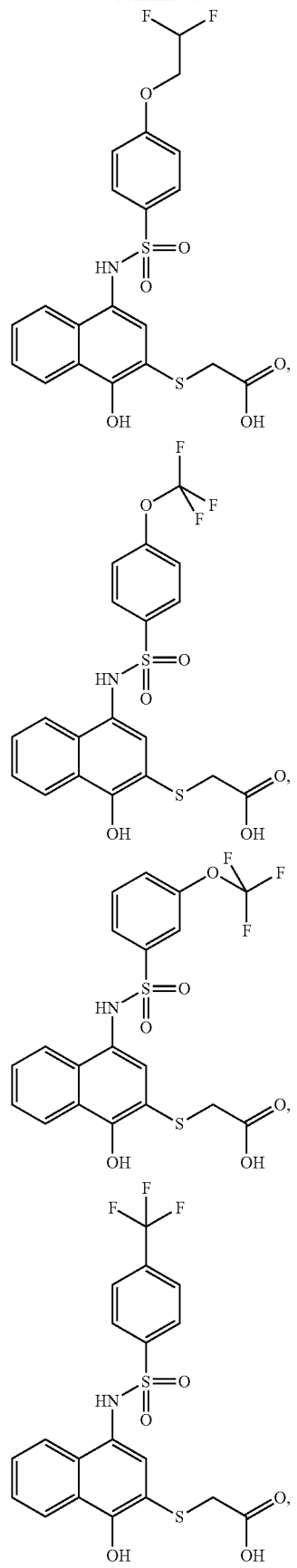

217
-continued
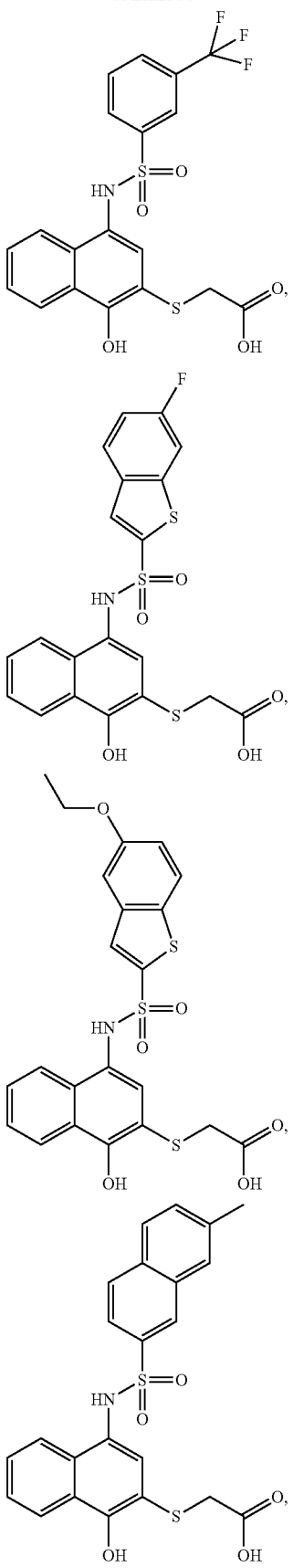
218
-continued
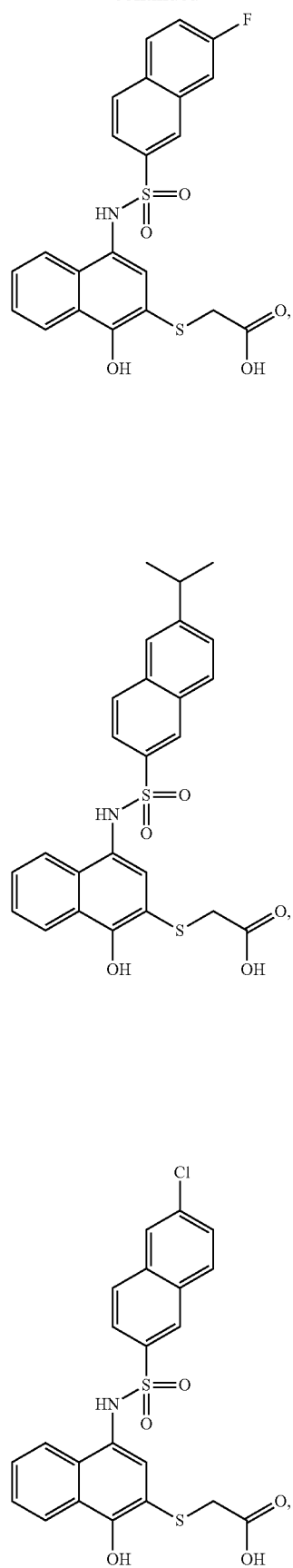

219
-continued
220
-continued

221
-continued
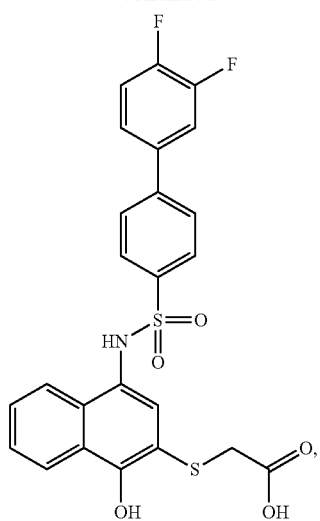
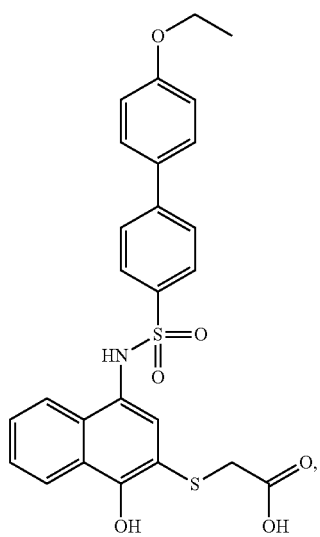
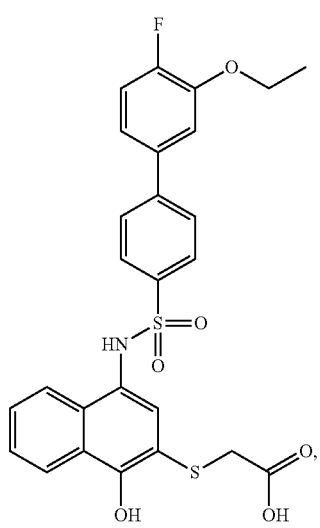
222
-continued
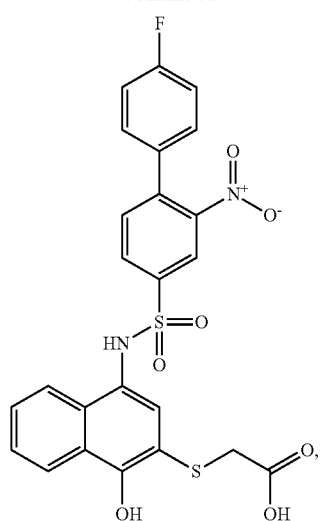
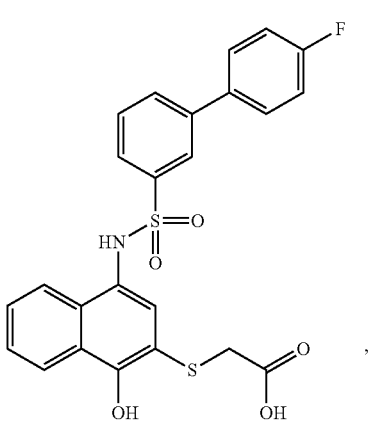
,
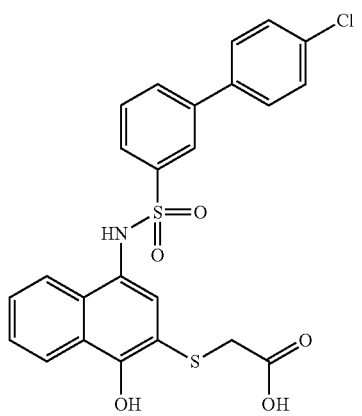
, 223
-continued
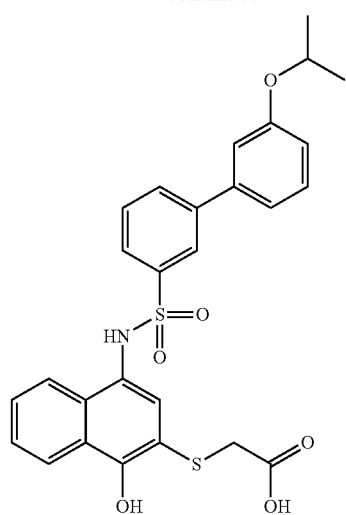
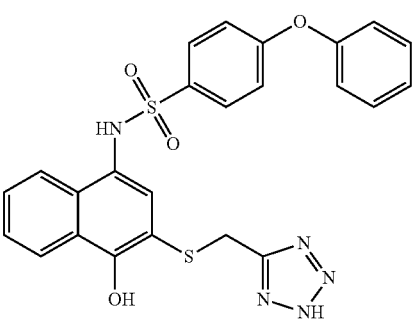
224
-continued
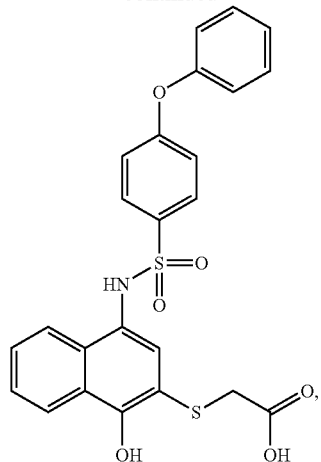
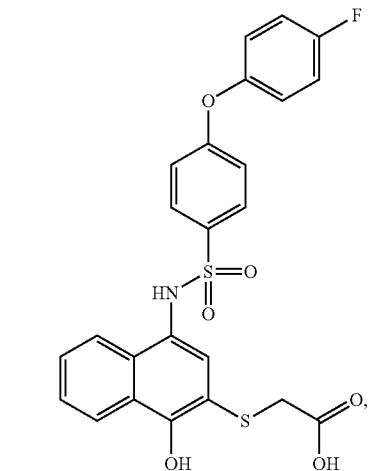
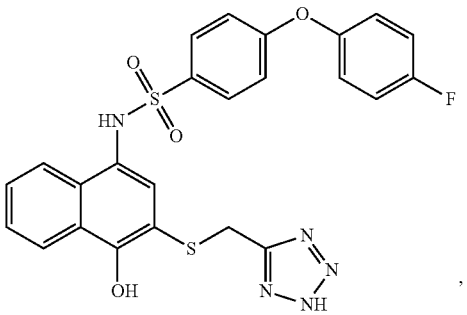

225
-continued
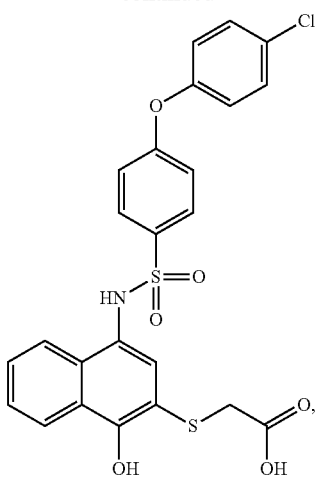
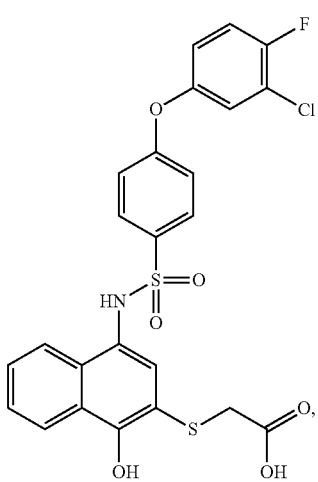
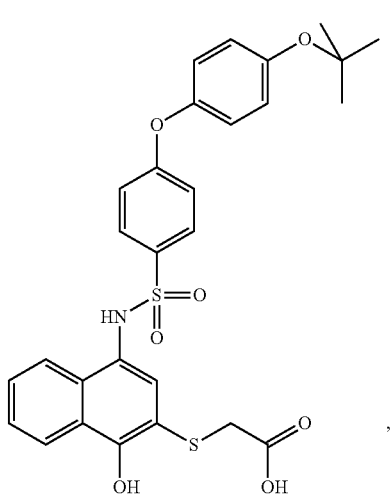
226
-continued
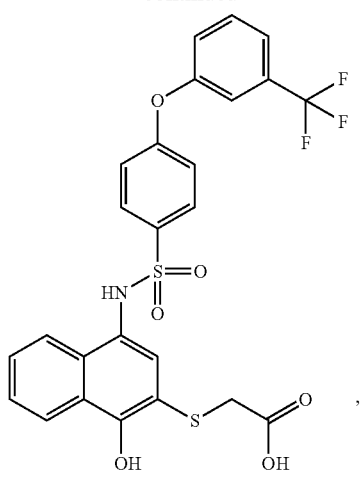
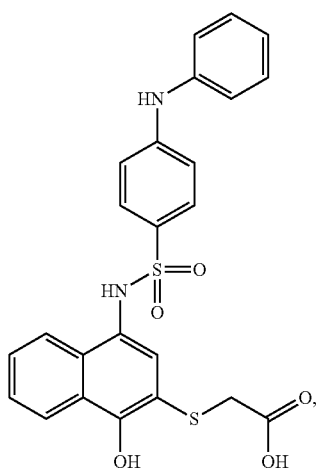
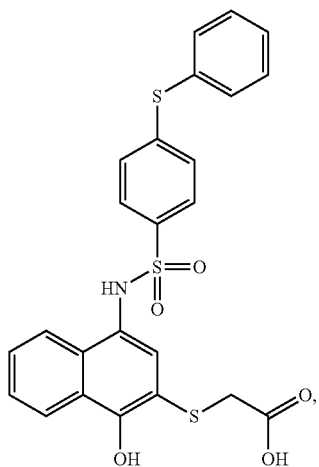

227
-continued
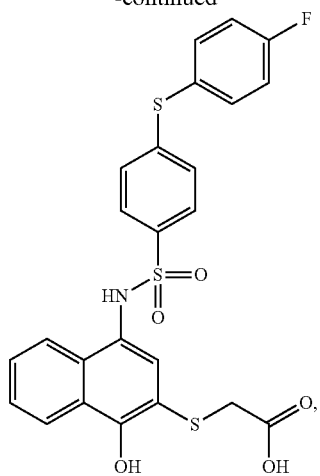
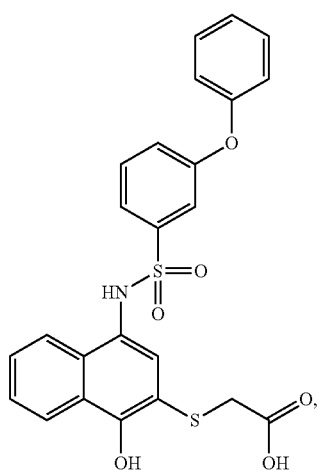
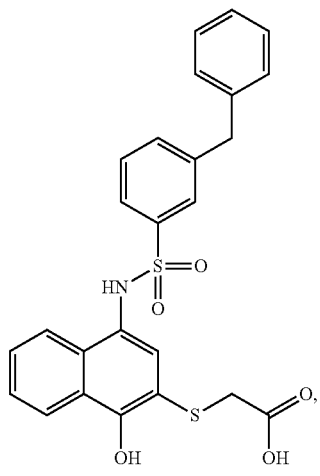
228
-continued
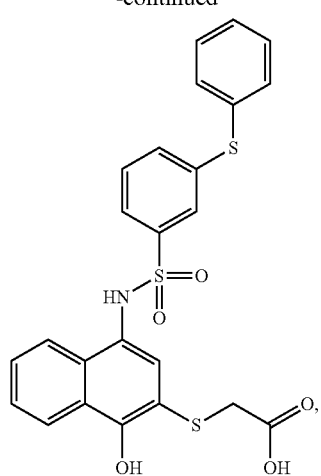
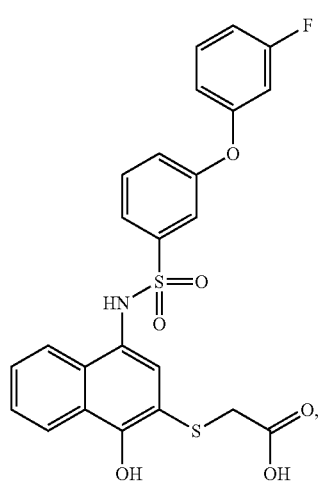
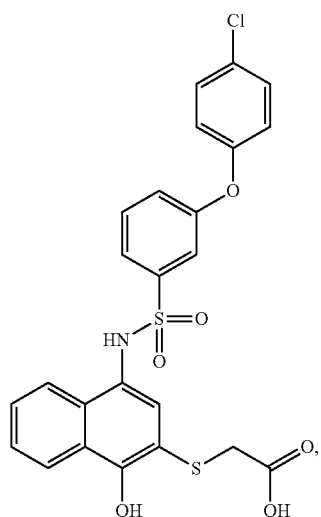

229
-continued
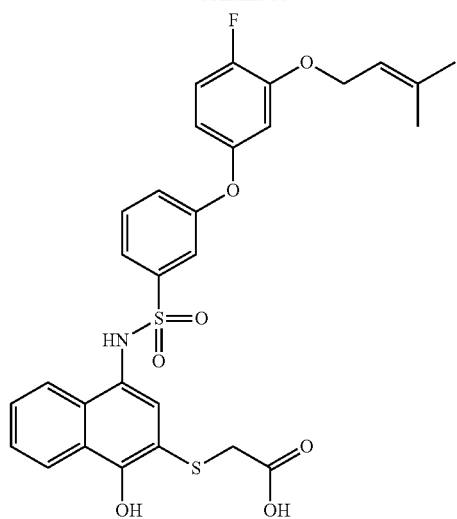
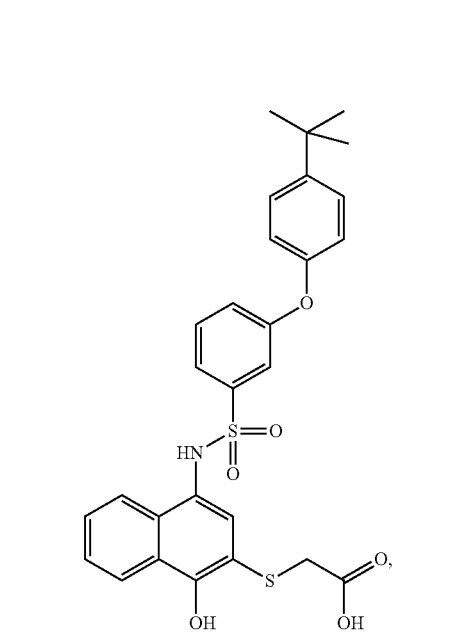
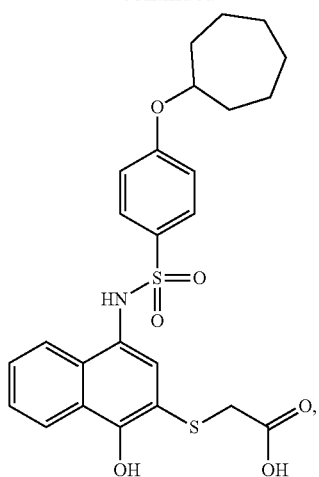
230
-continued
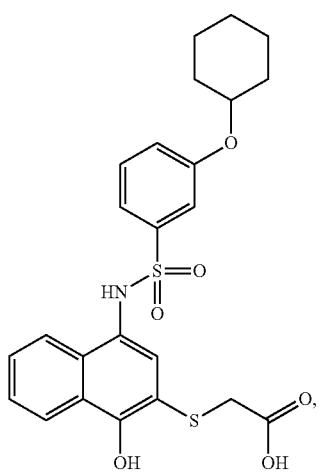
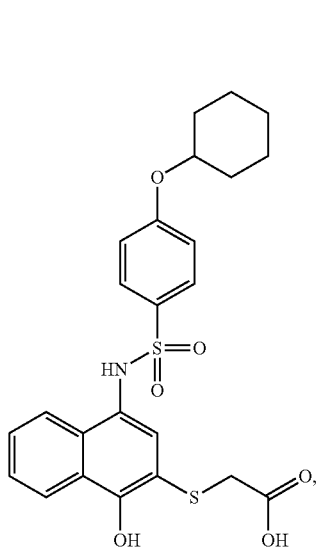

231
-continued
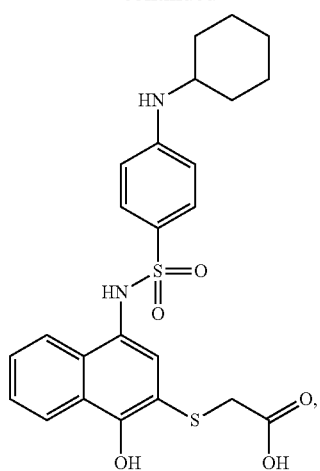
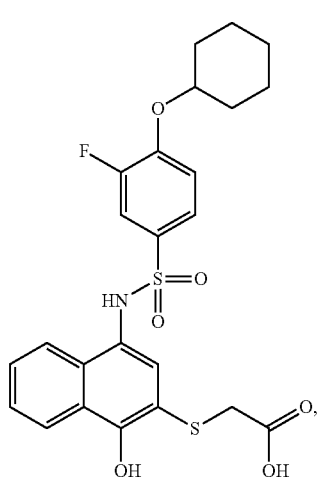
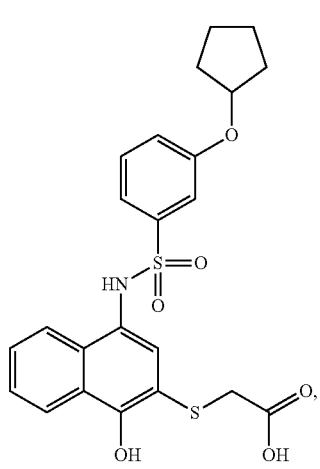
232
-continued
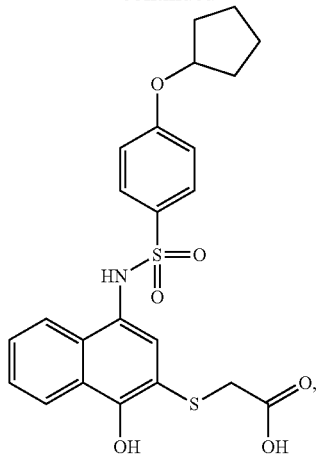
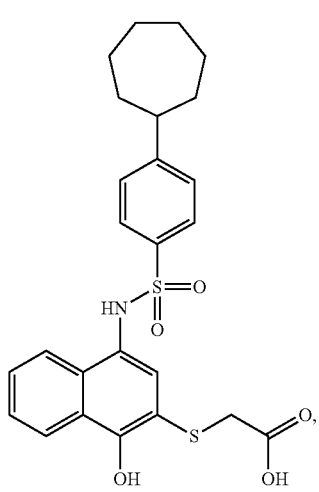
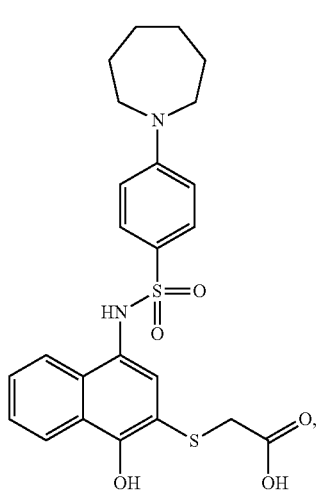

233
-continued
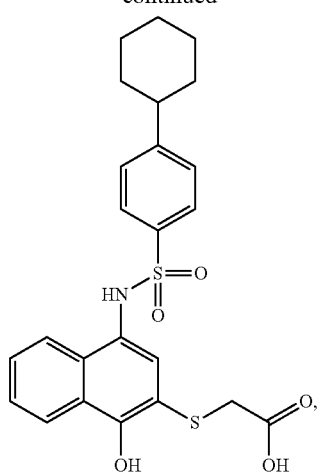
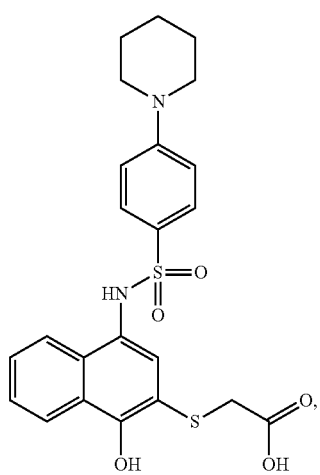
234
-continued
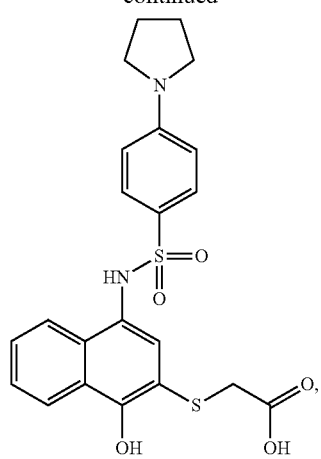
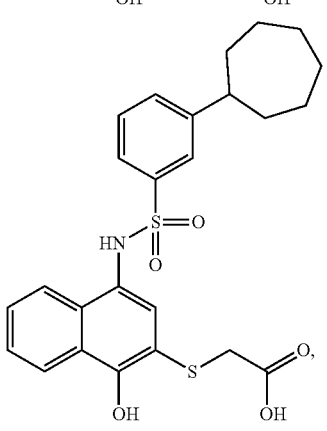
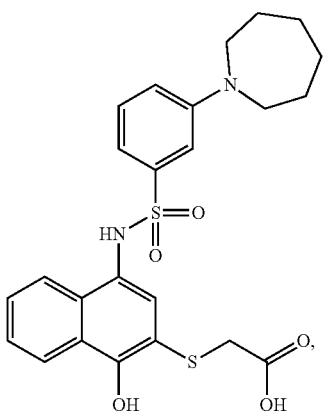
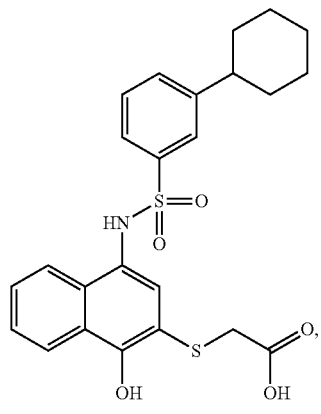

235
-continued
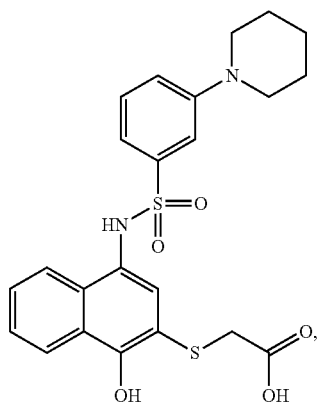
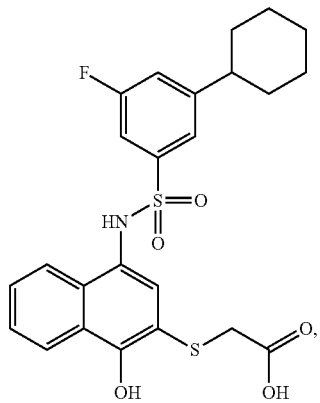
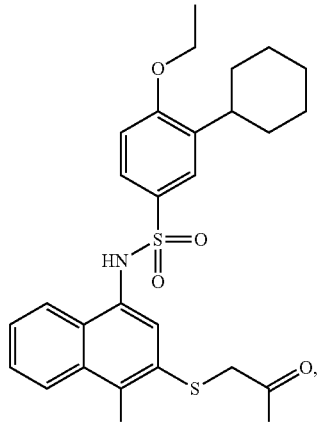
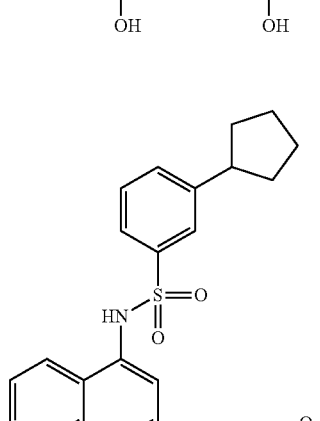
236
-continued
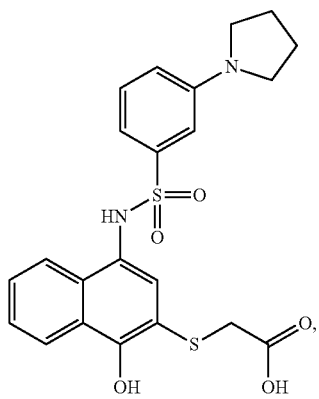
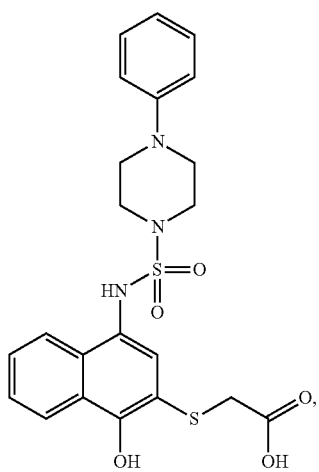
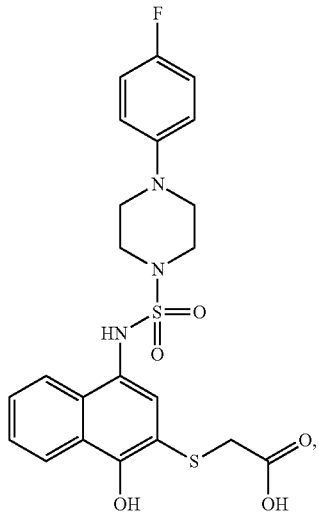

237
-continued
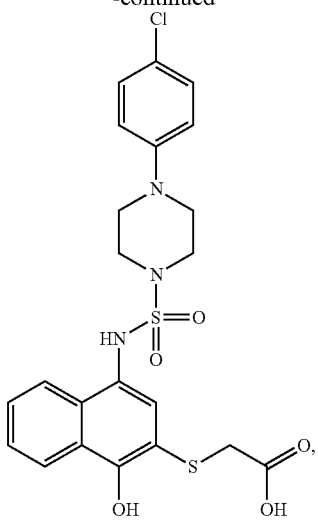
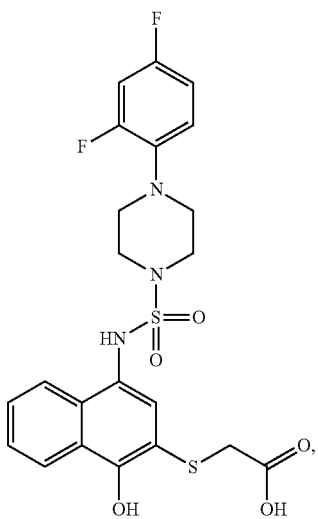
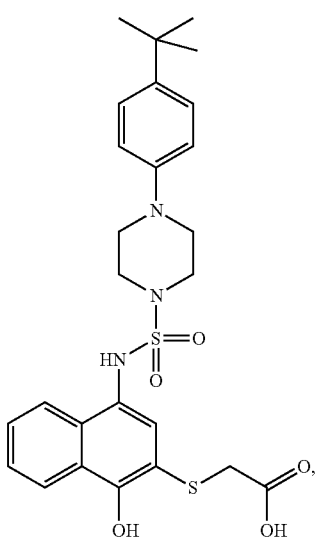
238
-continued
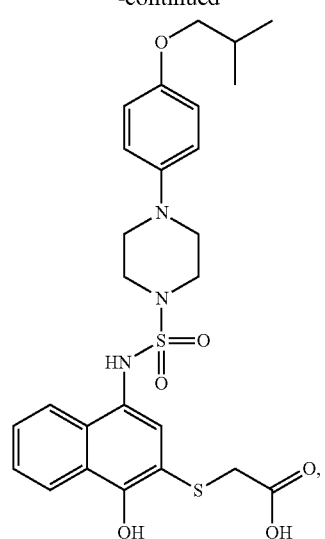
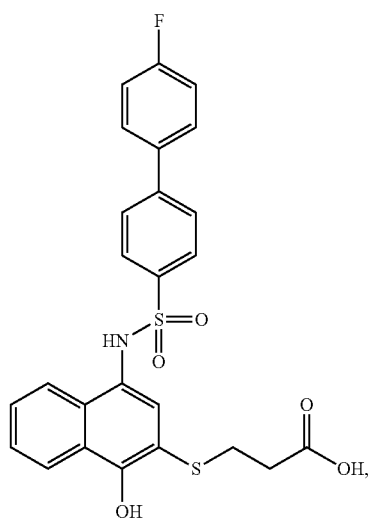

-continued
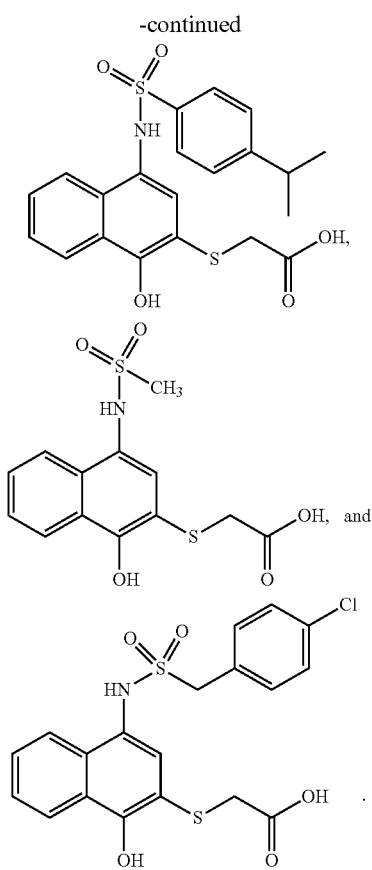
3. A compound selected from the group consisting of
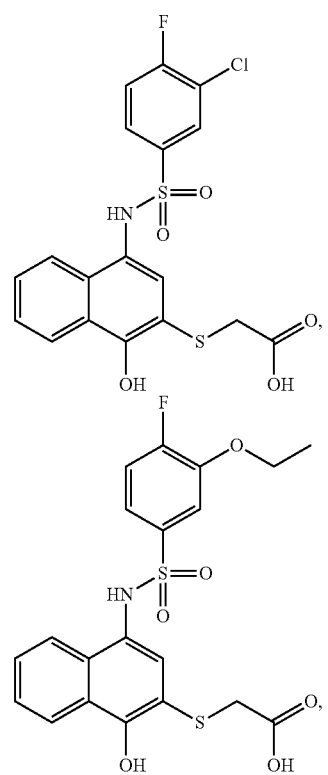
-continued
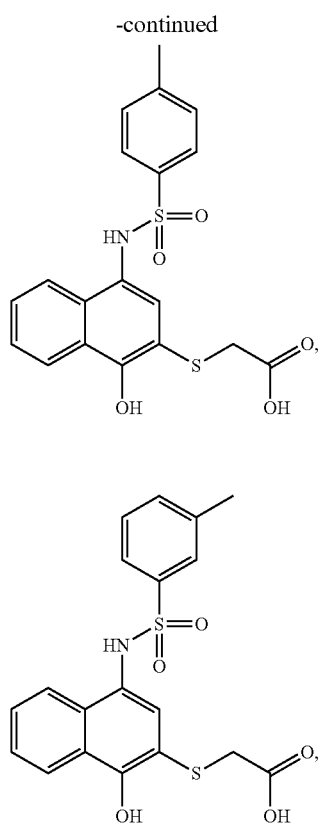
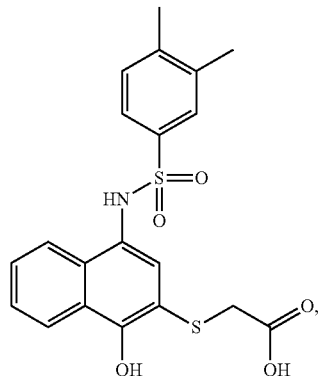
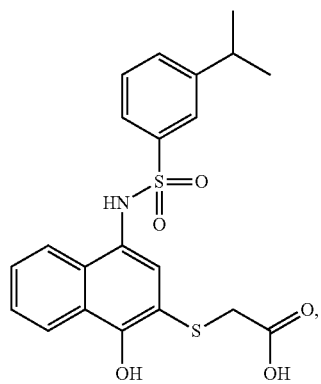

| 241 | 242 |
|---|---|
| -continued | -continued |
| 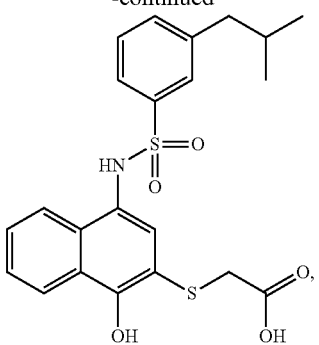 | 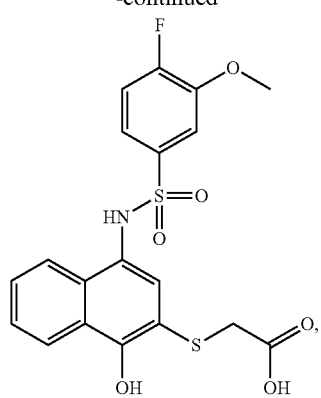 |
| 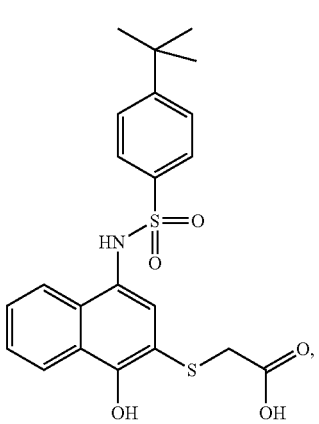 | 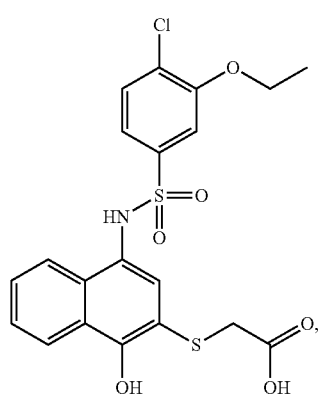 |
| 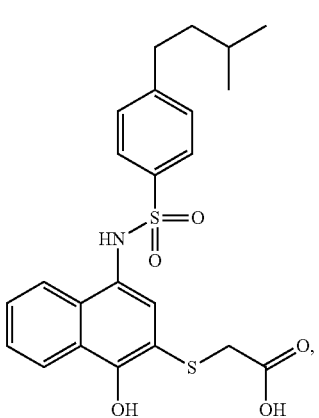 | 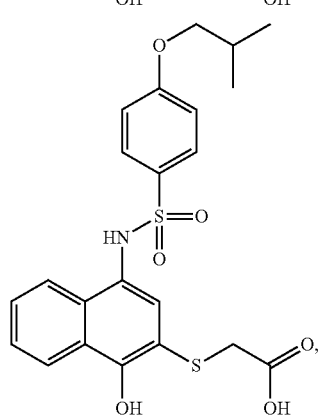 |
| 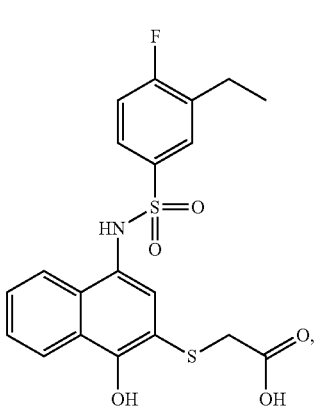 | 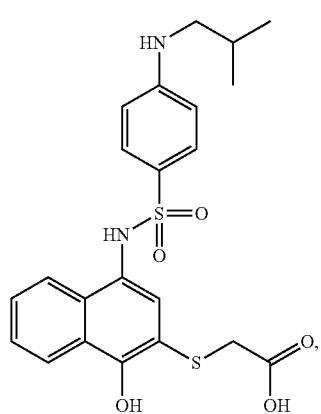 |